(12) United States Patent
Kularatne

(10) Patent No.: US 11,484,607 B2
(45) Date of Patent: *Nov. 1, 2022

(54) PSMA-TARGETED NIR DYES AND THEIR USES

(71) Applicant: On Target Laboratories, LLC, West Lafayette, IN (US)

(72) Inventor: Sumith A Kularatne, West Lafayette, IN (US)

(73) Assignee: On Target Laboratories, LLC, West Lafayette, IN (US)

( * ) Notice: Subject to any disclaimer, the term of this patent is extended or adjusted under 35 U.S.C. 154(b) by 23 days.

This patent is subject to a terminal disclaimer.

(21) Appl. No.: 17/029,226

(22) Filed: Sep. 23, 2020

(65) Prior Publication Data

US 2021/0046194 A1 Feb. 18, 2021

Related U.S. Application Data

(63) Continuation of application No. 16/126,140, filed on Sep. 10, 2018, now Pat. No. 10,842,887, which is a continuation-in-part of application No. 15/624,680, filed on Jun. 15, 2017, now Pat. No. 10,456,482, which is a continuation of application No.
(Continued)

(51) Int. Cl.
| | | |
|---|---|---|
| *A61B 5/00* | (2006.01) | |
| *A61B 8/00* | (2006.01) | |
| *A61B 10/00* | (2006.01) | |
| *A61K 49/00* | (2006.01) | |
| *G01N 21/64* | (2006.01) | |
| *C07K 5/087* | (2006.01) | |
| *C07K 5/11* | (2006.01) | |
| *C07K 7/06* | (2006.01) | |
| *C07K 5/062* | (2006.01) | |
| *C07D 209/20* | (2006.01) | |
| *C07K 5/083* | (2006.01) | |
| *G01N 33/574* | (2006.01) | |
| *C07K 7/02* | (2006.01) | |
| *C07K 5/072* | (2006.01) | |
| *C07K 5/078* | (2006.01) | |
| *C07K 5/065* | (2006.01) | |
| *C07K 5/09* | (2006.01) | |

(Continued)

(52) U.S. Cl.
CPC ...... *A61K 49/0052* (2013.01); *A61K 49/0032* (2013.01); *A61K 49/0034* (2013.01); *A61K 49/0056* (2013.01); *C07D 209/20* (2013.01); *C07K 5/0606* (2013.01); *C07K 5/06026* (2013.01); *C07K 5/06078* (2013.01); *C07K 5/06095* (2013.01); *C07K 5/06121* (2013.01); *C07K 5/06147* (2013.01); *C07K 5/06156* (2013.01); *C07K 5/0806* (2013.01); *C07K 5/0812* (2013.01); *C07K 5/0817* (2013.01); *C07K 5/1019* (2013.01); *C07K 7/02* (2013.01); *C07K 7/06* (2013.01); *G01N 21/6428* (2013.01); *G01N 33/57434* (2013.01); *G01N 33/57492* (2013.01); *G01N 33/582* (2013.01); *A61K 49/0017* (2013.01); *A61K 49/16* (2013.01); *C12Y 304/17021* (2013.01); *G01N 2021/6439* (2013.01); *G01N 2333/948* (2013.01)

(58) Field of Classification Search
CPC ............ A61K 49/0052; A61K 49/0032; A61K 49/0034; A61K 49/0056; A61K 49/0017; A61K 49/16; C07D 209/20; C07K 5/06026; C07K 5/0606; C07K 5/06078; C07K 5/06095; C07K 5/06121; C07K 5/06147; C07K 5/06156; C07K 5/0806; C07K 5/0812; C07K 5/0817; C07K 5/1019; C07K 7/02; C07K 7/06; G01N 33/57434; G01N 33/57492; G01N 33/582; G01N 2021/6439; G01N 2333/948; C12Y 304/17021
See application file for complete search history.

(56) References Cited

U.S. PATENT DOCUMENTS

| | | | |
|---|---|---|---|
| 6,329,531 B1 | 12/2001 | Turner et al. | |
| 9,801,956 B2* | 10/2017 | Kularatne | ................ C07K 7/02 |

(Continued)

FOREIGN PATENT DOCUMENTS

| | | |
|---|---|---|
| CN | 1237911 A | 12/1999 |
| CN | 104873982 A | 9/2015 |

(Continued)

OTHER PUBLICATIONS

Chinese Patent Offfice, Office Action regarding Serial No. 2018-512411, dated Jun. 23, 2020, 3 pages.
(Continued)

*Primary Examiner* — Michael G. Hartley
*Assistant Examiner* — Melissa J Perreira
(74) *Attorney, Agent, or Firm* — McAndrews, Held & Malloy, Ltd.

(57) ABSTRACT

The present disclosure relates to prostate specific membrane antigen (PSMA) targeted compounds conjugated to near-infra red (NIR) dyes and methods for their therapeutic and diagnostic use. More specifically, this disclosure provides compounds and methods for diagnosing and treating diseases associated with cells and/or vasculature expressing prostate specific membrane antigen (PSMA), such as prostate cancer and related diseases. The disclosure further describes methods and compositions for making and using the compounds, methods incorporating the compounds, and kits incorporating the compounds.

20 Claims, 92 Drawing Sheets

Related U.S. Application Data

15/623,353, filed on Jun. 14, 2017, now Pat. No. 9,968,691, which is a continuation of application No. 14/939,915, filed on Nov. 12, 2015, now Pat. No. 9,801,956, which is a continuation of application No. 14/937,169, filed on Nov. 10, 2015, now Pat. No. 9,808,538.

(60) Provisional application No. 62/216,157, filed on Sep. 9, 2015.

(51) Int. Cl.
*G01N 33/58* (2006.01)
*A61K 49/16* (2006.01)

(56) References Cited

U.S. PATENT DOCUMENTS

| | | | | |
|---|---|---|---|---|
| 9,808,538 | B2* | 11/2017 | Kularatne | C07K 5/1019 |
| 10,308,606 | B2* | 6/2019 | Kularatne | G01N 21/6428 |
| 10,456,482 | B2* | 10/2019 | Kularatne | G01N 21/6428 |
| 10,842,887 | B2* | 11/2020 | Kularatne | A61K 49/0034 |
| 2015/0110715 | A1 | 4/2015 | Eder et al. | |

FOREIGN PATENT DOCUMENTS

| WO | 2009026177 A1 | 2/2009 |
|---|---|---|
| WO | 20100108125 A2 | 9/2010 |
| WO | 20110106639 A1 | 9/2011 |
| WO | 2014127365 A1 | 8/2014 |
| WO | 2014149069 A1 | 9/2014 |

OTHER PUBLICATIONS

X. Wang, et al., "Development of Targeted Near-Infrared Imaging Agents for Prostate Cancer," Molecular Cancer Therapeutics, vol. 13, No. 11, Nov. 1, 2014, pp. 2595-2606.

Ying Chen, et al., "Synthesis and Biological Evaluation of Low Molecular Weight Fluorescent Imaging Agents for the Prostate-Specific Membran Antigen," Bioconjugate Chemistry, vol. 23, No. 12, Dec. 19, 2012, pp. 2377-2385.

J. Roy, et al., "DUPA Conjugation of a Cytotoxic Indenoisoquinoline Topoisomerase I Inhibitor for Selective Prostate Cancer Cell Targeting," Journal of Medicinal Chemistry, Mar. 30, 2015, pp. 3094-3103.

European Patent Office, Office Action regarding Serial No. 16 845 0245-1109, dated Jun. 11, 2019, 6 pages.

Office Action dated May 11, 2021, in connection with Chinese Application No. 201680059695.8.

PCT, International Search Report and Written Opinion regarding Application No. PCT/US2016/050709, dated Dec. 7, 2016, 19 pages.

Israel Patent Office, Office Action regarding Application No. 257669, dated Oct. 14, 2020, 145 pages.

China National Intellectual Property Administration, Office Action regarding Application No. 201680059695.08, dated Apr. 25, 2022, 12 pages.

\* cited by examiner

Synthesis of DUPA-Linker-NIR dye conjugates

FIG. 2A: Structure of PSMA-targeted DUPA-FITC (Fluorescein isothiocyanate) conjugate (14).
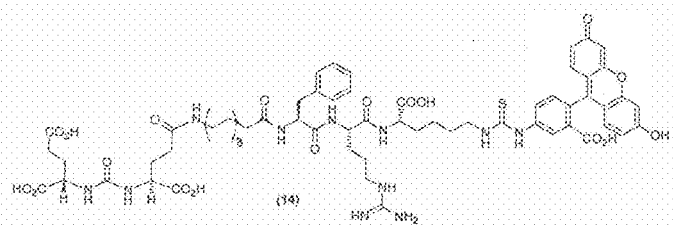
FIG. 2B: Structure of PSMA-targeted DUPA-FITC (Fluorescein isothiocyanate) conjugate (14) and its binding affinity ($K_D$) and specificity on PSMA-positive 22Rv1 human prostate cancer cells and on PSMA-negative A549 human alveolar basal epithelial cells in culture.
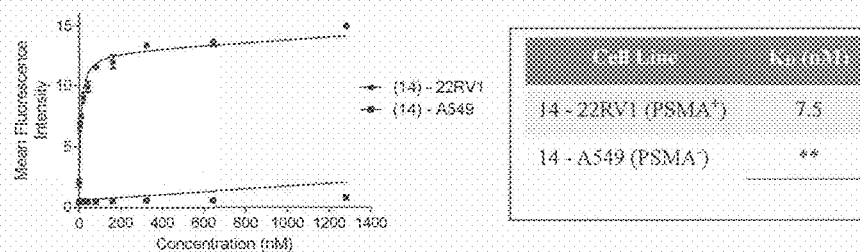

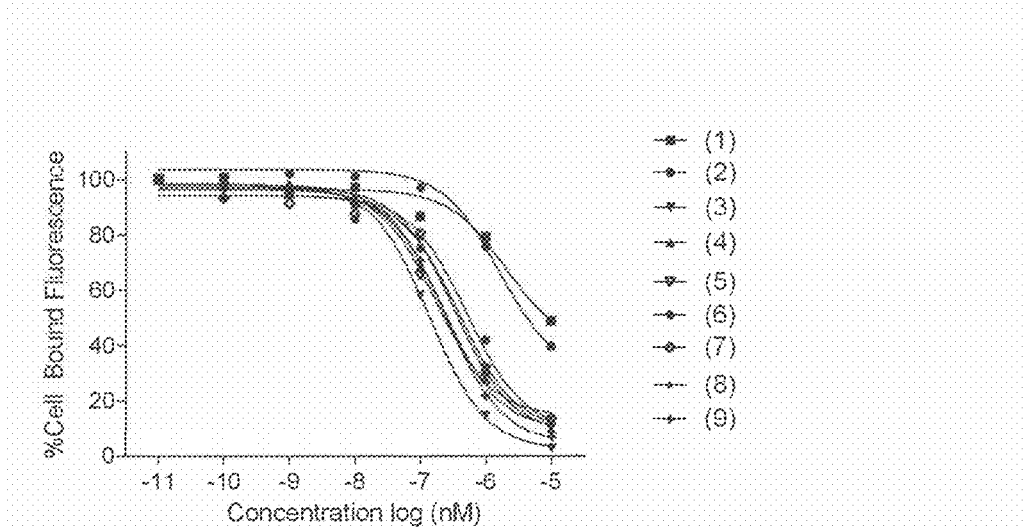
FIG. 3: Relative binding affinities of DUPA-NIR conjugates 1 – 9 with respect to DUPA-FITC (14).

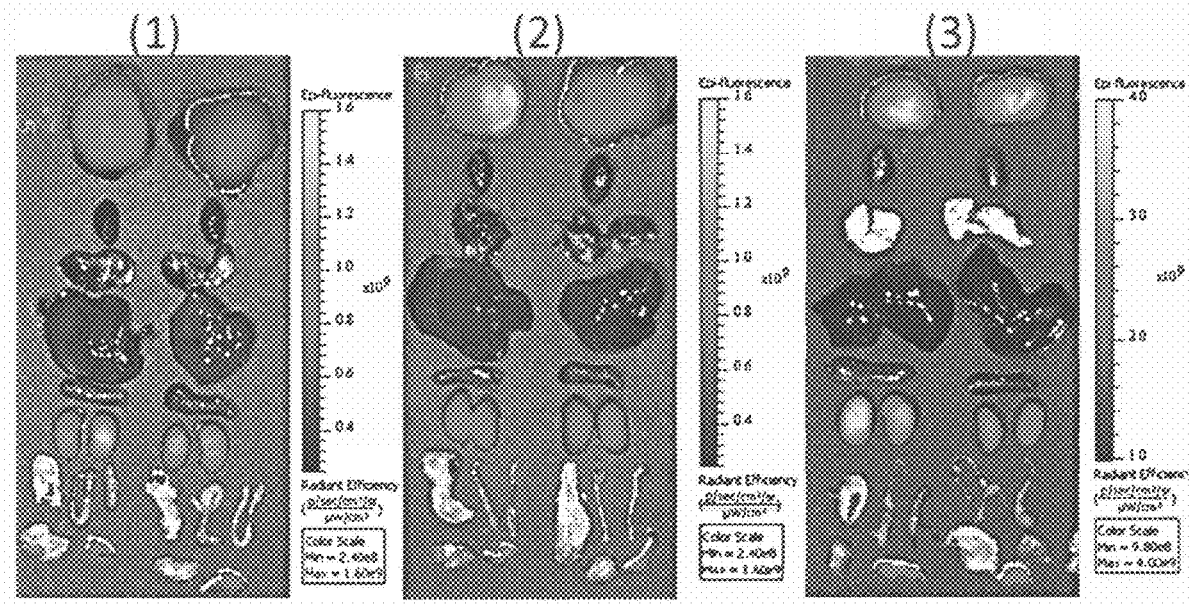
FIG. 4A: Tumor-to-tissue fluorescence ratio from tissue biodistribution data of PSMA-targeted DUPA-NIR conjugates 1 – 3.

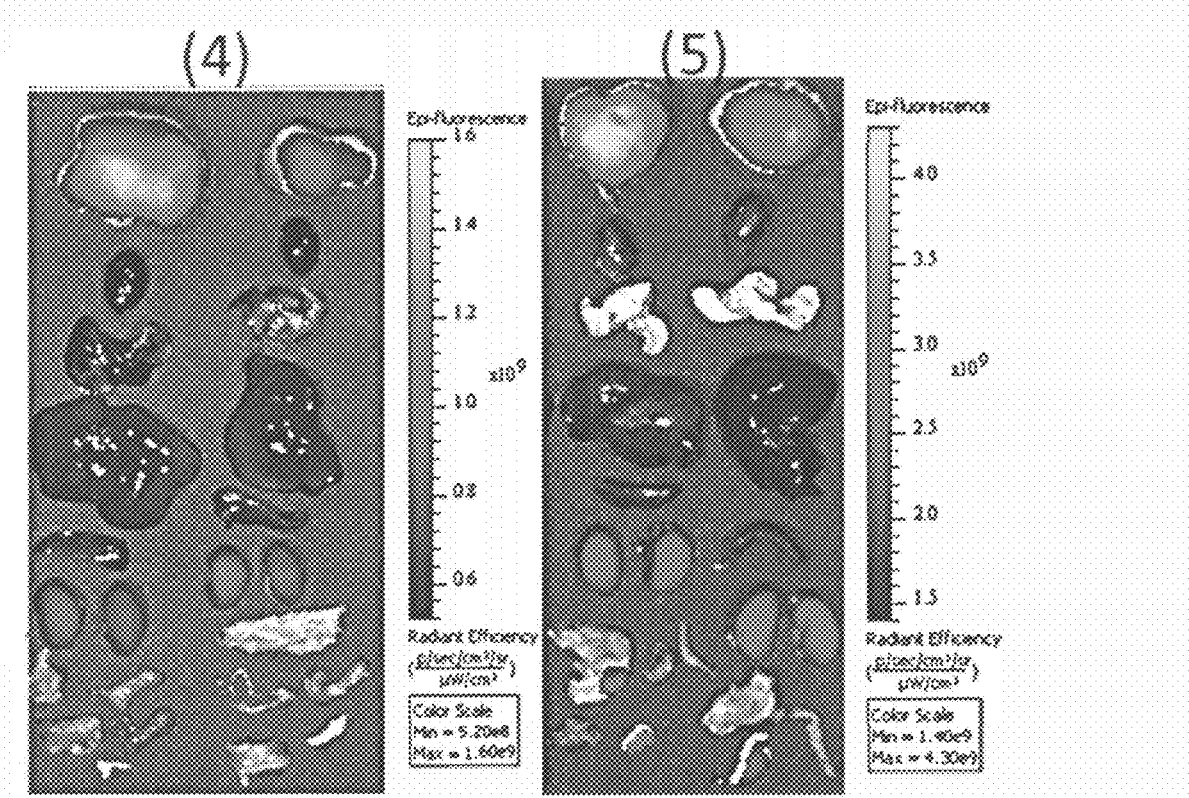
FIG. 4B: Tumor-to-tissue fluorescence ratio from tissue biodistribution data of PSMA-targeted DUPA-NIR conjugates 4 and 5.

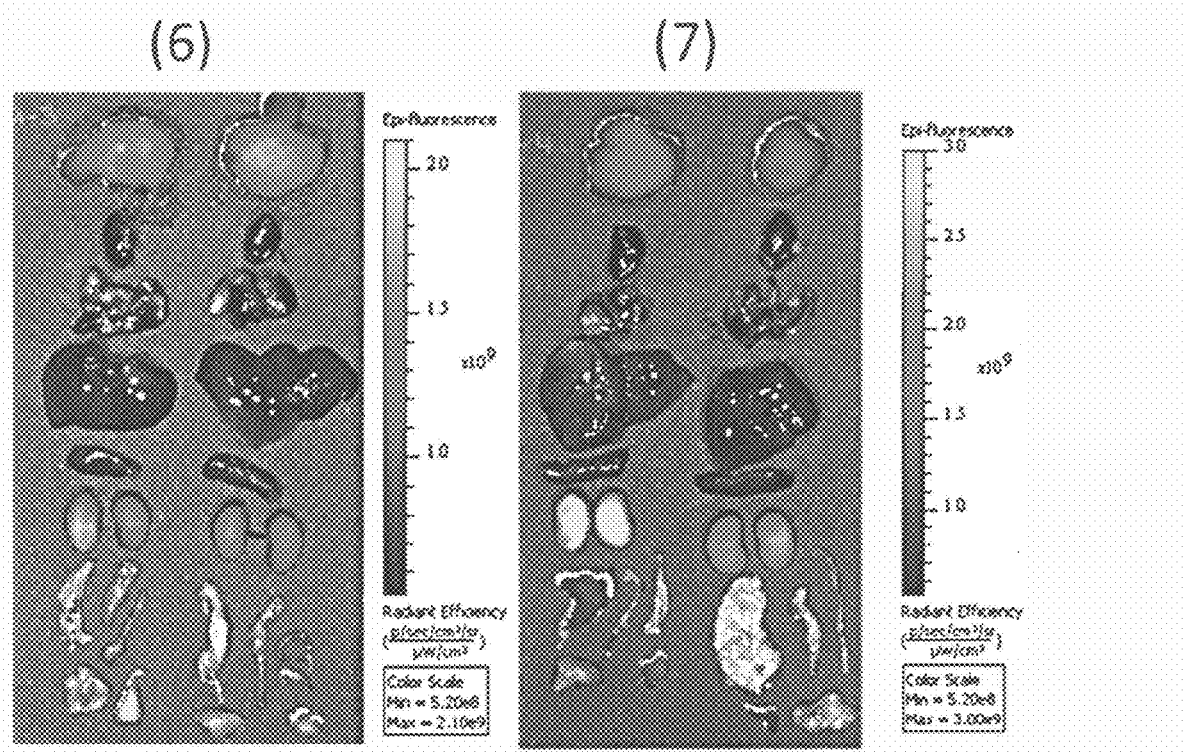
FIG. 4C: Tumor-to-tissue fluorescence ratio from tissue biodistribution data of PSMA-targeted DUPA-NIR conjugates 6 and 7.

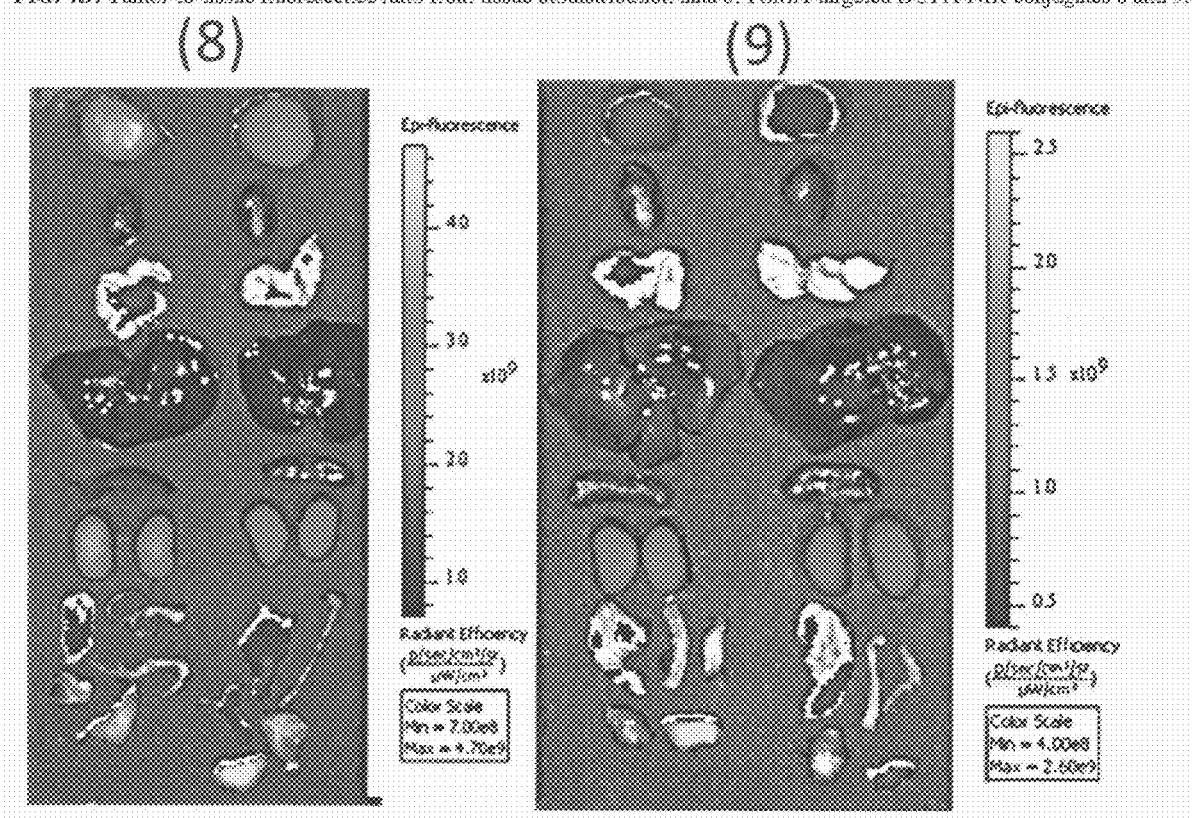
FIG. 4D: Tumor-to-tissue fluorescence ratio from tissue biodistribution data of PSMA-targeted DUPA-NIR conjugates 8 and 9.

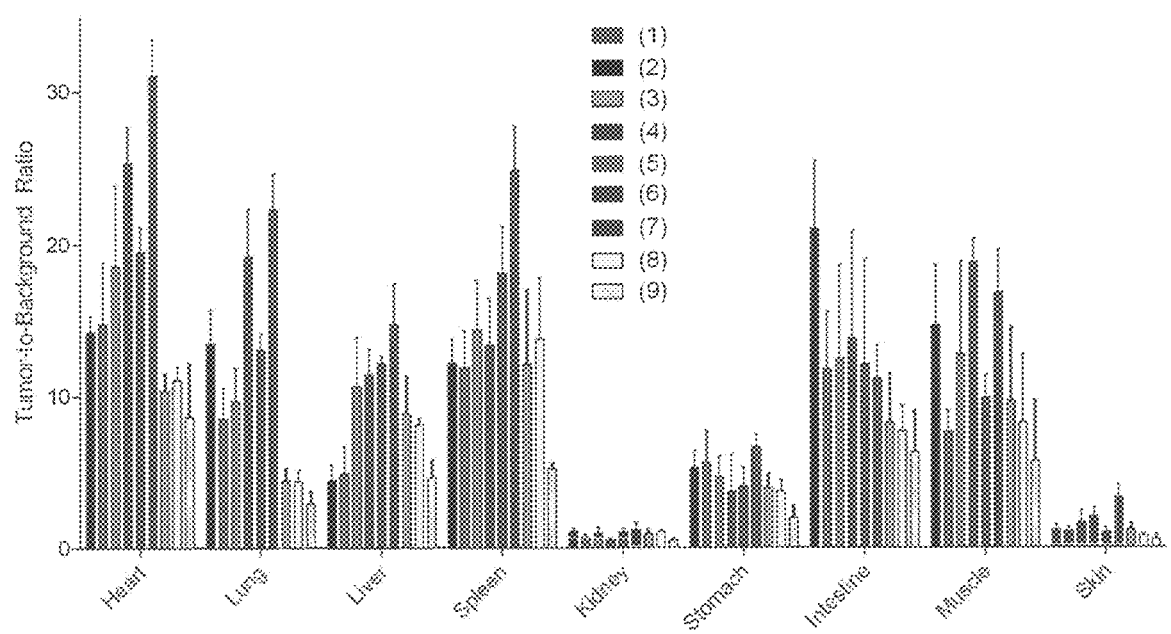
FIG. 4E: Biodistribution data of PSMA-targeted DUPA-NIR conjugates

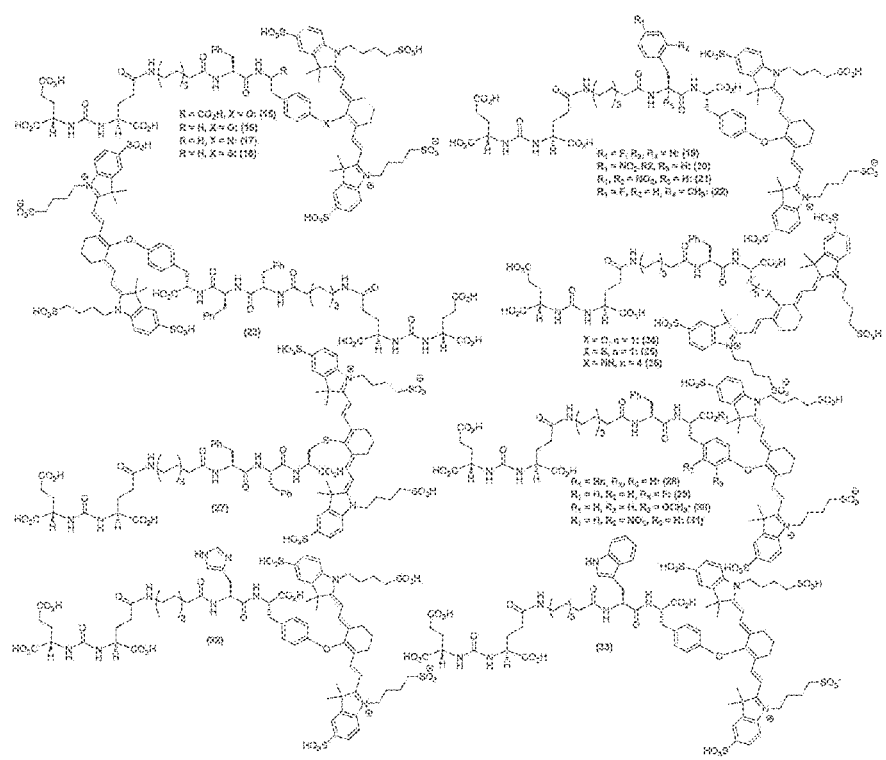
FIG. 5A: PSMA-targeted DUPA-Linker-NIR imaging agents

FIG. 5B: Additional: PSMA-targeted DUPA-Linker-NIR imaging agents
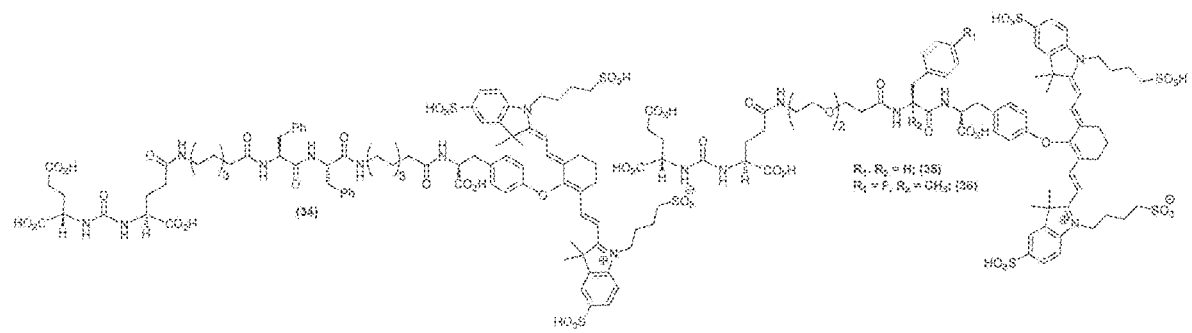

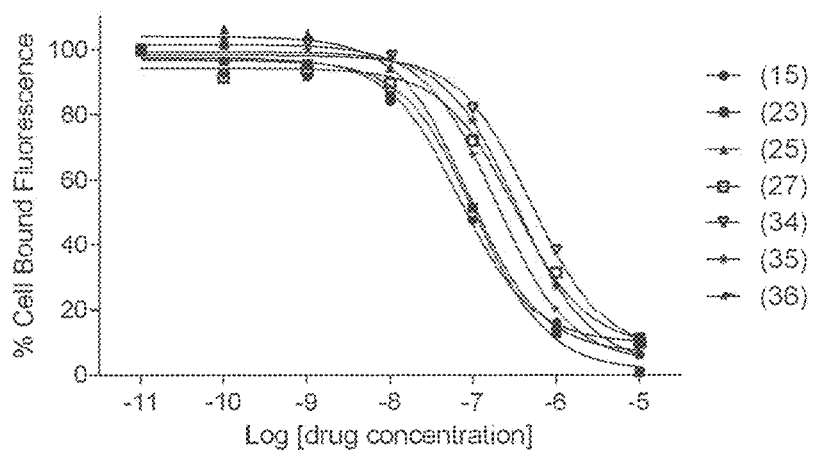
FIG. 6: Relative binding affinities of DUPA-NIR conjugates with aromatic amino acids linkers with respect to DUPA-FITC (14).

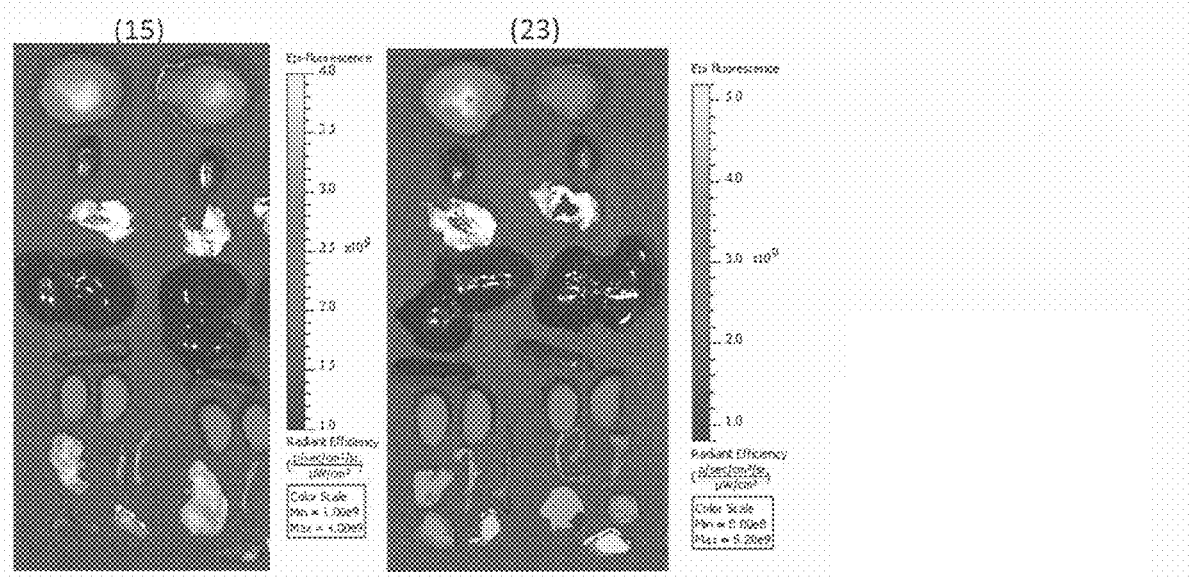
FIG. 7A: Tissue biodistribution analysis of DUPA-NIR conjugates 15 and 23 using fluorescence imaging of mice bearing human prostate tumor xenografts (22Rv1 cells).

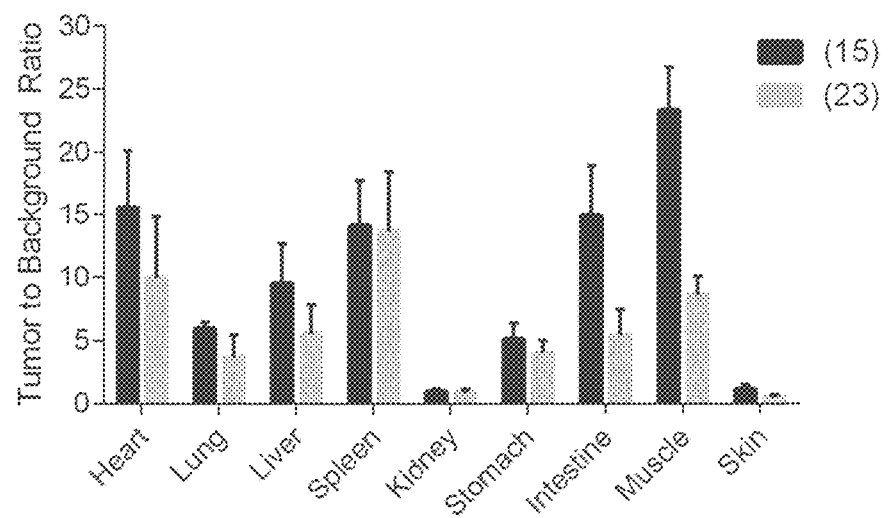
FIG. 7B – Tumor-to-tissue ratio of DUPA-NIR conjugates 15 and 23 using fluorescence imaging of mice bearing human prostate tumor xenografts (22Rv1 cells).

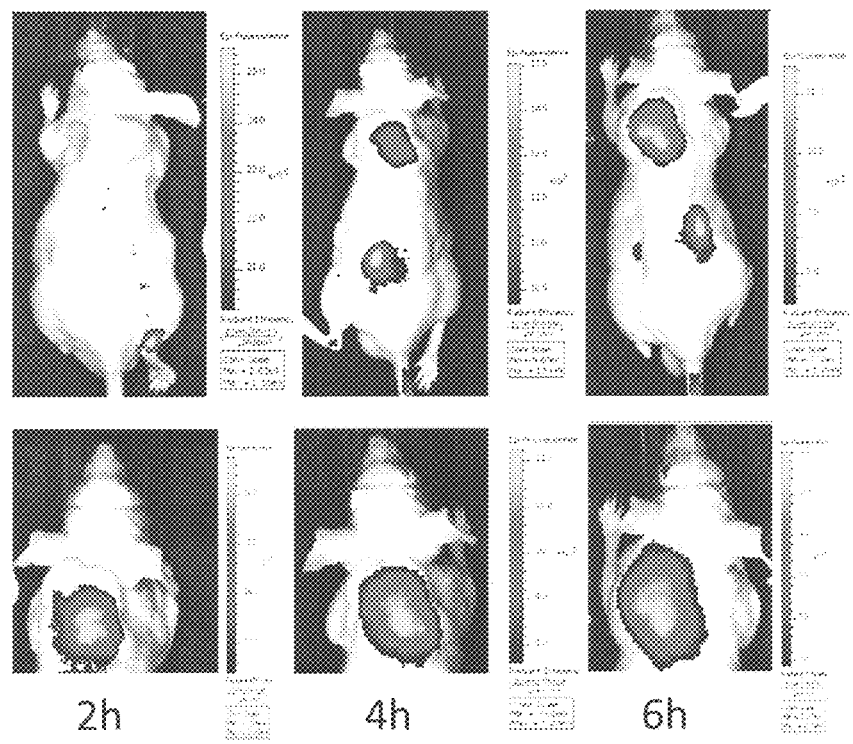
FIG. 8A: 22Rv1 human prostate tumor xenograft bearing mouse was injected with 20 nmol of 14 and imaged with IVIS imager and 2, 4, and 6 hr

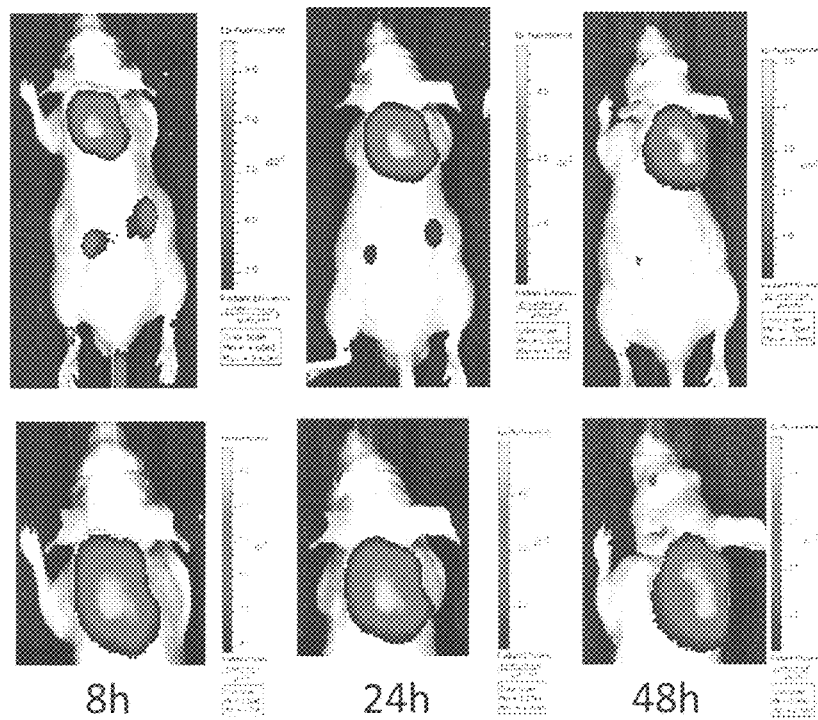
FIG. 8B: 22Rv1 human prostate tumor xenograft bearing mouse was injected with 20 nmol of 14 and imaged with IVIS imager and 8, 24, and 48 hr

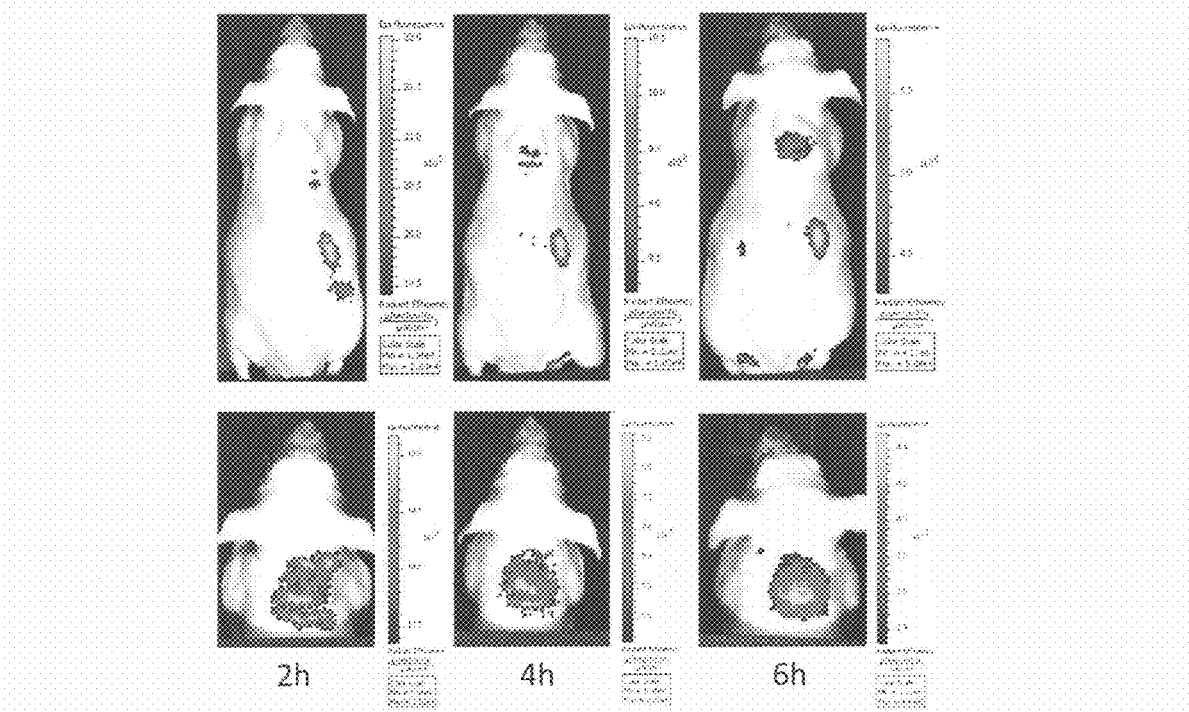
FIG. 9A: 22Rv1 human prostate tumor xenograft bearing mouse was injected with 20 nmol of 23 and imaged with IVIS imager at 2, 4, and 6 hr

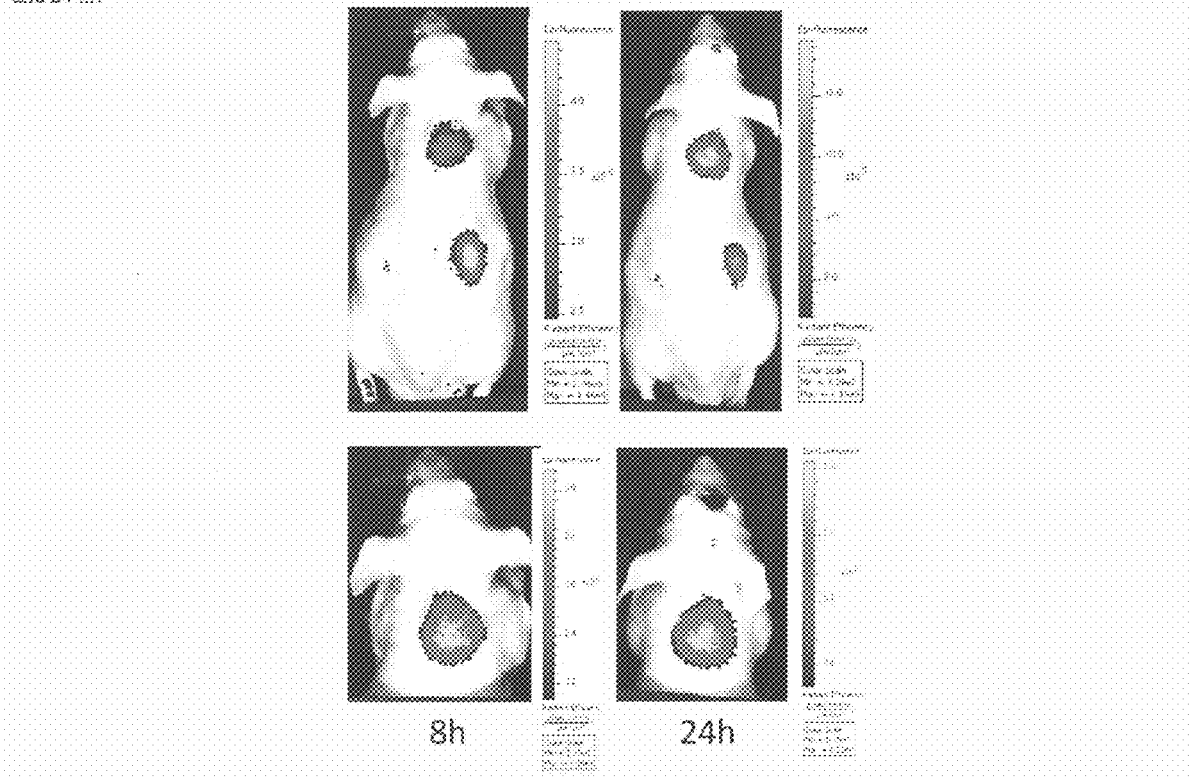
FIG. 9B: 22Rv1 human prostate tumor xenograft bearing mouse was injected with 20 nmol of 23 and imaged with IVIS imager at 8 and 24 hr.

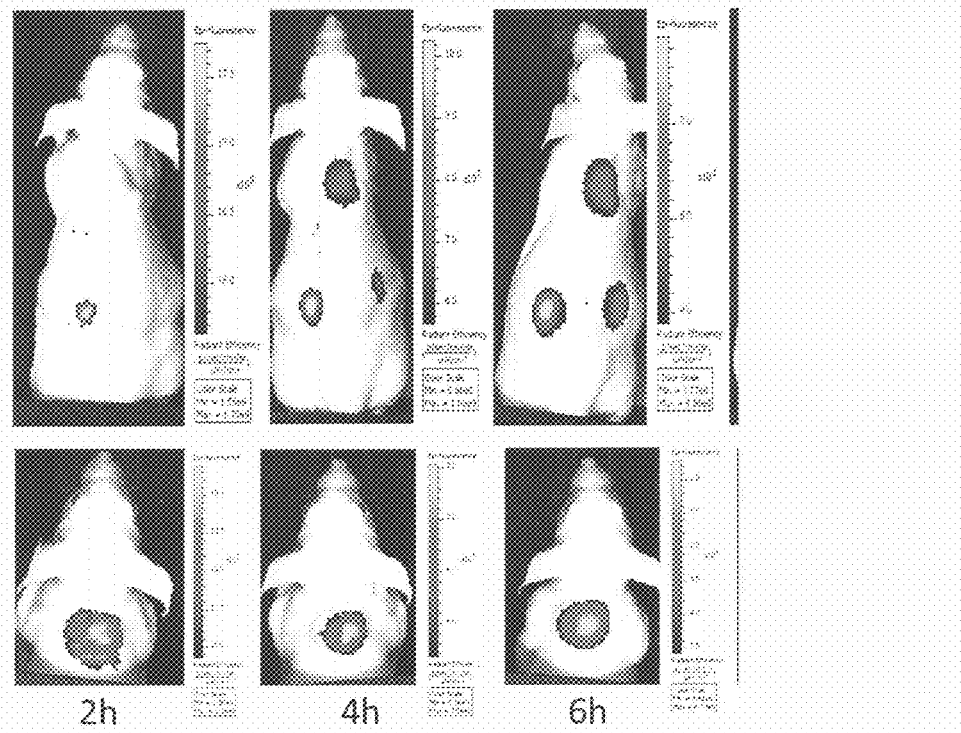
FIG. 10A: 22Rv1 human prostate tumor xenograft bearing mouse was injected with 20 nmol of 25 and imaged with IVIS imager at 2, 4, and 6 hr.

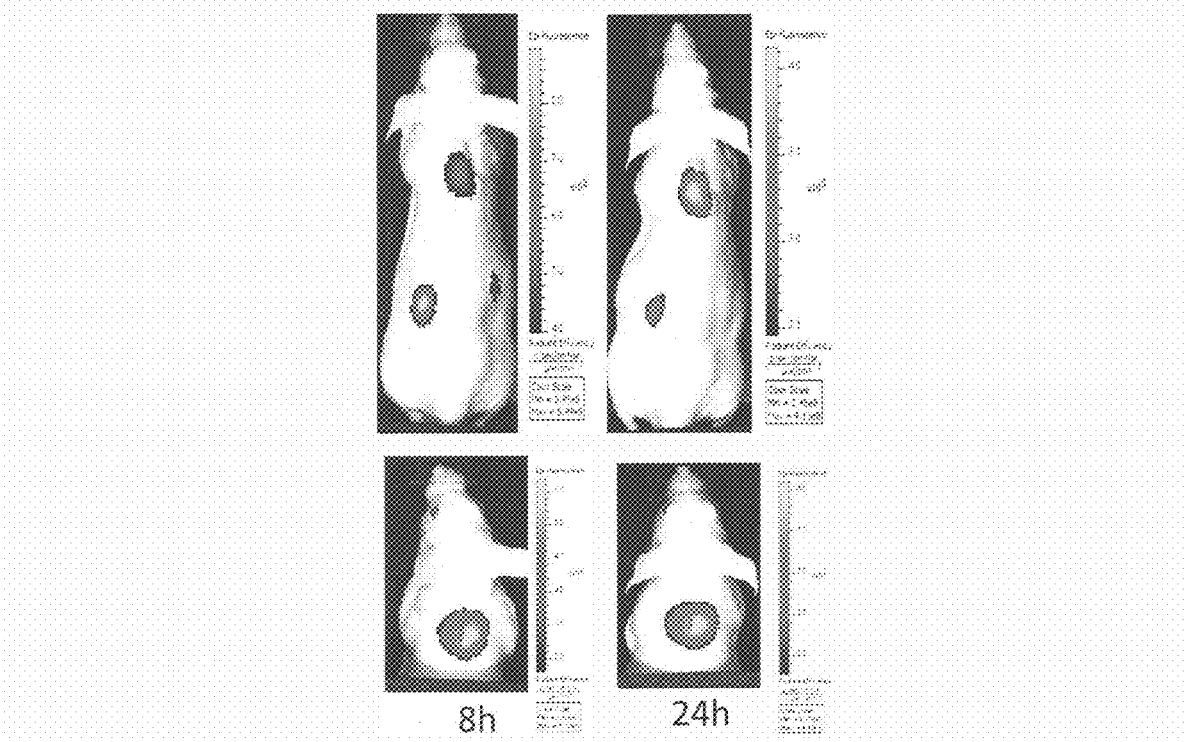
FIG. 10B: 22Rv1 human prostate tumor xenograft bearing mouse was injected with 20 nmol of 25 and imaged with IVIS imager at 8 and 24 hr.

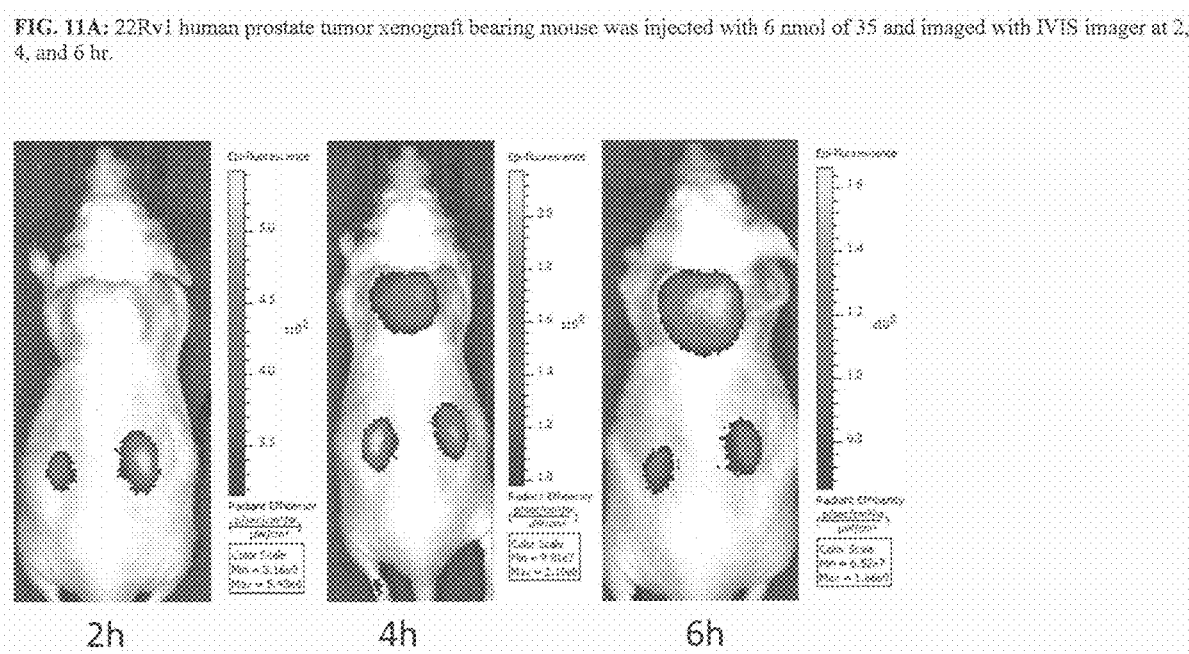
FIG. 11A: 22Rv1 human prostate tumor xenograft bearing mouse was injected with 6 nmol of 35 and imaged with IVIS imager at 2, 4, and 6 hr.

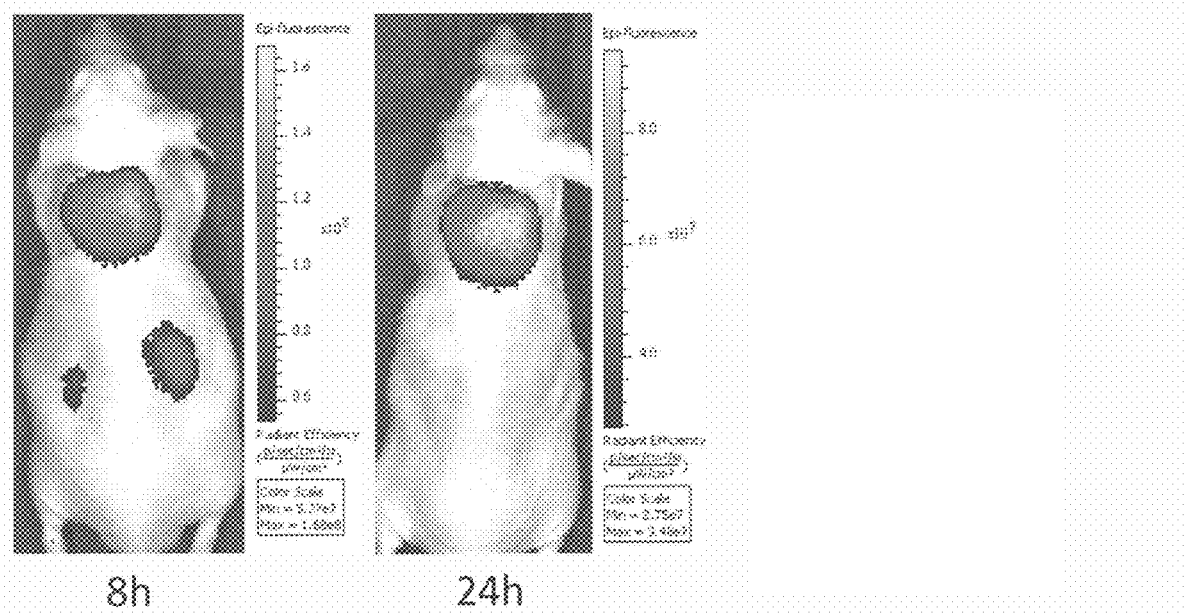
FIG. 11B: 22Rv1 human prostate tumor xenograft bearing mouse was injected with 6 nmol of 35 and imaged with IVIS imager at 8 and 24 hr.

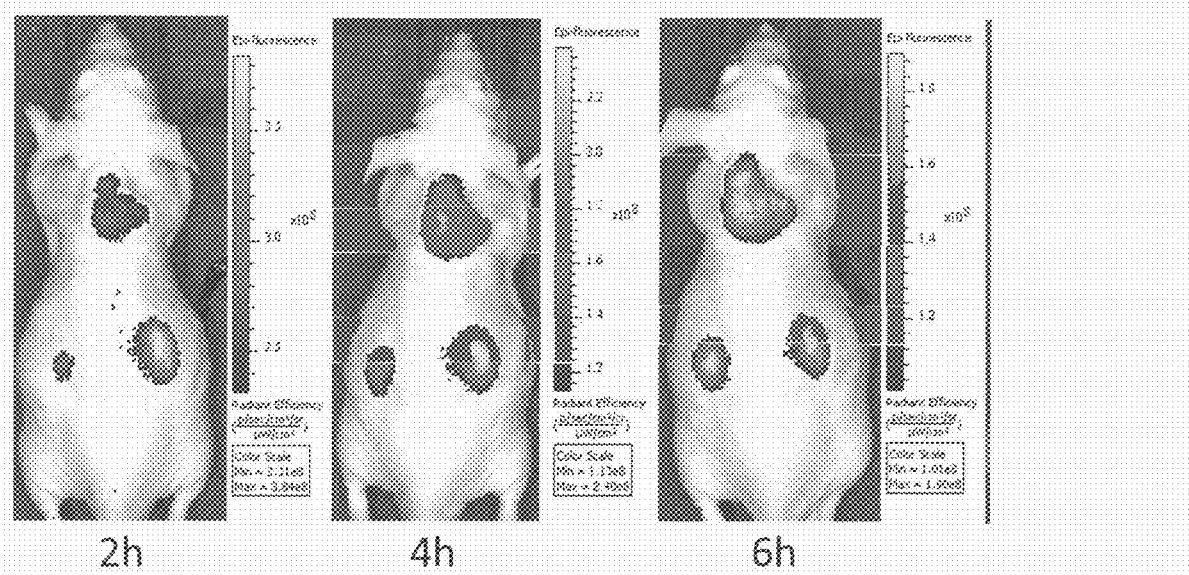

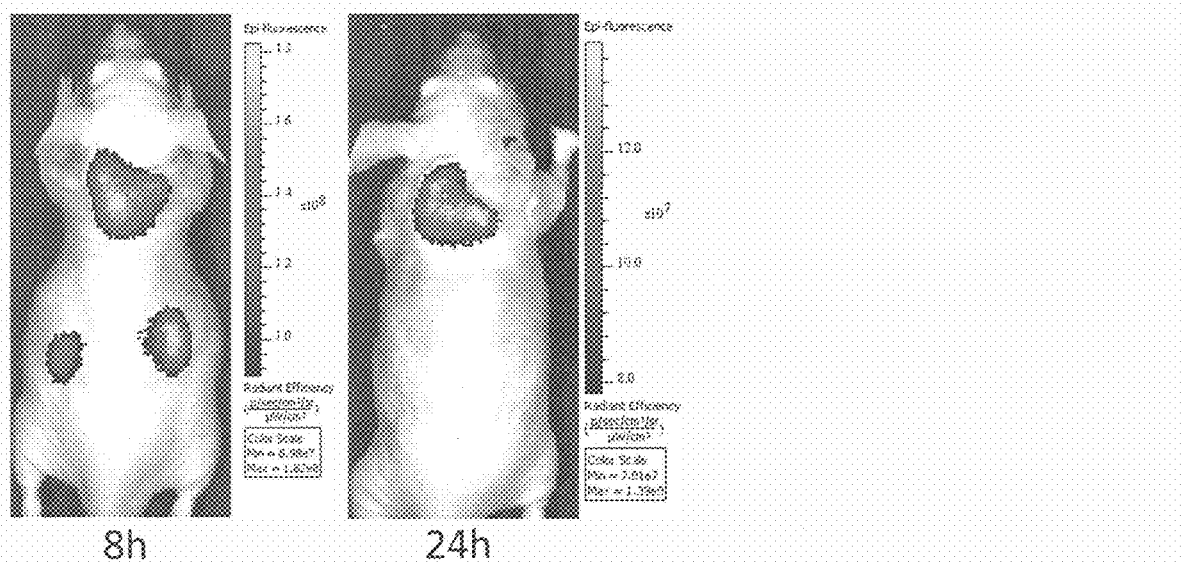
FIG. 12B: 22Rv1 human prostate tumor xenograft bearing mouse was injected with 6 nmol of 36 and imaged with IVIS imager at 8 and 24 hr.

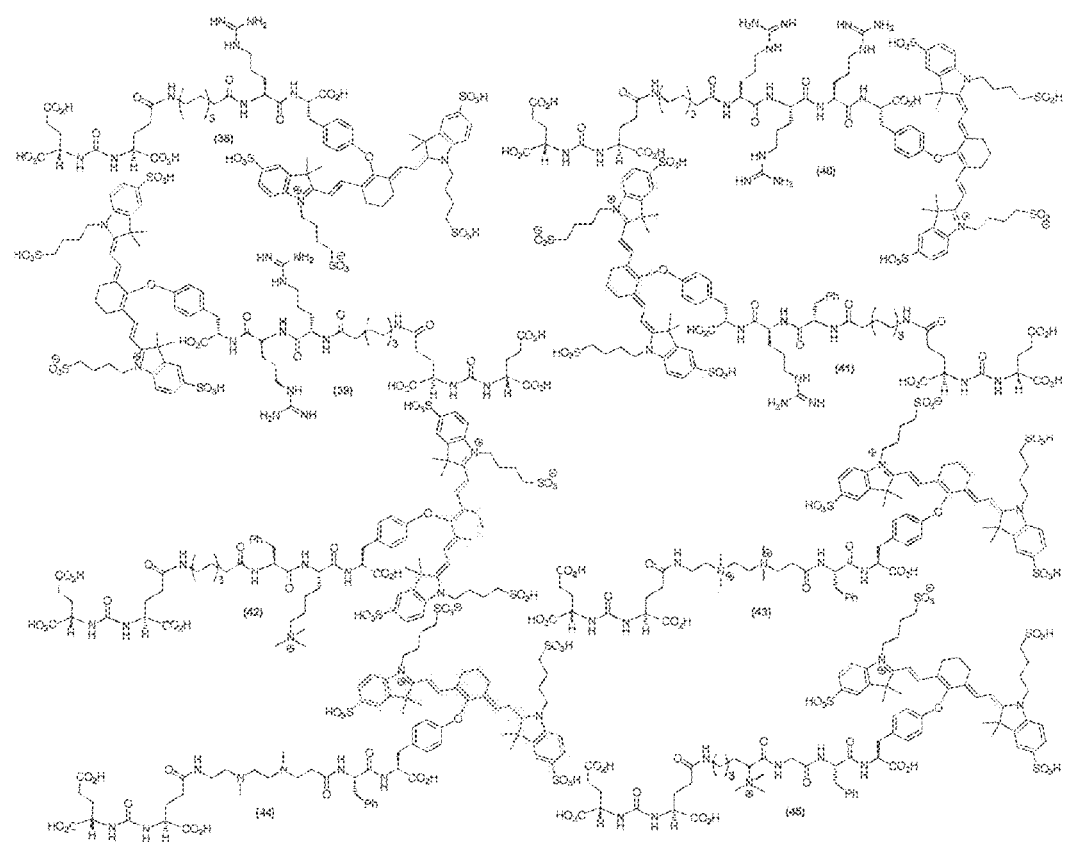
FIG. 13: Structures of PSMA-targeted DUPA-Linker-NIR imaging agents with positive charge linkers

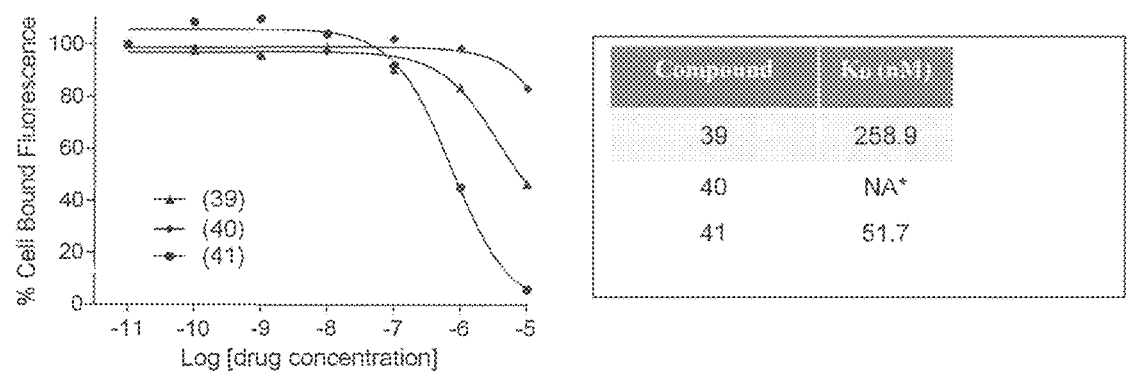
FIG. 14: Relative binding affinities of DUPA-NIR conjugates with respect to DUPA-FITC (14).

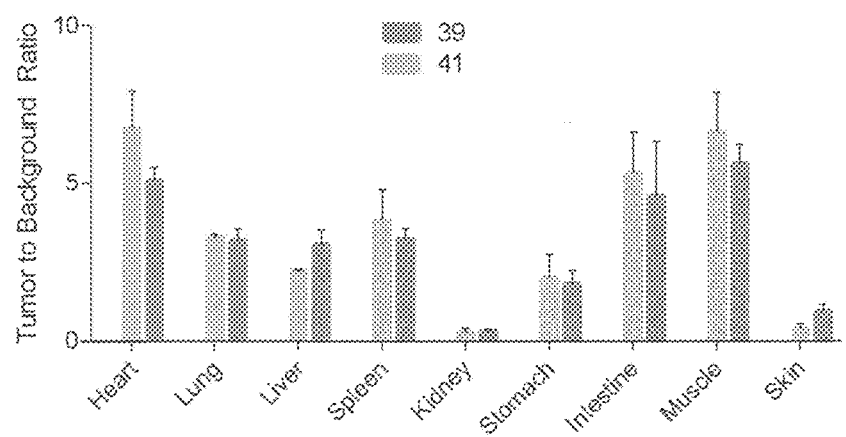
FIG. 16: Tumor-to-tissue ratio of DUPA-NIR conjugates 39 and 41 using fluorescence imaging of mice bearing human prostate tumor xenografts (22 Rv1 cells).

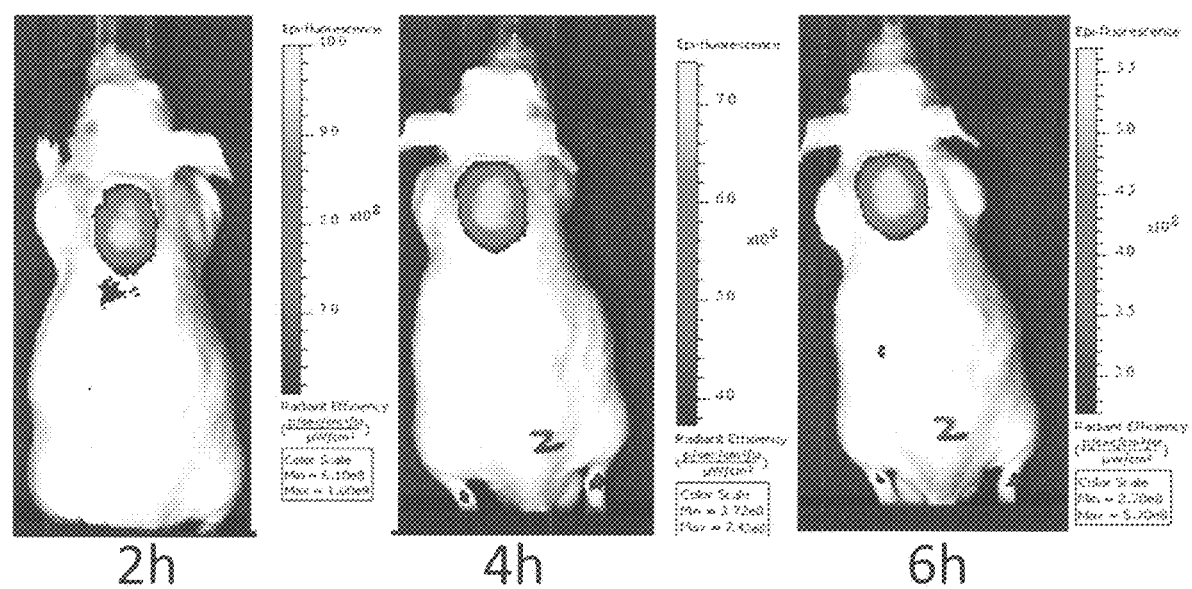
FIG. 16A: 22Rv1 human prostate tumor xenograft bearing mouse was injected with 20 nmol of 39 and imaged with IVIS imager at 2, 4, and 6 hr.

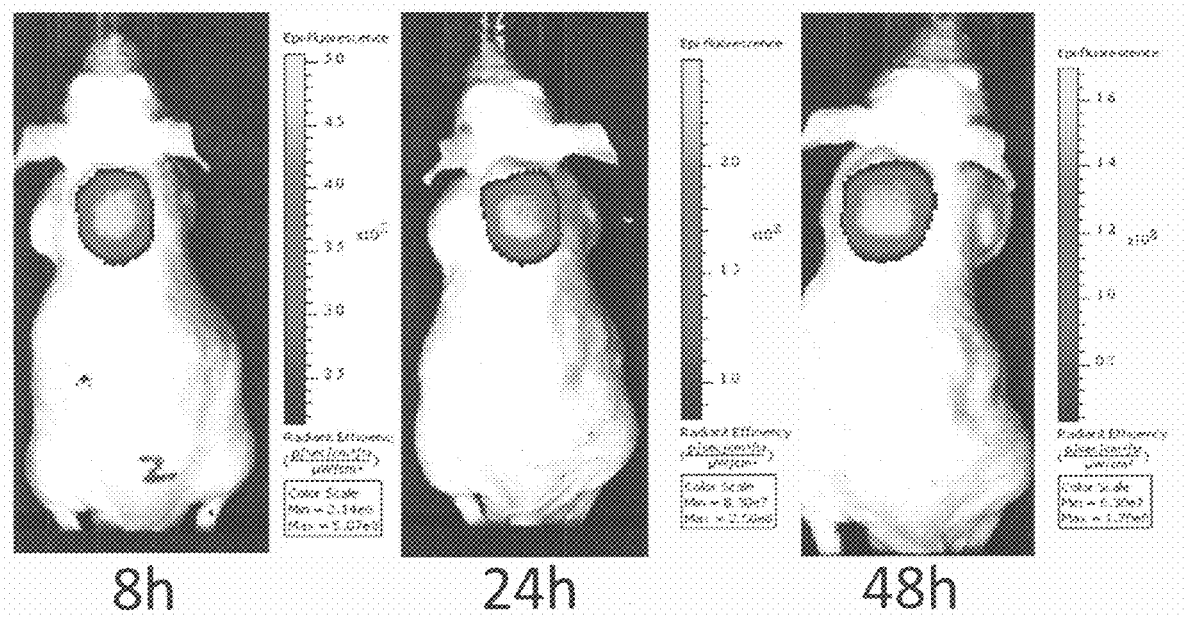
FIG. 16B: 22Rv1 human prostate tumor xenograft bearing mouse was injected with 20 nmol of 39 and imaged with IVIS imager at 8, 24, and 48 hr.

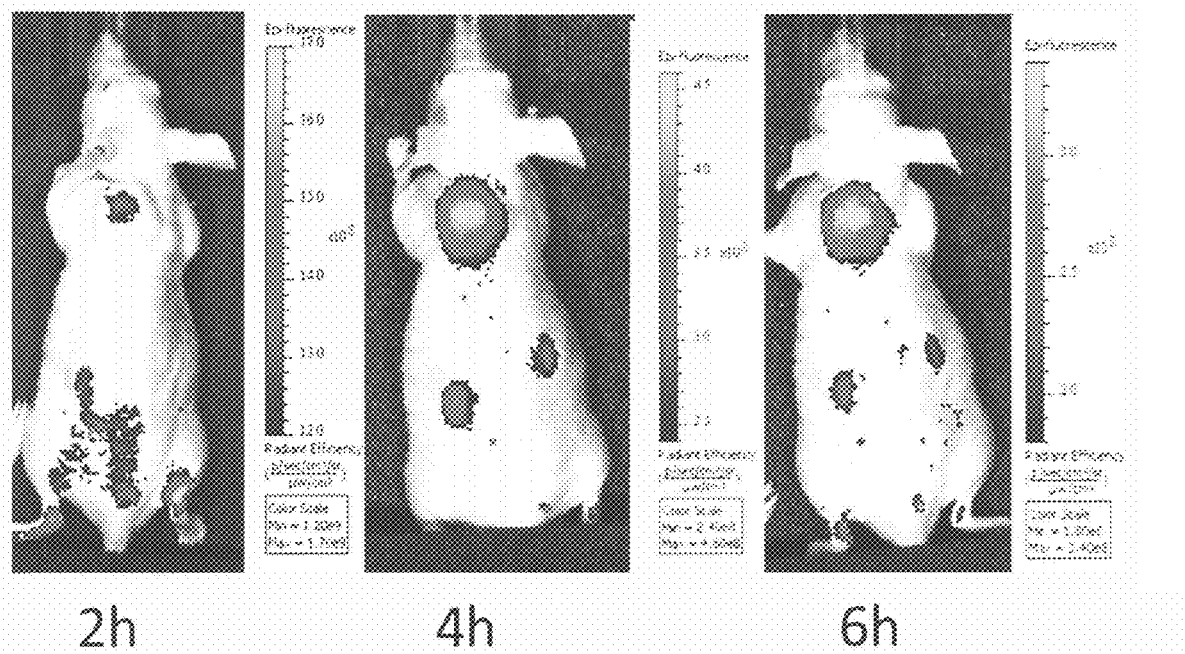
FIG. 17A: 22Rv1 human prostate tumor xenograft bearing mouse was injected with 20 nmol of 40 and imaged with IVIS imager at 2, 4, and 6 hr.

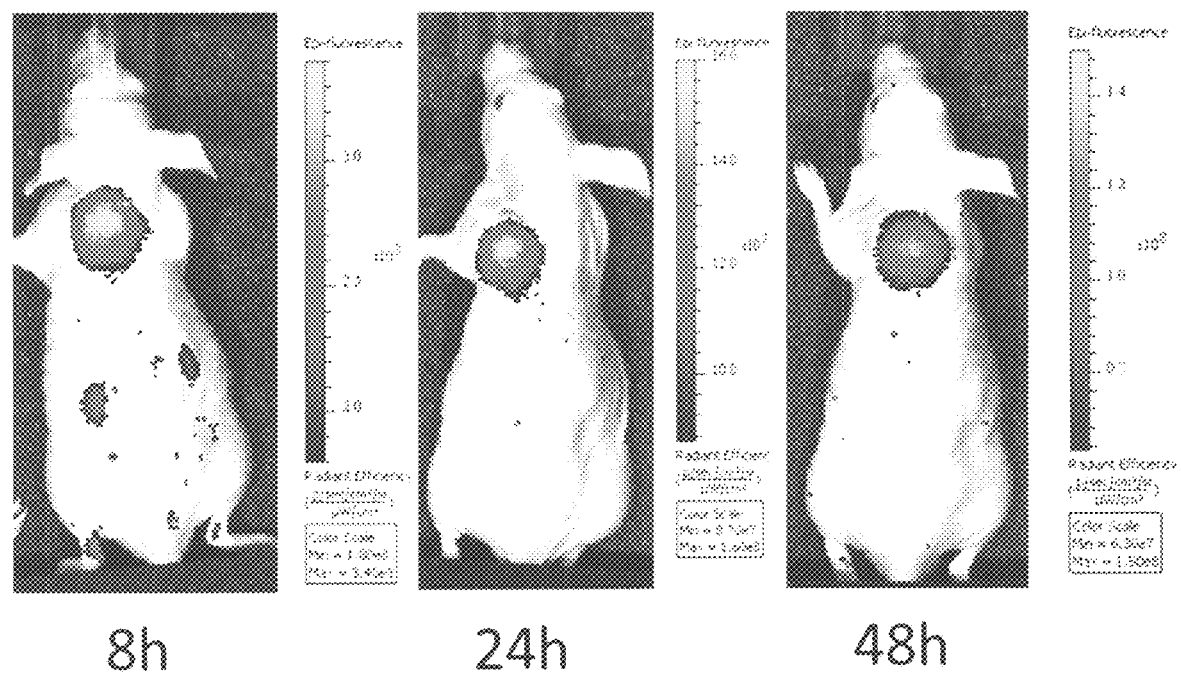
FIG. 17B: 22Rv1 human prostate tumor xenograft bearing mouse was injected with 20 nmol of 40 and imaged with IVIS imager at 8, 24, and 48 hr.

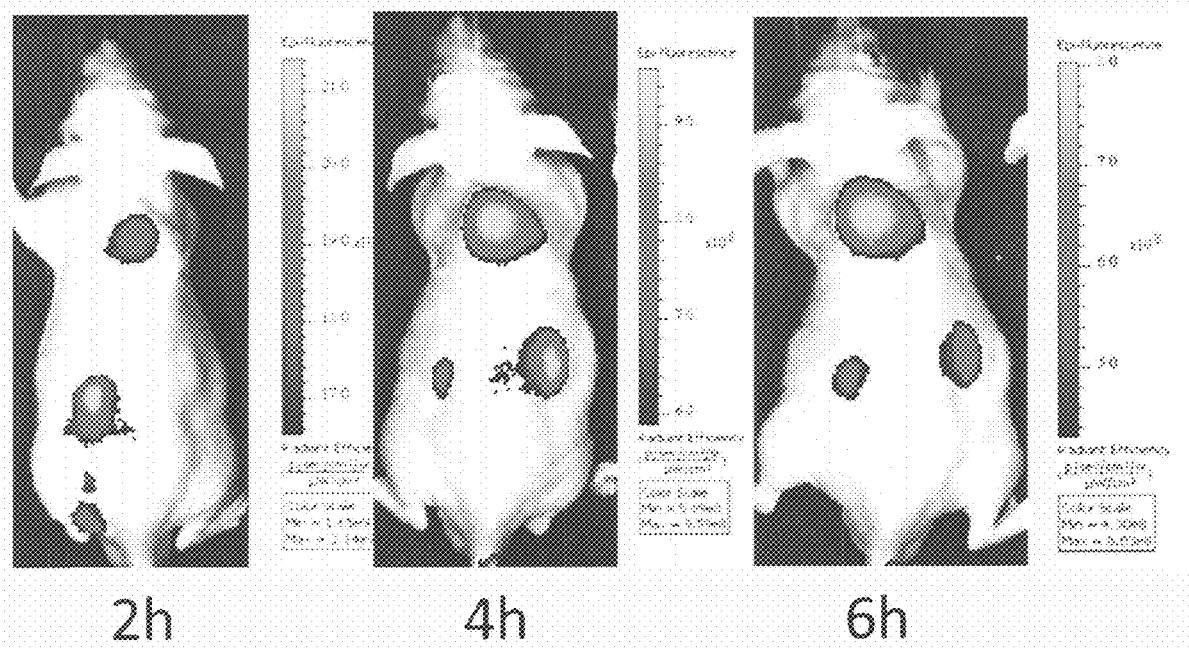

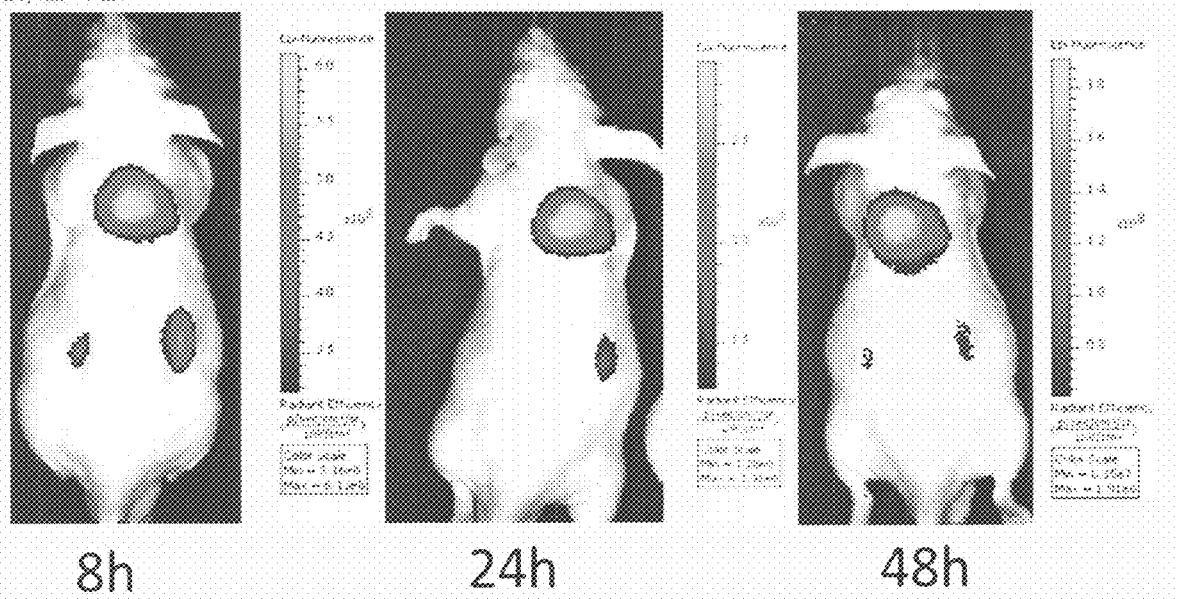
FIG. 18B: 22Rv1 human prostate tumor xenograft bearing mouse was injected with 20 nmol of 41 and imaged with IVIS imager at 8, 24, and 48 hr.

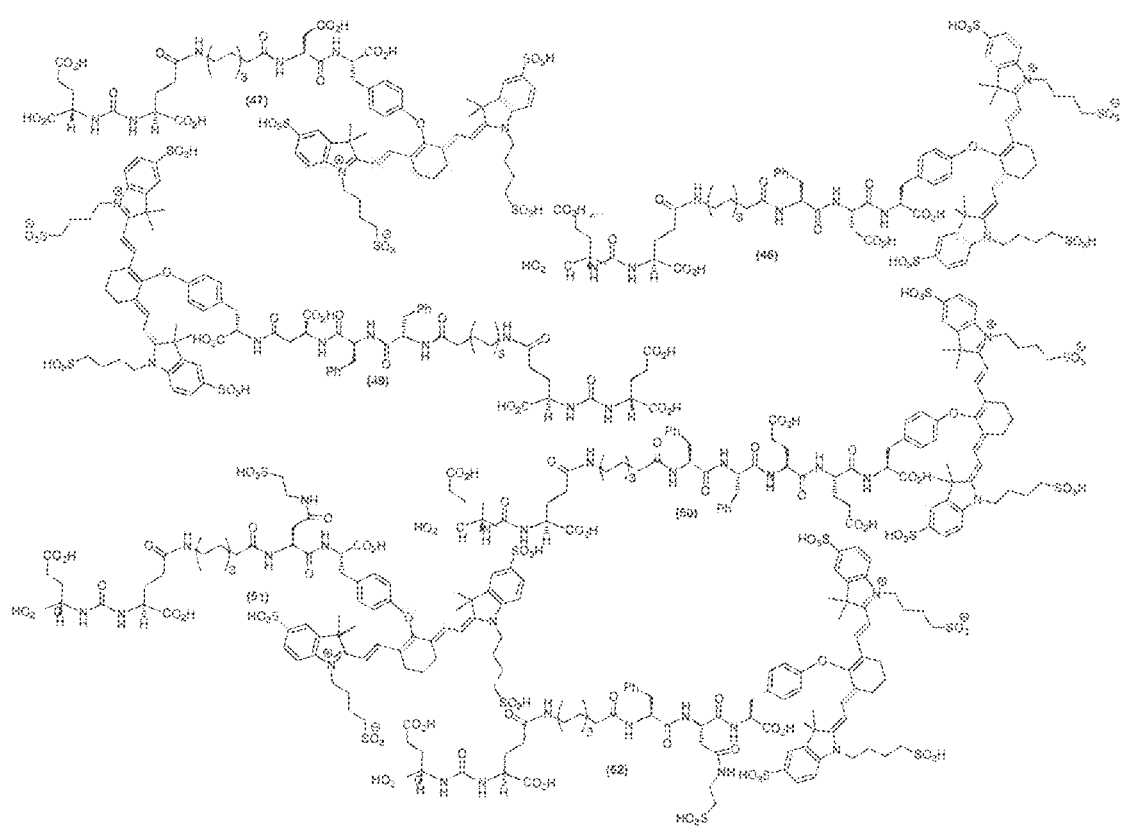
FIG. 19: Structures of PSMA-targeted DUPA-Linker-NIR imaging agents with negative charge linkers

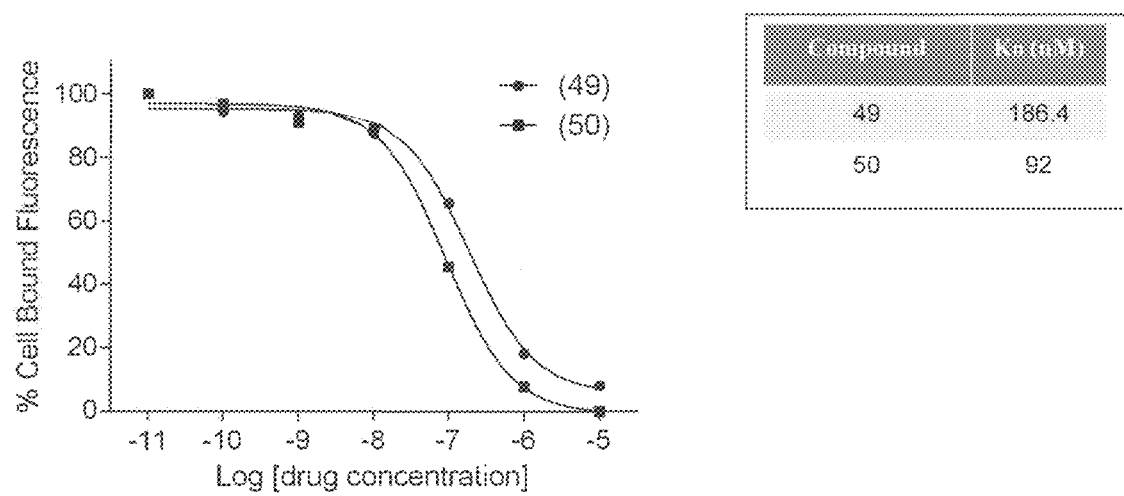
FIG. 20: Relative binding affinities of DUPA-NIR conjugates of 49 and 50 with respect to DUPA-FITC (14)

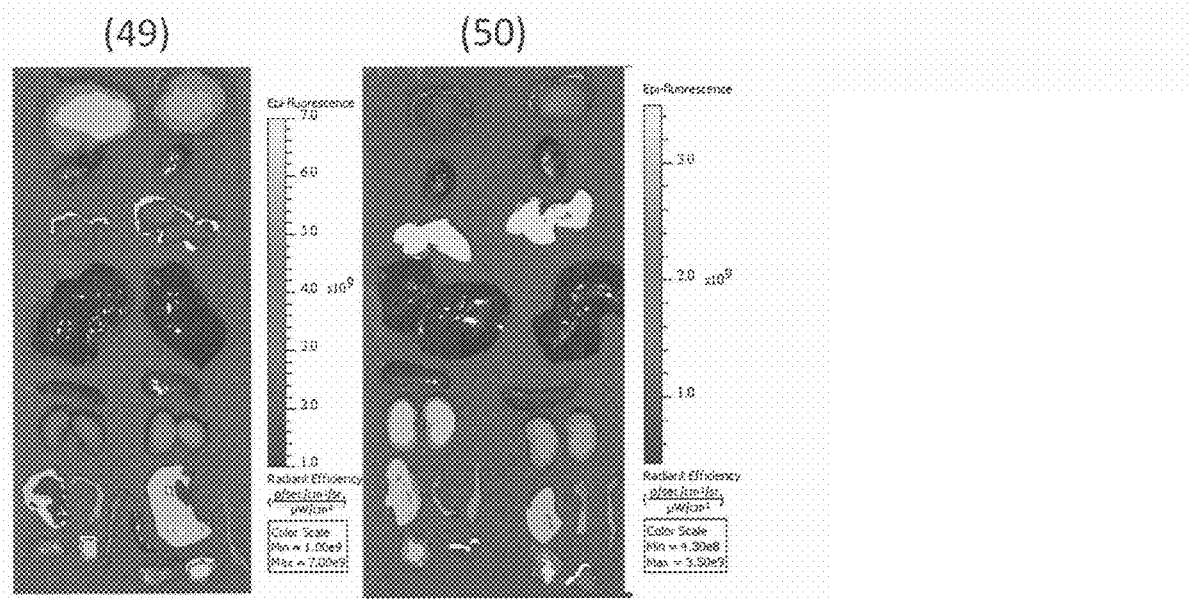
FIG. 21A: Tissue biodistribution analysis of DUPA-NIR (21B) conjugates 49 and 50 using fluorescence imaging of mice bearing human prostate tumor xenografts (22Rv1 cells).

FIG. 21B: Tumor-to-tissue ratio of DUPA-NIR conjugates 49 and 50 using fluorescence imaging of mice bearing human prostate tumor xenografts (22Rv1 cells).
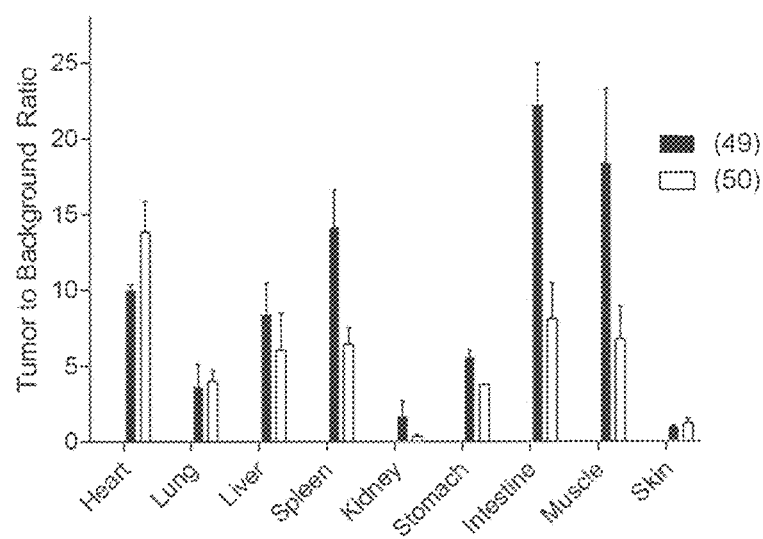

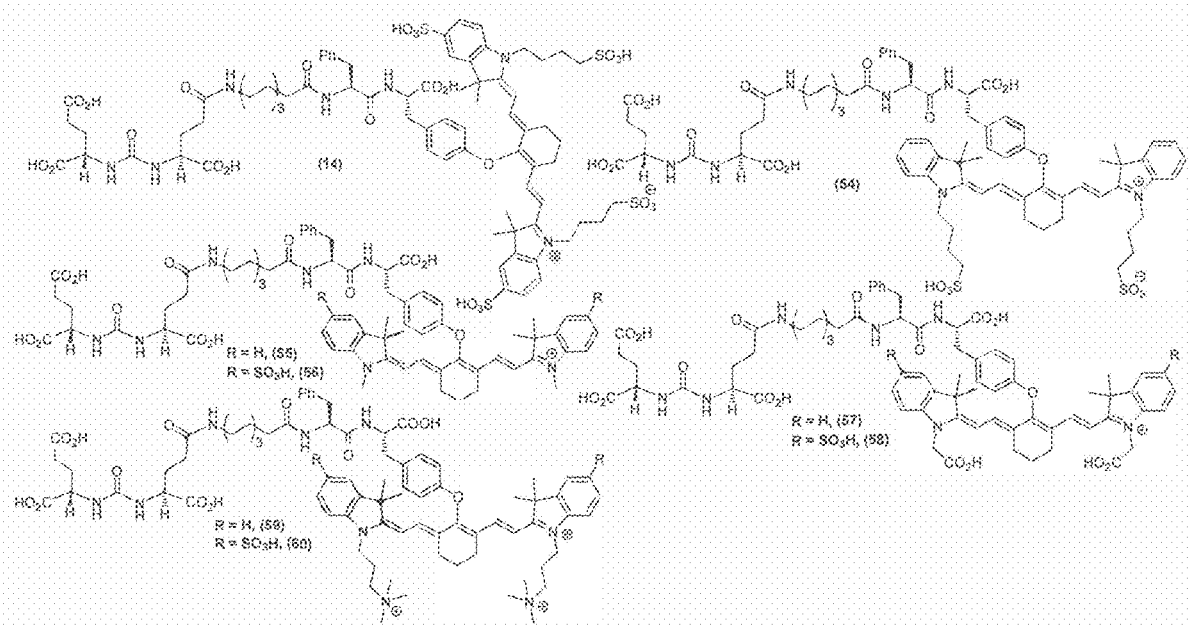
FIG. 22: Structures of PSMA-targeted DUPA-Linker-NIR imaging agents with variably charged NIR dye molecule.

FIG. 23: Relative binding affinities of DUPA-NIR conjugates with respect to DUPA-FITC (14).
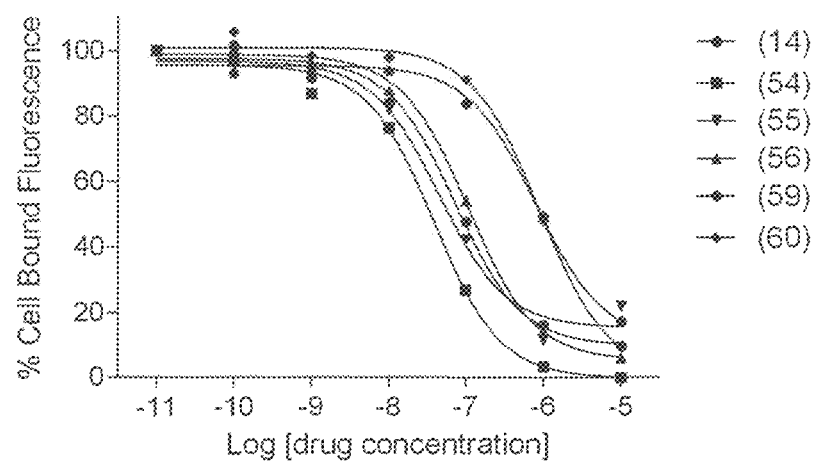

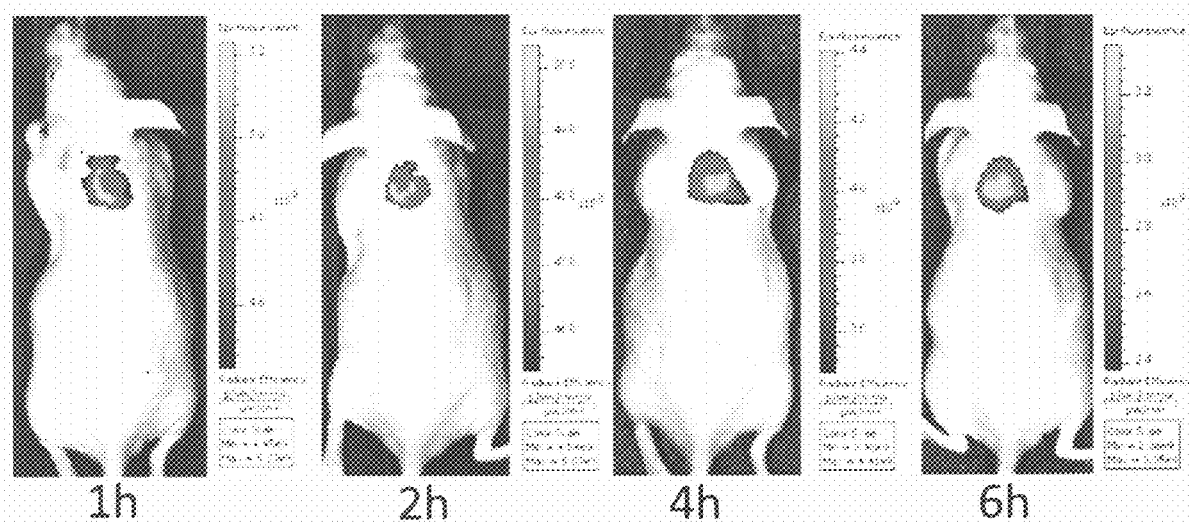
FIG. 24A: 22Rv1 human prostate tumor xenograft bearing mouse was injected with 20 nmol of 54 and imaged with IVIS imager at 1, 2, 4, and 6 hr.

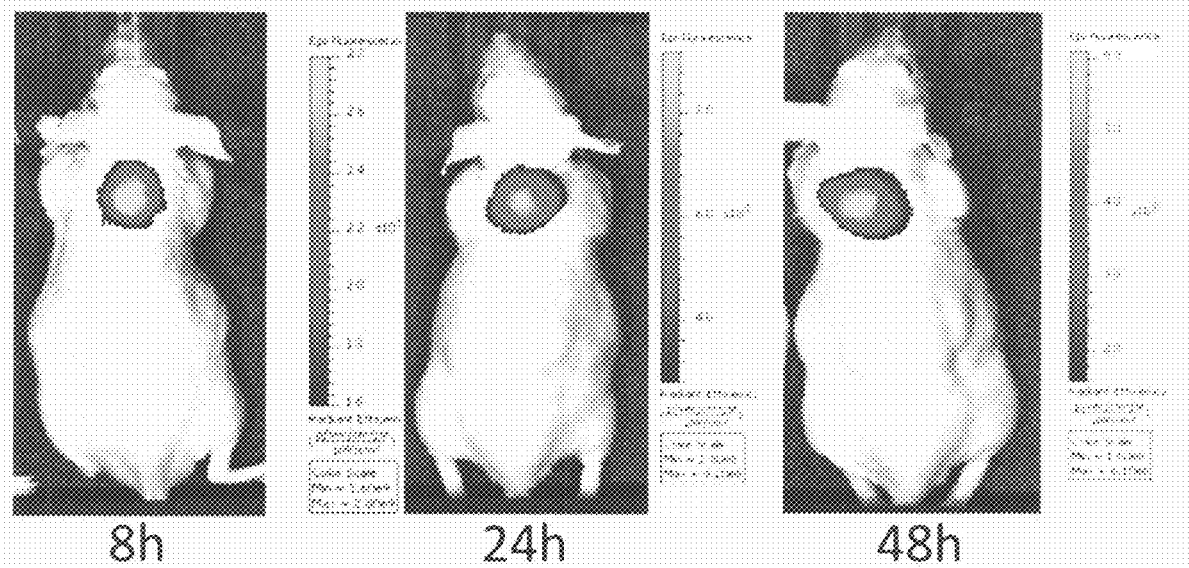
FIG. 24B: 22Rv1 human prostate tumor xenograft bearing mouse was injected with 20 nmol of 54 and imaged with IVIS imager at 8, 24, and 48 hr.

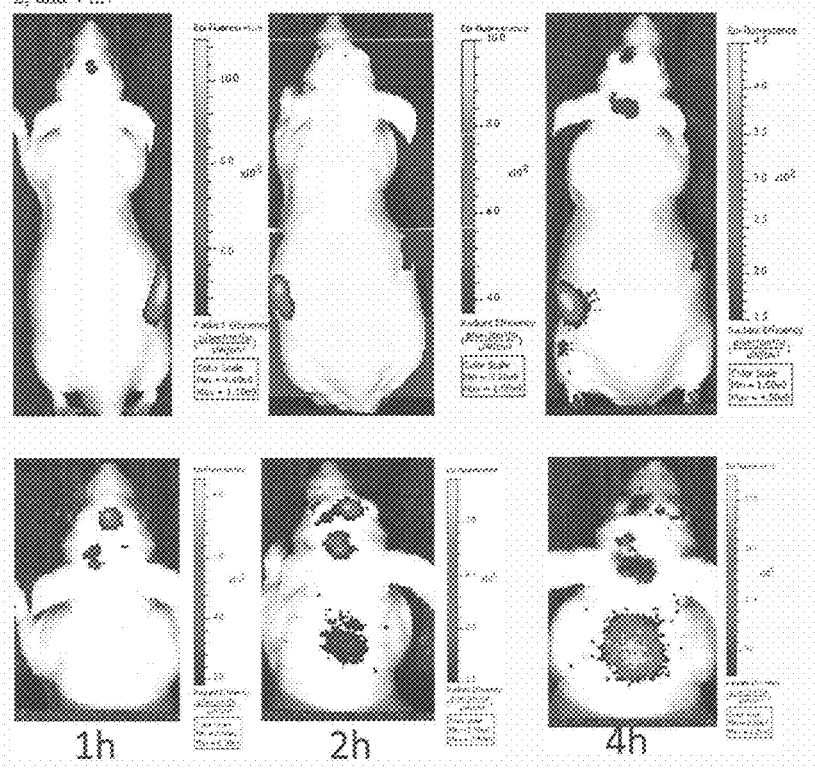
FIG. 25A: 22Rv1 human prostate tumor xenograft bearing mouse was injected with 20 nmol of 5S and imaged with IVIS imager at 1, 2, and 4 hr.

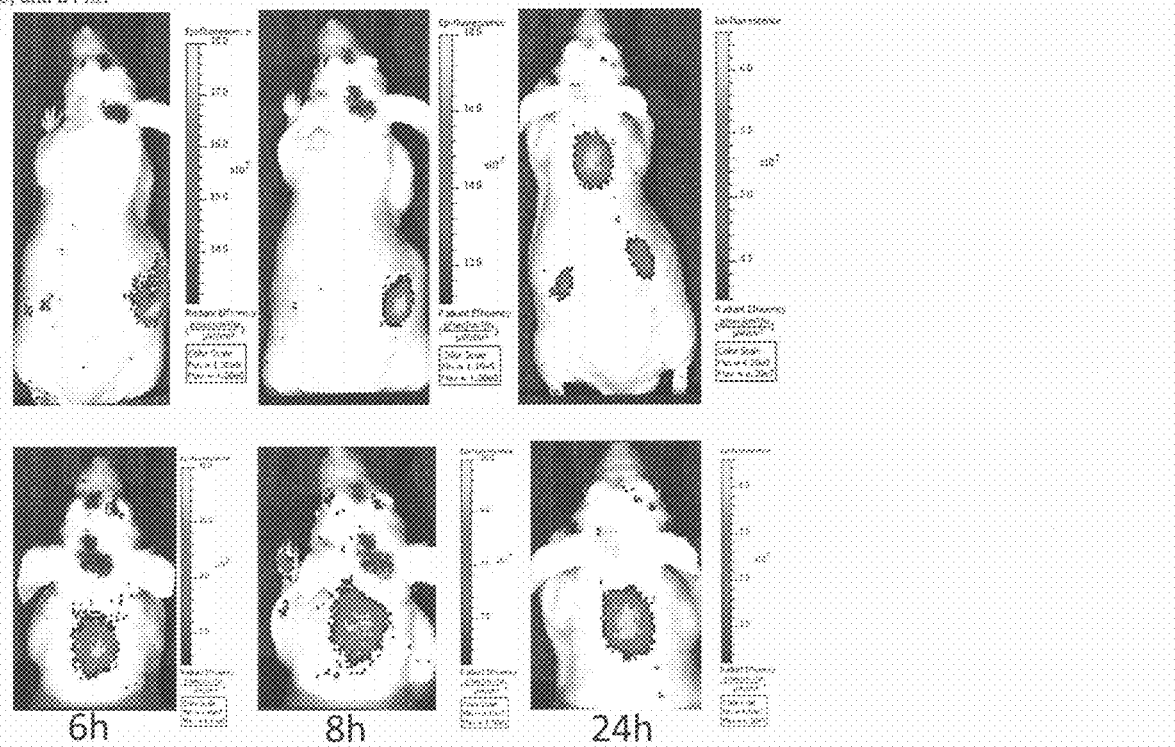
FIG. 25B: 22Rv1 human prostate tumor xenograft bearing mouse was injected with 20 nmol of 55 and imaged with IVIS imager at 6, 8, and 24 hr.

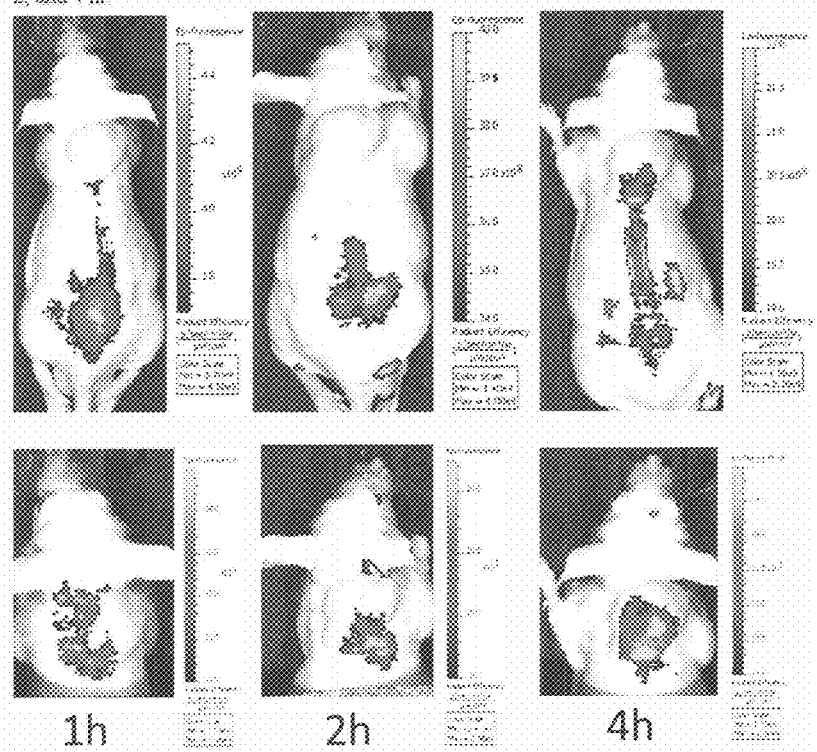
FIG. 26A: 22Rv1 human prostate tumor xenograft bearing mouse was injected with 20 nmol of 56 and imaged with IVIS imager at 1, 2, and 4 hr.

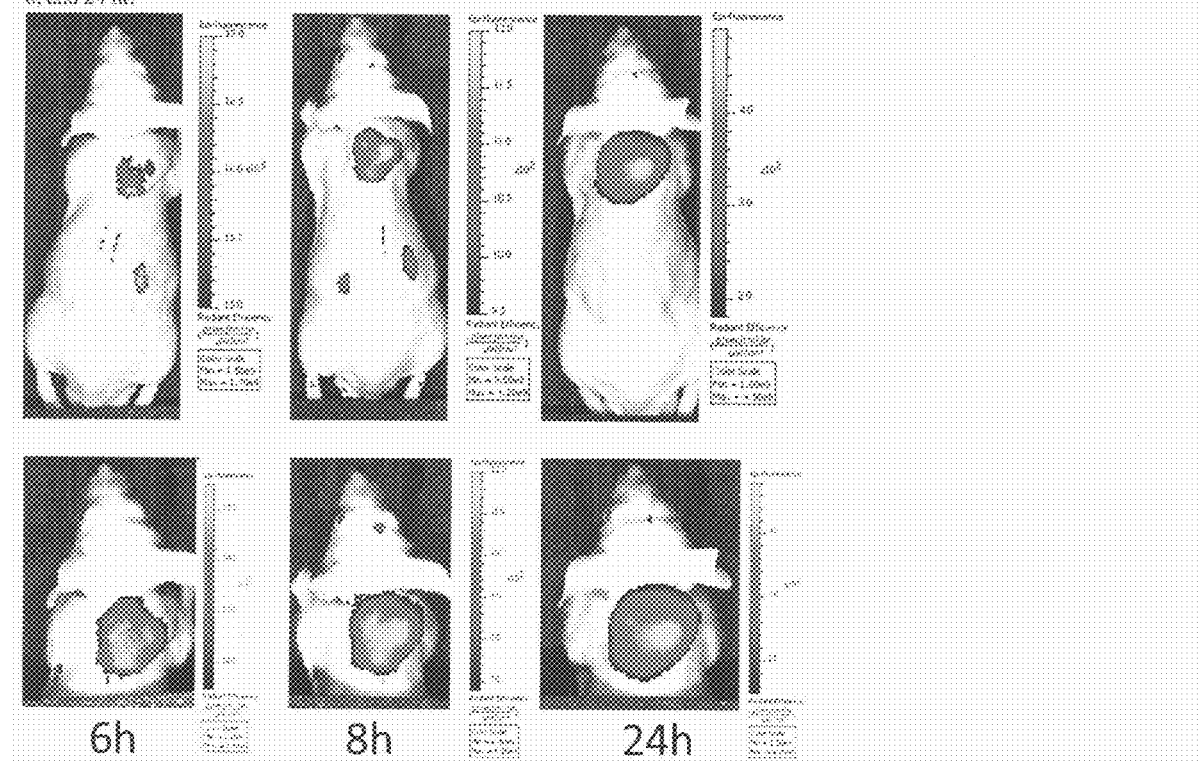
FIG. 26B: 22Rv1 human prostate tumor xenograft bearing mouse was injected with 20 nmol of 56 and imaged with IVIS imager at 6, 8, and 24 hr.

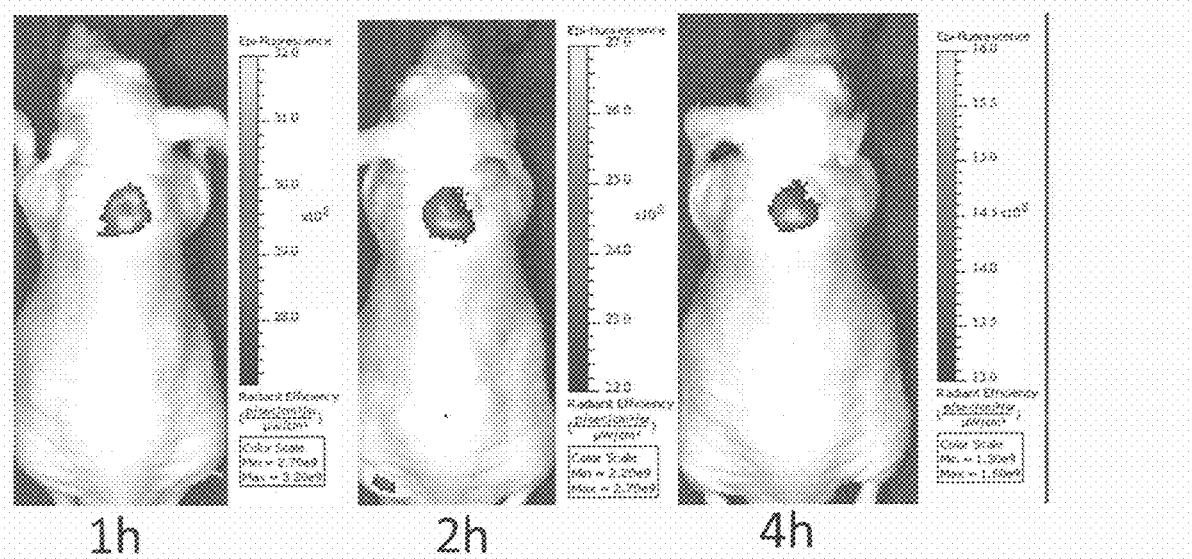
FIG. 27A: 22Rv1 human prostate tumor xenograft bearing mouse was injected with 20 nmol of 57 and imaged with IVIS imager at 1, 2, and 4 hr.

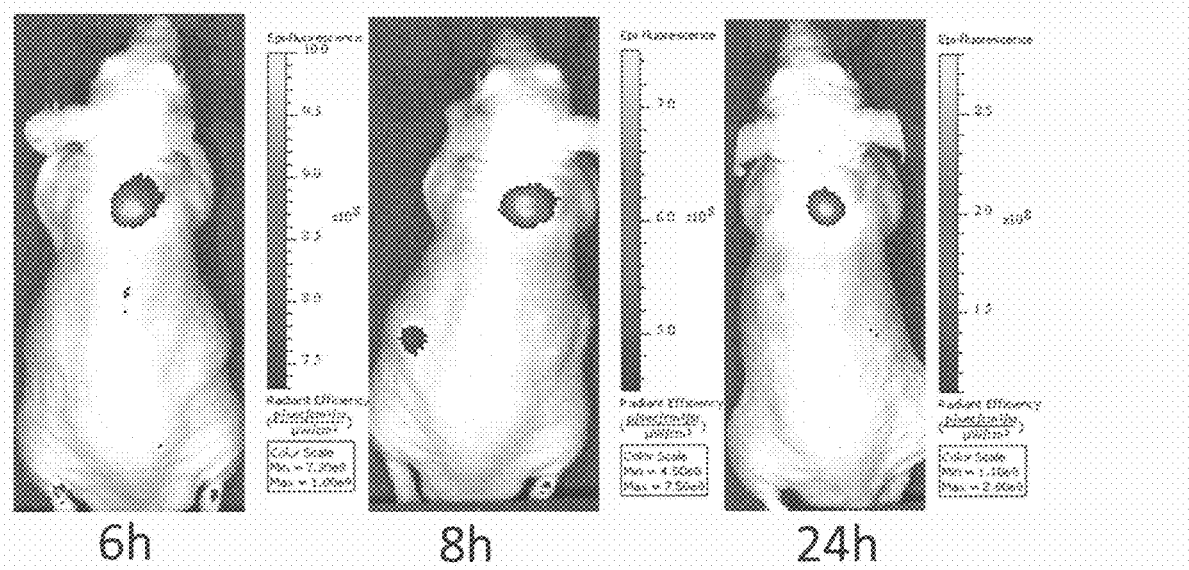
FIG. 27B: 22Rv1 human prostate tumor xenograft bearing mouse was injected with 20 nmol of 57 and imaged with IVIS imager at 6, 8, and 24 hr.

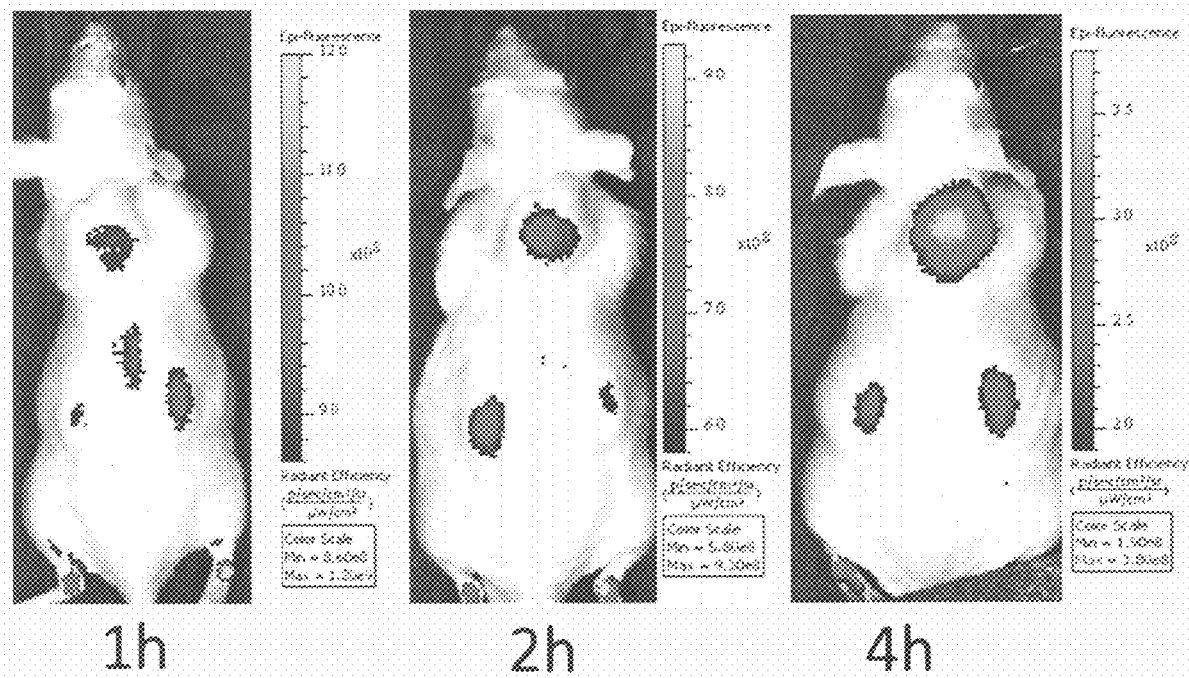
FIG. 28A: 22Rv1 human prostate tumor xenograft bearing mouse was injected with 20 nmol of 58 and imaged with IVIS imager at 1, 2, and 4 hr.

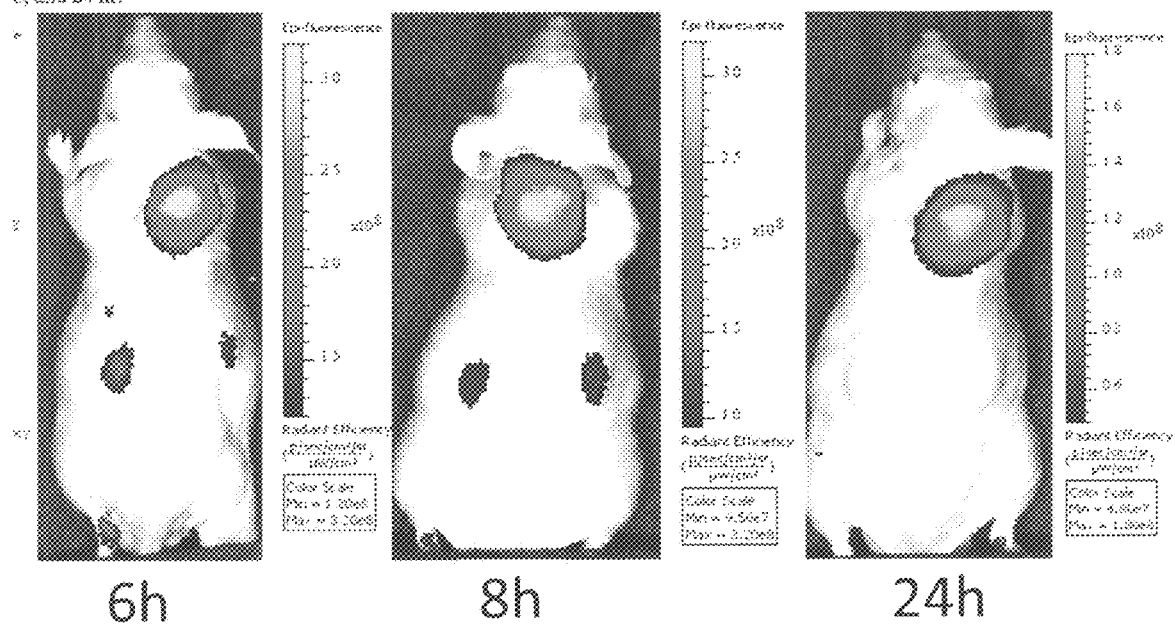
FIG. 28B: 22Rv1 human prostate tumor xenograft bearing mouse was injected with 20 nmol of 58 and imaged with IVIS imager at 6, 8, and 24 hr.

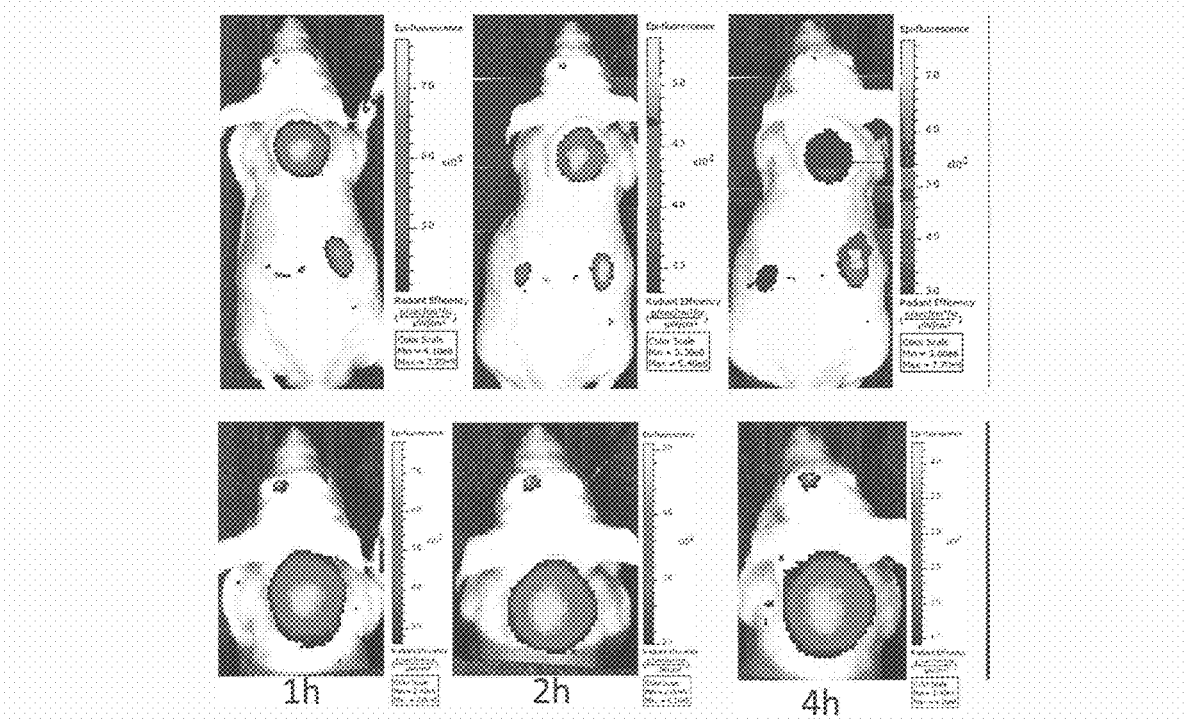
FIG. 29A: 22Rv1 human prostate tumor xenograft bearing mouse was injected with 20 nmol of 60 and imaged with IVIS imager at 1, 2, and 4 hr.

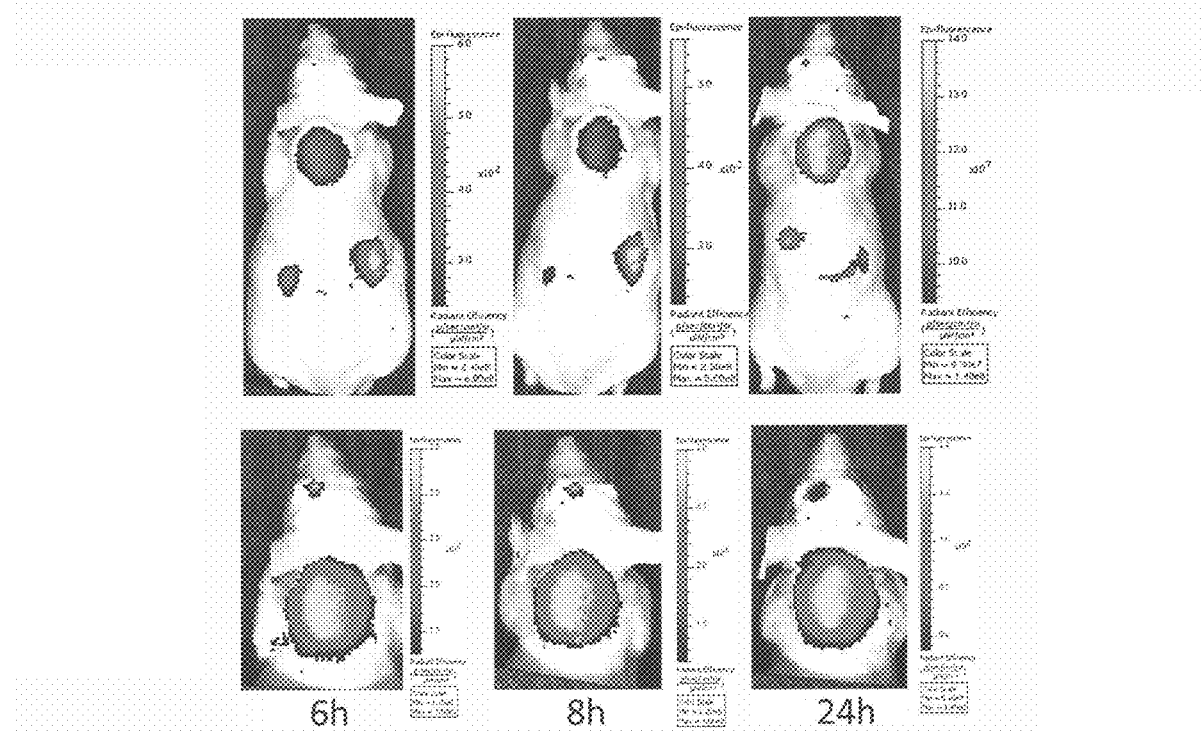
FIG. 29B: 22Rv1 human prostate tumor xenograft bearing mouse was injected with 20 nmol of 60 and imaged with IVIS imager at 6, 8, and 24 hr.

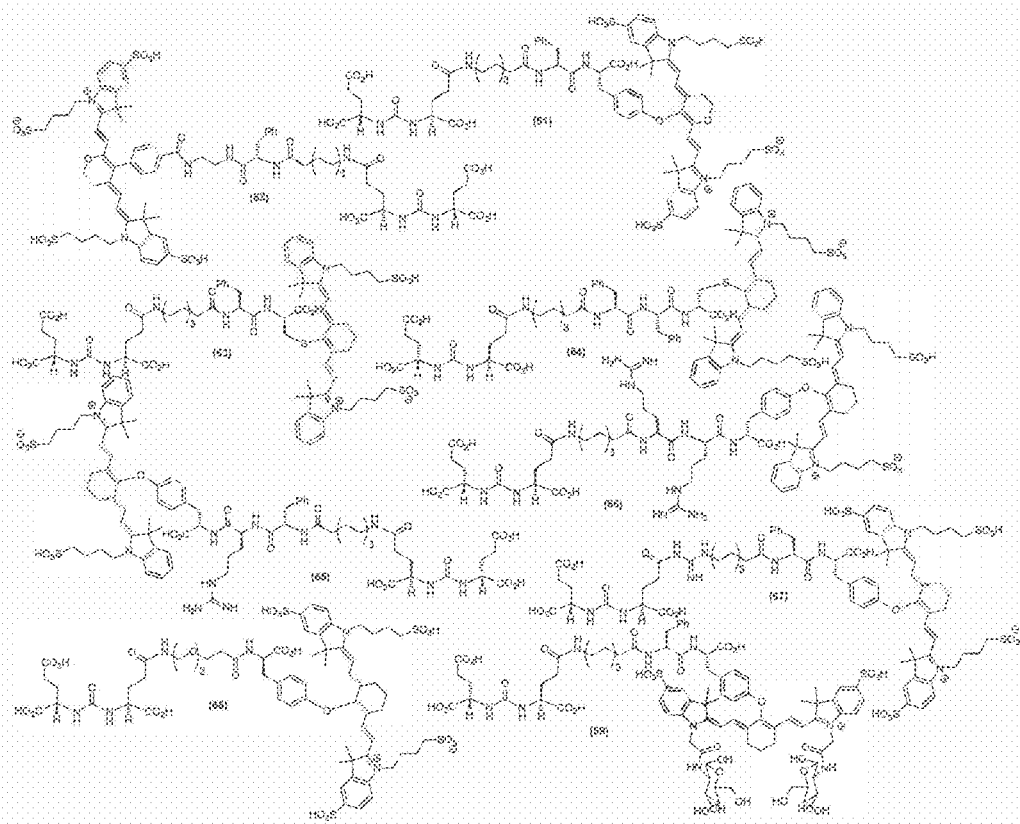
FIG. 30: Structures of PSMA-targeted DUPA-Linker-NIR imaging agents with miscellaneous linkers and NIR dyes.

FIG. 31: Relative binding affinities of DUPA-NIR conjugates with respect to DUPA-FITC (14).
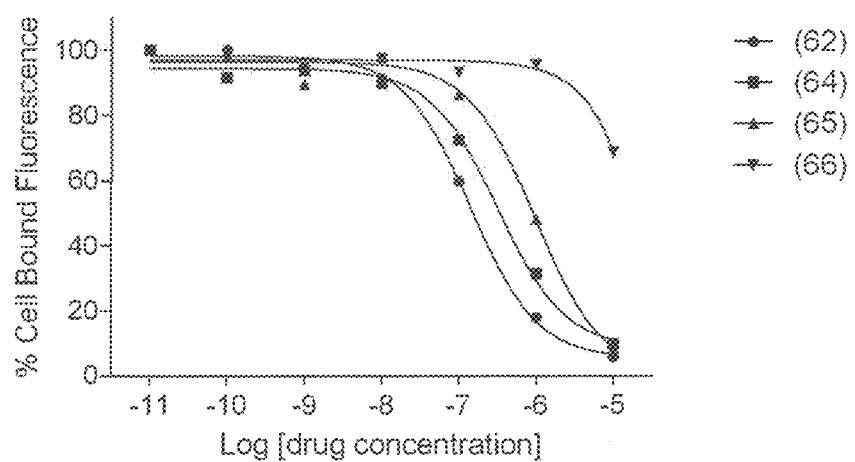

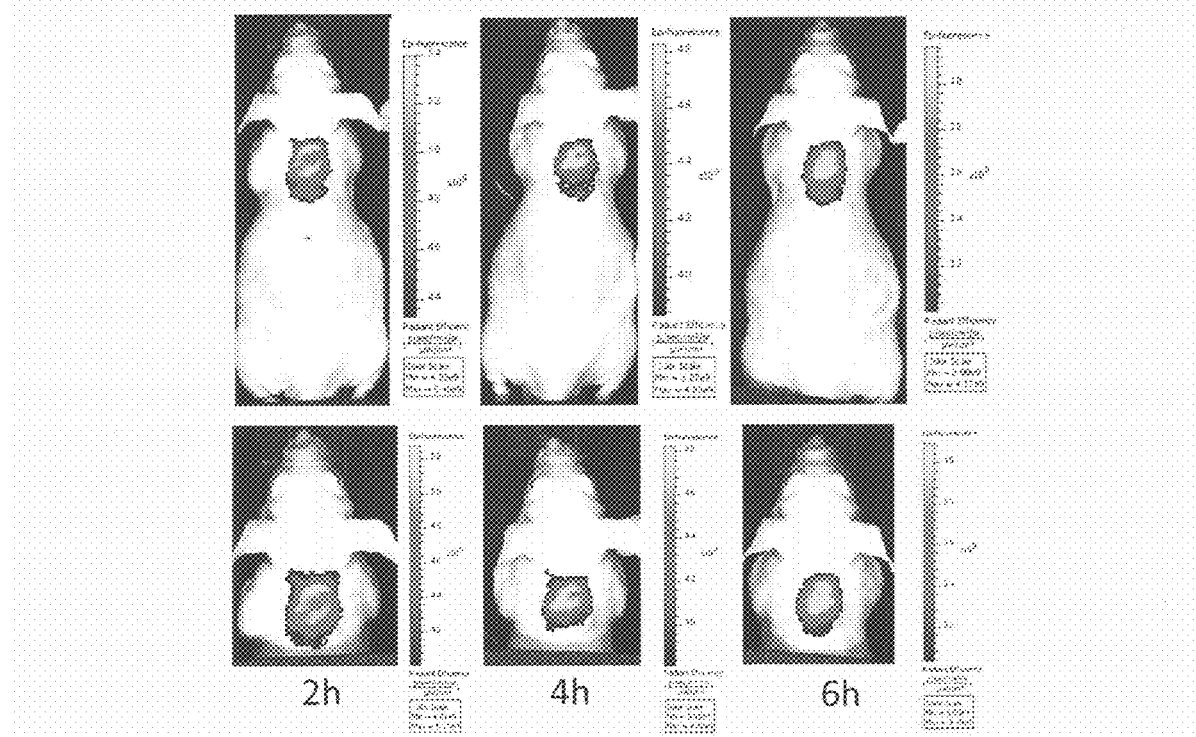
FIG. 32A: 22Rv1 human prostate tumor xenograft bearing mouse was injected with 20 nmol of 63 and imaged with IVIS imager at 2, 4, and 6 hr.

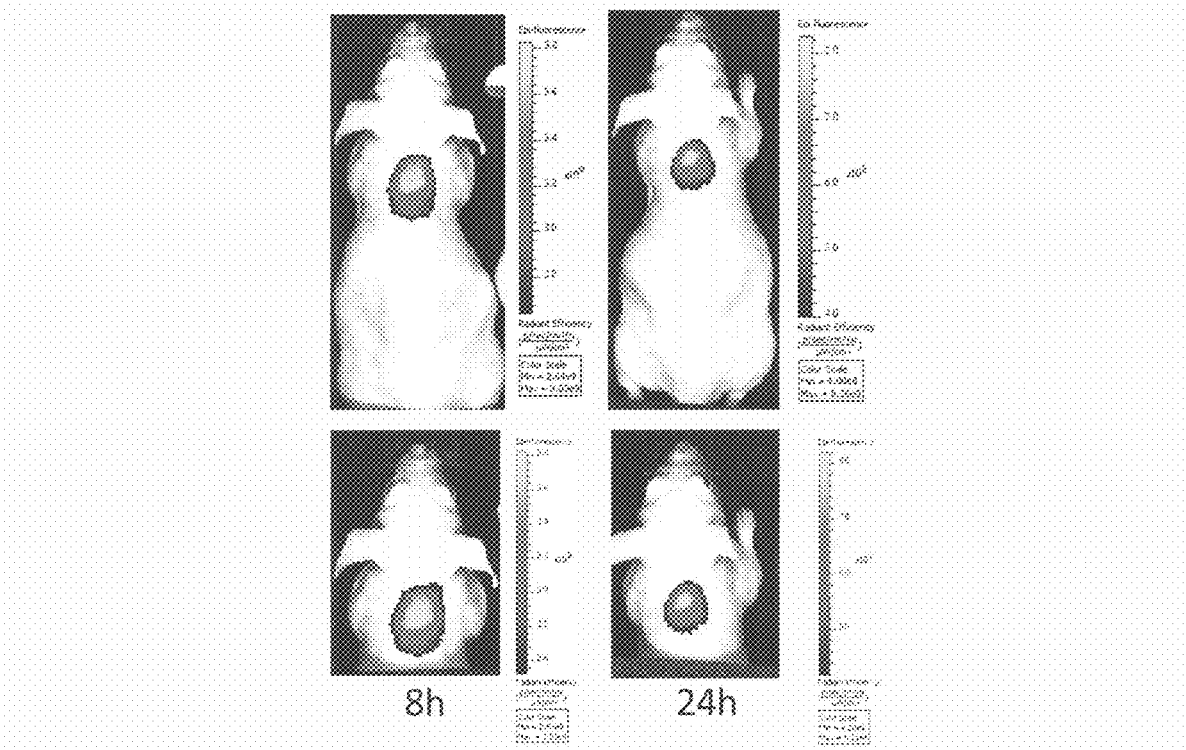
FIG. 32B: 22Rv1 human prostate tumor xenograft bearing mouse was injected with 20 nmol of 63 and imaged with IVIS imager at 8 and 24 hr.

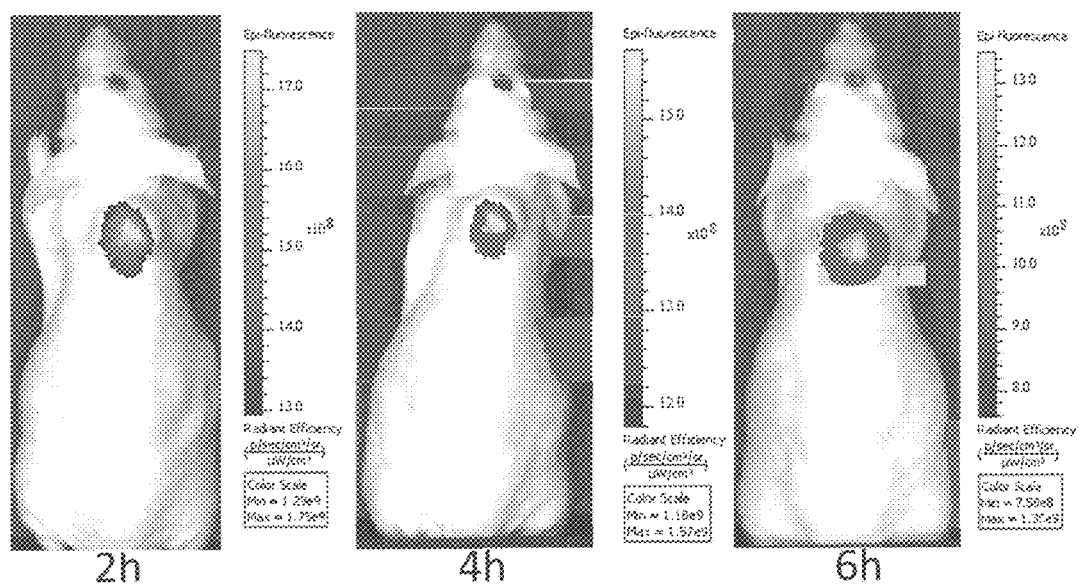
FIG. 33A: 22Rv1 human prostate tumor xenograft bearing mouse was injected with 6 nmol of 63 and imaged with IVIS imager at 2, 4, and 6 hr.

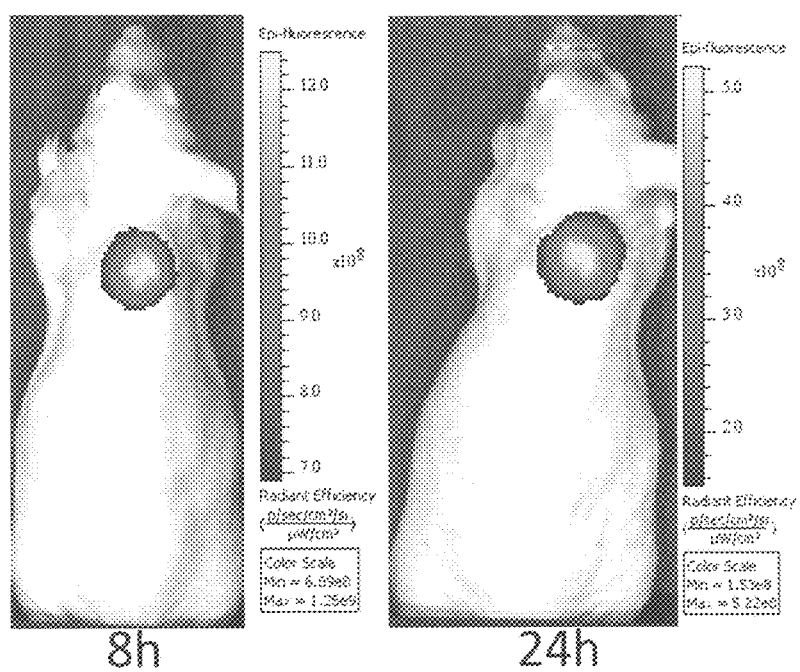
FIG. 33B: 22Rv1 human prostate tumor xenograft bearing mouse was injected with 6 nmol of 63 and imaged with IVIS imager at 8 and 24 hr.

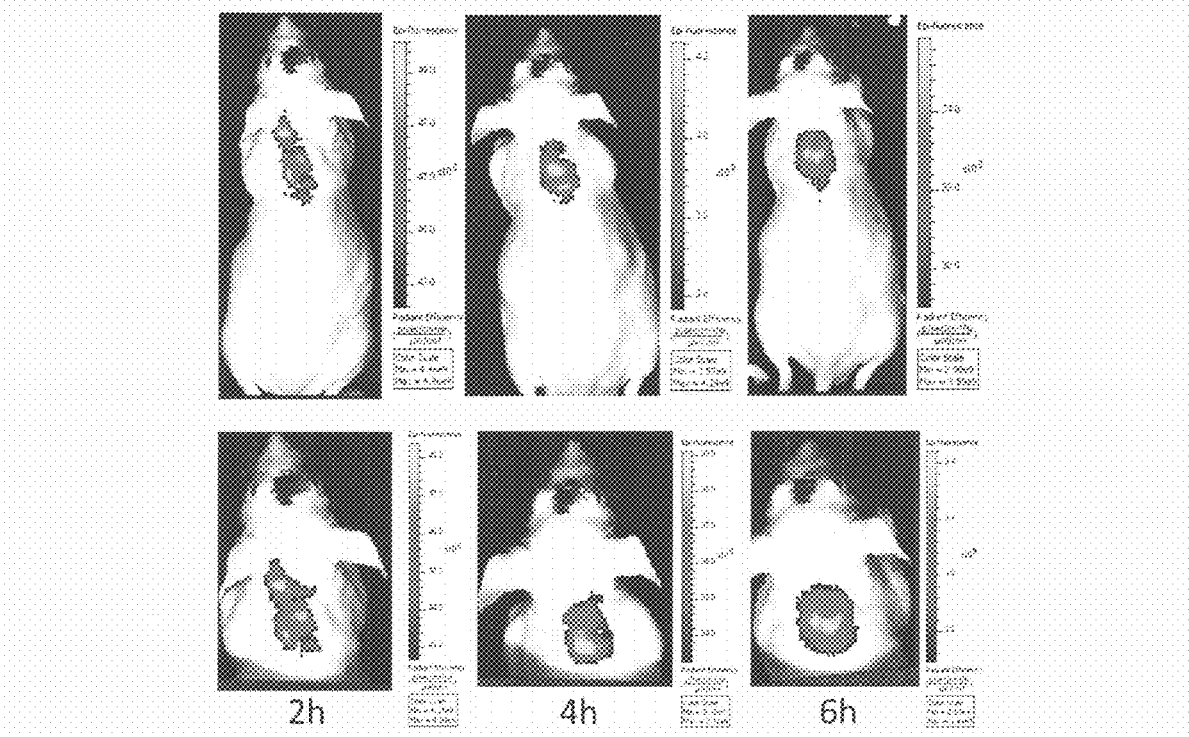
FIG. 34A: 22Rv1 human prostate tumor xenograft bearing mouse was injected with 20 nmol of 64 and imaged with IVIS imager at 2, 4, and 6 hr.

FIG. 34B: 22Rv1 human prostate tumor xenograft bearing mouse was injected with 20 nmol of 64 and imaged with IVIS imager at 8 and 24 hr.
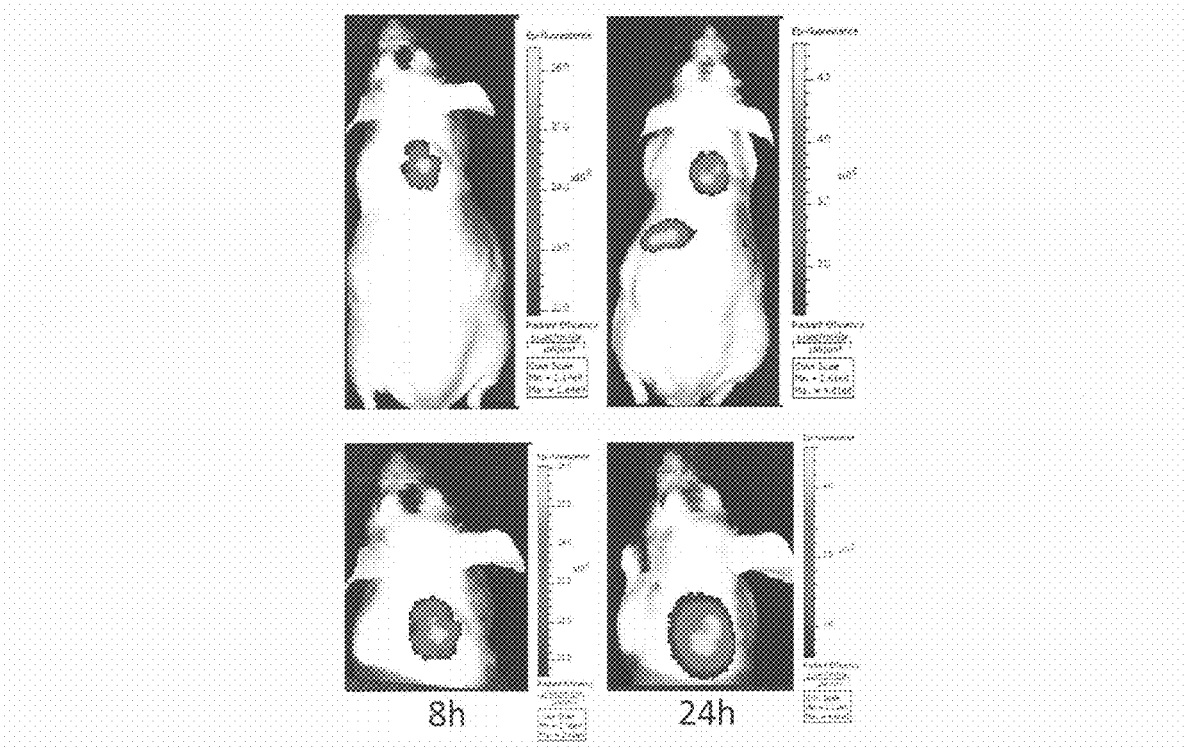

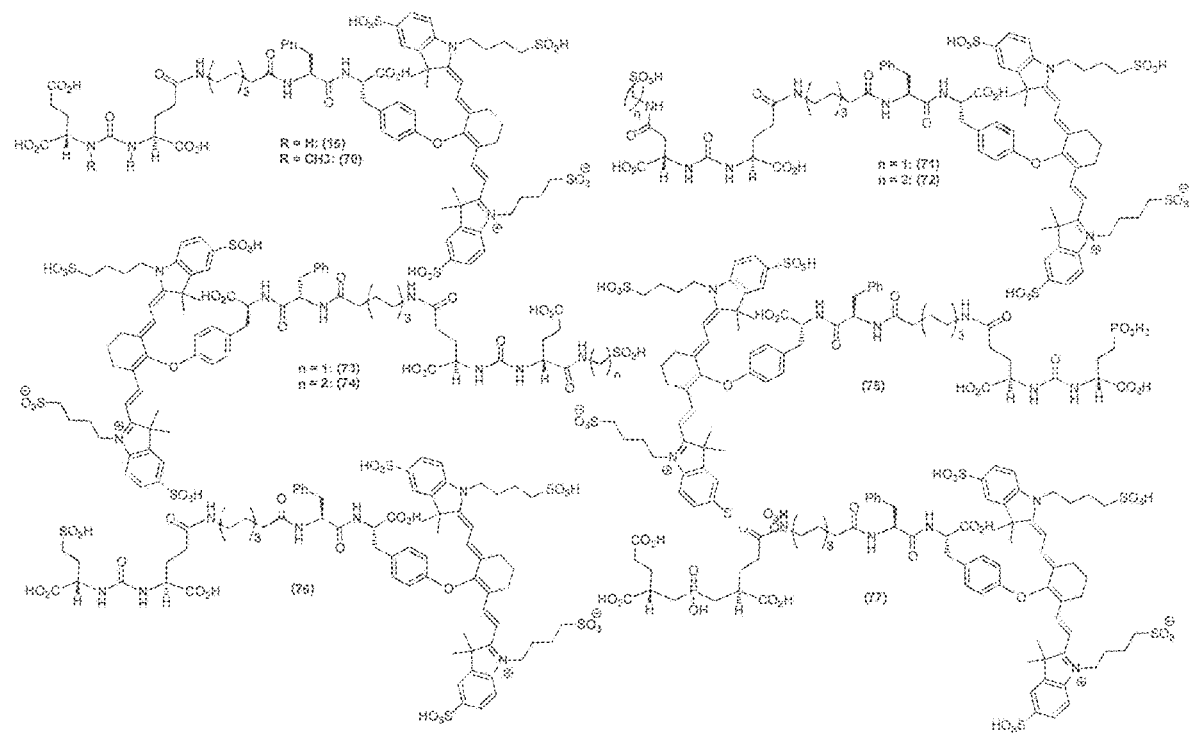
FIG. 35: Structures of PSMA-targeted NIR imaging agents with different ligands.

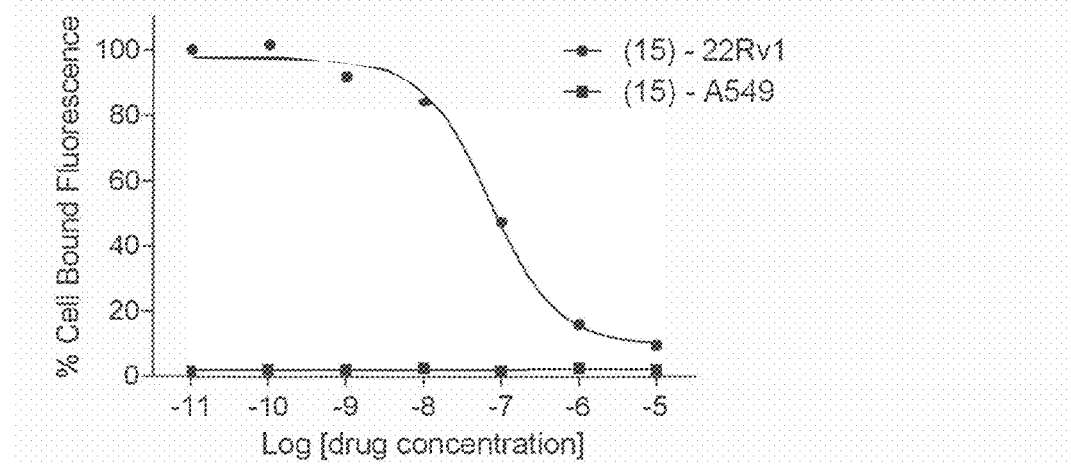
FIG. 36: Relative binding affinities of PSMA-targeted NIR conjugates with respect to DUPA-FITC (14).

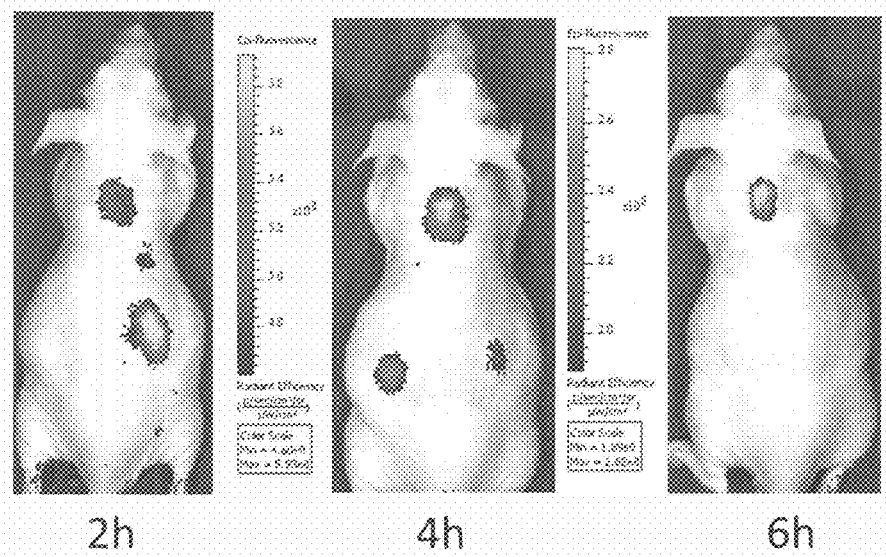
FIG. 37A: 22Rv1 human prostate tumor xenograft bearing mouse was injected with 6 nmol of 14 and imaged with IVIS imager at 2, 4, and 6 hr.

FIG. 37B: 22Rv1 human prostate tumor xenograft bearing mouse was injected with 6 nmol of 14 and imaged with IVIS imager at 8 and 24 hr.
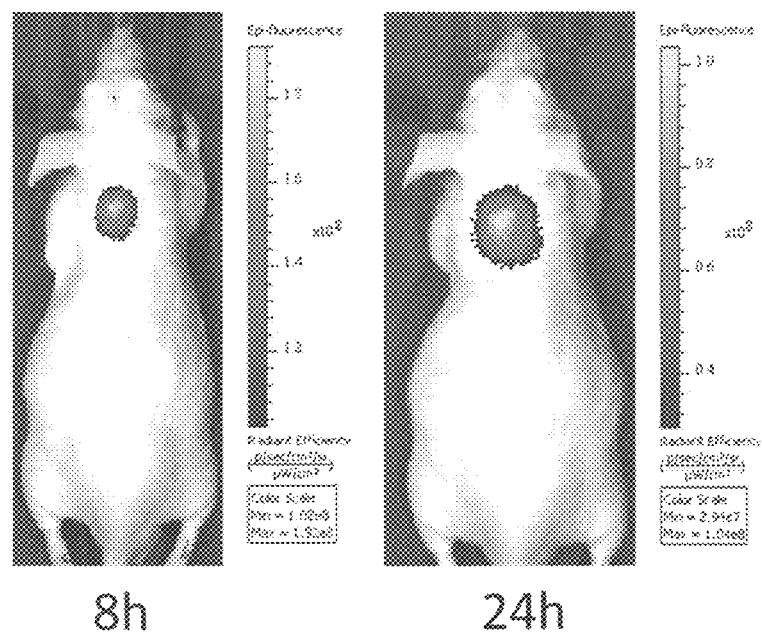

FIG. 38A: Chemical structures of S0456 and DUPA-FITC.
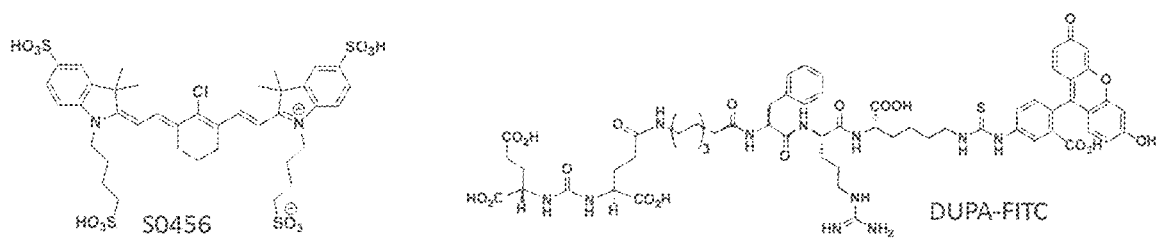

FIG. 38B: Excitation (Ex) & emission (Em) spectra of OTL78 (1 µM) and S0456 (1 µM) in 1 mL of PBS.
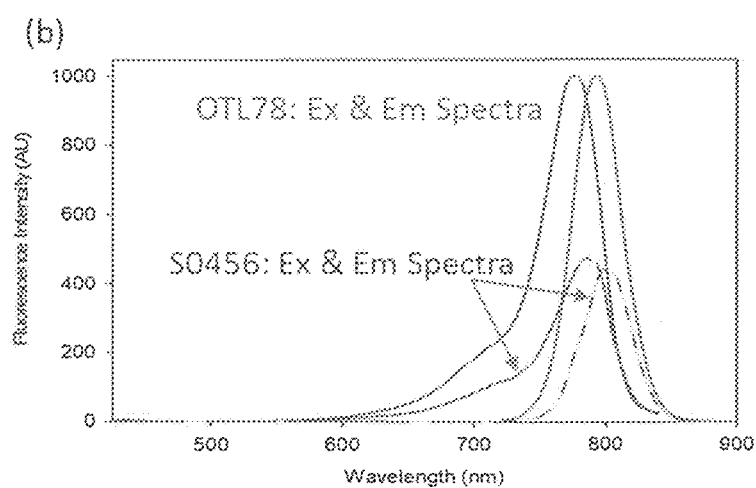

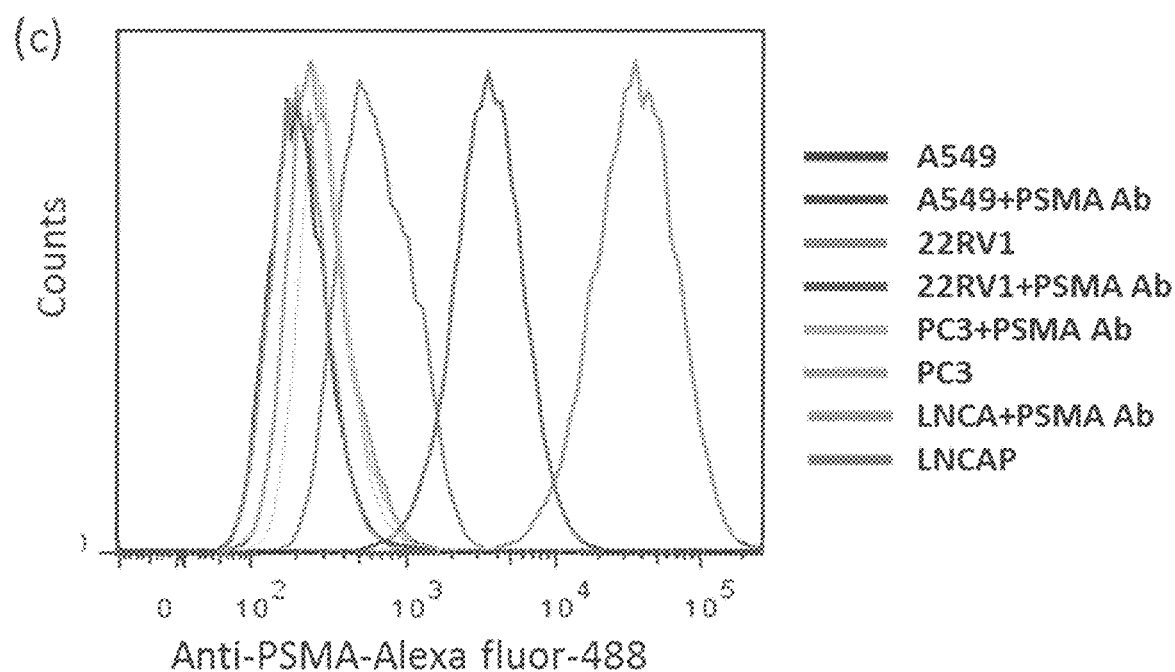
FIG. 38C: Evaluation of PSMA expression levels in LNCaP, 22Rv1, PC3, and A549 using flow cytometry.

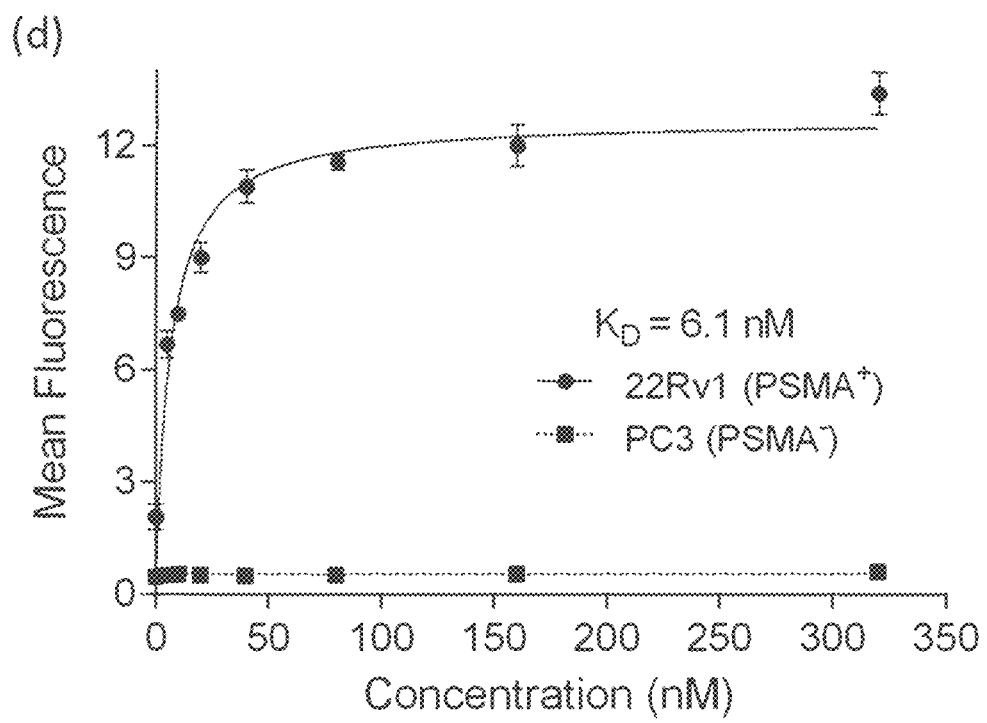
FIG. 38D: Dose dependent binding of DUPA-FITC

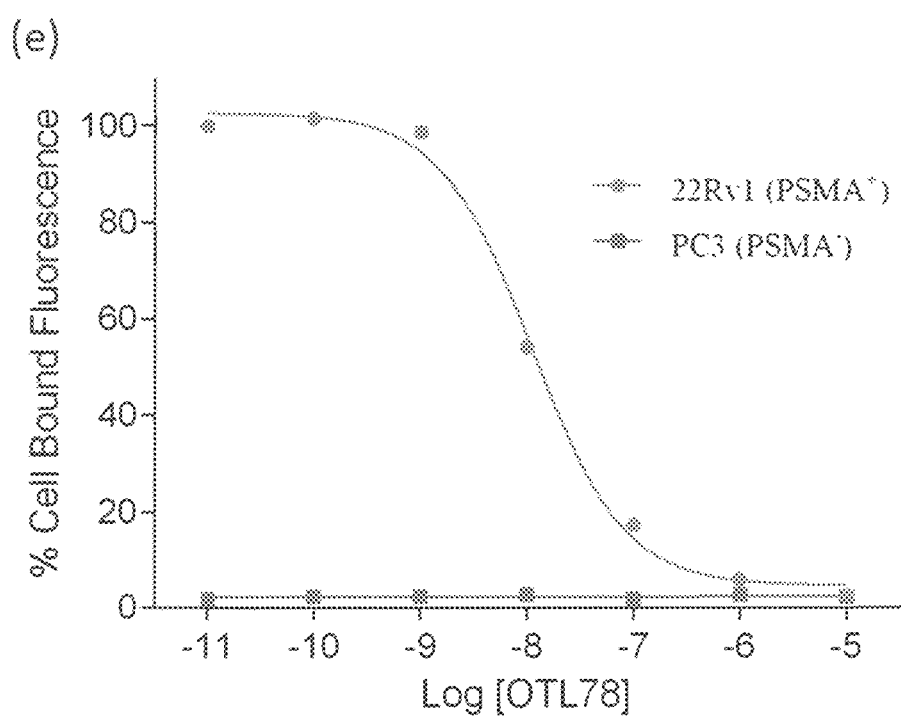
FIG. 38E: competitive binding of OTL78 with respect to DUPA-FITC to 22Rv1 and PC3 cells in culture.

FIG. 38F: Binding and internalization of OTL78 to (i) 22Rv1 and (ii) LNCaP at 4 °C by epifluorescence microscopy
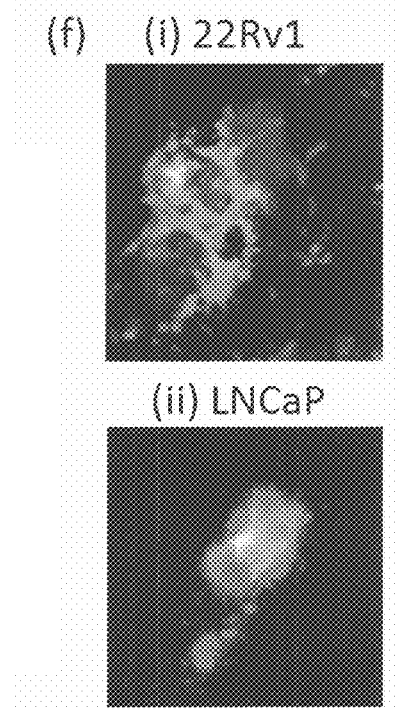

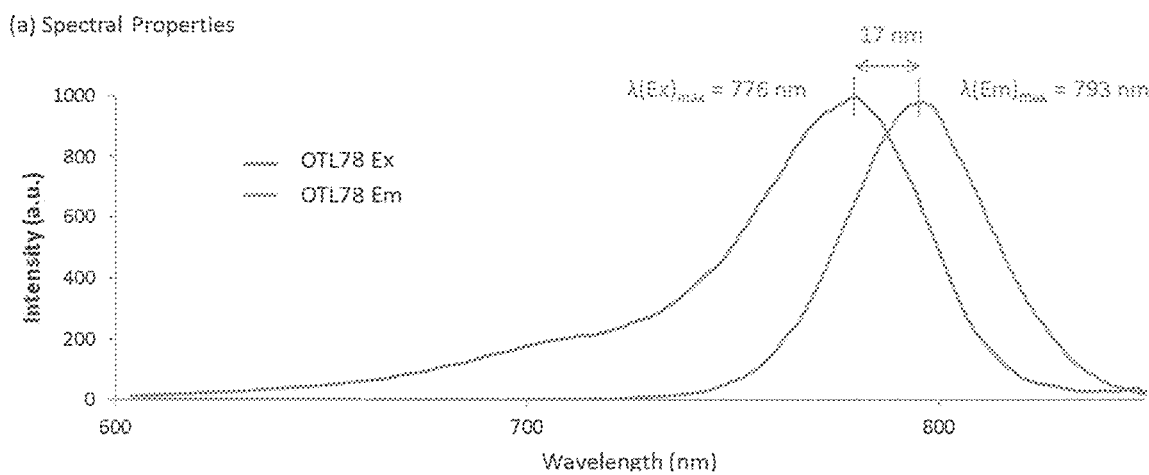
FIG. 39A: *In vitro* binding and specificity of OTL78. Excitation (Ex) & emission (Em) spectra of OTL78.

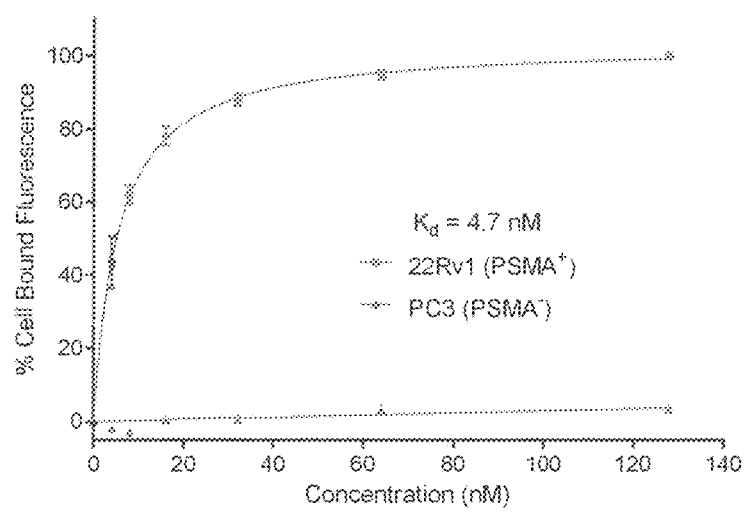
FIG. 39B: Dose dependent binding of OTL78 to prostate-specific membrane antigen (PSMA)+ 22Rv1 cells and PSMA-negative PC3 cells in culture (n=2).

FIG. 39C: Binding and internalization of OTL78 to (i) 22Rv1, (ii) LNCaP, or (iii) PC3 (fluorescence image) and (iv) PC3 (DIC image) cells by epifluorescence (epi) microscopy.
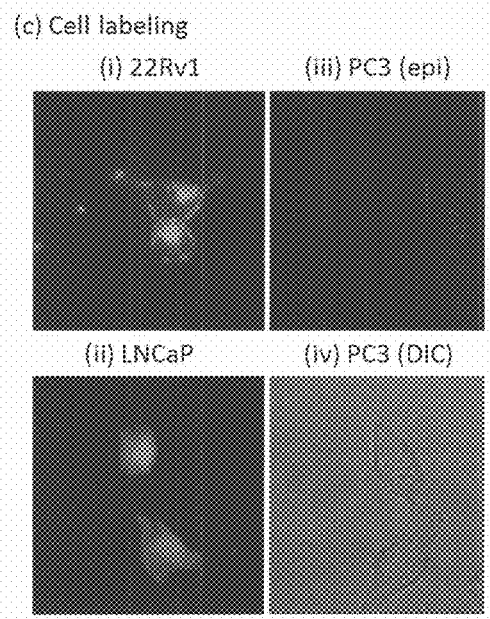

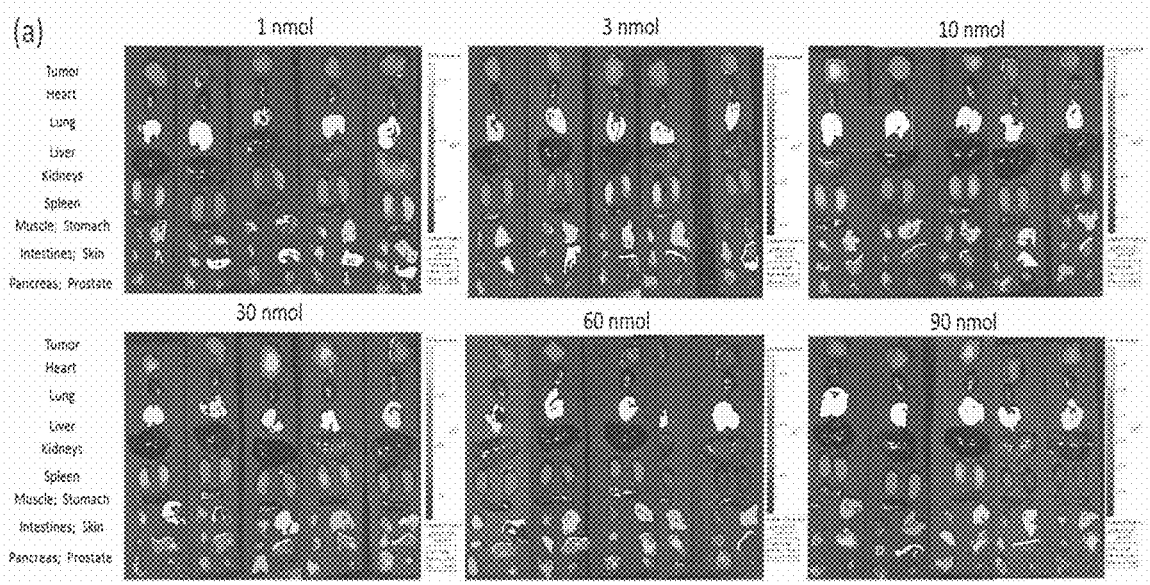
FIG. 40A: Tissue biodistribution analysis of OTL78: IVIS images showing overlay of fluorescence images over white light images of selected tissues.

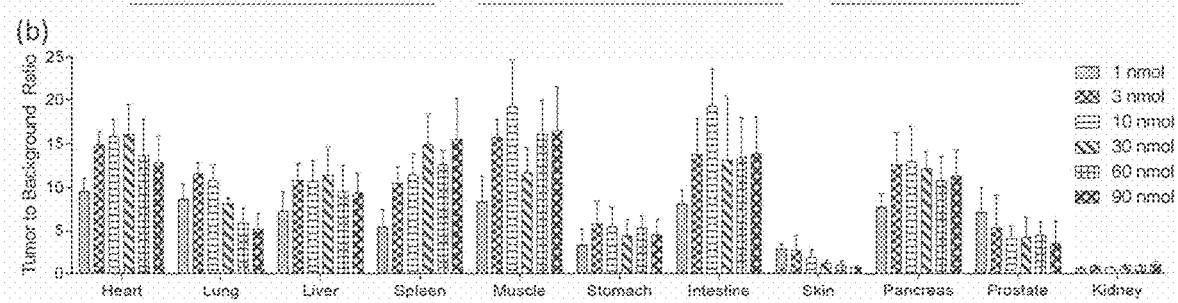
FIG. 40B: Tissue biodistribution analysis of OTL78.

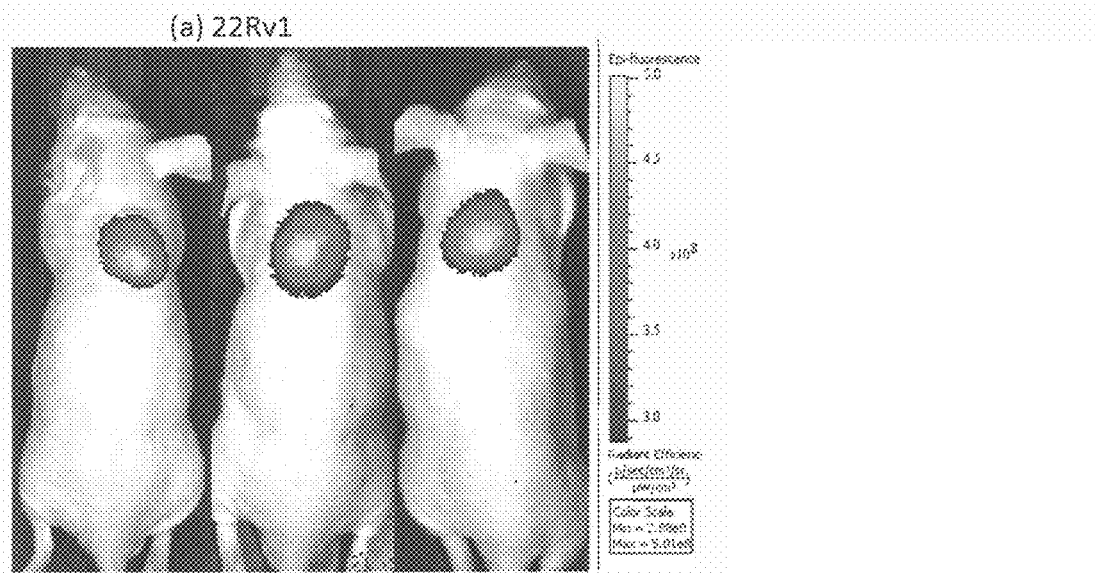
FIG. 41A: *In vivo* efficacy and specificity of OTL78 in subcutaneous tumor models using IVIS image system.

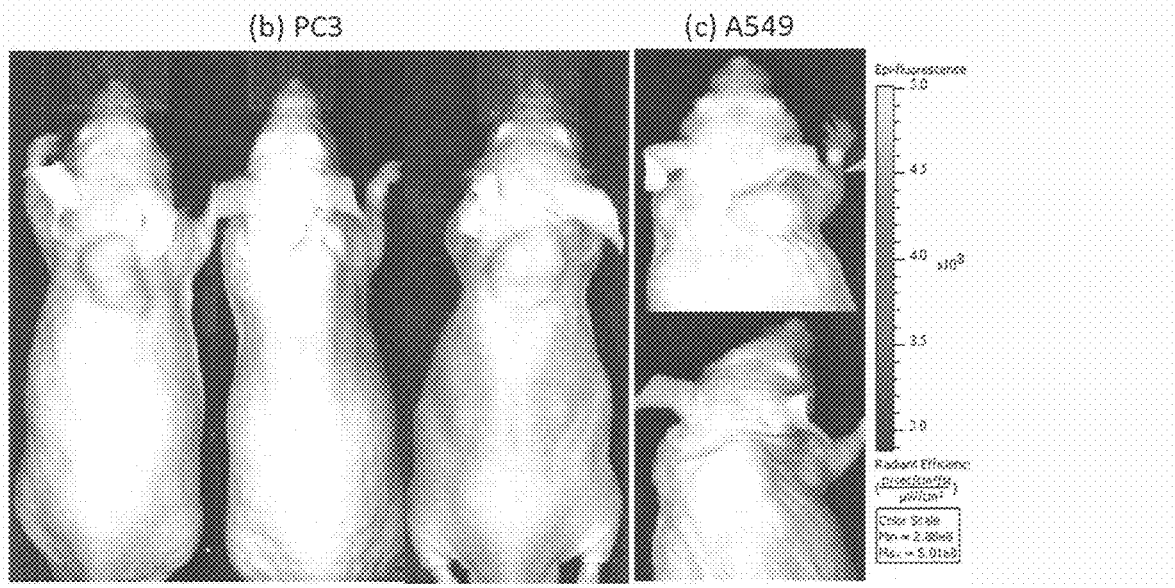
FIG. 41B–41C: : *In vivo* efficacy and specificity of OTL78 in subcutaneous tumor models using IVIS image system.

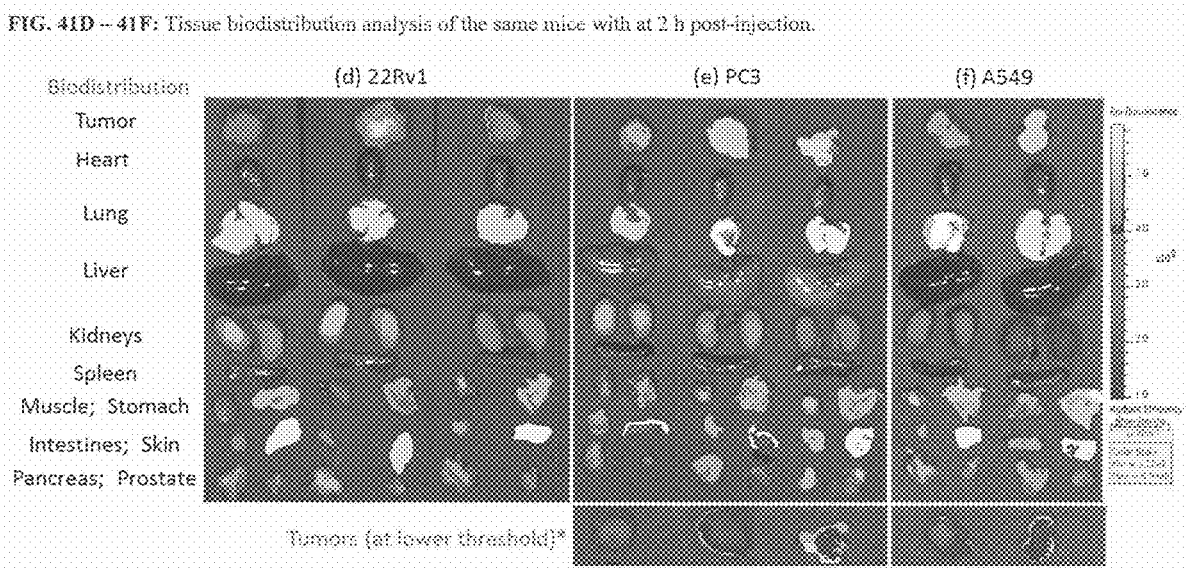
FIG. 41D – 41F: Tissue biodistribution analysis of the same mice with at 2 h post-injection.

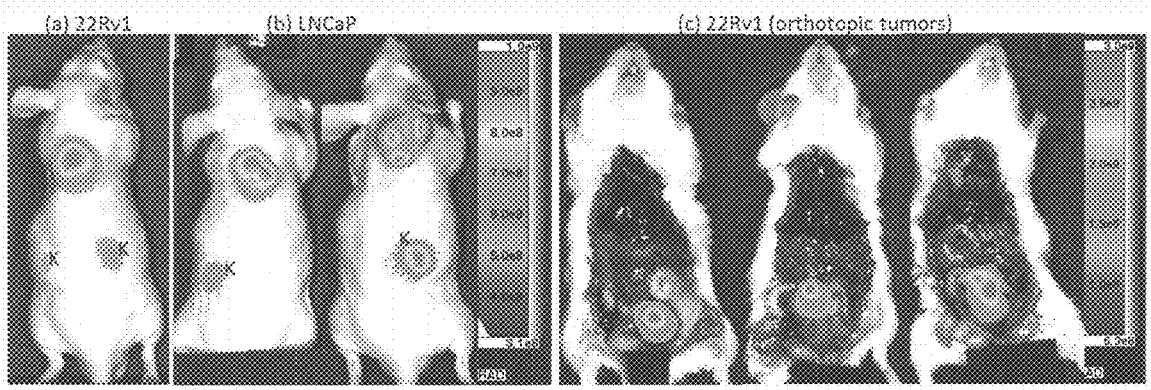
FIG. 42A-42C: *In vivo* efficacy and specificity of OTL78 in orthotopic and subcutaneous tumor models using AMI image system.

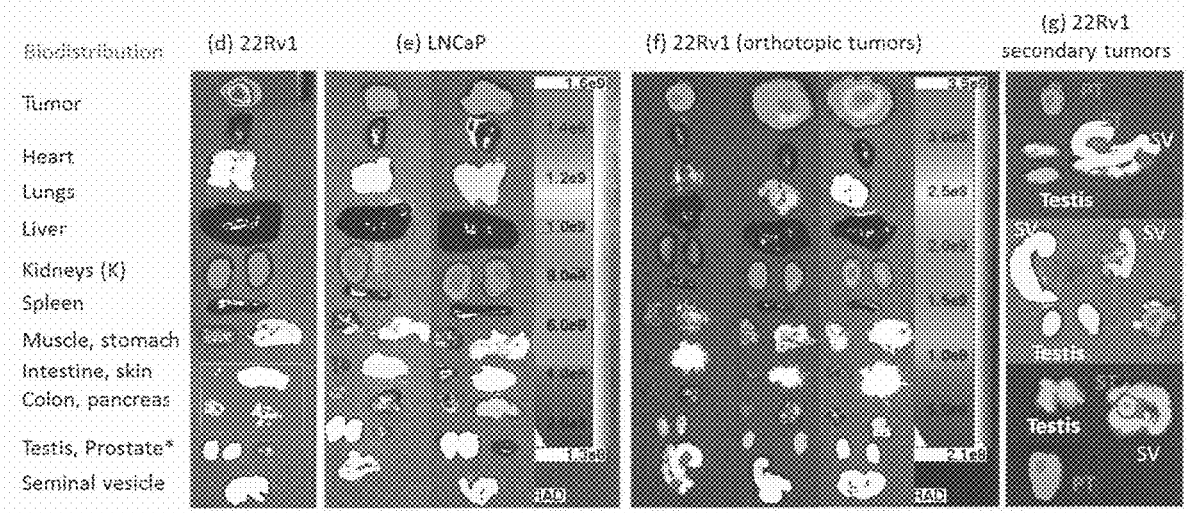
FIG. 42D-42G: Tissue biodistribution analysis of the same mice.

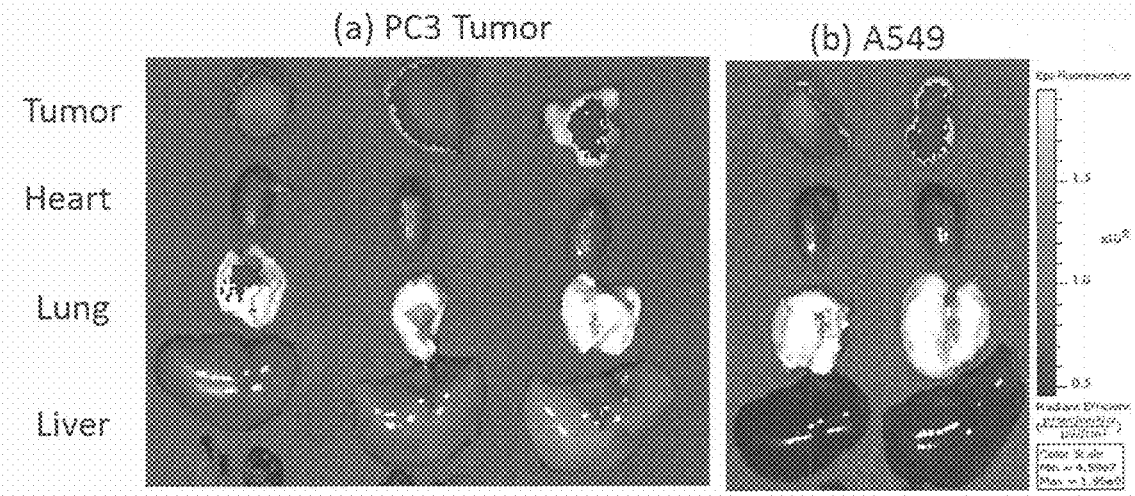
FIG. 43A-43B: In vivo efficacy of OTL78.

FIG. 43C-43D: Representative fluorescence images from AMI imager.
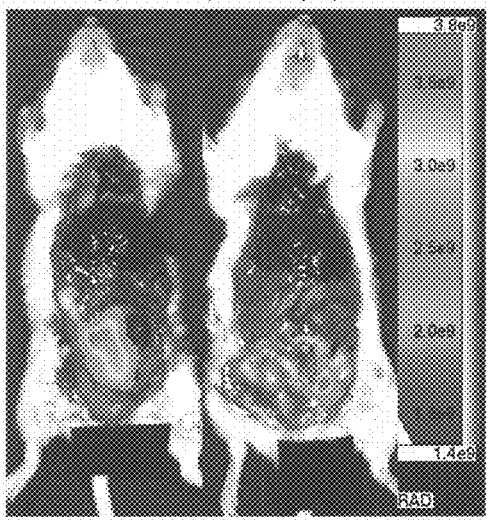 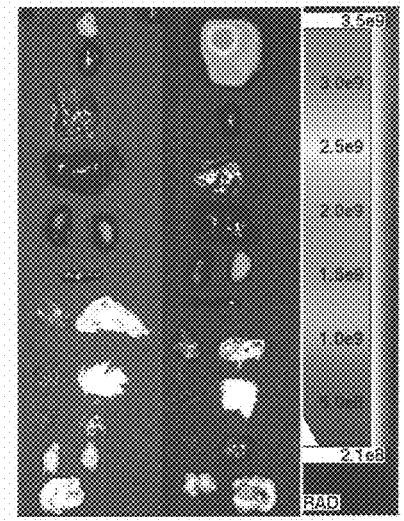

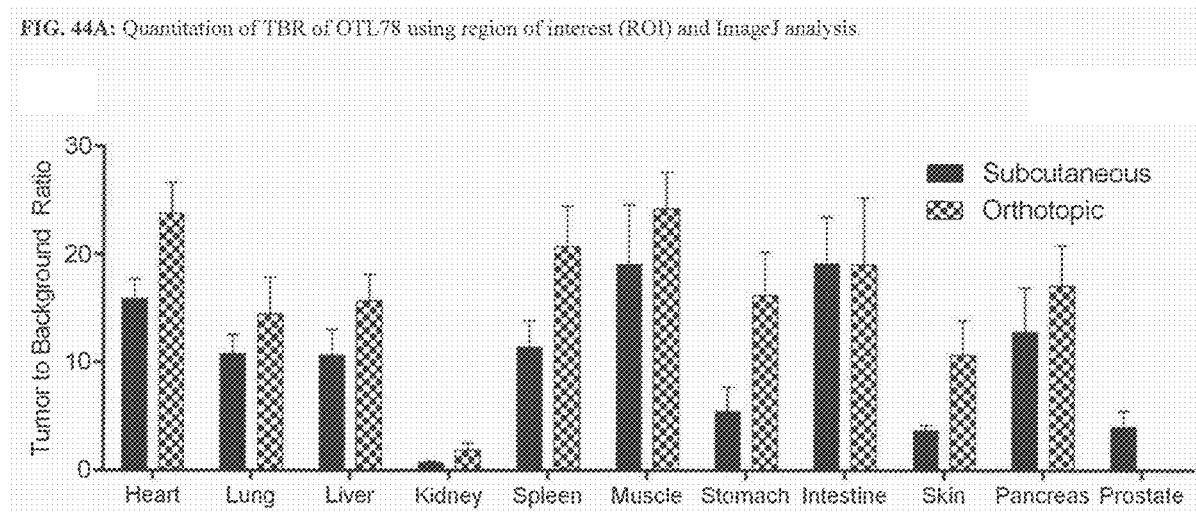
FIG. 44A: Quantitation of TBR of OTL78 using region of interest (ROI) and ImageJ analysis.

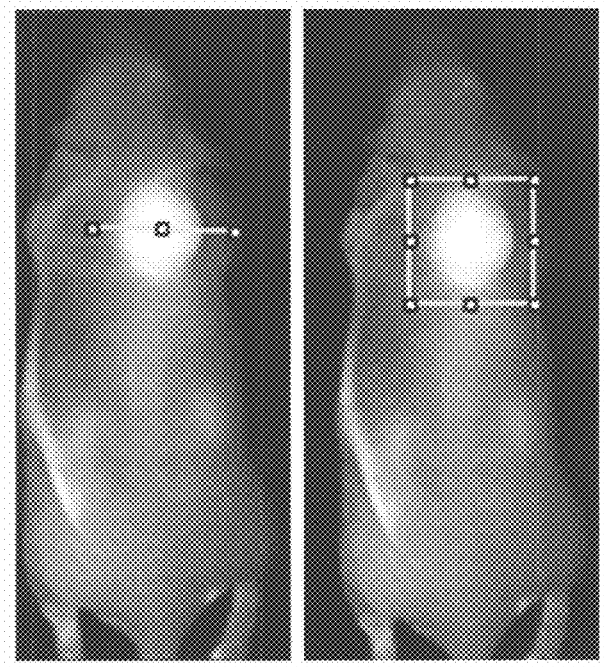
FIG. 44B: Representative fluorescence image (in gray scale) of mouse bearing 22Rv1 subcutaneous tumor after injecting 10 nmol of OTL78.

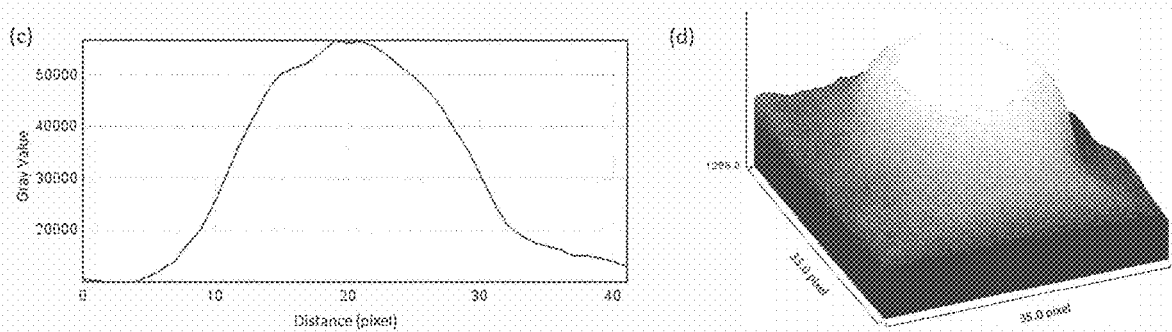
FIG. 44C – 44D: The plot of gray value versus distance (c) across the line and (d) within the box are shown in the Fig 41B.

FIG. 45A. Comparison of surgeries performed under conventional and fluorescence-guided techniques.
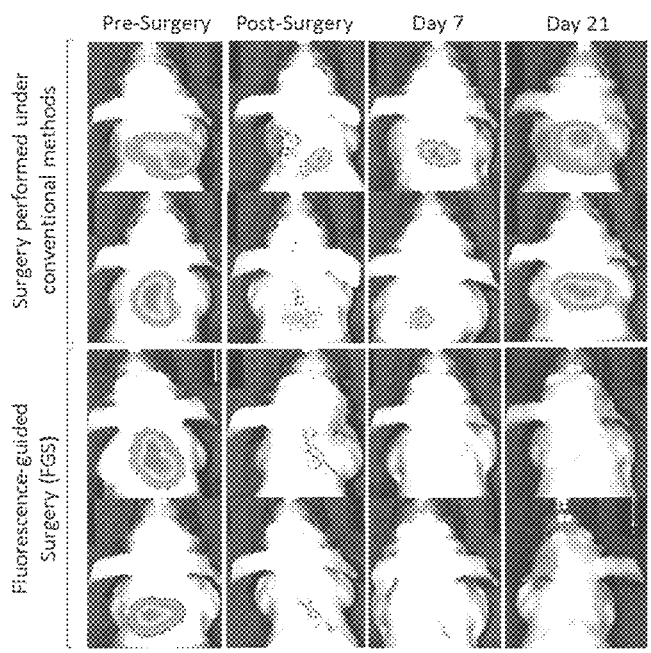

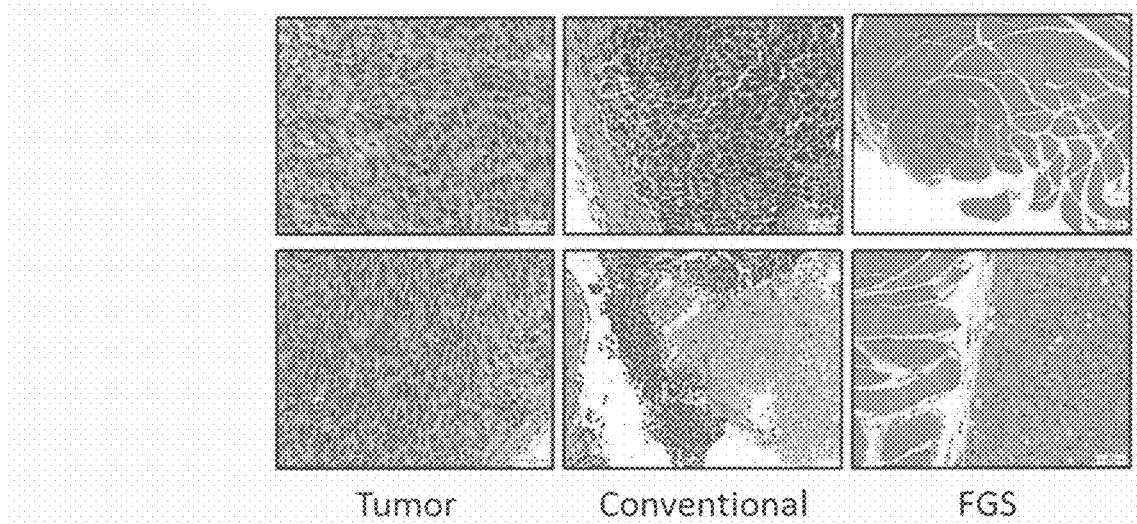
FIG. 45B: Representative H&E staining

FIG. 45C: Survival curve of the same mice (n=5 mice/group) over 30 days.
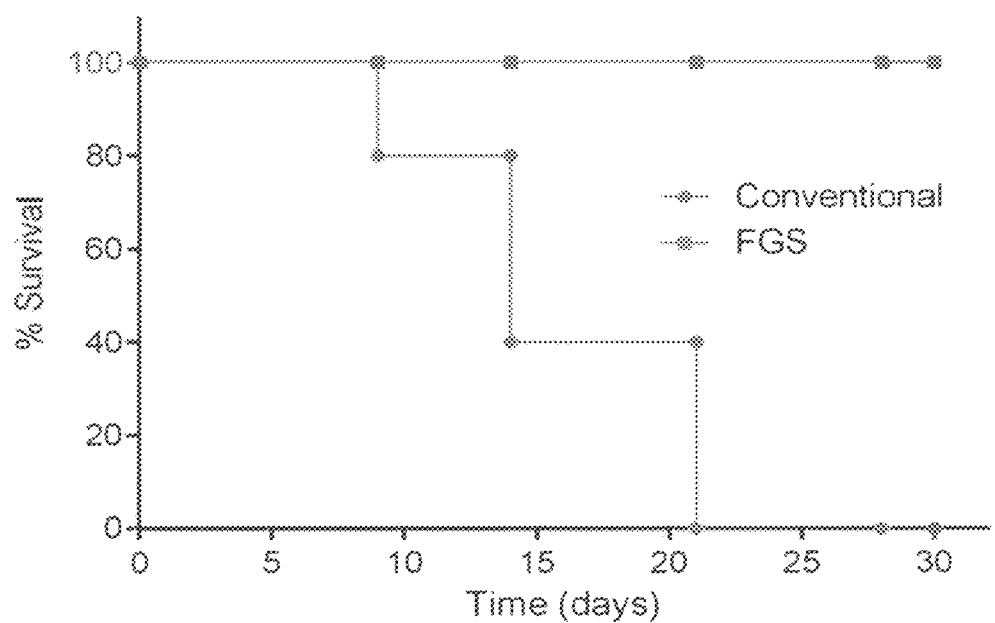

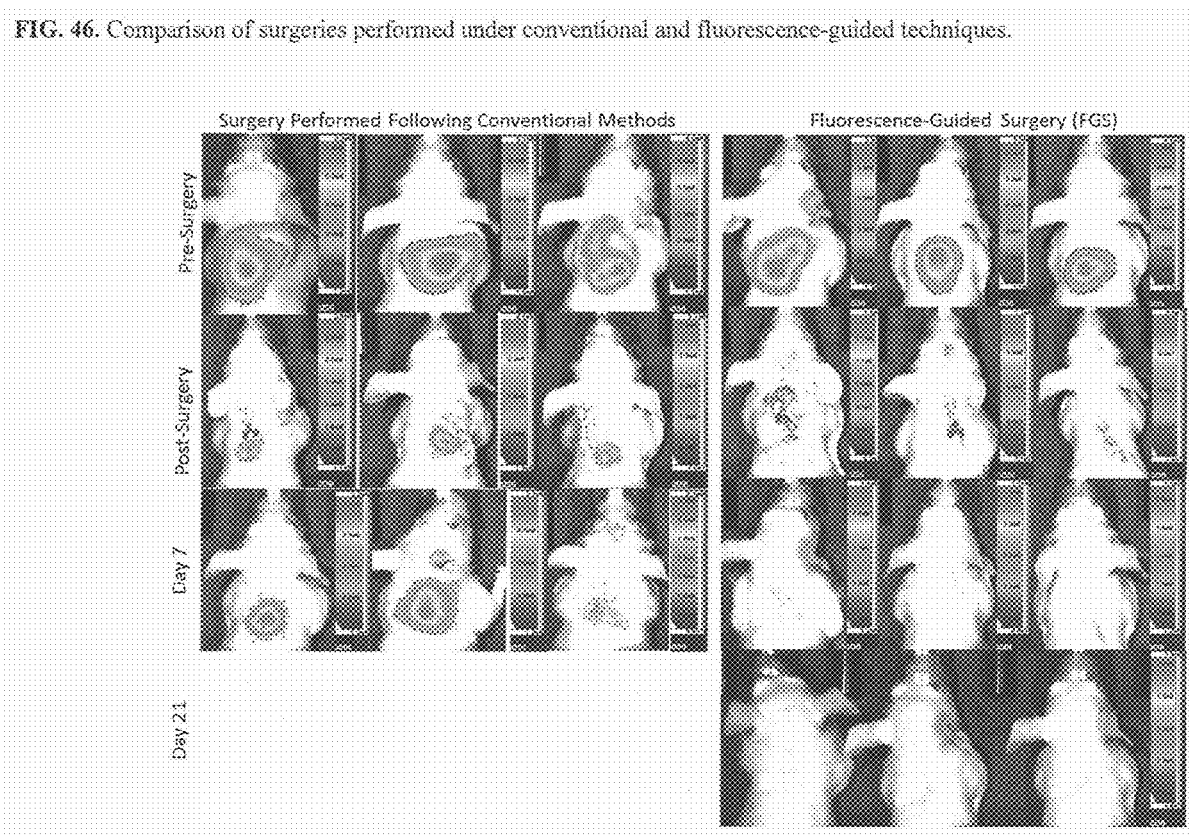
FIG. 46. Comparison of surgeries performed under conventional and fluorescence-guided techniques.

FIG. 47A-47B: Assessment of body weight change
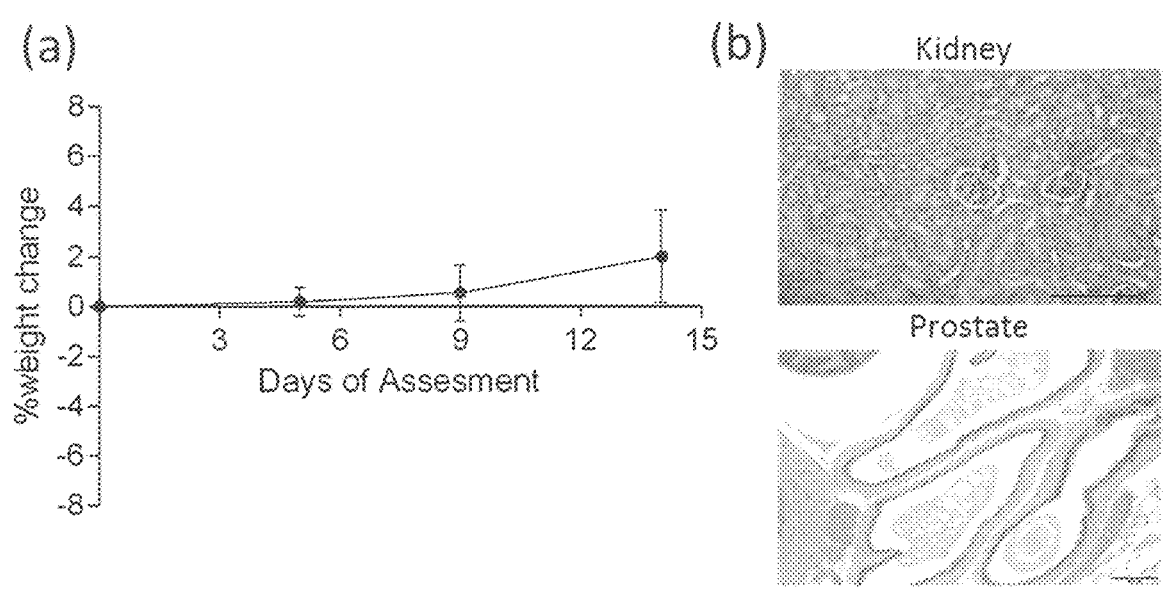

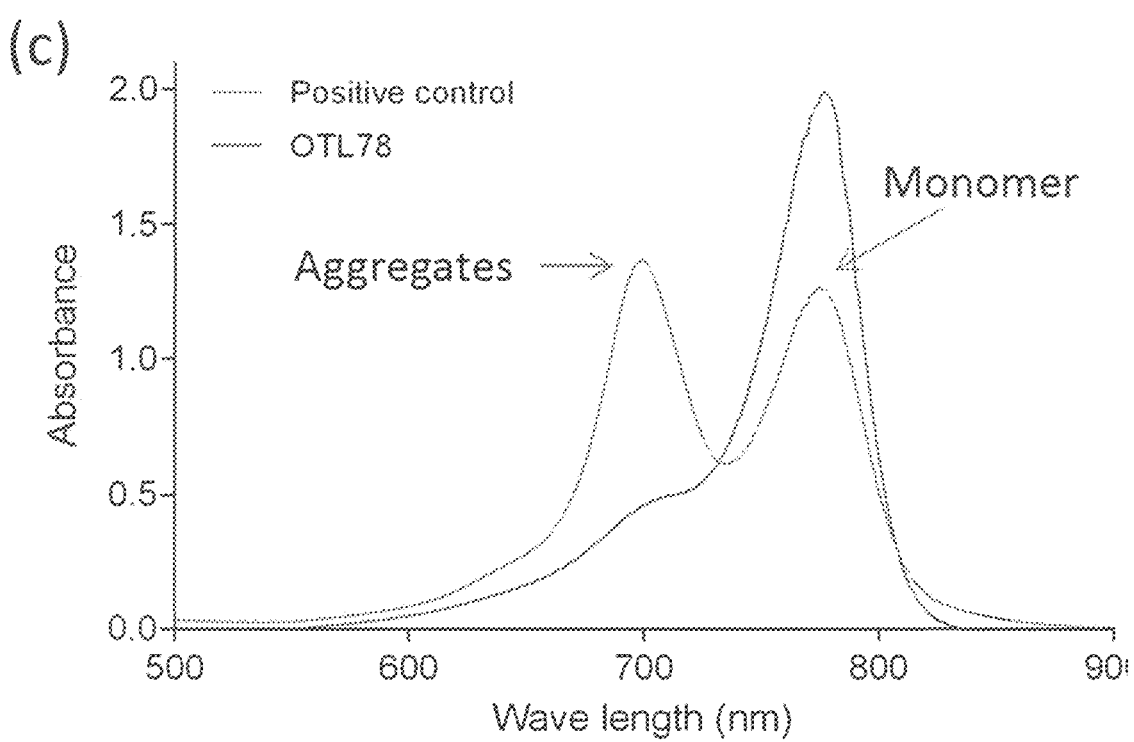
FIG. 47C: UV spectra of OTL78

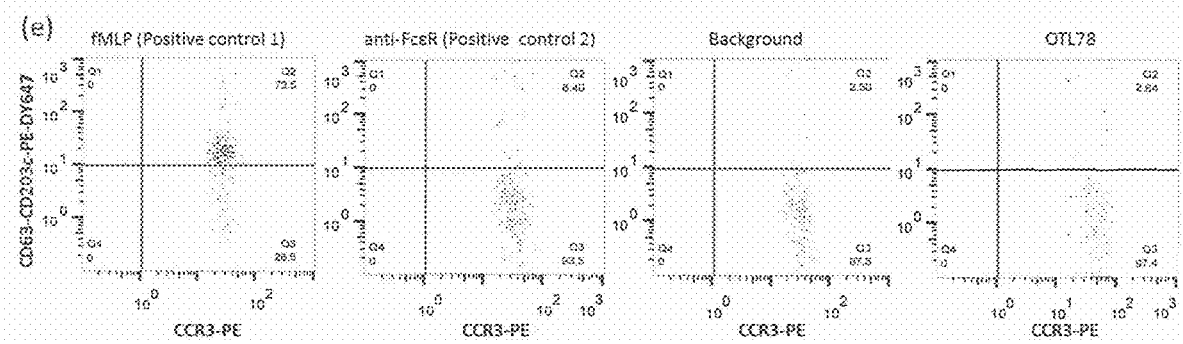
FIG. 47E: Evaluation of drug-related hypersensitivity in human blood samples using basophil activation assay by flow cytometry.

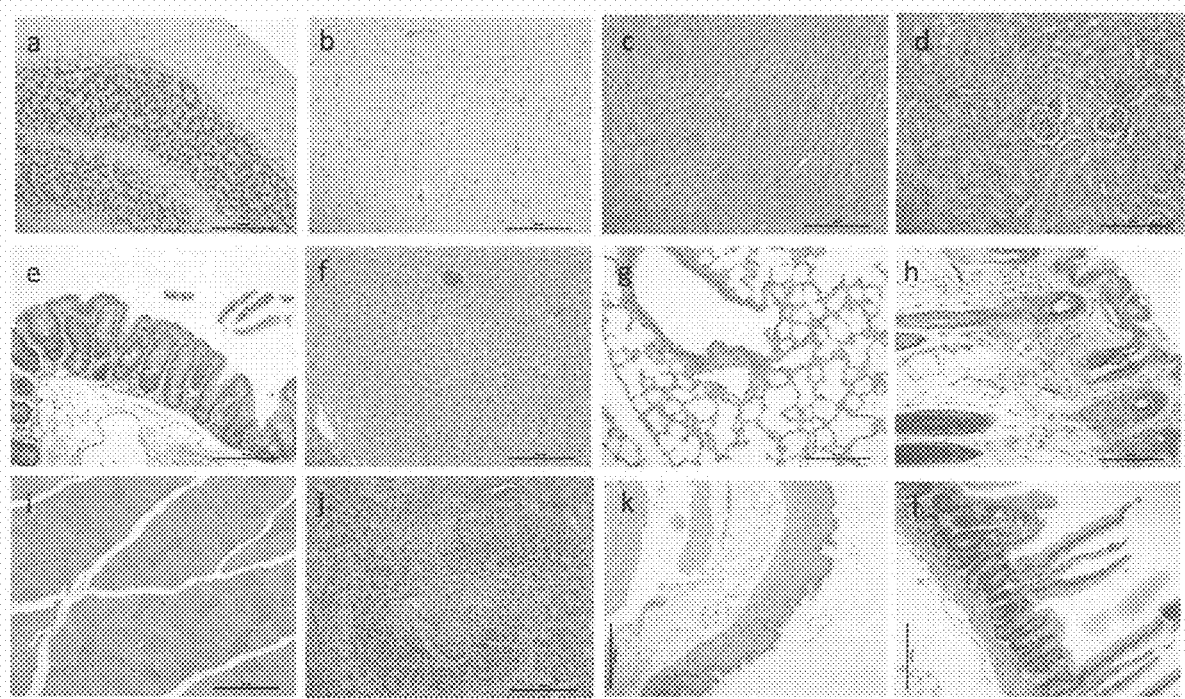
FIG. 48A-48L: Safety of OTL78. Histopathological analysis mice treated with OTL78 (10 μmol/mouse).

PSMA-TARGETED NIR DYES AND THEIR USES

RELATED APPLICATIONS

The present patent application is a continuation of U.S. patent application Ser. No. 16/126,140, which was filed Sep. 10, 2018, which is a continuation in part of U.S. patent application Ser. No. 15/624,680, which was filed Jun. 15, 2017, which is a continuation of U.S. Pat. No. 9,968,691, which was filed Jun. 14, 2017, which is a continuation of U.S. Pat. No. 9,801,956, which was filed on Nov. 12, 2015, which is a continuation of U.S. Pat. No. 9,808,538, which was filed on Nov. 10, 2015, and claimed the priority benefit of U.S. Provisional Patent Application Ser. No. 62/216,157, filed Sep. 9, 2015 the content of which is hereby incorporated by reference in its entirety into this disclosure.

FIELD OF THE INVENTION

The present disclosure relates to prostate specific membrane antigen (PSMA)-targeted near-infra red (NIR) dyes and methods for their therapeutic and diagnostic use. More specifically, this disclosure provides compounds and methods for diagnosing and surgical removal (image-guided surgery) of cells expressing prostate specific membrane antigen (PSMA), such as prostate cancer and related diseases. The disclosure further describes methods and compositions for making and using the compounds, methods incorporating the compounds, and kits incorporating the compounds.

BACKGROUND OF THE INVENTION

The prostate is one of the male reproductive organs found in the pelvis below the urinary bladder. It functions to produce and store seminal fluid which provides nutrients and fluids that are vital for the survival of sperm introduced into the vagina during reproduction. Like many other tissues, the prostate glands are also prone to develop either malignant (cancerous) or benign (non-cancerous) tumors. The American Cancer Society predicted that over 230,000 men would be diagnosed with prostate cancer and over 30,000 men would die from the disease in year 2005. In fact, prostate cancer is one of the most common male cancers in western societies, and is the second leading form of malignancy among American men. Current treatment methods for prostate cancer include hormonal therapy, radiation therapy, surgery, chemotherapy, photodynamic therapy, and combination therapy. The selection of a treatment generally varies depending on the stage of the cancer. However, many of these treatments affect the quality of life of the patient, especially those men who are diagnosed with prostate cancer over age 50. For example, the use of hormonal drugs is often accompanied by side effects such as osteoporosis and liver damage. Such side effects might be mitigated by the use of treatments that are more selective or specific to the tissue being responsible for the disease state, and avoid non-target tissues like the bones or the liver. As described herein, prostate specific membrane antigen (PSMA) represents a target for such selective or specific treatments.

Surgical removal of malignant disease constitutes one of the most common and effective therapeutic for primary treatment for cancer. Resection of all detectable malignant lesions results in no detectable return of the disease in approximately 50% of all cancer patients' and may extend life expectancy or reduce morbidity for patients in whom recurrence of the cancer is seen. Not surprisingly, surgical methods for achieving more quantitative cytoreduction are now receiving greater scrutiny.

Resection of all detectable malignant lesions results in no detectable return of the disease in approximately 50% of all cancer patients and may extend life expectancy or reduce morbidity for patients in whom recurrence of the cancer is seen. Given the importance of total resection of the malignant lesions, it is beneficial to ensure that the malignant lesions are accurately and completely identified. Identification of malignant tissue during surgery is currently accomplished by three methods. First, many tumor masses and nodules can be visually detected based on abnormal color, texture, and/or morphology. Thus, a tumor mass may exhibit variegated color, appear asymmetric with an irregular border, or protrude from the contours of the healthy organ. A malignant mass may also be recognized tactilely due to differences in plasticity, elasticity or solidity from adjacent healthy tissues. Finally, a few cancer foci can be located intraoperatively using fluorescent dyes that flow passively from the primary tumor into draining lymph nodes. In this latter methodology, fluorescent (sentinel) lymph nodes can be visually identified, resected and examined to determine whether cancer cells have metastasized to these lymph nodes.

PSMA is named largely due to its higher level of expression on prostate cancer cells; however, its particular function on prostate cancer cells remains unresolved. PSMA is over-expressed in the malignant prostate tissues when compared to other organs in the human body such as kidney, proximal small intestine, and salivary glands. PSMA also express in the neo-vasculature of most of the solid tumors. Though PSMA is expressed in brain, that expression is minimal, and most ligands of PSMA are polar and are not capable of penetrating the blood brain barrier. PSMA is a type II cell surface membrane-bound glycoprotein with ~110 kD molecular weight, including an intracellular segment (amino acids 1-18), a transmembrane domain (amino acids 19-43), and an extensive extracellular domain (amino acids 44-750). While the functions of the intracellular segment and the transmembrane domains are currently believed to be insignificant, the extracellular domain is involved in several distinct activities. PSMA plays a role in central nervous system, where it metabolizes N-acetyl-aspartyl glutamate (NAAG) into glutamic and N-acetyl aspartic acid. Accordingly, it is also sometimes referred to as an N-acetyl alpha linked acidic dipeptidase (NAALADase). PSMA is also sometimes referred to as a folate hydrolase I (FOLH I) or glutamate carboxypeptidase (GCP II) due to its role in the proximal small intestine where it removes γ-linked glutamate from poly-γ-glutamated folate and a-linked glutamate from peptides and small molecules.

PSMA also shares similarities with human transferrin receptor (TfR), because both PSMA and TfR are type II glycoproteins. More specifically, PSMA shows 54% and 60% homology to TfR1 and TfR2, respectively. However, though TfR exists only in dimeric form due to the formation of inter-strand sulfhydryl linkages, PSMA can exist in either dimeric or monomeric form.

Unlike many other membrane-bound proteins, PSMA undergoes rapid internalization into the cell in a similar fashion to cell surface bound receptors like vitamin receptors. PSMA is internalized through clathrin-coated pits and subsequently can either recycle to the cell surface or go to lysosomes. It has been suggested that the dimer and monomer form of PSMA are inter-convertible, though direct evidence of the interconversion is being debated. Even so, only the dimer of PSMA possesses enzymatic activity, and the monomer does not.

Though the role of the PSMA on the cell surface of the prostate cancer cells remains unknown, it has been recognized that PSMA represents a viable target for the selective and/or specific delivery of biologically active agents, including diagnostic agents, imaging agents, and therapeutic agents to such prostate cancer cells.

The radio-immunoconjugate of the anti-PSMA monoclonal antibody (mAb) 7E11, known as the PROSTASCINT® scan, is currently being used to diagnose prostate cancer metastasis and recurrence. However, this agent tends to produce images that are challenging to interpret (Lange, P. H. PROSTASCINT scan for staging prostate cancer. Urology 2001, 57, 402-406; Haseman, M. K.; et al. Cancer Biother Radiopharm 2000, 15, 131-140; Rosenthal, S. A.; et al. Tech Urol 2001, 7, 27-37). It binds to an intracellular epitope of PSMA in necrotic prostate cancer cells. More recently, monoclonal antibodies have been developed that bind to the extracellular domain of PSMA and have been radiolabeled and shown to accumulate in PSMA-positive prostate tumor models in animals. However, diagnosis and tumor detection using monoclonal antibodies has been limited by the low permeability due to their large size (150,000 Da) and slow clearance from non-targeted tissue. Moreover, the selective targeting of radio- or optical imaging agents either for imaging or therapeutic purposes is challenging due to their long half-life (~30 days). Especially, patients have to be stay in the hospital for longer days and spend more money on medical bills.

Two promising approaches to fluorescence-guided surgery are currently under intense investigation for use in the clinic. In one method, an activatable NIR fluorescent probe, which is minimally fluorescent in the steady state due to its proximity to an attached quencher, becomes highly fluorescent upon release of the quencher in malignant tissue. One of the most commonly used release mechanisms involves incorporation of a peptide sequence between the dye and the quencher that can be specifically cleaved by a tumor-enriched protease (i.e. cathepsins, caspases and matrix metalloproteinases). A major advantage of this strategy lies in the absence of fluorescence in tissues that lack the activating enzyme, allowing tissues along the excretion pathway (e.g. kidneys, bladder, liver) to remain nonfluorescent unless they fortuitously express the cleaving enzyme. Such tumor-activated NIR dyes can also generate substantial fluorescence in the tumor mass as long as the malignant lesion is enriched in the cleaving protease and the released dye is retained in the tumor. The major disadvantage of this methodology arises from the poor tumor specificities of many of the relevant hydrolases (most of which are also expressed in healthy tissues undergoing natural remodeling or experiencing inflammation). Moreover, the abundance of the desired proteases may vary among tumor masses, leading to slow or no activation of fluorescence in some malignant lesions and rapid development of fluorescence in others. Most of the time, these activatable peptides contain over 20 amino acids linked via peptide bonds that could lead to higher molecular weights, longer lead time (24*h*), cleavage of peptide bonds by peptidase in the circulation, high false positive results and very high manufacturing costs.

Other release mechanisms that activatable dyes use are pH difference between circulation and within the tumor or change in redox potential.

In the second, a fluorescent dye is conjugated to a tumor-specific targeting ligand that causes the attached dye to accumulate in cancers that over-express the ligand's receptor. While PSMA-targeted antibody-NIR dye conjugates have not yet been entered to clinical trials for fluorescence-guided surgery of cancer, several types of NIR dyes have been conjugated to monoclonal antibodies such as Her-2 with the intent of clinical development. Unfortunately, most of these dyes are tethered to antibodies non-specifically via amide, disulfide, or maleimide chemistry using either lysine or cysteine residues in the protein leading to heterogeneous chemical entities which result in variable affinities, efficacies, PK and safety profiles. Moreover, maleimide and disulfide bonds are known to be unstable in the circulation (half-life-≤2 h). On the other hand, lack of precise structural definition may limit progression of these conjugates into the clinical use due to challenges associated with the production process and safety. Moreover, production of these antibodies is highly expensive when compared to small molecular ligands. In contrast, small molecule ligand (Mr >0.5 Da), can penetrate solid tumors rapidly, and clears from PSMA-negative tissues in <2 h, shows high tumor-to-background ratios, easy of synthesis, and stable during the synthesis and storage.

Despite all the advantages those small molecular ligands have, development of NIR dye that maintains or enhances the properties of the small molecule is challenging. Recently, a variety of low molecular weight inhibitors of PSMA have been conjugated to visible light wave length dyes (400-600 nm) such as fluorescein and rhodamine and tested in in animal models [Kularatne S A, Wang K, Santhapuram H K, Low P S. Mol Pharm. 2009 May-June; 6(3):780-9] or in cells in culture [Liu T, Nedrow-Byers J R, Hopkins M R, Berkman C E. Bioorg Med Chem Lett. 2011 Dec. 1; 21(23)] or in human blood samples (He W, Kularatne S A, Kalli K R, Prendergast F G, Amato R J, Klee G G, Hartmann L C, Low P S. Int J Cancer. 2008 Oct. 15; 123(8):1968-73).

The visible light wave length dyes are not optimal for intra-operative image-guided surgery as these dyes are associated with a relatively high level of nonspecific background light due to the presence of collagen in the tissues. Hence the signal to noise ratio from these conventional compounds is low. Moreover, the absorption of visible light by biological chromophores, in particular hemoglobin, limits the penetration depth to a few millimeters. Thus tumors that are buried deeper than a few millimeters in the tissue typically remain undetected. Furthermore ionization equilibrium of fluorescein (pKa=6.4) leads to pH-dependent absorption and emission over the range of 5 to 9. Therefore, the fluorescence of fluorescein-based dyes is quenched at low pH (below pH 5).

Therefore, NIR dyes conjugated to small molecule ligands that target PSMA [(a) Humblet V, Lapidus R, Williams L R, Tsukamoto T, Rojas C, Majer P, Hin B, Ohnishi S, De Grand A M, Zaheer A, Renze J T, Nakayama A, Slusher B S, Frangioni J V. Mol Imaging. 2005 October-December; 4(4):448-62.; (b) Thomas M, Kularatne S A, Qi L, Kleindl P, Leamon C P, Hansen M J, Low P S.; (c) Chen Y, Dhara S, Banerjee S R, Byun Y, Pullambhatla M, Mease R C, Pomper M G. Biochem Biophys Res Commun. 2009 Dec. 18; 390(3):624-9; (d) Nakajima T, Mitsunaga M, Bander N H, Heston W D, Choyke P L, Kobayashi H. Bioconjug Chem. 2011 Aug. 17; 22(8):1700-5.; (e) Chen Y, Pullambhatla M, Banerjee S R, Byun Y, Stathis M, Rojas C, Slusher B S, Mease R C, Pomper M G. Bioconjug Chem. 2012 Dec. 19; 23(12):2377-85.; (f) Laydner H, Huang S S, Heston W D, Autorino R, Wang X, Harsch K M, Magi-Galluzzi C, Isac W, Khanna R, Hu B, Escobar P, Chalikonda S, Rao P K, Haber G P, Kaouk J H, Stein R J. Urology. 2013

February; 81(2):451-6.; (g) Kelderhouse L E, Chelvam V, Wayua C, Mahalingam S, Poh S, Kularatne S A, Low P S. Bioconjug Chem. 2013 Jun. 19; 24(6):1075-80.] have been tested as imaging agents in murine models of prostate cancer.

While these PSMA-targeted NIR dyes showed some labeling of prostate cancer cells in culture, they had very weak fluorescence in PSMA-expressing prostate tumor xenograft animal models. For example, the molecules described by, Humblet et al have shown very low tumor accumulation and florescence in the tumor xenograft models. It may be due the lack of proper spacer between the ligand the NIR dye may have hindered the binding of ligand to the binding pocket in PSMA. On the other hand, phosphorous based ligands have less affinity for PSMA when compared to DUPA. Moreover, phosphorous based ligands are difficult to synthesize, involve multiple steps, and will be expensive to manufacture.

PSMA—targeted NIR agent reported in Chen et al has taken over 20 h to reach the tumor and 72 h clear from the non-targeted tissues. Also notably, this PSMA-targeted NIR dye has very slowly skin clearance. While binding epitope of PSMA in transfected cells that they used can be artificial, it had very low uptake and low fluorescence in PSMA transfected prostate cancer cell tumor. Furthermore, there is substantial non-specific uptake of this molecule in all other tissues and there is accumulation and fluorescence in PSMA-negative cells indicating non-specific and non-targeted nature of NIR conjugate reported by Chen et al.

Chen et al and Laydner et al also have conjugated a small molecule ligand to IR800CW (a NIR dye). IR800CW is asymmetrical dye with activated carboxylic acid with n-hydroxysuccinimide ester (NHS). This is an extremely expensive molecule to synthesize and even more to purchase from commercially available resources (1 g is over $60,000). IR800CW also has the disadvantage that it is not stable during the synthesis due to two reasons:(a) hydrolysis of NHS ester, (b) hydrolysis of vinyl ether. The lack of stability of IR800CW conjugates during synthesis leads to formation of over 60% of undesired byproducts. This requires complex purification techniques indicating path for higher production cost, higher waiting period for clinical translation, and surgeons and patients will not have access to the drug.

Laydner et al conjugated a PSMA ligand to IR800CW via a long peptide space (6 amino acids) and bifunctional linker with NHS and maleimide. In addition to all the disadvantages caused by IR800CW, this PSMA-targeted IR800CW conjugate has a complicated synthesis scheme requiring synthesis in five stages (synthesis of ligand, conjugation of ligand to bifunctional linker via maleimide functional group, synthesis of peptide linker, conjugation of peptide linker to IR800CW, conjugation of peptide linker-IR800CW to ligand-bifunctional linker via amide bond) in multiple steps. Therefore, the manufacturing costs hamper the effective production of this molecule for clinical purposes. The synthesis scheme for these molecules is further complicated due to multiple chiral centers in the molecule. Peptide spacers, however, possess multiple chiral centers (stereoisomers) typically necessitating the need for production and assessment of all stereoisomers for FDA clearance. For example, a peptide spacer possessing only 3 amino acids (i.e. 3 chiral centers), would require toxicity profiles for 8 different drug products since these heterogeneous mixtures could result in different affinities, efficacies, PK and safety profiles.

The small molecule ligand used by Laydner et al is GluNHCONHCys-SH. The free thiol moiety in Cys tends to oxidize hence the molecule has to be handled under argon or nitrogen environment and generally leads to an unstable molecule. GluNHCONHCys-SH ligand is conjugated to bifunctional linker via maleimide reaction. It is well reported that reactions between thiols and maleimide are reversible and yield 50% of the diseased product. Moreover, maleimide bonds are not stable in circulation in the human body, hence use of maleimide bonds risk the release of the non-targeted dye leading to non-specific uptake thereof.

Kelderhouse et al conjugated DUPA-linker-Cys to Alexa flour 647 and Dylight 750 to DUPA via maleimide group. Again, these molecules have all the disadvantages associated with maleimide. Moreover, these low wave length NIR dyes, while being commercially available are very expensive. While molecules were tested on experimental metastatic mouse model, images were inconclusive.

Liu et al also reported PSMA-targeted NIR dye and some in vitro data but no animal data were reported. The lack of a proper spacer between the ligand and the NIR dye may have attributed to the lack of vivo data. Moreover, this dye has many drawbacks as other reported compounds. It is a phosphorous based ligand and asymmetrical dye. So, it has disadvantages described of both phosphorous based ligands as well as asymmetrical NIR dyes.

Nakajima et al reported anti-PSMA antibody (J591) conjugated to ICG. Unfortunately, this compound took 72 hours to clear from the other healthy tissues such as liver. In addition, the compound remained in circulation for 6 days indicating that it will remain the body for over 30 days in human body. Moreover, ICG was tethered to J591 non-specifically via amide using either lysine residues in the protein leading to heterogeneous chemical entities which result in variable affinities, efficacies, PK and safety profiles. Lack of precise structural definition may limit progression of these conjugates for clinical use due to challenges associated with the production process and safety.

Higher non-specificity and slow clearance from the skin of reported PSMA-targeted NIR dyes may be due to poor pharmacokinetic (PK) properties of these compounds.

Thus, there remains a need for a dye substance that can be used to specifically target PSMA expressing cancer cells or neo-vasculature of diseased tissue with increased stability, better PK properties, higher solubility, fast tumor accumulation, high fluorescence, fast skin clearance, and higher tumor-to-background ratios (TBR) for use in vivo tissue imaging and to use in image-guided surgery.

BRIEF SUMMARY OF THE INVENTION

This disclosure provides PSMA-targeted ligands linked to NIR dyes via different linkers to improve clinical properties (e.g. stability, PK properties, solubility, fast tumor accumulation, higher fluorescence, fast skin clearance, and higher tumor-to-background ratios) of the compounds. The disclosure provides uses of the compounds in image-guided surgery and methods for synthesizing the same. This disclosure further provides variation of the total charge of the Ligand-Linker-NIR dye conjugate by adding positive charges to the linker or reducing number of negative charges in the dye molecules. This disclosure also provides novel higher affinity ligands to improve in vivo affinity and PK properties of NIR conjugates. This disclosure also provides compounds for use in the targeted imaging of tumors expressing PSMA, including but not limited to prostate cancer, and methods of use, for example, in imaging and surgery involving PSMA positive tissues and tumors.

In certain aspects, compounds of the present invention have the form: B—X—Y—Z wherein B is a PSMA-targeted molecule;

X is a spacer;

Y is an amino acid spacer; and

Z is a NIR dye.

In some aspects, the PSMA-targeted molecule is chosen from the group consisting of a small molecule, a ligand, an inhibitor, an agonist or a derivative thereof. In some aspects, the PSMA-targeted compound is a ligand. In some aspects, the PSMA-targeted compound is DUPA. In other aspects, the PSMA-targeted compound is a small molecule that binds PSMA.

In some aspects, X is a hydrophobic spacer. In some aspects, X is selected from the group consisting of an eight aminooctonoic acid (EAOA), a chain of 7 atoms, a spacer 7 atoms in length, a chain from 7 to 24 atoms in length; a peptide comprising two aryl or aryl alkyl groups, each of which is optionally substituted, and where one aryl or aryl alkyl group is about 7 to about 11, or about 7 to about 14 atoms, and the other aryl or aryl alkyl group is about 10 to about 14, or about 10 to about 17 atoms. In another aspect, the spacer comprises about 1 to about 30 atoms, or about 2 to about 20 atoms. In some aspects, the spacer is 7 atoms in length. In some aspects, the spacer comprises EAOA. In some aspects, the spacer is variably charged. In some aspects, X has a positive charge. In other aspects, X has a negative charge.

In some aspects, Y is selected from the group consisting of: acidic (negatively charged) amino acids, such as aspartic acid and glutamic acid and derivative thereof; basic (positively charged) amino acids such as arginine, histidine, and lysine and derivative thereof; neutral polar amino acids, such as glycine, serine, threonine, cysteine, tyrosine, asparagine, and glutamine and derivative thereof; neutral nonpolar (hydrophobic) amino acids, such as alanine, leucine, isoleucine, valine, proline, phenylalanine, tryptophan, and methionine; and derivatives thereof. In some aspects, Y is an aromatic amino acid and derivative thereof. In some aspects, Y has a positive charge. In other aspects, Y has a negative charge.

In some aspects, Z is selected from the group consisting of near-infra red dyes, including but not limited to, LS288, IR800, SP054, S0121, KODAK, S2076, S0456 and/or the dyes selected from group consisting of:

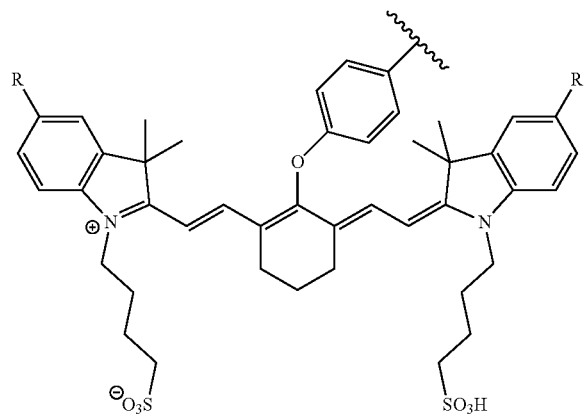

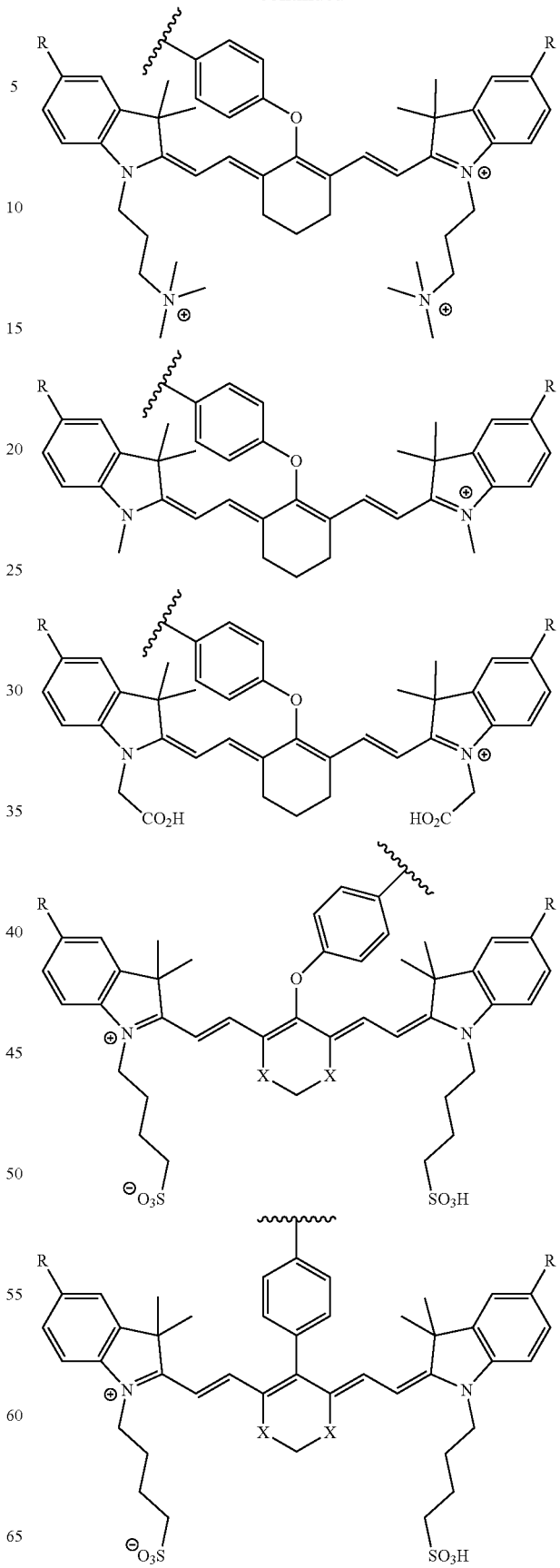

-continued

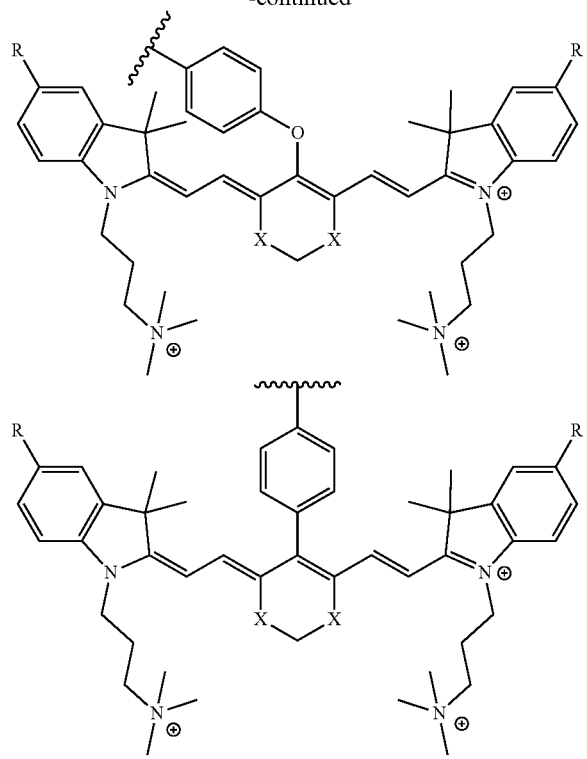

R = H or R = SO₃H; X = O, S, N

In certain aspects, the Z is variably charged. In some aspects, Z has a positive charge. In other aspects, Z has a negative charge.

In certain aspects, compounds of the present invention have the formula:

B—X—Y—Z wherein B is a PSMA-targeted compound; X is a spacer; Y is an amino acid spacer with a sulfur-containing side chain group; and Z is an NIR dye. In some aspects, the amino acid spacer with a sulfur-containing side group is cysteine. In some aspects, the amino acid spacer with a sulfur-containing side group is methionine. In some aspects, the amino acid spacer with a sulfur-containing side group is molecule containing thiophenol moiety.

In some aspects, compounds of the present invention have the form:

B—X—Y—Z wherein B is a PSMA-targeted compound; X is a spacer; Y is an amino acid spacer with a chalcogen-containing side chain group; and Z is an NIR dye.

In some aspects the present invention provides compounds of the form:

B—X—Y—Z

Wherein, B is a PSMA-targeted compound; X is a spacer; Y is an amino acid chosen from the group consisting of tyrosine, cysteine, lysine, or a derivative thereof; and Z is an NIR dye. In some aspects, Y comprises a tyrosine or tyrosine derivative. In some aspects, Y comprises a tyrosine and a carbon isotope is on the aromatic ring of tyrosine. In some aspects, Y comprises an amino acid with an aromatic ring with a hydrogen isotope.

In some aspects the invention includes the compound B—X—Y—Z wherein B comprises DUPA or a derivative thereof, X comprises an EAOA, Y comprises tyrosine, and Z comprises S0456.

The present invention also relates to a compound having the structural formula:

(I)

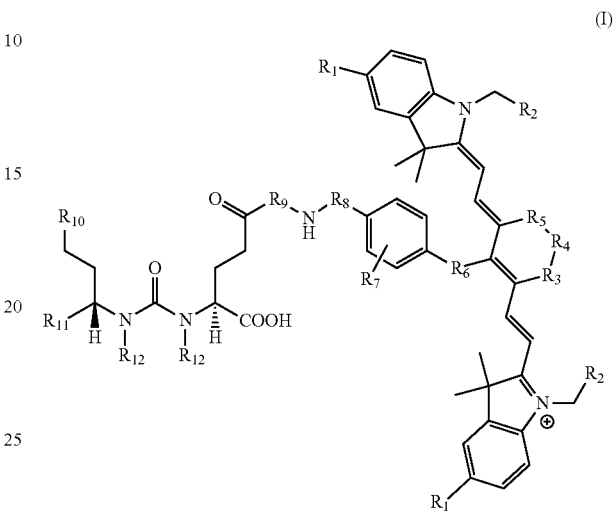

or a pharmaceutically acceptable salt thereof, or isotopes thereof, wherein:

$R_1$ represents a hydrogen or $SO_3H$;

$R_2$ represents a hydrogen, $CH_3$, $C_3H_6SO_3^-$, $C_3H_6SO_3H$ or $C_4H_8SO_3^-$, or $C_4H_8SO_3H$ or $C_3H_6N^+(CH_3)_3$;

$R_3$, and $R_5$ each represents a carbon, optionally one or more sharing bonds, $R_4$ represents a carbon with optionally one or more sharing bonds;

$R_6$ represents nitrogen, oxygen, or sulfur or no atom (direct C—C bond between aromatic ring and vinyl ring);

$R_7$ is optional and when present represents aromatic substitution group to enhance the spectral properties such as increase brightness and stability of the vinyl ether bridge;

$R_8$ is optional and when present represents linkers with aromatic amino acids such as Phe, Trp, His or derivative thereof, cationic amino acids such Arg, Lys, or derivative thereof, anionic amino acids such as Asp, Glu or derivative of them, unnatural amino acids of aromatic/cationic/anionic acids or derivative thereof;

$R_9$ is optional and when present represents a linear carbon chain, or polyethylene glycol linker, cationic linker, or derivative thereof;

$R_{10}$ represents a $CO_2H$, $PO_3H_2$, $SO_3H$, $CH_2SO_3H$, $CH_2CONHCH_2SO_3H$, $CH_2CONHCH_2CH_2SO_3H$;

$R_{11}$ represents $CO_2H$, $SO_3H$, $CH_2CONHCH_2SO_3H$, $CH_2CONHCH_2CH_2SO_3H$; and $R_{12}$ represents a hydrogen, a methyl group, a $CH_2$ and may optionally represent each a $CH_2$ sharing a bond.

In some aspects compounds of the present invention have an absorption and emission maxima between about 500 nm and about 900 nm. In some aspects compounds of the present invention have an absorption and emission maxima between about 600 nm and 800 nm.

In some aspects compounds of the present invention are made to fluoresce after distribution thereof in the tissue cells.

In some aspects compounds of the present invention are made to fluoresce by subjecting the compounds to excitation light of near infrared wavelength. In some aspects compounds of the present invention have a binding affinity to PSMA that is similar to the binding affinity of DUPA. In some aspects compounds of the present invention are highly selective for targeting to a tumor cell. In particularly preferred aspects, the compounds of the present invention are targeted to prostate cancer cells.

In certain aspects compounds of the present invention are administered to a subject in need thereof and in some aspects the administered composition comprises, in addition to the compound, a pharmaceutically acceptable carrier, excipient or diluent.

Some aspects of the present invention provide methods of optical imaging of PSMA-expressing biological tissue, said method comprising:
  (a) contacting the biological tissue with a composition comprising a PSMA-targeted NIR dye compound,
  (b) allowing time for the compound in the composition to distribute within the biological target;
  (c) illuminating the tissue with an excitation light of a wavelength absorbable by the compound; and
  (d) detecting the optical signal emitted by the compound.

In some aspects, these methods are used in detection of diseases associated with high PSMA expression. In some aspects, further comprising the step of constructing an image from the signal emitted in (d). In some aspects, the invention provides the aforementioned method wherein step (a) includes two or more fluorescent compounds whose signal properties are distinguishable are contacted with the tissue, and optionally the tissue is in a subject. In some aspects the present invention provides use of an endoscope, catheter, tomographic system, hand-held optical imaging system, surgical goggles, or intra-operative microscope for the illuminating and/or detecting method steps.

In some aspects, compositions and methods of the present invention are used to treat cancer. In some aspects, the cancer is selected from the group consisting of prostate cancer, lung cancer, bladder cancer, pancreatic cancer, liver cancer, kidney cancer, sarcoma, breast cancer, brain cancer, neuroendocrine carcinoma, colon cancer, testicular cancer or melanoma. In some aspects, PSMA-targeted NIR dye compounds of the present invention are used for imaging of PSMA-expressing cells. In certain aspects those cells are chosen from the group consisting of prostate cells, prostate cancer cells, bladder cancer cells, pancreatic cancer cells, liver cancer cells, lung cancer cells, kidney cancer cells, sarcoma cells, breast cancer cells, brain cancer cells, neuroendocrine carcinoma cells, colon cancer cells, testicular cancer cells or melanoma cells.

The present invention also provides methods of targeting a cell type in a biological sample comprising: (a) contacting the biological sample with a PSMA-targeted NIR dye compound for a time and under conditions that allow for binding of the compound to at least one cell of the target cell type; and (b) optically detecting the presence or absence of the compound of in the biological sample, wherein presence of the compound in detecting step (b) indicates that the target cell type is present in the biological sample. In some aspects the present invention provides methods for optical detection of PSMA-expressing cells comprising administering PSMA-targeting NIR dye compounds of the present invention and subjecting the compound to an excitation light source and detecting fluorescence from the compound. In some aspects, the excitation light source is near-infrared wavelength light. In some aspects the excitation light wavelength is within a range from about 600 to 1000 nanometers. In some aspects the excitation light wavelength is within a range from about 670 to 850 nanometers.

In certain aspects the present invention provides methods of performing image guided surgery on a subject comprising:
  a) administering a composition comprising a PSMA-targeting NIR dye compound under conditions and for a time sufficient for the compound to accumulate at a given surgical site;
  b) illuminating the compound to visualize the compound using infrared light; and
  c) performing surgical resection of the areas that fluoresce upon excitation by the infrared light.

In some aspects methods of the present invention the infrared light wavelength is within a range from about 600 to 1000 nanometers. In some aspects methods of the present invention use an infrared light wavelength is within a range from about 670 to 850 nanometers.

Some aspects of the present invention provide a method of diagnosing a disease in a subject comprising:
  a) administering to a subject in need of diagnosis an amount of a PSMA-targeted NIR dye compound for a time and under conditions that allow for binding of the compound to at least one PSMA-expressing cell;
  b) measuring the signal from the compound of present in the biological sample;
  c) comparing the signal measured in b) with at least one control data set, wherein the at least one control data set comprises signals from the compound of claim 1 contacted with a biological sample that does not comprise the target cell type; and
  d) providing a diagnosis of disease wherein the comparison in step c) indicates the presence of the disease.

Some aspects of the present invention provide a kit comprising a PSMA-targeting NIR dye compound. In some aspects, the kit is used for the imaging of PSMA-expressing cells. In some aspects the PSMA-expressing cells are tumor cells. In some aspects the PSMA-expressing cells are non-prostate cancer cells. In certain aspects the PSMA-expressing cells are prostate tumor cells. In certain aspects the PSMA-expressing cells are cancer cells. In certain aspects the PSMA-expressing area is neo-vasculature of tumor cells. In some aspects the present invention is used for detection of metastatic disease. In some aspects compounds of the present invention are used for improved surgical resection and/or improved prognosis. In some aspects methods of the present invention provide cleaner surgical margins than non-NIR conjugated fluorescing dyes. In some aspects PSMA-targeted NIR dye compounds of the present invention have an improved tumor-to-background ratio.

In other aspects compounds of the present invention are used to image, diagnose, or detect non-prostate cancer cells chosen from the group consisting of bladder cancer cells, pancreatic cancer cells, liver cancer cells, lung cancer cells, kidney cancer cells, sarcoma cells, breast cancer cells, brain cancer cells, neuroendocrine carcinoma cells, colon cancer cells, testicular cancer cells or melanoma cells. In other aspects, the cells being detected are more than 5 mm below the skin. In some aspects, the tissue being detected is more than 5 mm below the skin. In other aspects, the tumor being detected is more than 5 mm below the skin. In some aspects, the cells being detected are more than 6 mm, 7 mm, 8 mm, 9 mm, or 10 mm below the subject's skin. In some aspects of the present invention dye probes that are detectable outside of the visible light spectrum. In some aspects dye probes greater than the visible light spectrum are used. In some aspects compounds of the present invention comprise dye probes sensitive to wavelengths between 650 nm and 900 nm. In some aspects the PSMA-targeted NIR dye compounds of the present invention have maximum light absorption wavelengths in the near infrared region of between about 650 nm and 1000 nm, for example and in one aspect, at approximately 800 nm.

In still another aspect of the methods provided, the non-prostate cancer is bladder cancer, pancreatic cancer, liver cancer, lung cancer, kidney cancer, sarcoma, breast cancer, brain cancer, neuroendocrine carcinoma, colon cancer, testicular cancer or melanoma.

In a further aspect of the methods provided, the PSMA-expressing cancer cells are of a tumor. In still a further aspect of the methods provided, the PSMA-expressing cancer is a tumor. In some aspects, the volume of the tumor is at least 1000 mm$^3$. In some aspects, the volume of the tumor is less than 1000 mm$^3$. In some aspects, the volume of the tumor is less than 950 mm$^3$. In some aspects, the volume of the tumor is less than 900 mm$^3$. In some aspects, the volume of the tumor is less than 850 mm$^3$. In some aspects, the volume of the tumor is less than 800 mm$^3$. In some aspects, the volume of the tumor is less than 750 mm$^3$. In some aspects, the volume of the tumor is less than 700 mm$^3$. In some aspects, the volume of the tumor is less than 650 mm$^3$. In some aspects, the volume of the tumor is less than 600 mm$^3$. In some aspects, the volume of the tumor is less than 550 mm$^3$. In some aspects, the volume of the tumor is less than 500 mm$^3$. In some aspects, the volume of the tumor is less than 450 mm$^3$. In some aspects, the volume of the tumor is less than 400 mm$^3$. In some aspects, the volume of the tumor is less than 350 mm$^3$. In some aspects, the volume of the tumor is less than 300 mm$^3$. In some aspects, the volume of the tumor is less than 250 mm$^3$. In some aspects, the volume of the tumor is less than 200 mm$^3$. In some aspects, the volume of the tumor is less than 150 mm$^3$. In some aspects, the volume of the tumor is less than 100 mm$^3$. In one aspect, the volume of the tumor is at least 75 mm$^3$. In another aspect, the volume of the tumor is less than 75 mm$^3$. In another aspect, the volume of the tumor is less than 70 mm$^3$. In another aspect, the volume of the tumor is less than 65 mm$^3$. In another aspect, the volume of the tumor is less than 60 mm$^3$. In another aspect, the volume of the tumor is less than 55 mm$^3$. In one aspect, the volume of the tumor is at least 50 mm$^3$. In other aspects, the tumor is less than 50 mm$^3$. In another aspect, the volume of the tumor is less than 45 mm$^3$. In other aspects, the volume of the tumor is less than 40 mm$^3$. In another aspect, the volume of the tumor is less than 35 mm$^3$. In still another aspect, the volume of the tumor is less than 30 mm$^3$. In another aspect, the volume of the tumor is less than 25 mm$^3$. In still another aspect, the volume of the tumor is less than 20 mm$^3$. In another aspect, the volume of the tumor is less than 15 mm$^3$. In still another aspect, the volume of the tumor is less than 10 mm$^3$. In still another aspect, the volume of the tumor is less than 12 mm$^3$. In still another aspect, the volume of the tumor is less than 9 mm$^3$. In still another aspect, the volume of the tumor is less than 8 mm$^3$. In still another aspect, the volume of the tumor is less than 7 mm$^3$. In still another aspect, the volume of the tumor is less than 6 mm$^3$. In still another aspect, the volume of the tumor is less than 5 mm$^3$.

In one aspect, the tumor has a length of at least 5 mm prior to surgical recession using a PSMA-targeted NIR dye compound of the present invention. In one aspect, these methods detect tumors less than 5 mm. In other aspects the methods herein detect tumors less than 4 mm. In some aspects, the methods herein detect tumors less than 3 mm. In another aspect, the tumor has a length of at least 6 mm. In still another aspect, the tumor has a length of at least 7 mm. In yet another aspect, the tumor has a length of at least 8 mm. In another aspect, the tumor has a length of at least 9 mm. In still another aspect, the tumor has a length of at least 10 mm. In yet another aspect, the tumor has a length of at least 11 mm. In a further aspect, the tumor has a length of at least 12 mm. In still a further aspect, the tumor has a length of at least 13 mm. In still a further aspect, the tumor has a length of at least 14 mm. In another aspect, the tumor has a length of at least 15 mm. In yet another aspect, the tumor has a length of at least 16 mm. In still another aspect, the tumor has a length of at least 17 mm. In a further aspect, the tumor has a length of at least 18 mm. In yet a further aspect, the tumor has a length of at least 19 mm. In still a further aspect, the tumor has a length of at least 20 mm. In another aspect, the tumor has a length of at least 21 mm. In still another aspect, the tumor has a length of at least 22 mm. In yet another aspect, the tumor has a length of at least 23 mm. In a further aspect, the tumor has a length of at least 24 mm. In still a further aspect, the tumor has a length of at least 25 mm. In yet a further aspect, the tumor has a length of at least 30 mm.

In some aspects the present disclosure relates to prostate specific membrane antigen (PSMA) targeted compounds conjugated to near-infra red (NIR) dyes and methods for their therapeutic and diagnostic use. More specifically, this disclosure provides compounds and methods for diagnosing and treating diseases associated with cells expressing prostate specific membrane antigen (PSMA), such as prostate cancer, solid tumors, and related diseases. The disclosure further describes methods and compositions for making and using the compounds, methods incorporating the compounds, and kits incorporating the compounds. It has been discovered that a PSMA-targeted compound, such as DUPA conjugated to an NIR dye via a linker (L) may be useful in the imaging, diagnosis, and/or treatment of prostate cancer, and related diseases that involve pathogenic cell populations expressing or over-expressing PSMA. PSMA is a cell surface protein that is internalized in a process analogous to endocytosis observed with cell surface receptors, such as vitamin receptors. Accordingly, it has been discovered that certain conjugates that include a linker having a predetermined length, and/or a predetermined diameter, and/or preselected functional groups along its length may be used to treat, image, and/or diagnose such diseases.

In one illustrative aspect, the linker L may be a releasable or non-releasable linker. In one aspect, the linker L is at least about 7 atoms in length. In one variation, the linker L is at least about 10 atoms in length. In one variation, the linker L is at least about 14 atoms in length. In another variation, the linker L is between about 7 and about 22, between about 7 and about 20, or between about 7 and about 18 atoms in length. In another variation, the linker L is between about 14 and about 22, between about 15 and about 12, or between about 14 and about 20 atoms in length.

In an alternative aspect, the linker L is at least about 10 angstroms (Å) in length.

In one variation, the linker L is at least about 15 Å in length. In another variation, the linker L is at least about 20 Å in length. In another variation, the linker L is in the range from about 10 Å to about 30 Å in length.

In an alternative aspect, at least a portion of the length of the linker L is about 5 Å in diameter or less at the end connected to the binding ligand B. In one variation, at least a portion of the length of the linker L is about 4 Å or less, or about 3 Å or less in diameter at the end connected to the binding ligand B. It is appreciated that the illustrative aspects that include a diameter requirement of about 5 Å or less, about 4 Å or less, or about 3 Å or less may include that requirement for a predetermined length of the linker, thereby defining a cylindrical-like portion of the linker. Illustratively, in another variation, the linker includes a cylindrical portion at the end connected to the binding ligand that is at least about 7 Å in length and about 5 Å or less, about 4 Å or less, or about 3 Å or less in diameter.

In another aspect, the linker L includes one or more hydrophilic linkers capable of interacting with one or more residues of PSMA, including amino acids that have hydrophilic side chains, such as Ser, Thr, Cys, Arg, Orn, Lys, Asp, Glu, Gln and like residues. In another aspect, the linker L includes one or more hydrophobic linkers capable of interacting with one or more residues of PSMA, including amino acids that have hydrophobic side chains, such as Val, Leu, Phe, Tyr, Met, and like residues. It is to be understood that the foregoing aspects and aspects may be included in the linker L either alone or in combination with each other. For example, linkers L that are at least about 7 atoms in length and about 5 Å, about 4 Å or less, or about 3 Å or less in diameter or less are contemplated and described herein, and also include one or more hydrophilic linkers capable of interacting with one or more residues of PSMA, including Val, Leu, Phe, Tyr, Met, and like residues are contemplated and described herein.

In another aspect, one end of the linker is not branched and comprises a chain of carbon, oxygen, nitrogen, and sulfur atoms. In one aspect, the linear chain of carbon, oxygen, nitrogen, and sulfur atoms is at least 5 atoms in length. In one variation, the linear chain is at least 7 atoms, or at least 10 atoms in length. In another aspect, the chain of carbon, oxygen, nitrogen, and sulfur atoms are not substituted. In one variation, a portion of the chain of carbon, oxygen, nitrogen, and sulfur atoms is cyclized with a divalent fragment. For example, a linker (L) comprising the dipeptide Phe-Phe may include a piperazin-1,4-diyl structure by cyclizing two nitrogens with an ethylene fragment, or substituted variation thereof.

In another aspect, pharmaceutical compositions are described herein, where the pharmaceutical composition includes the conjugates described herein in amounts effective to treat diseases and disease states, diagnose diseases or disease states, and/or image tissues and/or cells that are associated with pathogenic populations of cells expressing or over expressing PSMA. Illustratively, the pharmaceutical compositions also include one or more carriers, diluents, and/or excipients.

In another aspect, methods for treating diseases and disease states, diagnosing diseases or disease states, and/or imaging tissues and/or cells that are associated with pathogenic populations of cells expressing or over expressing PSMA are described herein. Such methods include the step of administering the conjugates described herein, and/or pharmaceutical compositions containing the conjugates described herein, in amounts effective to treat diseases and disease states, diagnose diseases or disease states, and/or image tissues and/or cells that are associated with pathogenic populations of cells expressing or over expressing PSMA.

BRIEF DESCRIPTION OF THE DRAWINGS

FIG. 2A—Structure of PSMA-targeted DUPA-FITC (Fluorescein isothiocyanate) conjugate (14).

FIG. 2B—PSMA-targeted DUPA-FITC (Fluorescein isothiocyanate) conjugate (14) and its binding affinity ($K_D$) and specificity on PSMA-positive 22Rv1 human prostate cancer cells and on PSMA-negative A549 human alveolar basal epithelial cells in culture. DUPA-FITC dissolved in RPMI medium was added at the indicated concentrations to 22Rv1 or A549 cells in RPMI culture media and allowed to incubate for 1 h at 37° C. Media was then removed, washed with fresh media (3×), and replaced with PBS (phosphate buffered saline). Samples were analyzed using flow cytometry. Error bars represent SD (n=3). s are contained within the antigen recognition site.

FIG. 3—Relative binding affinities of DUPA-NIR conjugates 1-9 with respect to DUPA-FITC (14). PSMA-positive 22Rv1 human prostate cancer cells were incubated for 1 h at 37° C. in the presence of 100 nM DUPA-FITC with increasing concentrations of DUPA-NIR conjugates. Media was then removed, washed with fresh media (3×), and replaced with PBS. Cell bound fluorescence was assayed as using flow cytometry.

FIG. 4A—tumor-to-tissue fluorescence ratio from tissue biodistribution data of PSMA-targeted DUPA-NIR conjugates 1-3

FIG. 4B—Tumor-to-tissue fluorescence ratio from tissue biodistribution data of PSMA-targeted DUPA-NIR conjugates 4 and 5.

FIG. 4C—Tumor-to-tissue fluorescence ratio from tissue biodistribution data of PSMA-targeted DUPA-NIR conjugates 6 and 7.

FIG. 4D—Tumor-to-tissue fluorescence ratio from tissue biodistribution data of PSMA-targeted DUPA-NIR conjugates 8 and 9.

FIG. 4E—Biodistribution data of PSMA-targeted DUPA-NIR conjugates.

FIG. 5A—PSMA-targeted DUPA-Linker-NIR imaging agents with aromatic amino acid linkers between the ligand and the NIR dye.

FIG. 5B—Additional: PSMA-targeted DUPA-Linker-NIR imaging agents

FIG. 6—Relative binding affinities of DUPA-NIR conjugates with aromatic amino acids linkers with respect to DUPA-FITC (14). PSMA-positive 22Rv1 human prostate cancer cells were incubated for 1 h at 37° C. in the presence of 100 nM DUPA-FITC with increasing concentrations of DUPA-NIR conjugates. Media was then removed, washed with fresh media (3×), and replaced with PBS. Cell bound fluorescence was assayed as using flow cytometry.

FIGS. 7A and 7B—Tissue biodistribution analysis (7A) and tumor-to-tissue ratio (7B) of DUPA-NIR conjugates 15 and 23 using fluorescence imaging of mice bearing human prostate tumor xenografts (22Rv1 cells). Male nude mice with 22Rv1 tumor xenografts were injected with DUPA-NIR dye conjugates via tail vein. The mice were euthanized 2 h after administration of the DUPA-NIR dye conjugate, selected tissues were harvested, and tissues were imaged with IVIS imager (ex=745 nm, em=ICG, exposure time=1 s). After imaging, fluorescence within a Region of interest (ROI) was measured for each tissue using In Vivo imaging software and tumor-to-tissue fluorescence was then calculated.

FIG. 8A—Overlay of whole or half body fluorescence image over white light images after adjusting the threshold. 22Rv1 human prostate tumor xenograft bearing mouse was injected with 20 nmol of 14 and imaged with IVIS imager (ex=745 nm, em=ICG, exposure time=1 s) at 2, 4, and 6 hr.

FIG. 8B—Overlay of whole or half body fluorescence image over white light images after adjusting the threshold. 22Rv1 human prostate tumor xenograft bearing mouse was injected with 20 nmol of 14 and imaged with IVIS imager at 8, 24, and 48 hr.

FIG. 9A—Overlay of whole body or half body fluorescence image over white light images after adjusting the threshold. 22Rv1 human prostate tumor xenograft bearing mouse was injected with 20 nmol of 23 and imaged with IVIS imager (ex=745 nm, em=ICG, exposure time=1 s) at 2, 4, and 6 hr.

FIG. 9B—Overlay of whole body or half body fluorescence image over white light images after adjusting the threshold. 22Rv1 human prostate tumor xenograft bearing mouse was injected with 20 nmol of 23 and imaged with IVIS imager at 8 and 24 hr.

FIG. 10A—Overlay of whole body or half body fluorescence image over white light images after adjusting the threshold. 22Rv1 human prostate tumor xenograft bearing mouse was injected with 20 nmol of 25 and imaged with IVIS imager (ex=745 nm, em=ICG, exposure time=1 s) at 2, 4, and 6 hr.

FIG. 10B—Overlay of whole body or half body fluorescence image over white light images after adjusting the threshold. 22Rv1 human prostate tumor xenograft bearing mouse was injected with 20 nmol of 25 and imaged with IVIS imager (ex=745 nm, em=ICG, exposure time=1 s) at 8 and 24 hr.

FIG. 11A—Overlay of whole body or half body fluorescence image over white light images after adjusting the threshold. 22Rv1 human prostate tumor xenograft bearing mouse was injected with 6 nmol of 35 and imaged with IVIS imager (ex=745 nm, em=ICG, exposure time=1 s) at 2, 4, and 6 hr.

FIG. 11B—Overlay of whole body or half body fluorescence image over white light images after adjusting the threshold. 22Rv1 human prostate tumor xenograft bearing mouse was injected with 6 nmol of 35 and imaged with IVIS imager (ex=745 nm, em=ICG, exposure time=1 s) at 8 and 24 hr.

FIG. 12A—Overlay of whole body or half body fluorescence image over white light images after adjusting the threshold. 22Rv1 human prostate tumor xenograft bearing mouse was injected with 6 nmol of 36 and imaged with IVIS imager (ex=745 nm, em=ICG, exposure time=1 s) at 2, 4, and 6 hr.

FIG. 12B—Overlay of whole body or half body fluorescence image over white light images after adjusting the threshold. 22Rv1 human prostate tumor xenograft bearing mouse was injected with 6 nmol of 36 and imaged with IVIS imager (ex=745 nm, em=ICG, exposure time=1 s) at 8 and 24 hr.

FIG. 13—Structures of PSMA-targeted DUPA-Linker-NIR imaging agents with positive charge linkers between the ligand and the NIR dye FIG. 14—Relative binding affinities of DUPA-NIR conjugates with respect to DUPA-FITC (14). PSMA-positive 22Rv1 human prostate cancer cells were incubated for 1 h at 37° C. in the presence of 100 nM DUPA-FITC with increasing concentrations of DUPA-NIR conjugates. Media was then removed, washed with fresh media (3×), and replaced with PBS. Cell bound fluorescence was assayed as using flow cytometry.

FIG. 15—Tumor-to-tissue ratio of DUPA-NIR conjugates 39 and 41 using fluorescence imaging of mice bearing human prostate tumor xenografts (22 Rv1 cells). Male nude mice with 22Rv1 tumor xenografts were injected with DUPA-NIR dye conjugates via tail vein. The mice were euthanized 2 h after administration of the DUPA-NIR dye conjugate, selected tissues were harvested, and tissues were imaged with IVIS imager (ex=745 nm, em=ICG, exposure time=1 s). After imaging, fluorescence within a Region of interest (ROI) was measured for each tissue using In Vivo imaging software and tumor-to-tissue fluorescence was then calculated.

FIG. 16A—Overlay of whole body or half body fluorescence image over white light images after adjusting the threshold. 22Rv1 human prostate tumor xenograft bearing mouse was injected with 20 nmol of 39 and imaged with IVIS imager (ex=745 nm, em=ICG, exposure time=1 s) at 2, 4, and 6 hr.

FIG. 16B—Overlay of whole body or half body fluorescence image over white light images after adjusting the threshold. 22Rv1 human prostate tumor xenograft bearing mouse was injected with 20 nmol of 39 and imaged with IVIS imager (ex=745 nm, em=ICG, exposure time=1 s) at 8, 24, and 48 hr.

FIG. 17A—Overlay of whole body or half body fluorescence image over white light images after adjusting the threshold. 22Rv1 human prostate tumor xenograft bearing mouse was injected with 20 nmol of 40 and imaged with IVIS imager (ex=745 nm, em=ICG, exposure time=1 s) at 2, 4, and 6 hr.

FIG. 17B—Overlay of whole body or half body fluorescence image over white light images after adjusting the threshold. 22Rv1 human prostate tumor xenograft bearing mouse was injected with 20 nmol of 40 and imaged with IVIS imager (ex=745 nm, em=ICG, exposure time=1 s) at 8, 24, and 48 hr.

FIG. 18A—Overlay of whole body or half body fluorescence image over white light images after adjusting the threshold. 22Rv1 human prostate tumor xenograft bearing mouse was injected with 20 nmol of 41 and imaged with IVIS imager (ex=745 nm, em=ICG, exposure time=1 s) at 2, 4, and 6 hr.

FIG. 18B—Overlay of whole body or half body fluorescence image over white light images after adjusting the threshold. 22Rv1 human prostate tumor xenograft bearing mouse was injected with 20 nmol of 41 and imaged with IVIS imager (ex=745 nm, em=ICG, exposure time=1 s) at 8, 24, and 48 hr.

FIG. 19—Structures of PSMA-targeted DUPA-Linker-NIR imaging agents with negative charge linkers between the ligand and the NIR dye FIG. 20—Relative binding affinities of DUPA-NIR conjugates of 49 and 50 with respect to DUPA-FITC (14). PSMA-positive 22Rv1 human prostate cancer cells were incubated for 1 h at 37° C. in the presence of 100 nM DUPA-FITC with increasing concentrations of DUPA-NIR conjugates. Media was then removed, washed with fresh media (3×), and replaced with PBS. Cell bound fluorescence was assayed as using flow cytometry.

FIGS. 21A and 21B—Tissue biodistribution analysis (21A) and tumor-to-tissue ratio of DUPA-NIR (21B) conjugates 49 and 50 using fluorescence imaging of mice bearing human prostate tumor xenografts (22Rv1 cells). Male nude mice with 22Rv1 tumor xenografts were injected with DUPA-NIR dye conjugates via tail vein. The mice were euthanized 2 h after administration of the DUPA-NIR dye conjugate, selected tissues were harvested, and tissues were imaged with IVIS imager (ex=745 nm, em=ICG, exposure time=1 s). After imaging, fluorescence within a Region of interest (ROI) was measured for each tissue using In Vivo imaging software and tumor-to-tissue fluorescence was then calculated.

FIG. 22—Structures of PSMA-targeted DUPA-Linker-NIR imaging agents with variably charged NIR dye molecule.

FIG. 23—Relative binding affinities of DUPA-NIR conjugates with respect to DUPA-FITC (14). PSMA-positive 22Rv1 human prostate cancer cells were incubated for 1 h at 37° C. in the presence of 100 nM DUPA-FITC with increasing concentrations of DUPA-NIR conjugates. Media was then removed, washed with fresh media (3×), and replaced with PBS. Cell bound fluorescence was assayed as using flow cytometry.

FIG. 24A—Overlay of whole body or half body fluorescence image over white light images after adjusting the threshold. 22Rv1 human prostate tumor xenograft bearing mouse was injected with 20 nmol of 54 and imaged with IVIS imager (ex=745 nm, em=ICG, exposure time=1 s) at 1, 2, 4, and 6 hr.

FIG. 24B—Overlay of whole body or half body fluorescence image over white light images after adjusting the threshold. 22Rv1 human prostate tumor xenograft bearing mouse was injected with 20 nmol of 54 and imaged with IVIS imager (ex=745 nm, em=ICG, exposure time=1 s) at 8, 24, and 48 hr.

FIG. 25A—Overlay of whole body or half body fluorescence image over white light images after adjusting the threshold. 22Rv1 human prostate tumor xenograft bearing mouse was injected with 20 nmol of 55 and imaged with IVIS imager (ex=745 nm, em=ICG, exposure time=1 s) at 1, 2, and 4 hr.

FIG. 25B—Overlay of whole body or half body fluorescence image over white light images after adjusting the threshold. 22Rv1 human prostate tumor xenograft bearing mouse was injected with 20 nmol of 55 and imaged with IVIS imager (ex=745 nm, em=ICG, exposure time=1 s) at 6, 8, and 24 hr.

FIG. 26A—Overlay of whole body or half body fluorescence image over white light images after adjusting the threshold. 22Rv1 human prostate tumor xenograft bearing mouse was injected with 20 nmol of 56 and imaged with IVIS imager (ex=745 nm, em=ICG, exposure time=1 s) at 1, 2, and 4 hr.

FIG. 26B—Overlay of whole body or half body fluorescence image over white light images after adjusting the threshold. 22Rv1 human prostate tumor xenograft bearing mouse was injected with 20 nmol of 56 and imaged with IVIS imager (ex=745 nm, em=ICG, exposure time=1 s) at 6, 8, and 24 hr.

FIG. 27A—Overlay of whole body or half body fluorescence image over white light images after adjusting the threshold. 22Rv1 human prostate tumor xenograft bearing mouse was injected with 20 nmol of 57 and imaged with IVIS imager (ex=745 nm, em=ICG, exposure time=1 s) at 1, 2, and 4 hr.

FIG. 27B—Overlay of whole body or half body fluorescence image over white light images after adjusting the threshold. 22Rv1 human prostate tumor xenograft bearing mouse was injected with 20 nmol of 57 and imaged with IVIS imager (ex=745 nm, em=ICG, exposure time=1 s) at 6, 8, and 24 hr.

FIG. 28A—Overlay of whole body or half body fluorescence image over white light images after adjusting the threshold. 22Rv1 human prostate tumor xenograft bearing mouse was injected with 20 nmol of 58 and imaged with IVIS imager (ex=745 nm, em=ICG, exposure time=1 s) at 1, 2, and 4 hr.

FIG. 28B—Overlay of whole body or half body fluorescence image over white light images after adjusting the threshold. 22Rv1 human prostate tumor xenograft bearing mouse was injected with 20 nmol of 58 and imaged with IVIS imager (ex=745 nm, em=ICG, exposure time=1 s) at 6, 8, and 24 hr.

FIG. 29A—Overlay of whole body or half body fluorescence image over white light images after adjusting the threshold. 22Rv1 human prostate tumor xenograft bearing mouse was injected with 20 nmol of 60 and imaged with IVIS imager (ex=745 nm, em=ICG, exposure time=1 s) at 1, 2, and 4 hr.

FIG. 29B—Overlay of whole body or half body fluorescence image over white light images after adjusting the threshold. 22Rv1 human prostate tumor xenograft bearing mouse was injected with 20 nmol of 60 and imaged with IVIS imager (ex=745 nm, em=ICG, exposure time=1 s) at 6, 8, and 24 hr.

FIG. 30—Structures of PSMA-targeted DUPA-Linker-NIR imaging agents with miscellaneous linkers and NIR dyes.

FIG. 31—Relative binding affinities of DUPA-NIR conjugates with respect to DUPA-FITC (14). PSMA-positive 22Rv1 human prostate cancer cells were incubated for 1 h at 37° C. in the presence of 100 nM DUPA-FITC with increasing concentrations of DUPA-NIR conjugates. Media was then removed, washed with fresh media (3×), and replaced with PBS. Cell bound fluorescence was assayed as using flow cytometry.

FIG. 32A—Overlay of whole body or half body fluorescence image over white light images after adjusting the threshold. 22Rv1 human prostate tumor xenograft bearing mouse was injected with 20 nmol of 63 and imaged with IVIS imager (ex=745 nm, em=ICG, exposure time=1 s) at 2, 4, and 6 hr.

FIG. 32B—Overlay of whole body or half body fluorescence image over white light images after adjusting the threshold. 22Rv1 human prostate tumor xenograft bearing mouse was injected with 20 nmol of 63 and imaged with IVIS imager (ex=745 nm, em=ICG, exposure time=1 s) at 8 and 24 hr.

FIG. 33A—Overlay of whole body or half body fluorescence image over white light images after adjusting the threshold. 22Rv1 human prostate tumor xenograft bearing mouse was injected with 6 nmol of 63 and imaged with IVIS imager (ex=745 nm, em=ICG, exposure time=1 s) at 2, 4, and 6 hr FIG. 33B—Overlay of whole body or half body fluorescence image over white light images after adjusting the threshold. 22Rv1 human prostate tumor xenograft bearing mouse was injected with 6 nmol of 63 and imaged with IVIS imager (ex=745 nm, em=ICG, exposure time=1 s) at 8 and 24 hr.

FIG. 34A—Overlay of whole body or half body fluorescence image over white light images after adjusting the threshold. 22Rv1 human prostate tumor xenograft bearing mouse was injected with 20 nmol of 64 and imaged with IVIS imager (ex=745 nm, em=ICG, exposure time=1 s) at 2, 4, and 6 hr FIG. 34B—Overlay of whole body or half body fluorescence image over white light images after adjusting the threshold. 22Rv1 human prostate tumor xenograft bearing mouse was injected with 6 nmol of 63 and imaged with IVIS imager (ex=745 nm, em=ICG, exposure time=1 s) at 8 and 24 hr.

FIG. 35—Structures of PSMA-targeted NIR imaging agents with different ligands.

FIG. 36—Relative binding affinities of PSMA-targeted NIR conjugates with respect to DUPA-FITC (14). PSMA-positive 22Rv1 human prostate cancer cells were incubated for 1 h at 37° C. in the presence of 100 nM DUPA-FITC with increasing concentrations of DUPA-NIR conjugates. Media was then removed, washed with fresh media (3×), and replaced with PBS. Cell bound fluorescence was assayed as using flow cytometry.

FIG. 37A—Overlay of whole body or half body fluorescence image over white light images after adjusting the threshold. 22Rv1 human prostate tumor xenograft bearing mouse was injected with 6 nmol of 14 and imaged with IVIS imager (ex=745 nm, em=ICG, exposure time=1 s) at 2, 4, and 6 hr FIG. 37B—Overlay of whole body or half body fluorescence image over white light images after adjusting the threshold. 22Rv1 human prostate tumor xenograft bearing mouse was injected with 6 nmol of 14 and imaged with IVIS imager (ex=745 nm, em=ICG, exposure time=1 s) at 8 and 24 hrs.

FIG. 38A—Chemical structures of S0456 and DUPA-FITC.

FIG. 38B—Excitation (Ex) & emission (Em) spectra of OTL78 (1 µM) and S0456 (1 µM) in 1 mL of PBS obtained using fluorometer.

FIG. 38C—Evaluation of PSMA expression levels in LNCaP, 22Rv1, PC3, and A549 using flow cytometry.

FIG. 38D—Dose dependent binding of DUPA-FITC.

FIG. 38E—competitive binding of OTL78 with respect to DUPA-FITC to 22Rv1 and PC3 cells in culture. Error bars represent SD (n=2).

FIG. 38F—Binding and internalization of OTL78 to (i) 22Rv1 and (ii) LNCaP at 4° C. by epifluorescence microscopy. Nuclear is stained with DAPI (a blue dye).

FIG. 39A—In vitro binding and specificity of OTL78. (a) Excitation (Ex) & emission (Em) spectra of OTL78.

FIG. 39B—Dose dependent binding of OTL78 to prostate-specific membrane antigen (PSMA)+22Rv1 cells and PSMA-negative PC3 cells in culture (n=2).

FIG. 39C—Binding and internalization of OTL78 to (i) 22Rv1, (ii) LNCaP, or (iii) PC3 (fluorescence image) and (iv) PC3 (DIC image) cells by epifluorescence (epi) microscopy. Note: OTL78 is highly concentrated in the acidic endosomes of 22Rv1 and LNCaP cells. DIC=Deferential Interference Contrast Images.

FIG. 40A—Tissue biodistribution analysis of OTL78: IVIS images showing overlay of fluorescence images over white light images of selected tissues.

FIG. 40B—Tissue biodistribution analysis of OTL78: tumor-to-tissue ratio from tissue biodistribution data from mice bearing 22Rv1 tumor xenografts after administering increasing doses of OTL78. Error bars represents SD (n=5).

FIG. 41A-41C: In vivo efficacy and specificity of OTL78 in subcutaneous tumor models using IVIS image system. Representative fluorescence images from IVIS imager showing mice bearing (A) 22Rv1 (n=5 mice/group), (B) PC3 (n=5 mice/group), and (C) A549 (n=3 mice/group) tumors 2 h after administering 10 nmol of OTL78.

FIG. 41D-41F: Tissue biodistribution analysis of the same mice with (D) 22Rv1, (E) PC3, and (F) A549 tumors at 2 h post-injection. Note: * Representative fluorescence images of PC3 and A549 after lowering threshold to ~1×10$^8$ [(p/sec/cm$^3$/sr)/(µW/cm$^2$)].

FIGS. 42A-42C—In vivo efficacy and specificity of OTL78 in orthotopic and subcutaneous tumor models using AMI image system. Representative fluorescence images from AMI image system showing mice bearing (A) 22Rv1 subcutaneous (n=3 mice/group), (B) LNCaP subcutaneous (n=3 mice/group), and (C) 22Rv1 orthotopic (n=5 mice/group) tumors 2 h after administering 10 nmol of OTL78.

FIGS. 42D-42G: Tissue biodistribution analysis of the same mice with (D) 22Rv1, (E) LNCaP, (F) 22Rv1, (G) 22Rv1 secondary tumors at 2 h post-injection. Note: *Primary tumor is in the prostate in Fig (F) and K=Kidneys. Note: PT=Primary Tumor, SC=Secondary Tumor, & SV=Seminal Vesicle.

FIGS. 43A-43B—In vivo efficacy of OTL78. Tissue biodistribution analysis using fluorescence imaging of the mice with (a) PC3 and (b) A549 at 2 h post-injection.

FIGS. 43C-43D—Representative fluorescence images from AMI imager showing mice bearing (c) 22Rv1 orthotopic (n=5 mice/group) and (d) tissue biodistribution analysis using fluorescence imaging of the same mice 2 h after administering 10 nmol of OTL78.

FIG. 44A—Quantitation of TBR of OTL78 using region of interest (ROI) and ImageJ analysis. TBR calculated using ROI values obtained from IVIS or AMI imager after tissue biodistribution studies of 22Rv1 subcutaneous or orthotopic tumors bearing mice injected with 10 nmol of OTL78. Note: Since the primary tumor is in the prostate, tumor-to-prostate ratio is equal to one in orthotopic model. Error bars represents SD (n=5 mice/group).

FIG. 44B—Representative fluorescence image (in gray scale) of mouse bearing 22Rv1 subcutaneous tumor after injecting 10 nmol of OTL78.

FIGS. 44C-44D: The plot of gray value versus distance (c) across the line and (d) within the box are shown in the FIG. 41B.

FIG. 45A—Comparison of surgeries performed under conventional and fluorescence-guided techniques. Representative fluorescence images of tumor beds of mice before and after surgically removing 22Rv1 tumor xenografts by conventional (n=5 mice/group) or fluorescence-guided (n=5 mice/group) techniques. Mice were administered with OTL78 (10 nmol/mouse) 2 h before imaging with AMI image system.

FIG. 45B—Representative H&E staining of 22Rv1 tumor (left column) after surgical resection, the residual fluorescent tissues after conventional surgery showing positive tumor margins (middle column), and tumor bed tissues after FGS showing negative tumor margins.

FIG. 45C—Survival curve of the same mice (n=5 mice/group) over 30 days. Growth of tumors was monitored during the study and any animal with tumor volume ≥1000 mm3 were euthanized.

FIG. 46—Comparison of surgeries performed under conventional and fluorescence-guided techniques. Representative fluorescence images of mice before and after surgically removing 22Rv1 tumor xenografts by conventional (n=5 mice/group) or fluorescence-guided (n=5 mice/group) techniques till day 21. Mice were administered with OTL78 (10 nmol/mouse) 2 h before imaging using AMI image system. The cohort underwent on fluorescence-guided surgery were monitored over a 30 days.

FIGS. 47A-47B—Assessment of body weight change after administering 6 µmol (i.e. 600× of normal dose) of OTL78 to healthy balb/c mice and (b) representative H&E staining of kidney and prostate of mouse injected with 6 µmol of OTL78 at 14 days post-injection (n=5 mice/group).

FIG. 47C—UV spectra of OTL78 showing no aggregates whereas the positive control (OTL38) demonstrating >50% higher aggregates at 75 µM concentration in saline.

FIG. 47E: Evaluation of drug—related hypersensitivity in human blood samples using basophil activation assay by flow cytometry. fMLP: N-formylmethionyl-leucyl-phenylalanine is a non-specific cell activator, anti-FcεR: a high affinity monoclonal antibody binding to IgE, CCR3 (CD193): specific biomarker on basophils, CD63 and CD203c: receptors that upregulated upon activation of basophils, PE: phycoerythrin, background: negative control, and CD63-CD203c-PE-DY647+/CCR3-PE+(Q2) cell population considered as the positive response for basophil activation.

FIGS. 48A-48L—Safety of OTL78. Histopathological analysis mice treated with OTL78 (10 mol/mouse). A: Cerebellum, B: Cerebrum, C: Heart, D: Kidney, E: Large intestine, F: Liver, G: Lung, H: Skin, I: Muscle, J: Spleen, K: Stomach, L: Small intestine (n=5 mice/group).

DEFINITIONS

Figure 1:
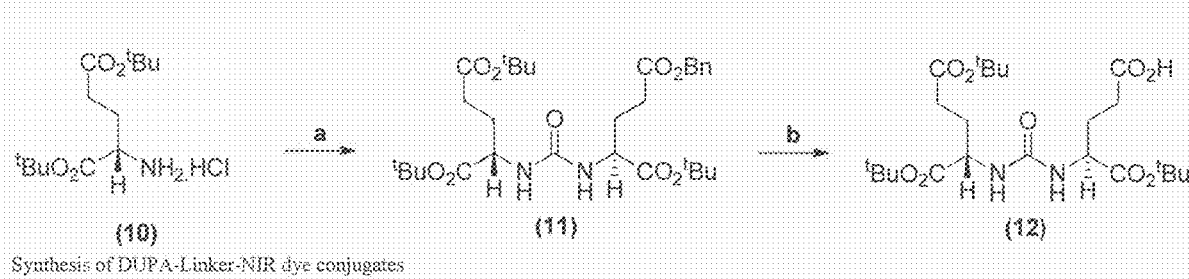
FIG. 1 shows the synthesis of DUPA-Linker-NIR dye conjugates.

It is to be understood that this invention is not limited to the particular methodology, protocols, cell lines, constructs, and reagents described herein and as such may vary. It is also to be understood that the terminology used herein is for the purpose of describing particular aspects only, and is not intended to limit the scope of the present invention, which will be limited only by the appended claims.

As used herein and in the appended claims, the singular forms "a," "an," and "the" include plural reference unless the context clearly indicates otherwise. Thus, for example, reference to a "prostate specific membrane antigen ligand" "PSMA ligand" is a reference to one or more such ligands and includes equivalents thereof known to those skilled in the art, and so forth.

Unless defined otherwise, all technical and scientific terms used herein have the same meaning as commonly understood to one of ordinary skill in the art to which this invention belongs. Although any methods, devices, and materials similar or equivalent to those described herein can be used in the practice or testing of the invention, the preferred methods, devices and materials are now described.

All publications and patents mentioned herein are incorporated herein by reference for the purpose of describing and disclosing, for example, the constructs and methodologies that are described in the publications, which might be used in connection with the presently described invention. The publications discussed herein are provided solely for their disclosure prior to the filing date of the present application. Nothing herein is to be construed as an admission that the inventors are not entitled to antedate such disclosure by virtue of prior invention or for any other reason.

With respect to PSMA-targeted NIR conjugates of the present invention, the term "antigenically specific" or "specifically binds" refers to PSMA-targeting compounds that bind to one or more epitopes of PSMA, but which do not substantially recognize and bind other molecules in a sample containing a mixed population of antigens.

The term "epitope" as used herein refers to a site on PSMA that is recognized by DUPA. An epitope may be a linear or conformationally formed sequence or the shape of amino acids.

As used herein, "PSMA-targeting compound" or "PSMA-targeted compound" shall include those small molecules, ligands, polypeptides and proteins that have at least the biological activity of specific binding to PSMA or an epitope of PSMA. These compounds include ligands, receptors, peptides, or any amino acid sequence that binds to PSMA or to at least one PSMA epitope.

Compounds of the present invention comprise a PSMA-targeting compound, they may bind a portion of PSMA itself, or they may bind a cell surface protein or receptor that is associated with PSMA.

The terms "functional group", "active moiety", "activating group", "leaving group", "reactive site", "chemically reactive group" and "chemically reactive moiety" are used in the art and herein to refer to distinct, definable portions or units of a molecule. The terms are somewhat synonymous in the chemical arts and are used herein to indicate the portions of molecules that perform some function or activity and are reactive with other molecules.

The term "amino acid" refers to naturally occurring and non-naturally occurring amino acids, as well as amino acid analogs and amino acid mimetics that function in a manner similar to the naturally occurring amino acids. Naturally encoded amino acids are the 20 common amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine) and pyrolysine and selenocysteine. Amino acid analogs refers to compounds that have the same basic chemical structure as a naturally occurring amino acid, i.e., an a carbon that is bound to a hydrogen, a carboxyl group, an amino group, and an R group, such as, homoserine, norleucine, methionine sulfoxide, methionine methyl sulfonium. Such analogs have modified R groups (such as, norleucine) or modified peptide backbones, but retain the same basic chemical structure as a naturally occurring amino acid.

Amino acids may be referred to herein by either their commonly known three letter symbols or by the one-letter symbols recommended by the IUPAC-IUB Biochemical Nomenclature Commission.

The present invention addresses, among other things, problems associated with the early diagnosis and surgical treatment of PSMA-expressing cells involved in disease and/or cancer, and in particular PSMA-targeted dye conjugates with improved imaging, diagnostic, biological properties including, as non-limiting examples, higher specificity, decreased background signal and increased tumor fluorescence.

DETAILED DESCRIPTION

Surgery cures 50% of patients with solid tumors in the US, while chemo- and radiotherapy cure less than 5% of all cancer patients. Over 700,000 patients undergo cancer surgery every year in the US and 40% of surgical patients have a recurrence of locoregional disease within 5 years. Despite major advances in the field of oncology there remains a need for early detection, methods to overcome hurdles to complete surgical resection of the primary tumor with negative margins, and removal of metastatic cancer cells and identification of satellite disease. Achieving these three goals not only improves disease clearance but also guides decisions regarding postoperative chemotherapy and radiation. While non-targeted fluorescent dyes have been shown to passively accumulate in some tumors, the resulting tumor-to-background ratios are often poor and the boundaries between malignant and healthy tissues can be difficult to define. Although ligand targeted fluorescence dyes (e.g., EC17: Folate-EDA-FITC) have been used for imaging a tissue, those dyes have been ineffective as they would not penetrate deep tissue and hence only identified the specific cells on the surface of a tissue rather than deeper within the tissue sample. In addition, fluorescein-based dyes have the disadvantages that of low shelf-life stability. Thiourea bridge formed by Fluorescence isothiocynate (FITC) compounds easily decomposes making unstable compound. In addition, as EC17 uses fluorescein which has the drawback of a relatively high level of nonspecific background noise from collagen in the tissues surrounding the imaging site. Moreover, the absorption of visible light by biological chromophores, in particular hemoglobin, further limits the usefulness of dyes that incorporate fluorescein. Therefore, conventional dyes cannot readily detect tumors that may be buried deeper than a few millimeters in the tissue. Furthermore, fluorescence from fluorescein is quenched at low pH (below pH 5).

In order for a dye material to be useful in detecting and guiding surgery or providing detection of early, metastatic, and other tissue imaging it is important to overcome these drawbacks. The present invention provides PSMA-targeted conjugates of near infrared dyes that are stable, fluoresce in the infrared range, penetrate deep within targeted tissue to produce a specific and bright identification of areas of tissue that express PSMA, fast clearance from tissues that do not express PSMA to obtain high tumor-to-background ratio, and fast skin clearance. More specifically, the PSMA-targeted conjugates are linked to the near infrared dyes through a linker consisting of one or more atomic spacers, amino acids, amino acid derivatives. Even more specifically, it has been found that where the atomic spacer is hydrophobic 7-atom spacer with neutral or charged atoms and amino acid spacer is aromatic amino acid or a derivative of aromatic amino acid, or negative or positive charge amino acid and tyrosine or a derivative of tyrosine. Charge of the linker can be varied to obtain fast skin clearance and fast tumor accumulation to obtain higher tumor-to-background ratio. Moreover, the fluorescence intensity of the NIR dye is maintained or even enhanced by having the aromatic amino acid or tyrosine or derivative of tyrosine and charge of the NIR dye can be varied to accomplish fast skin clearance.

This disclosure provides PSMA-targeted ligands linked to NIR dyes and methods for synthesizing the same. This disclosure also provides compounds for use in the targeted imaging of tumors expressing PSMA, including but not limited to prostate cancer, and methods of use, for example, in imaging and surgery involving PSMA positive tissues and tumors.

In certain aspects, compounds of the present invention have the form: B—X—Y—Z
wherein B is a PSMA-targeted compound;
X is a spacer;
Y is an amino acid spacer; and
Z is an NIR dye.

In some aspects, the PSMA-targeted compound is chosen from the group consisting of a small molecule, a ligand, or a derivative thereof. In some aspects, the PSMA-targeted compound is a ligand. In some aspects, the PSMA-targeted compound is DUPA. In other aspects, the PSMA-targeted compound is a small molecule that binds PSMA.

In some aspects, X is a hydrophobic spacer. In some embodiments, X is selected from the group consisting of an eight aminooctonoic acid (EAOA), a chain of 7 atoms, polyethylene glycol spacer, a spacer 7 atoms in length, cationic spacer, chain of 7 atoms, a chain from 7 to 24 atoms in length; a peptide comprising two aryl or aryl alkyl groups, each of which is optionally substituted, and where one aryl or aryl alkyl group is about 7 to about 11, or about 7 to about 14 atoms, and the other aryl or aryl alkyl group is about 10 to about 14, or about 10 to about 17 atoms. In another aspect, the spacer comprises about 1 to about 30 atoms, or about 2 to about 20 atoms. In some aspects, the spacer is 7 atoms in length. In some aspects, the spacer comprises EAOA. In some aspects, the spacer is variably charged. In some aspects, X has a positive charge. In other aspects, X has a negative charge.

In some aspects, Y is selected from the group consisting of: acidic (negatively charged) amino acids, such as aspartic acid and glutamic acid; basic (positively charged) amino acids such as arginine, histidine, and lysine; neutral polar amino acids, such as glycine, serine, threonine, cysteine, tyrosine, asparagine, and glutamine; neutral nonpolar (hydrophobic) amino acids, such as alanine, leucine, isoleucine, valine, proline, phenylalanine, tryptophan, and methionine; and derivatives thereof. In some aspects, Y is an aromatic amino acid. In some aspects, Y has a positive charge. In other aspects, Y has a negative charge.

In some aspects, Z is selected from the group consisting of near-infra red dyes, including but not limited to, LS288, IR800, SP054, S0121, KODAK, S2076 S0456 and/or the dyes selected from group consisting of.

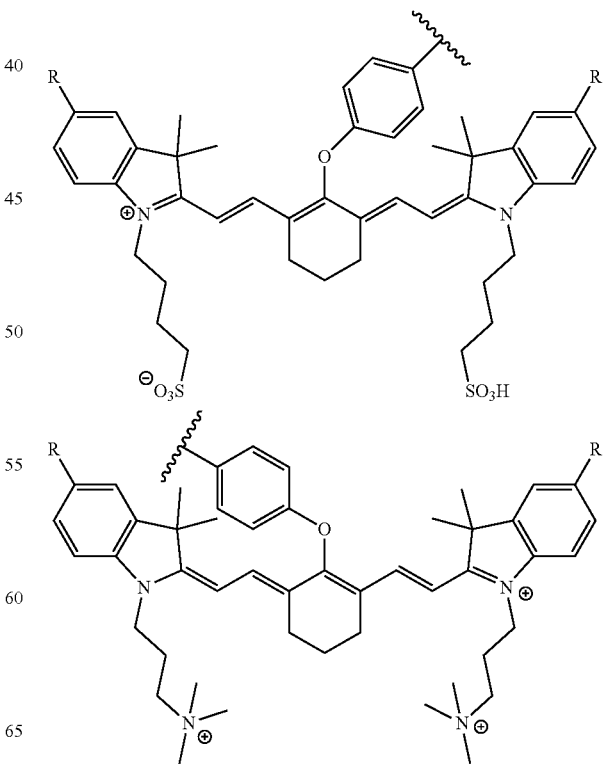

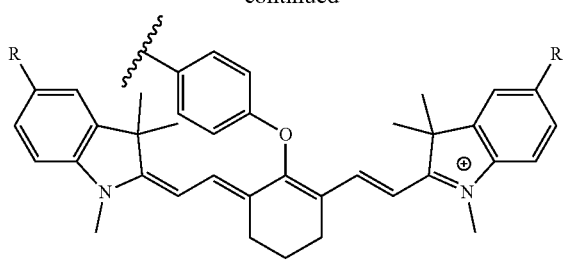

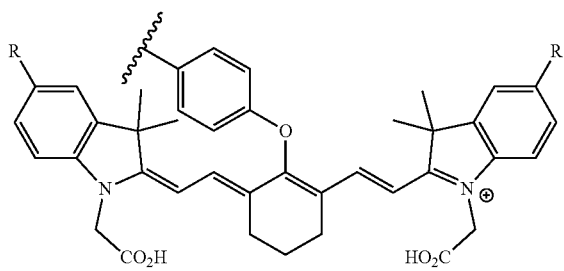

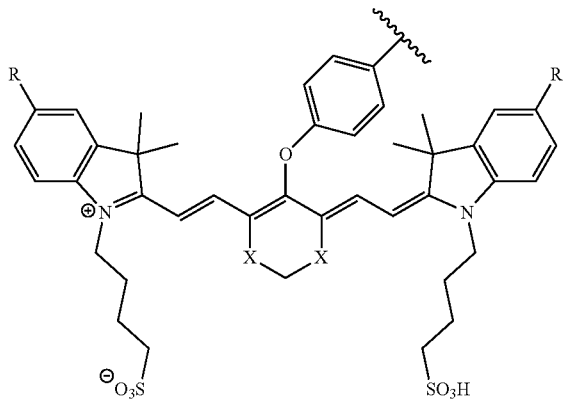

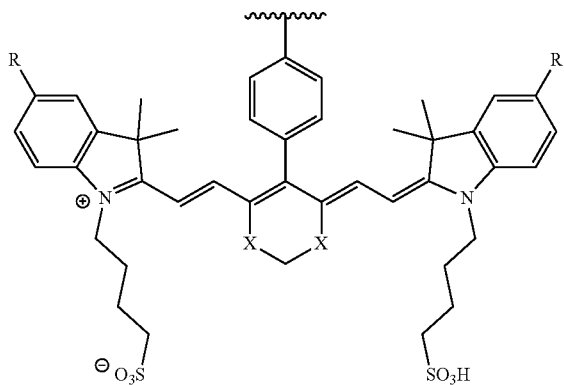

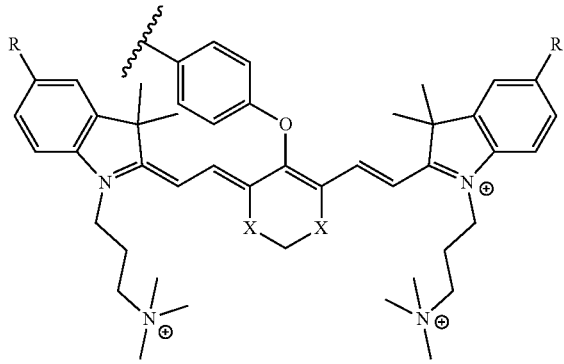

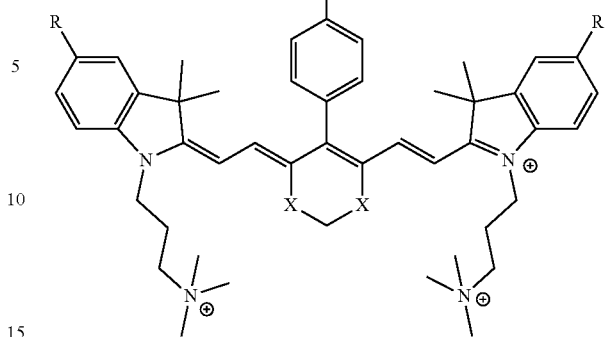

R = H or R = SO₃H; X = O, S, N

In certain aspects, the Z is variably charged. In some aspects, Z has a positive charge. In other aspects, Z has a negative charge.

In certain aspects, compounds of the present invention have the form:

B—X—Y—Z wherein B is a PSMA-targeted compound; X is a spacer; Y is an amino acid spacer with a sulfur-containing side chain group; and Z is an NIR dye. In some aspects, the amino acid spacer with a sulfur-containing side group is cysteine. In some aspects, the amino acid spacer with a sulfur-containing side group is methionine. In some aspects, the amino acid spacer with a sulfur-containing side group is molecule containing thiophenol moiety. In some aspects, compounds of the present invention have the form:

B—X—Y—Z wherein B is a PSMA-targeted compound; X is a spacer; Y is an amino acid spacer with a chalcogen-containing side chain group; and Z is an NIR dye. In some aspects the present invention provides compounds of the form:

B—X—Y—Z wherein B is a PSMA-targeted compound; X is a spacer; Y is an amino acid chosen from the group consisting of tyrosine, cysteine, lysine, or a derivative thereof; and Z is an NIR dye. In some aspects, Y comprises a tyrosine or tyrosine derivative. In some aspects, Y comprises a tyrosine and a carbon isotope is on the aromatic ring of tyrosine. In some aspects, Y comprises an amino acid with an aromatic ring with a hydrogen isotope.

In some aspects, compounds of the present invention have the form:

B—X—Y—Z wherein B is a PSMA-targeted compound; X is a spacer; Z is an NIR dye; and Y comprises a derivative of tyrosine selected from the group consisting of:

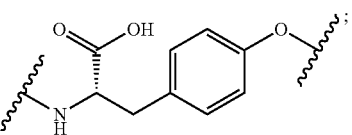

-continued

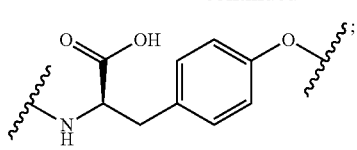

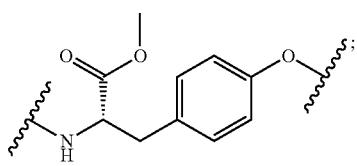

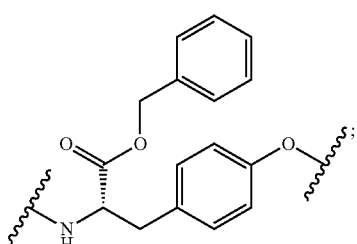

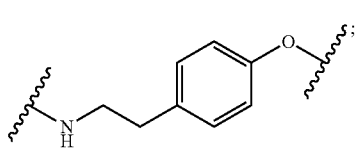

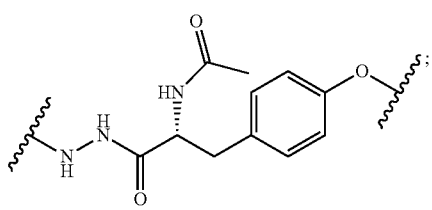

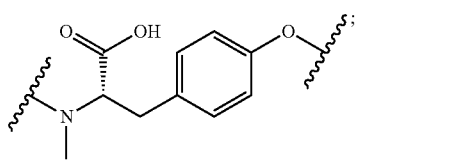

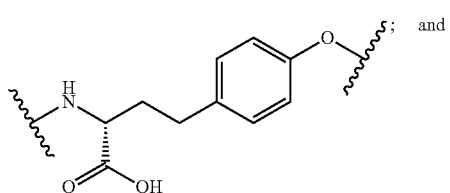

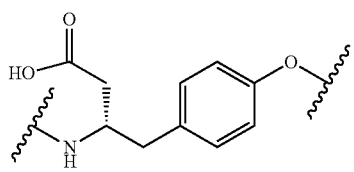

or racemic mixtures thereof.

In some aspects the invention includes the compound B—X—Y—Z wherein B comprises DUPA or a derivative thereof, X comprises an EAOA, Y comprises tyrosine, and Z comprises S0456.

Some aspects of the present invention include a compound having the structural formula:

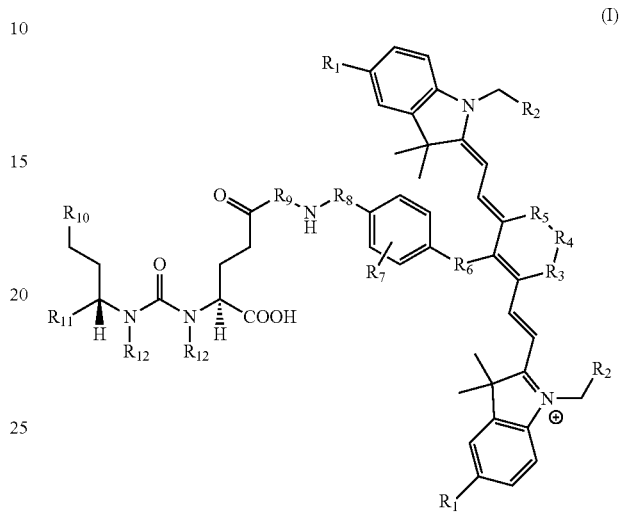

(I)

or a pharmaceutically acceptable salt thereof, or isotopes thereof, wherein:

$R_1$ represents a hydrogen or $SO_3H$;

$R_2$ represents a hydrogen, $CH_3$, $C_3H_6SO_3$, $C_3H_6SO_3H$ or $C_4H_8SO_3$, or $C_4H_8SO_3H$ or $C_3H_6N^+(CH_3)_3$;

$R_3$, and $R_5$ each represents a carbon, optionally one or more sharing bonds, $R_4$ represents a carbon with optionally one or more sharing bonds;

$R_6$ represents nitrogen, oxygen, or sulfur or no atom (direct C—C bond between aromatic ring and vinyl ring);

$R_7$ is optional and when present represents aromatic substitution group to enhance the spectral properties such as increase brightness and stability of the vinyl ether bridge;

$R_8$ is optional and when present represents linkers with aromatic amino acids such as Phe, trp, His or derivative of them, cationic amino acids such Arg, Lys, or derivative of them, anionic amino acids such as Asp, Glu or derivative of them, unnatural amino acids of aromatic/cationic/anionic acids or derivative;

$R_9$ is optional and when present represents a linear carbon chain, or polyethylene glycol linker, cationic linker, or derivative of them;

$R_{10}$ represents a $CO_2H$, $PO_3H_2$, $SO_3H$, $CH_2SO_3H$, $CH_2CONHCH_2SO_3H$, $CH_2CONHCH_2CH_2SO_3H$;

$R_{11}$ represents $CO_2H$, $SO_3H$, $CH_2CONHCH_2SO_3H$, $CH_2CONHCH_2CH_2SO_3H$; and Rig represents a hydrogen, a methyl group, a $CH_2$ and may optionally represent each a $CH_2$ sharing a bond.

In some aspects the present invention includes a compound that has the structural formula:

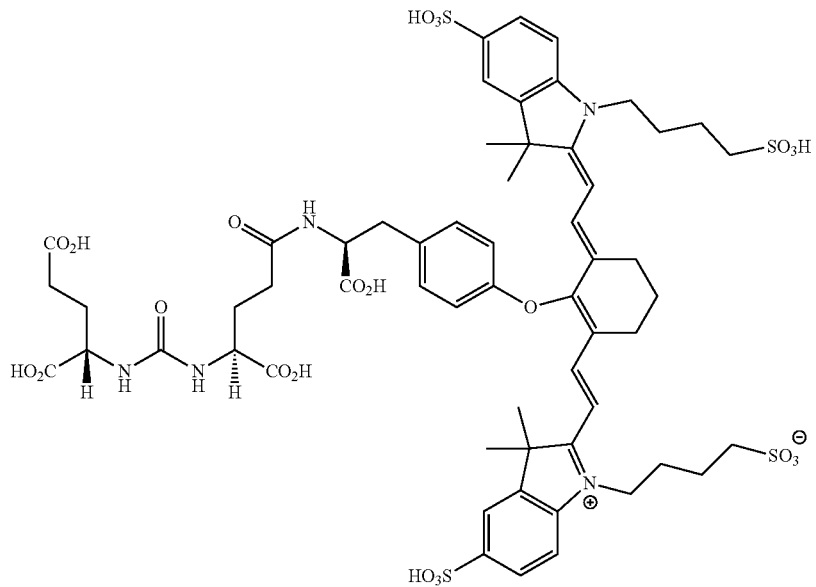
(1)
In some aspects the present invention includes a compound that has the structural formula:
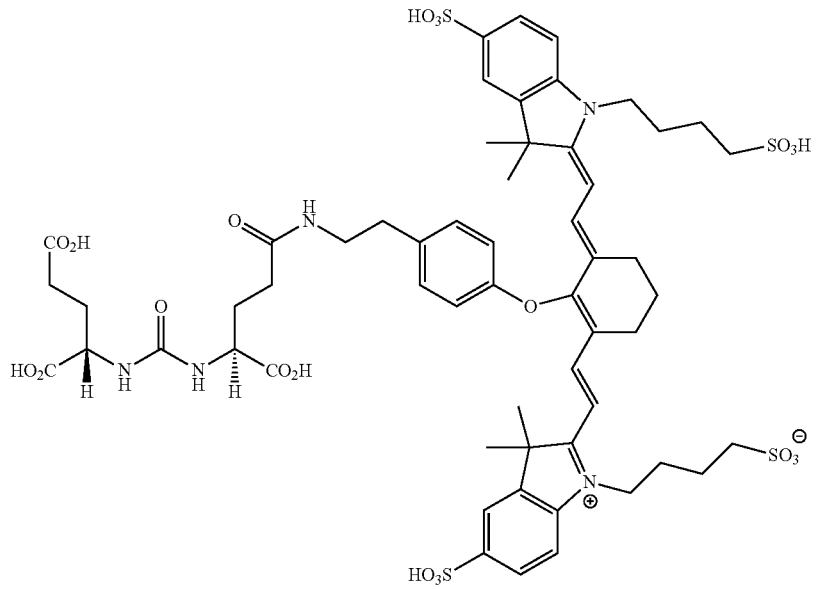
(2)
In some aspects the present invention includes a compound that has the structural formula:

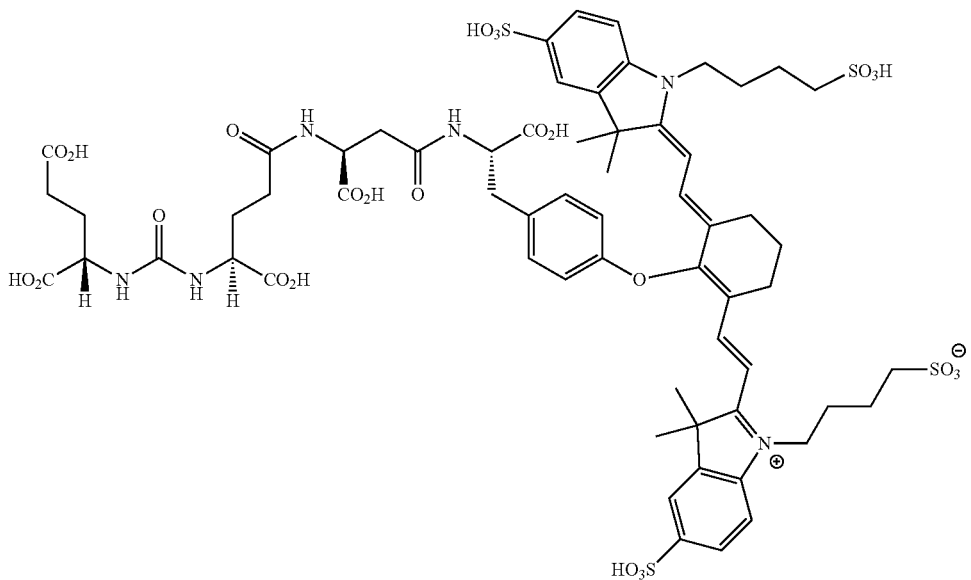
(3)
In some aspects the present invention includes a compound that has the structural formula:
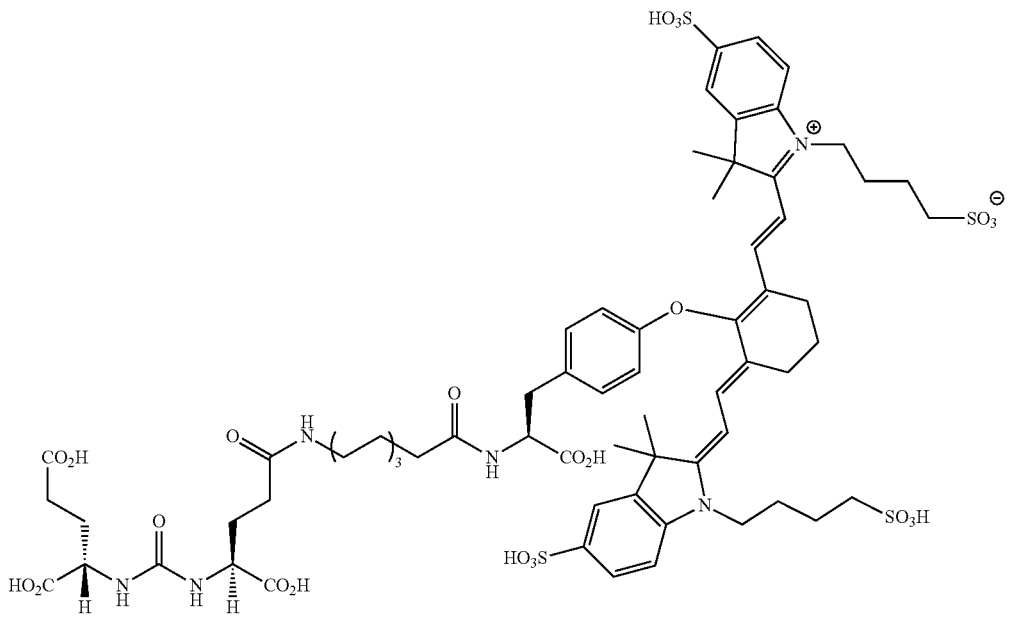
(4)
In some aspects the present invention includes a compound that has the structural formula:

(5)
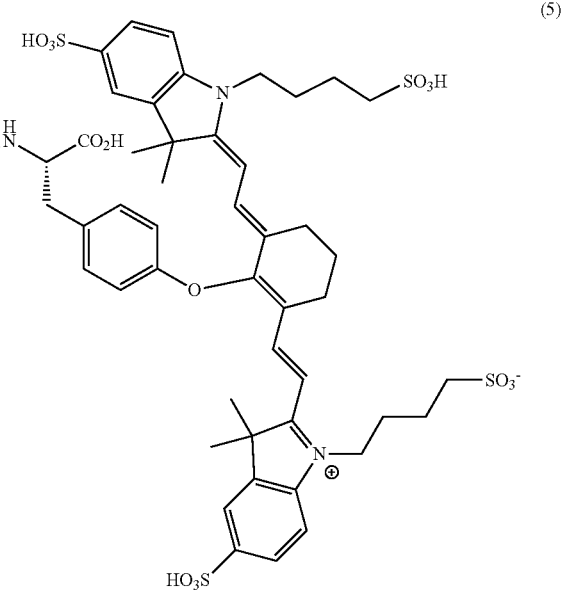
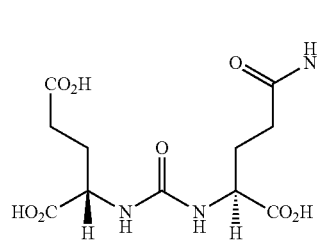
In some aspects the present invention includes a compound that has the structural formula:
(6)
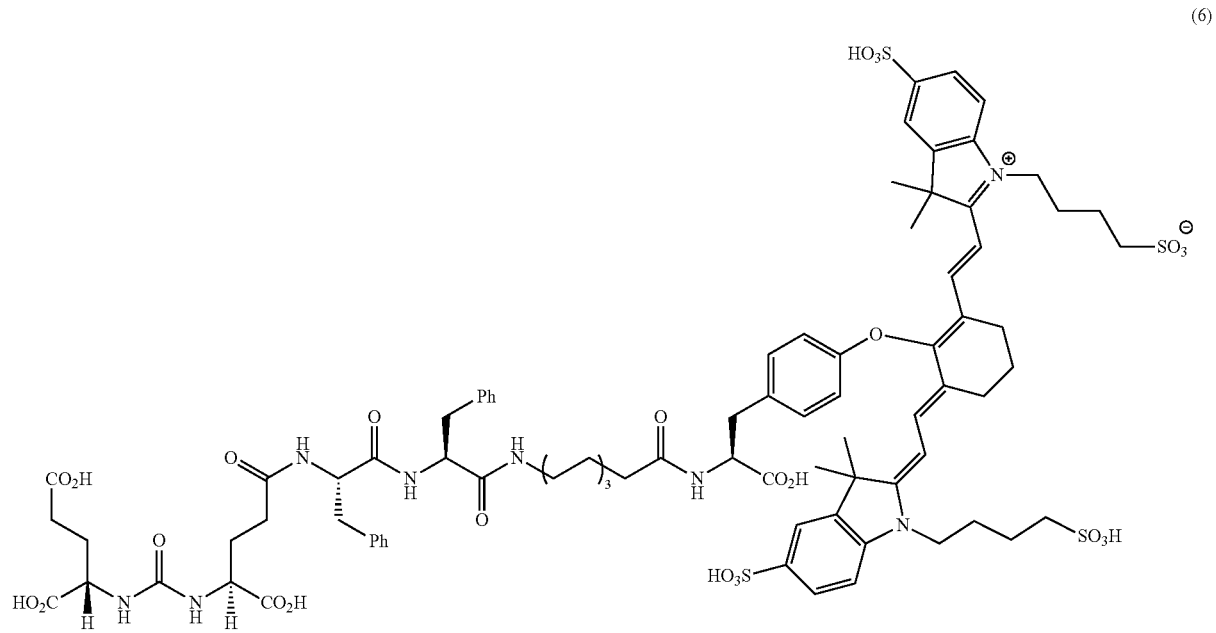
In some aspects the present invention includes a compound that has the structural formula:

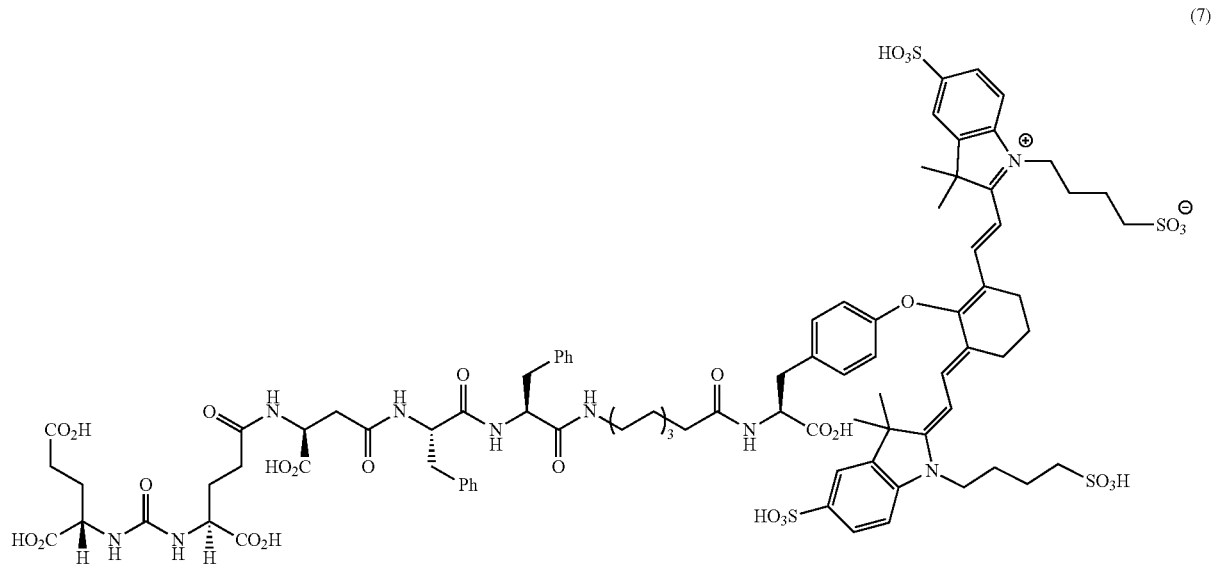
(7)
In some aspects the present invention includes a compound that has the structural formula:
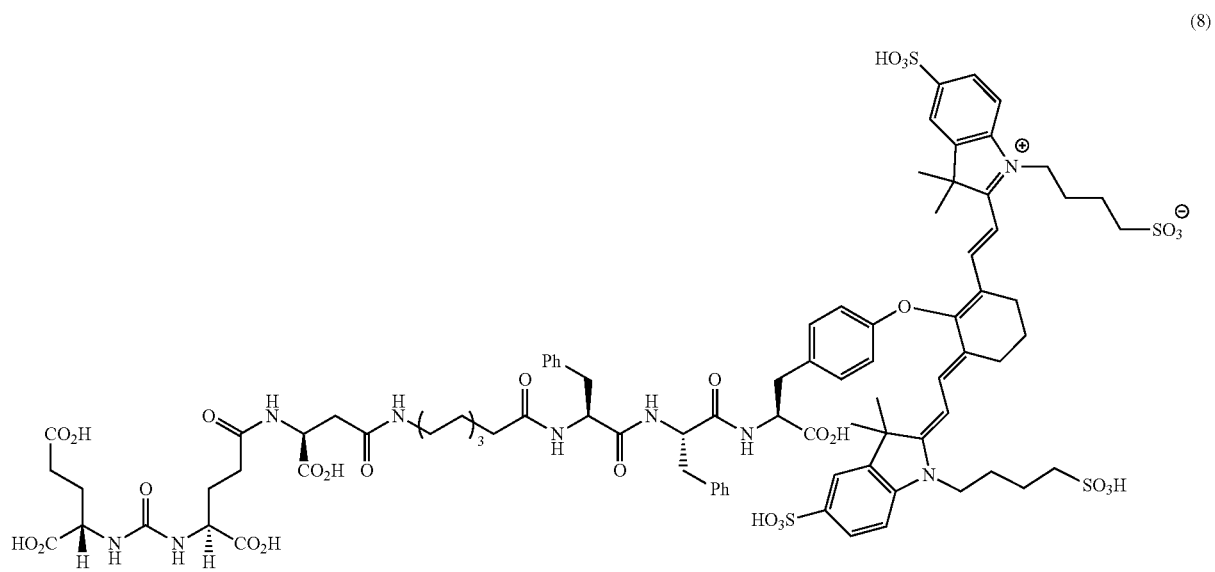
(8)
In some aspects the present invention includes a compound that has the structural formula:

(9)
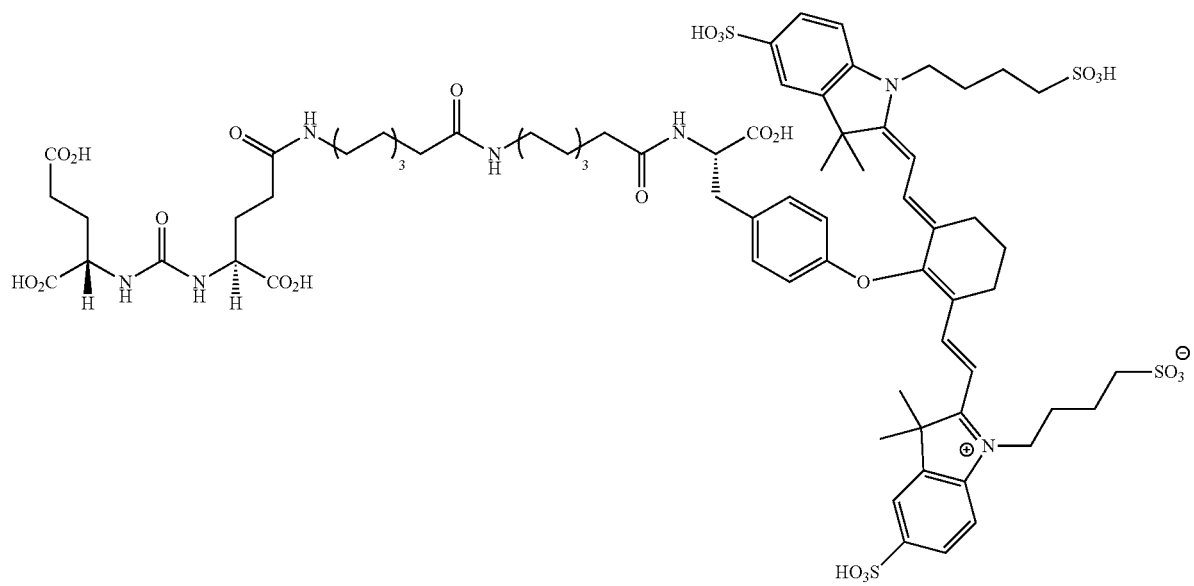
In some aspects the present invention includes a compound that has the structural formula:
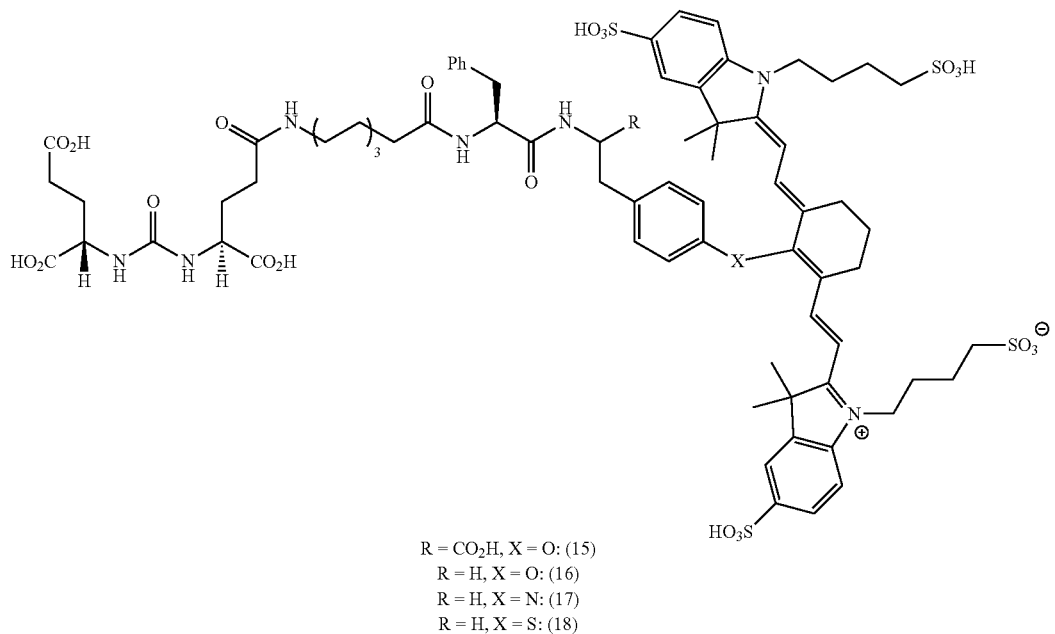
R = CO₂H, X = O: (15)
R = H, X = O: (16)
R = H, X = N: (17)
R = H, X = S: (18)
In some aspects the present invention includes a compound that has the structural formula:

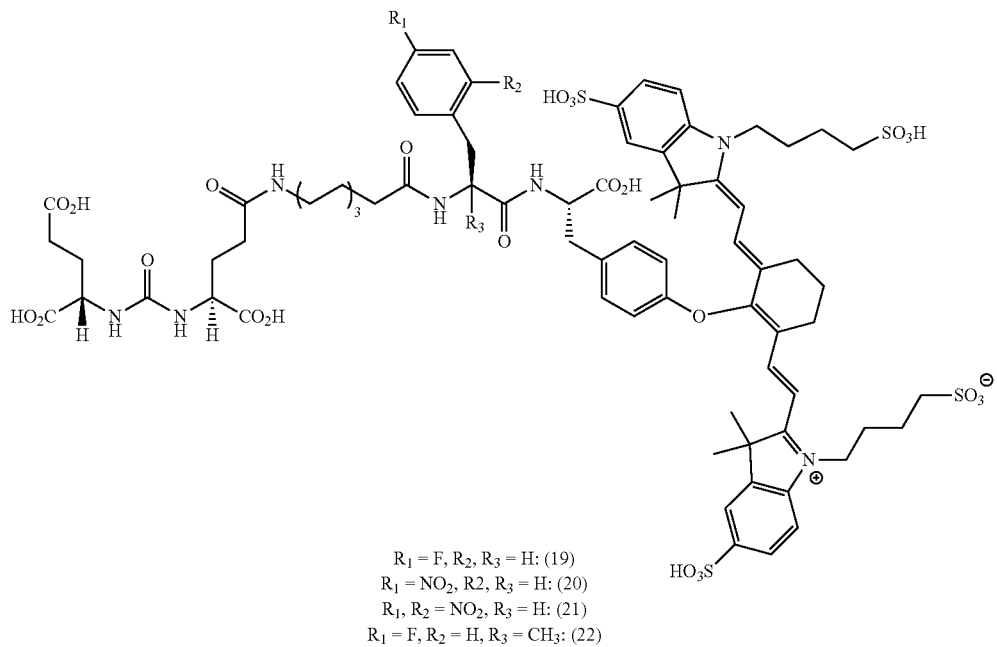
R₁ = F, R₂, R₃ = H: (19)
R₁ = NO₂, R2, R₃ = H: (20)
R₁, R₂ = NO₂, R₃ = H: (21)
R₁ = F, R₂ = H, R₃ = CH₃: (22)
In some aspects the present invention includes a compound that has the structural formula:
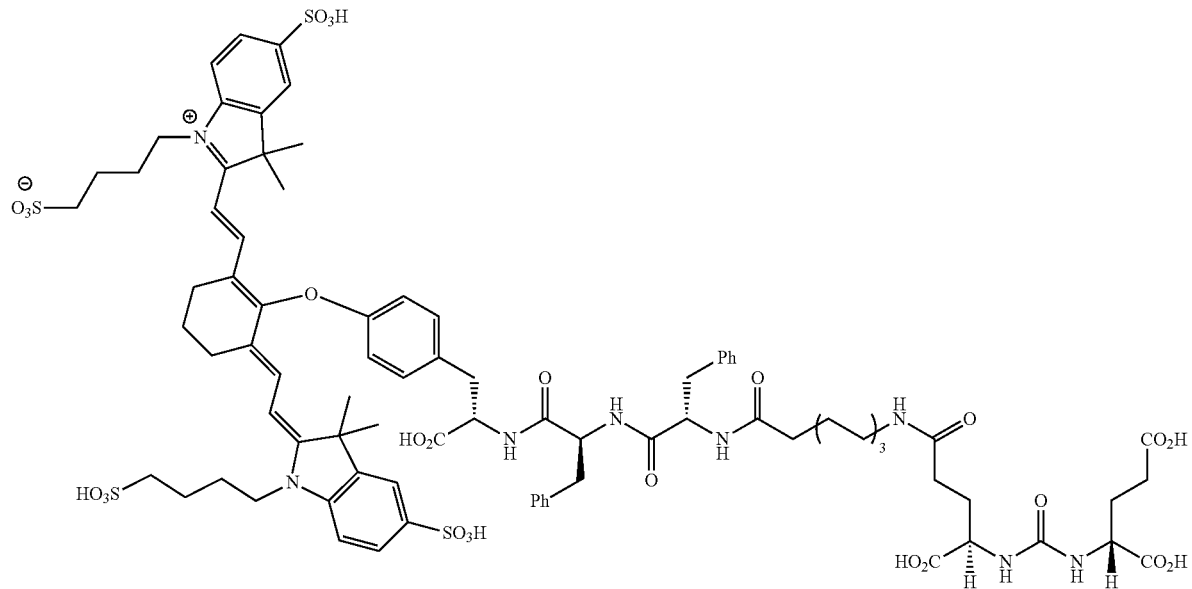
(23)
In some aspects the present invention includes a compound that has the structural formula:

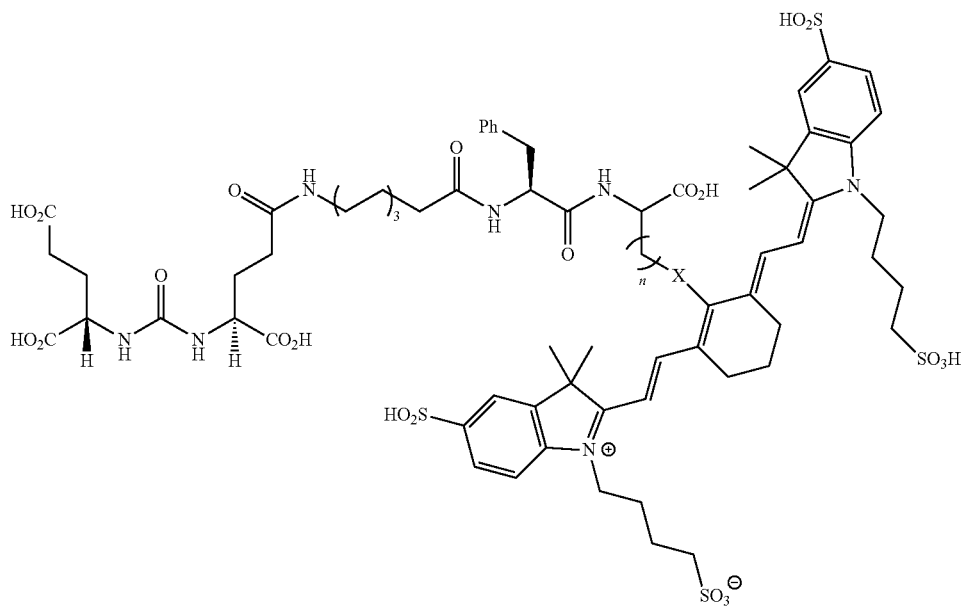
X = O, n = 1: (24)
X = S, n = 1: (25)
X = NH, n = 4 (26)
In some aspects the present invention includes a compound that has the structural formula:
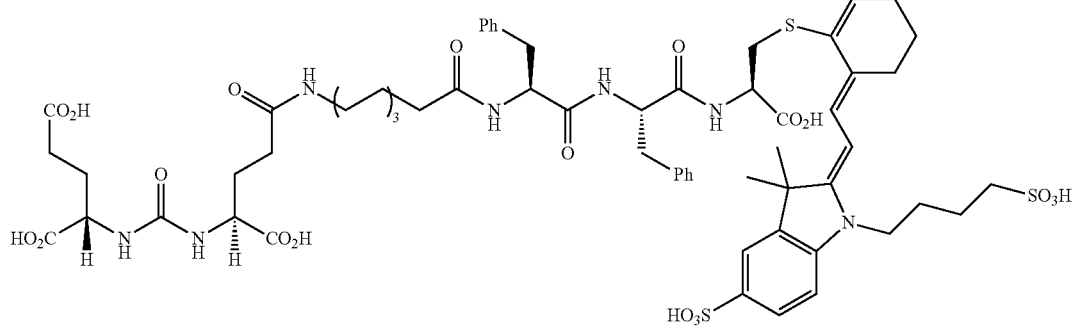
(27)
In some aspects the present invention includes a compound that has the structural formula:

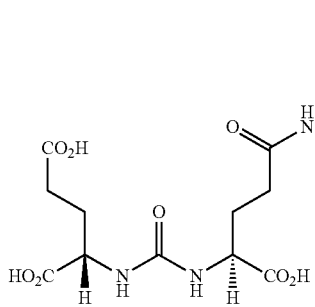
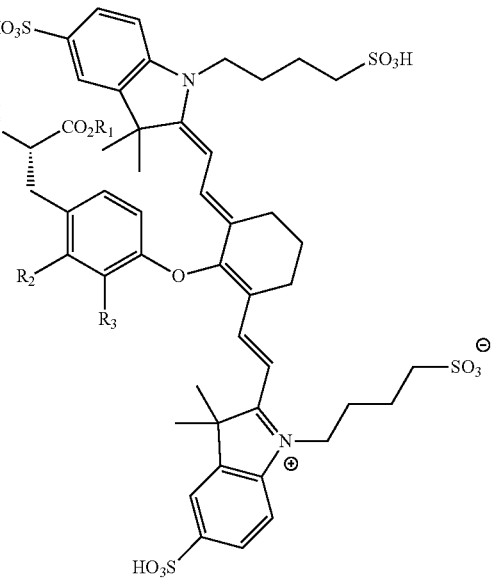
$R_1$ = Bn, $R_2$, $R_3$ = H: (28)
$R_1$ = H, $R_2$ = H, $R_3$ = F: (29)
$R_1$ = H, $R_2$ = H, $R_3$ = OCH$_3$: (30)
$R_1$ = H, $R_2$ = NO$_2$, $R_3$ = H: (31)
In some aspects the present invention includes a compound that has the structural formula:
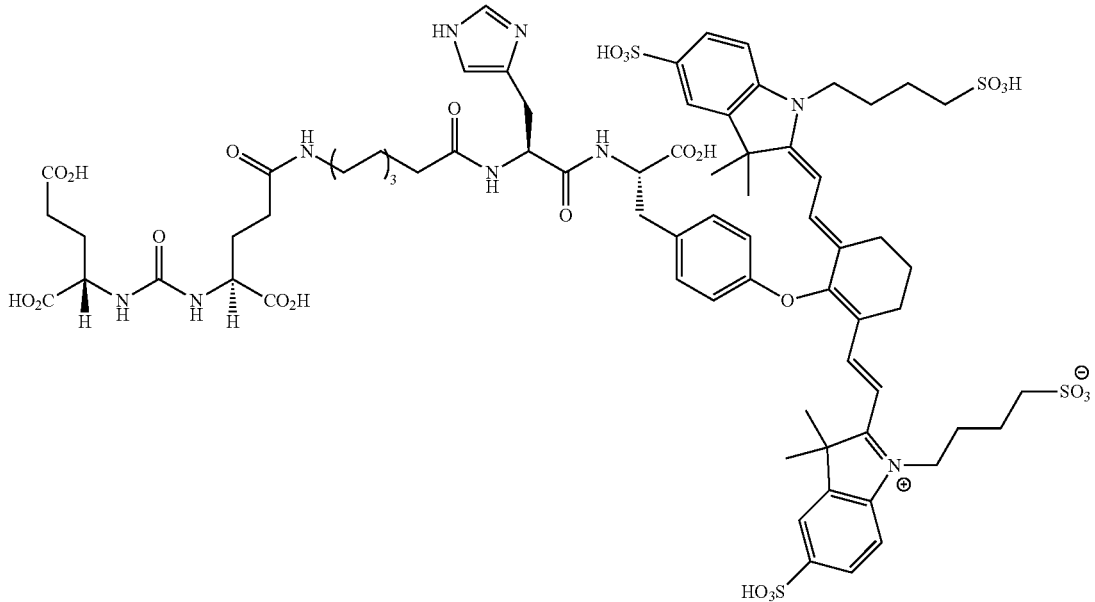
(32)
In some aspects the present invention includes a compound that has the structural formula:

(33)
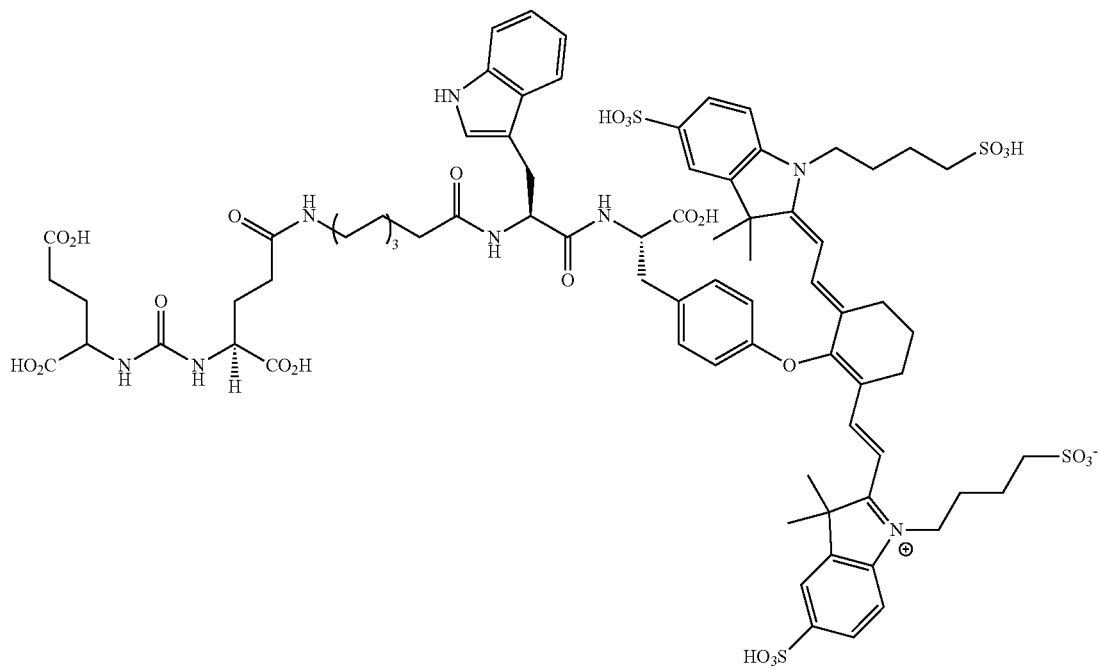
In some aspects the present invention a compound that has the structural formula:
(34)
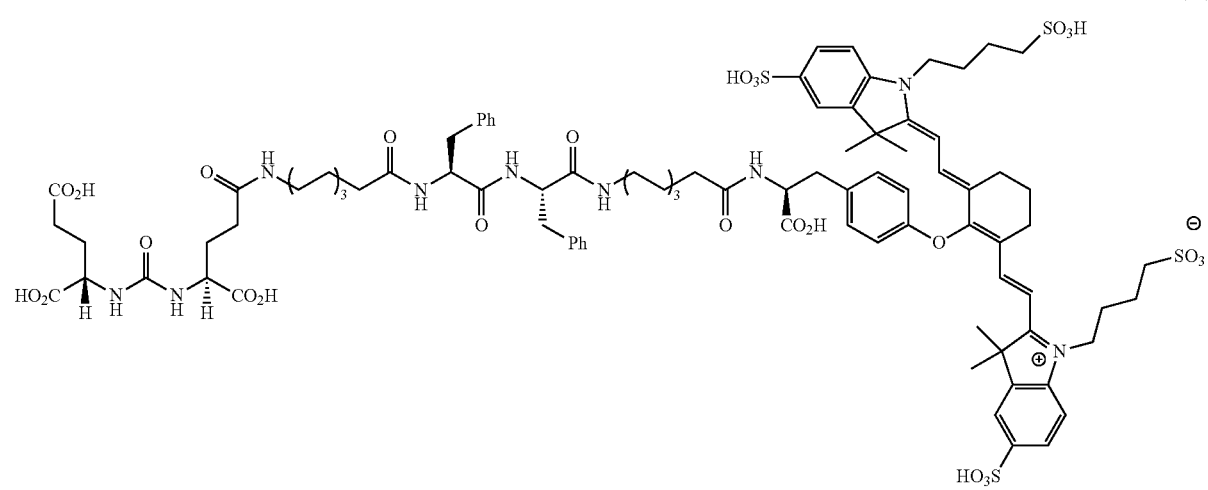
In some aspects the present invention a compound that has the structural formula:

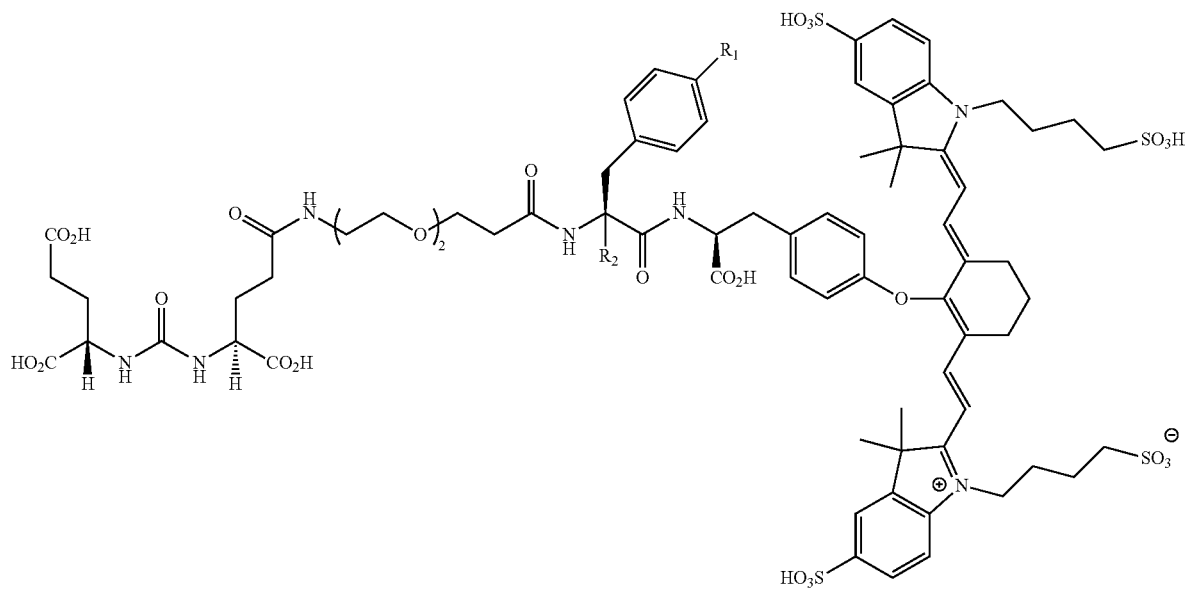
R₁, R₂ = H; (35)
R₁ = F, R₂ = CH₃; (36)
In some aspects the present invention includes a compound that has the structural formula:
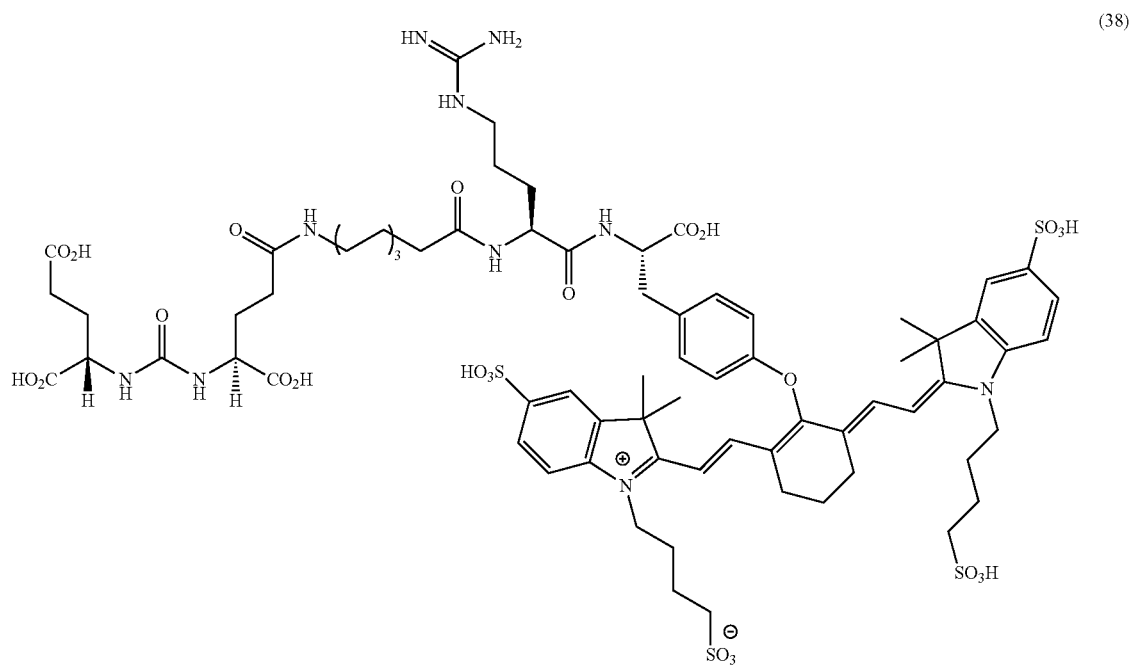
(38)
In some aspects the present invention includes a compound that has the structural formula:

(39)
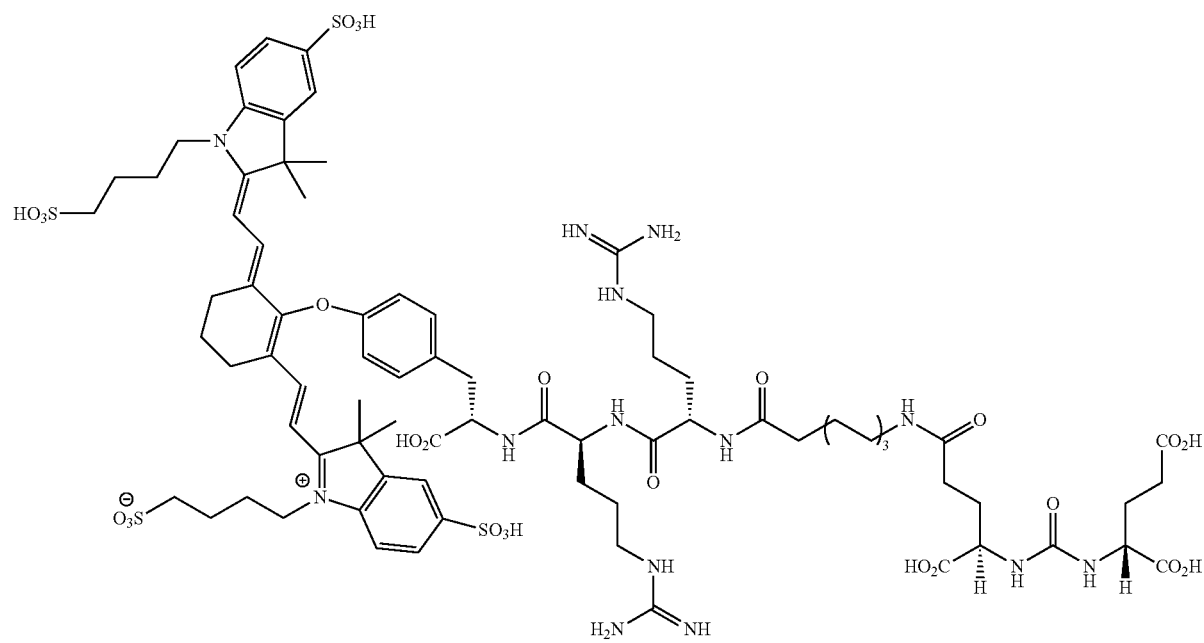
In some aspects the present invention includes a compound that has the structural formula:
(40)
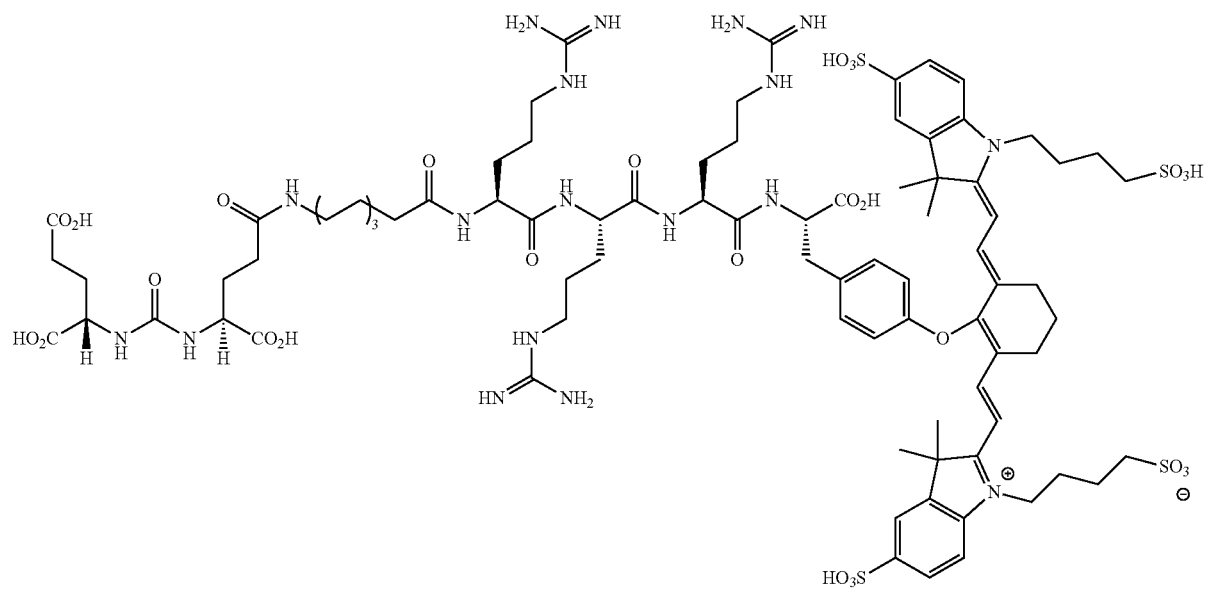
In some aspects the present invention includes a compound that has the structural formula:

(41)
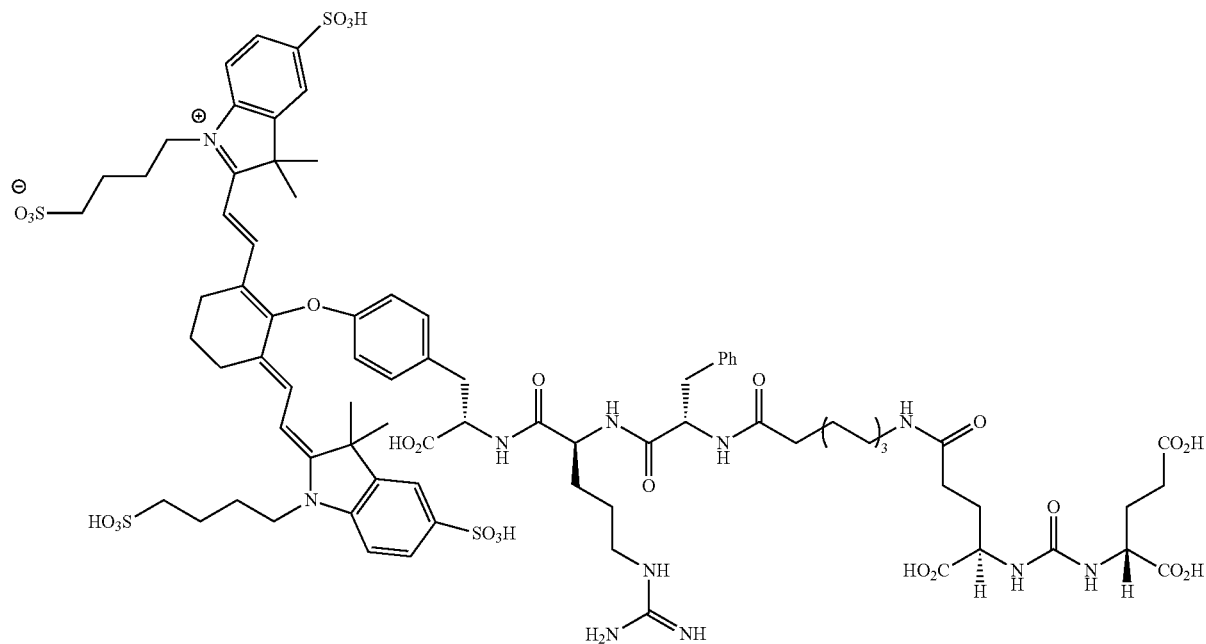
In some aspects the present invention includes a compound that has the structural formula:
(42)
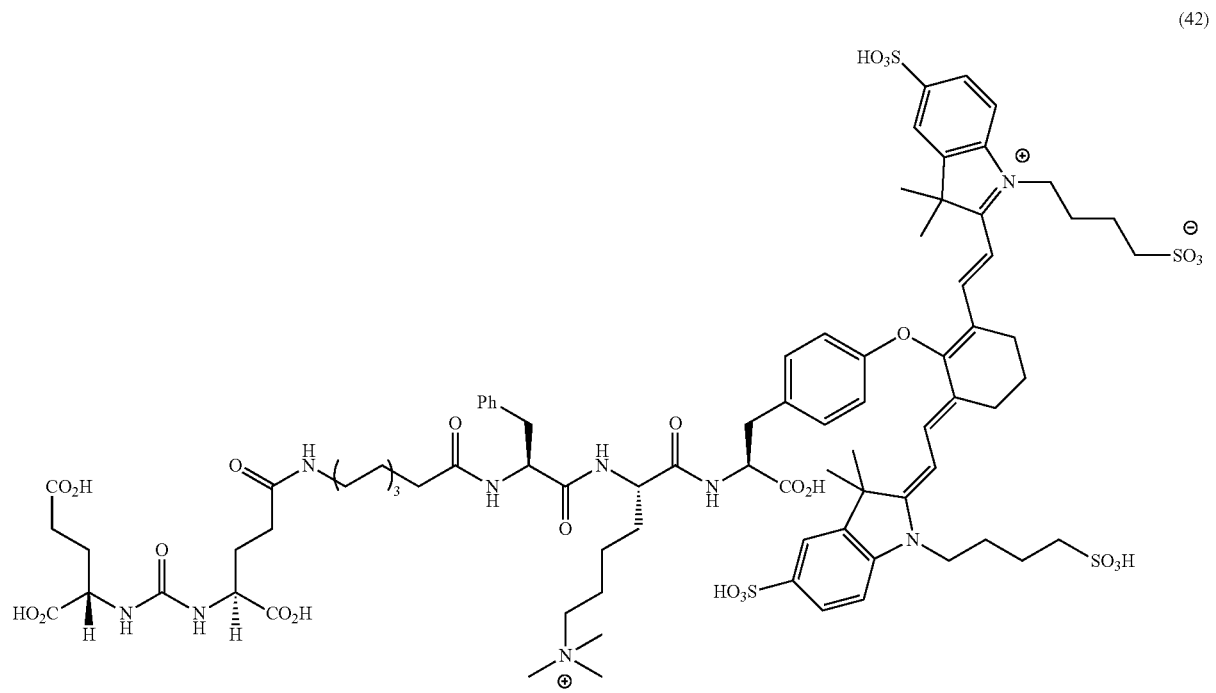
In some aspects the present invention includes a compound that has the structural formula:

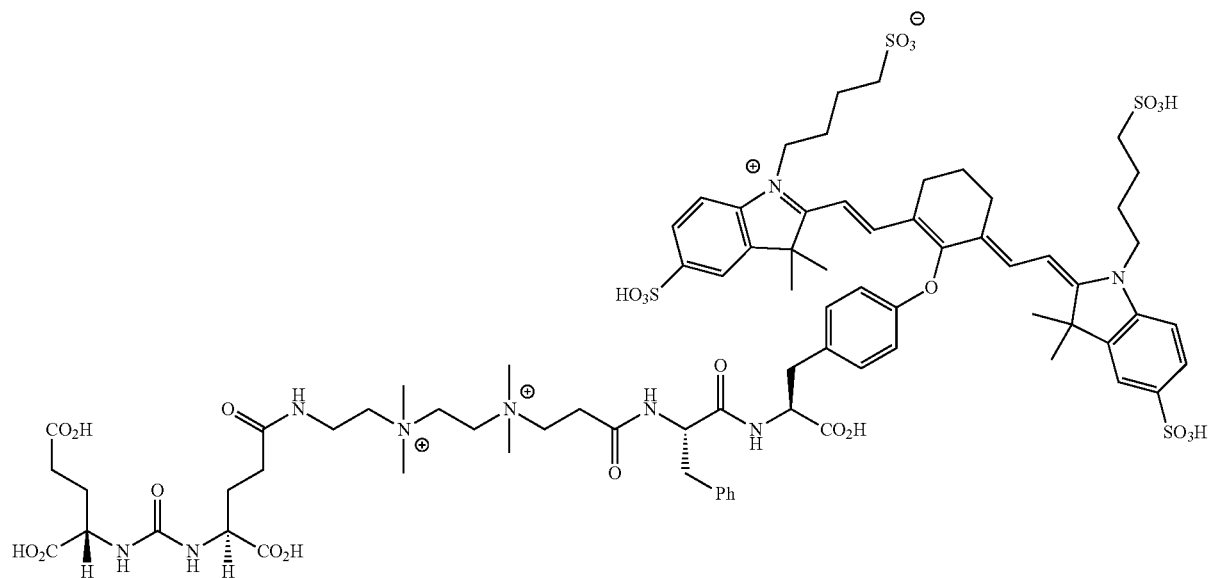
(43)
In some aspects the present invention includes a compound that has the structural formula:
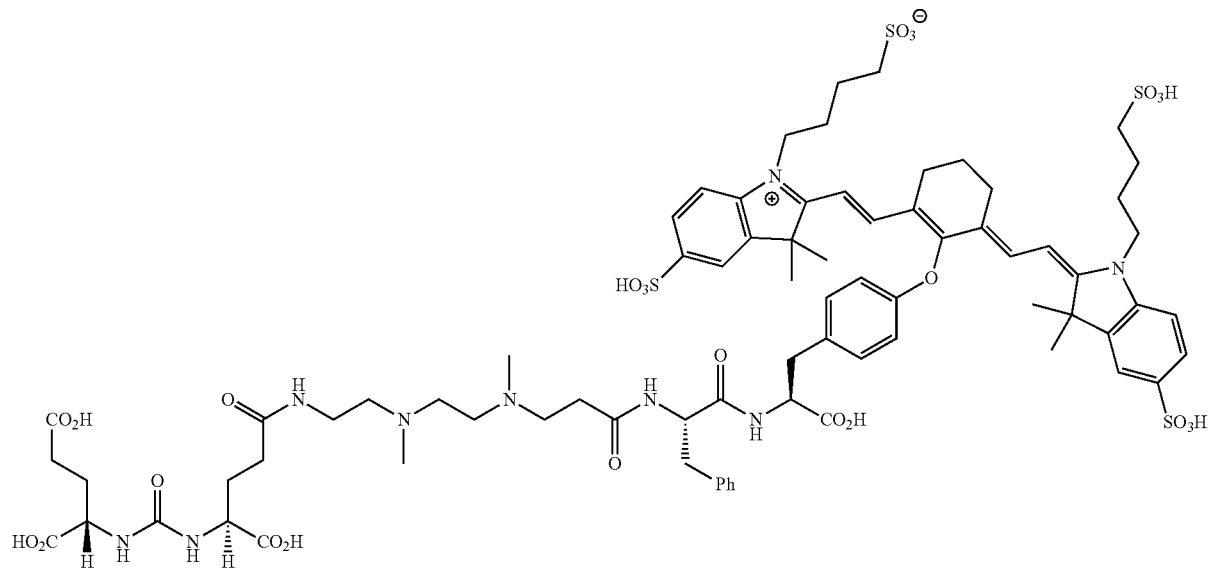
(44)
In some aspects the present invention includes a compound that has the structural formula:

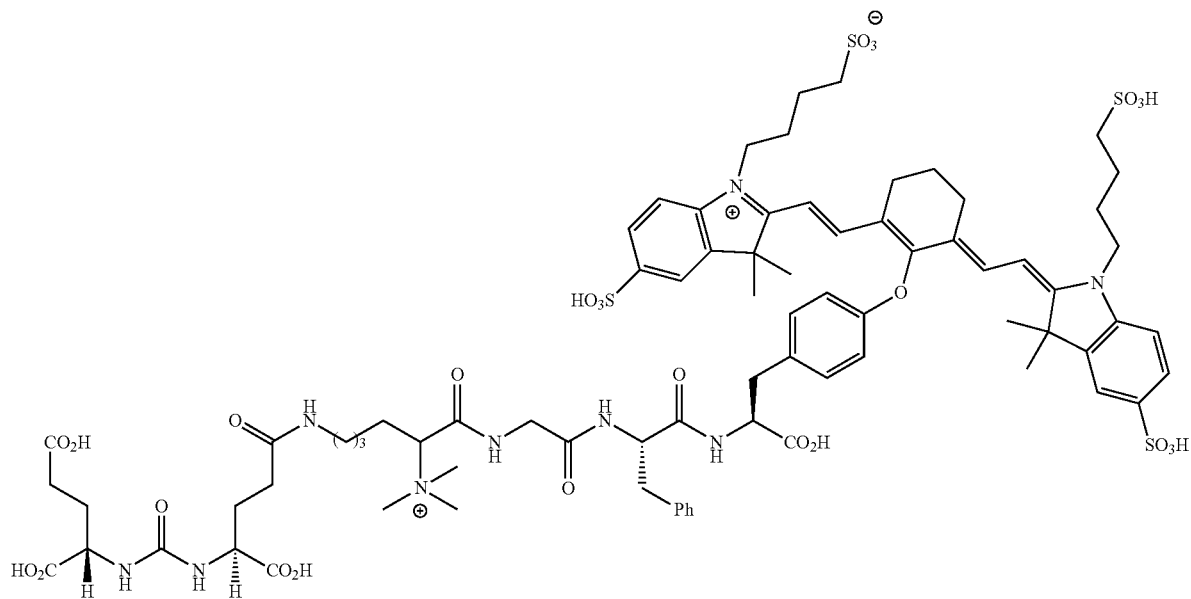
(45)
In some aspects the present invention includes a compound that has the structural formula:
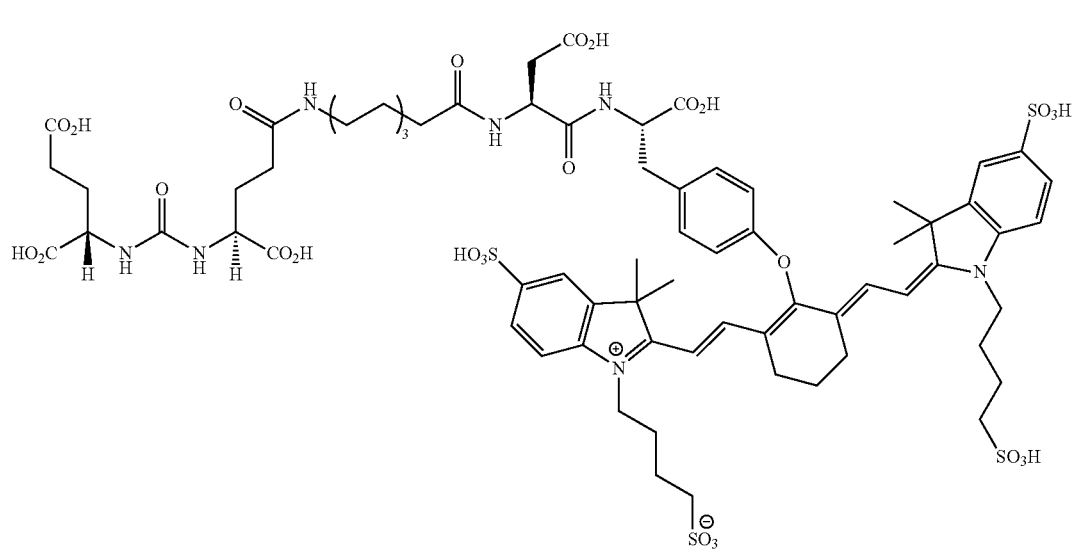
(47)
In some aspects the present invention includes a compound that has the structural formula:

(48)
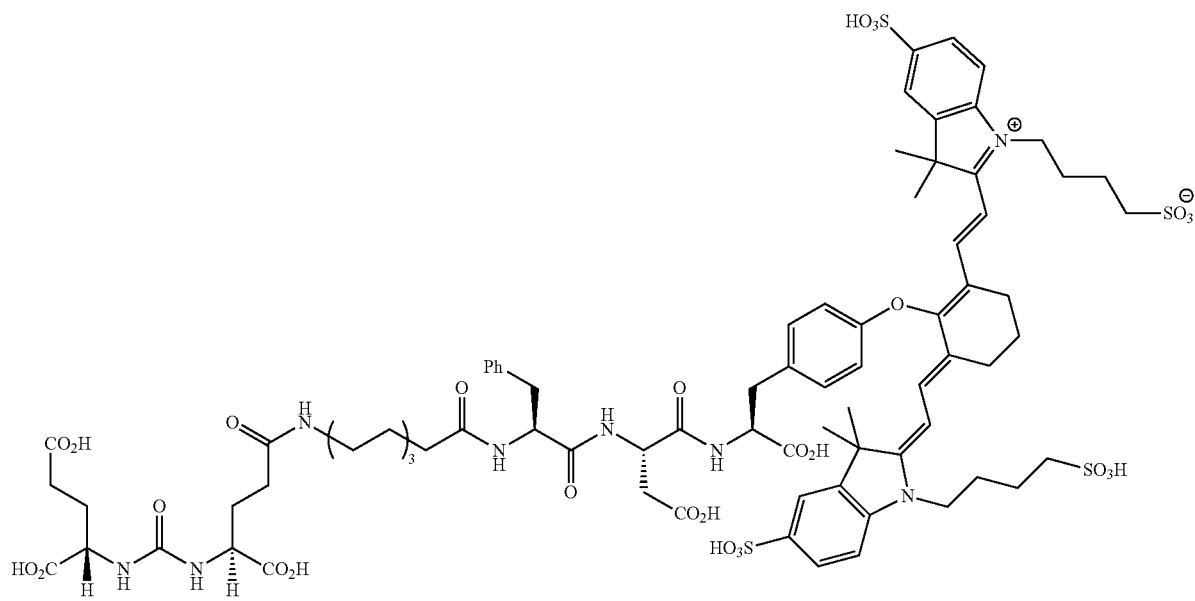
In some aspects the present invention includes a compound that has the structural formula:
(49)
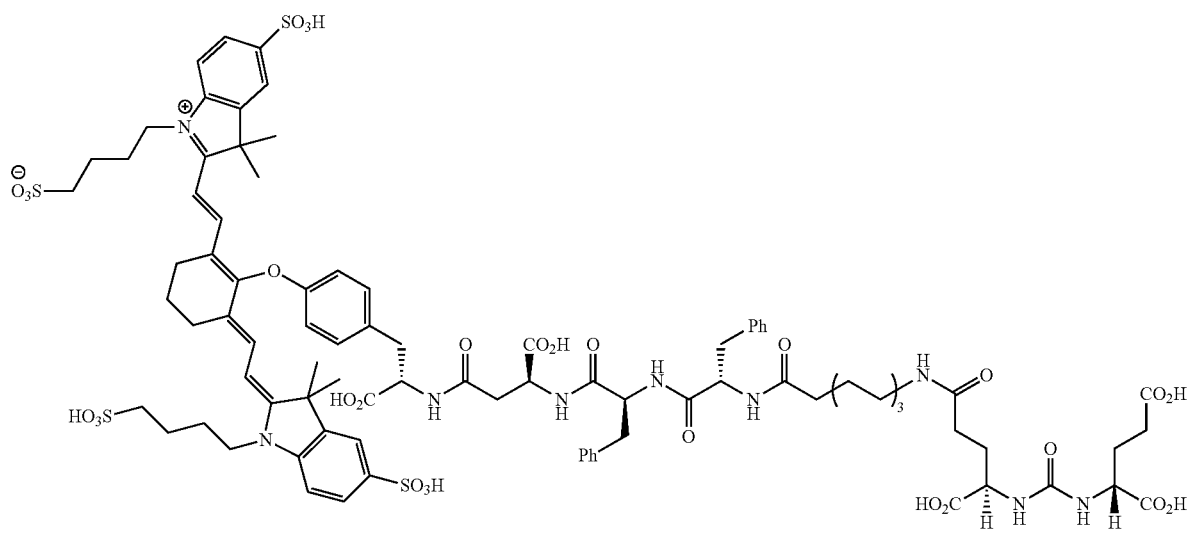
In some aspects the present invention includes a compound that has the structural formula:

(50)
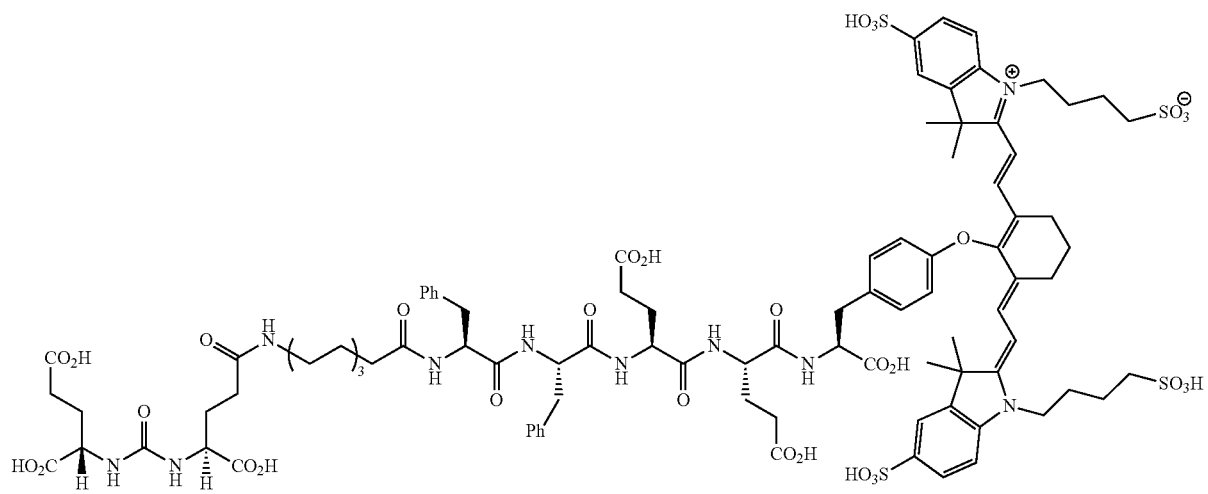
In some aspects the present invention includes a compound that has the structural formula:
(51)
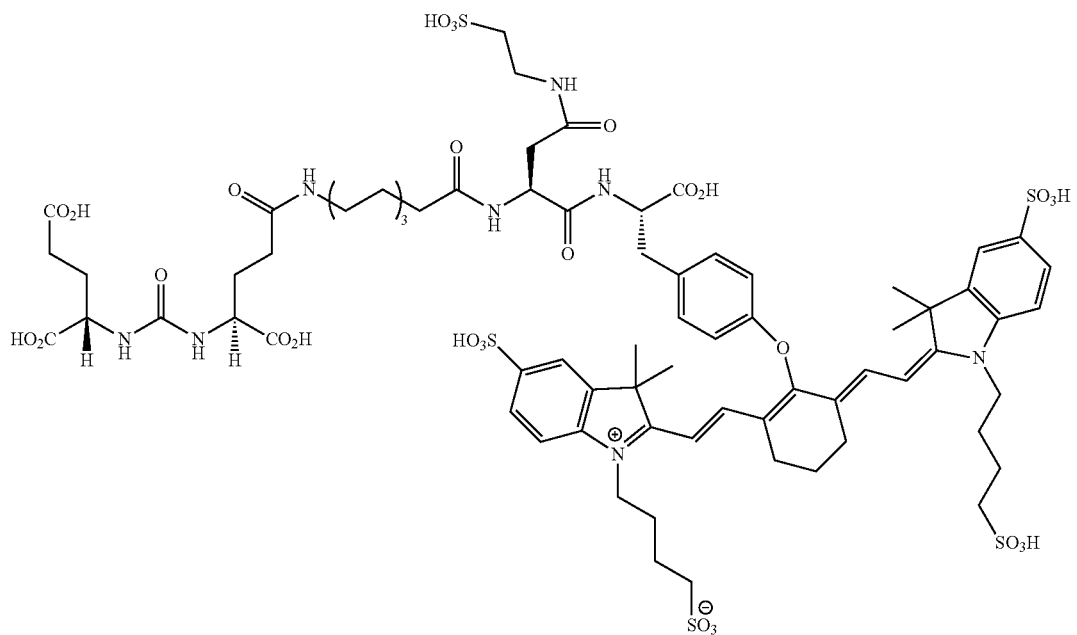
In some aspects the present invention includes a compound that has the structural formula:

(52)
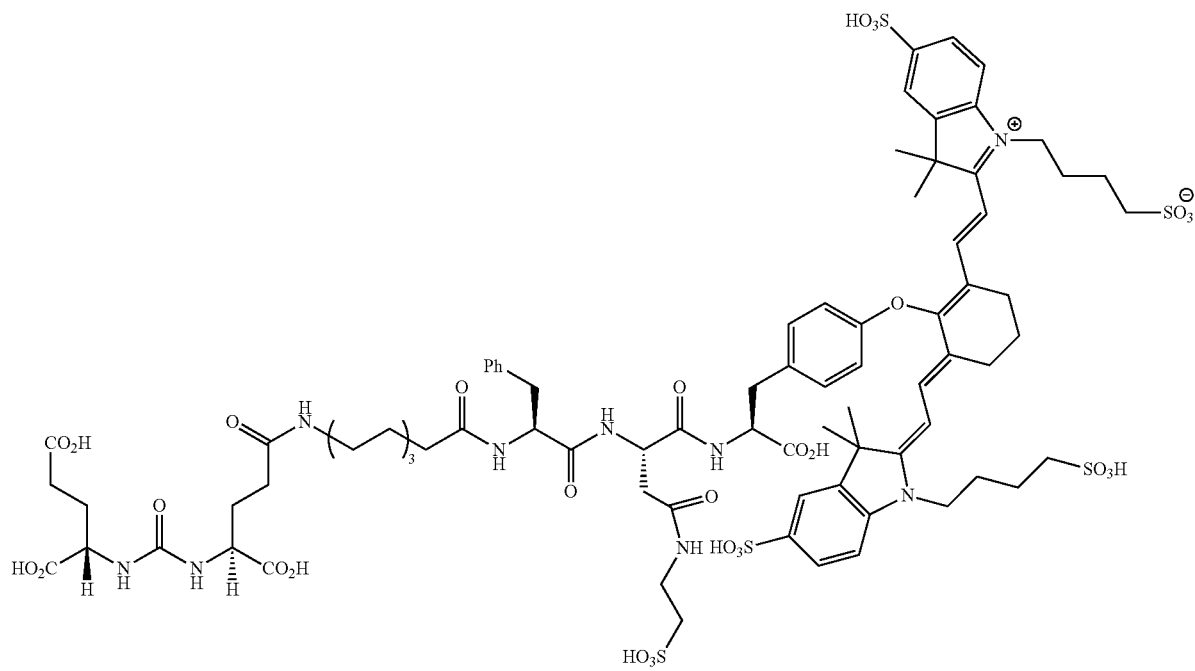
In some aspects the present invention includes a compound that has the structural formula:
(54)
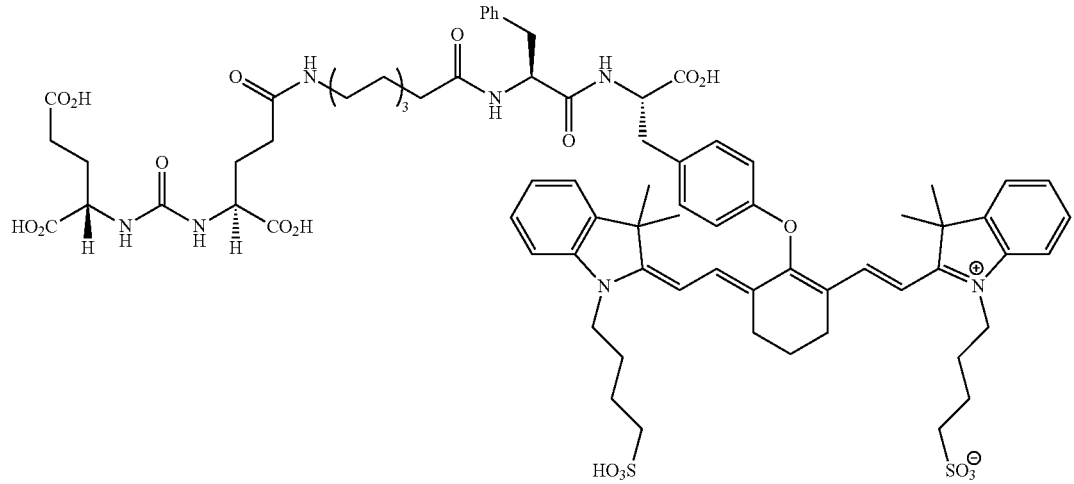
In some aspects the present invention includes a compound that has the structural formula:

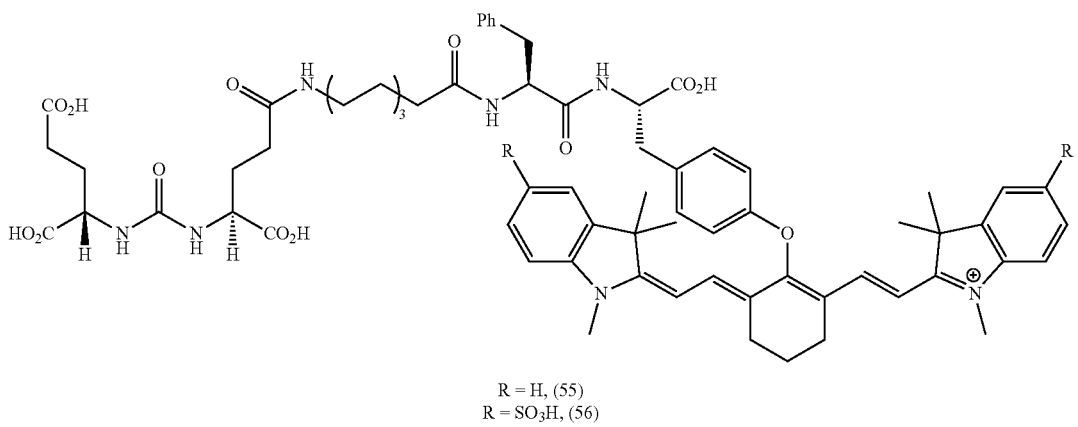
R = H, (55)
R = SO₃H, (56)
In some aspects the present invention includes a compound that has the structural formula:
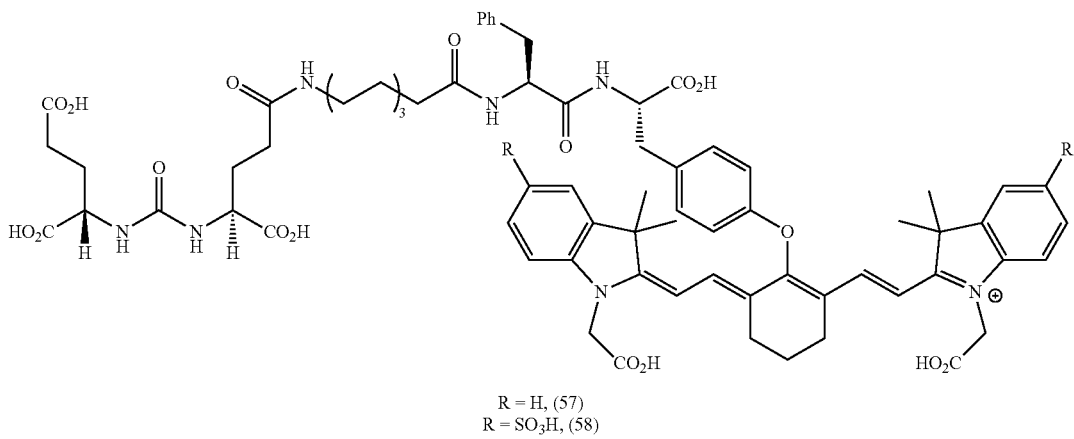
R = H, (57)
R = SO₃H, (58)
In some aspects the present invention includes a compound that has the structural formula:
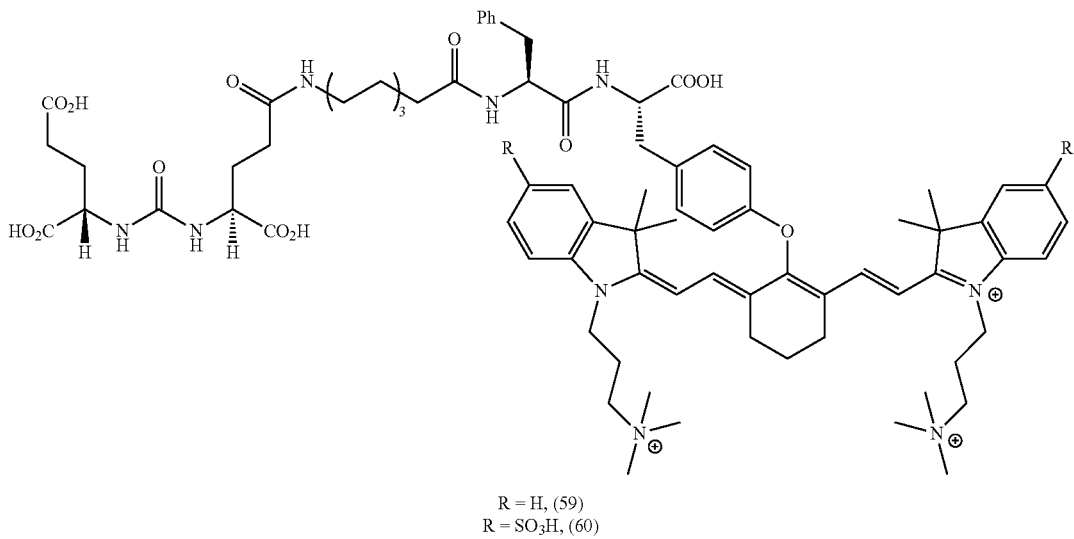
R = H, (59)
R = SO₃H, (60)

In some aspects the present invention includes a compound that has the structural formula:
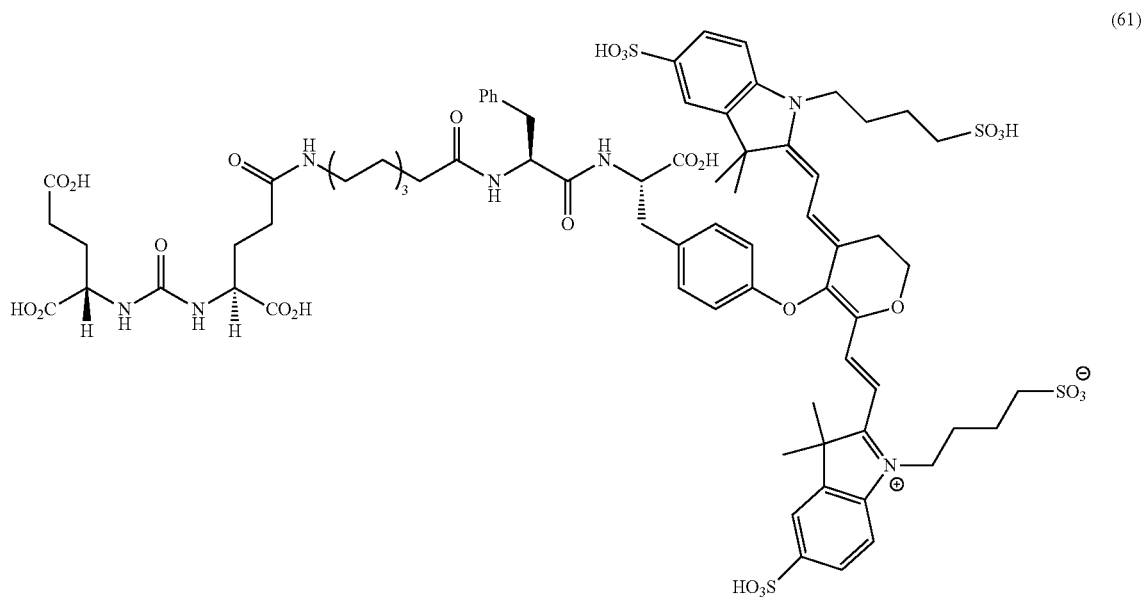
(61)
In some aspects the present invention includes a compound that has the structural formula:
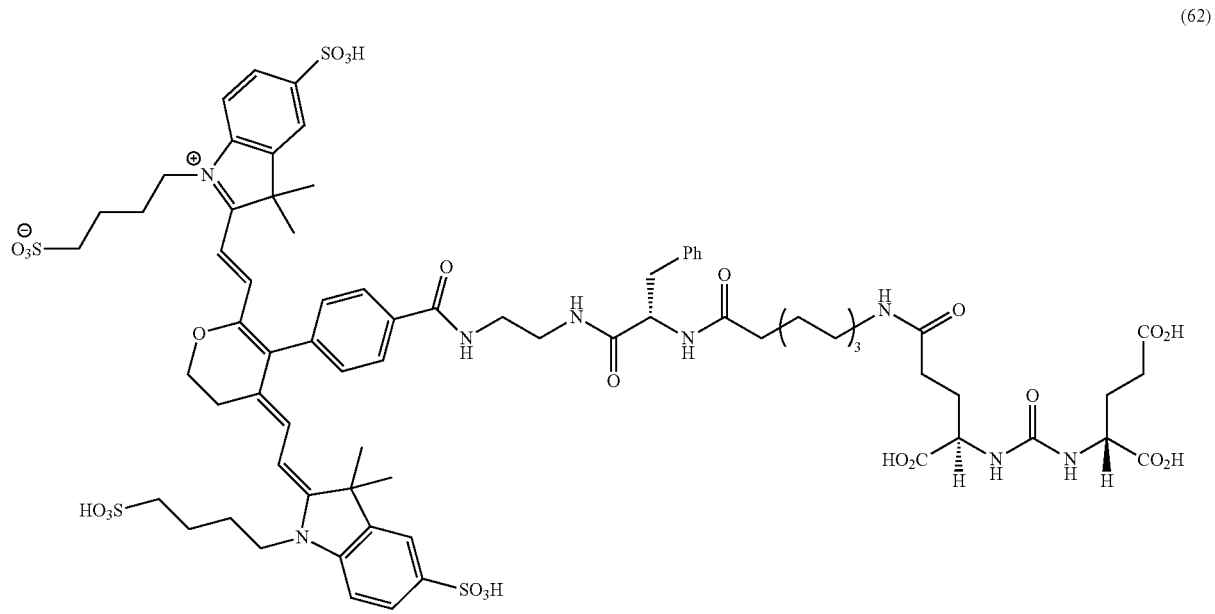
(62)
In some aspects the present invention includes a compound that has the structural formula:

(63)
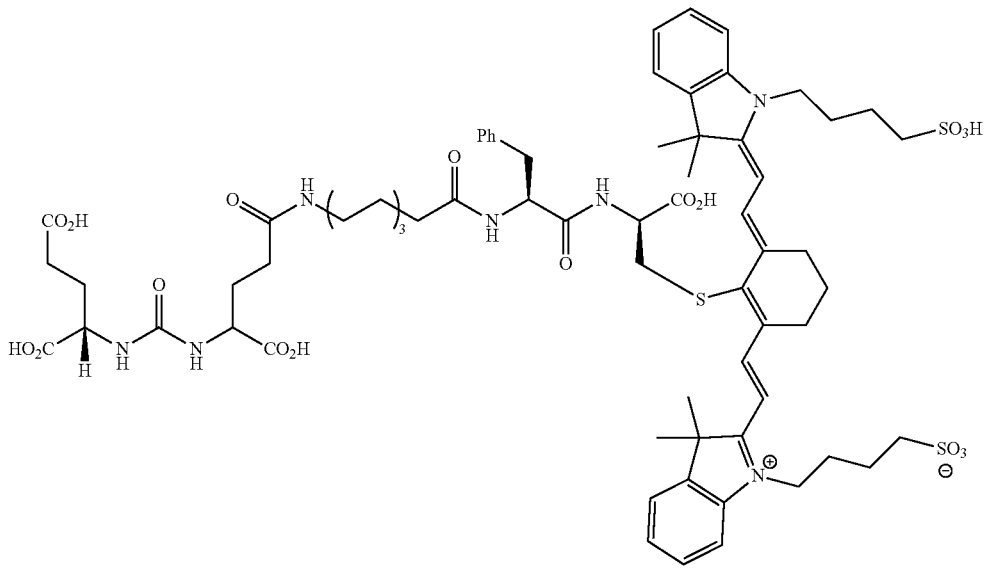
In some aspects the present invention includes a compound that has the structural formula:
(64)
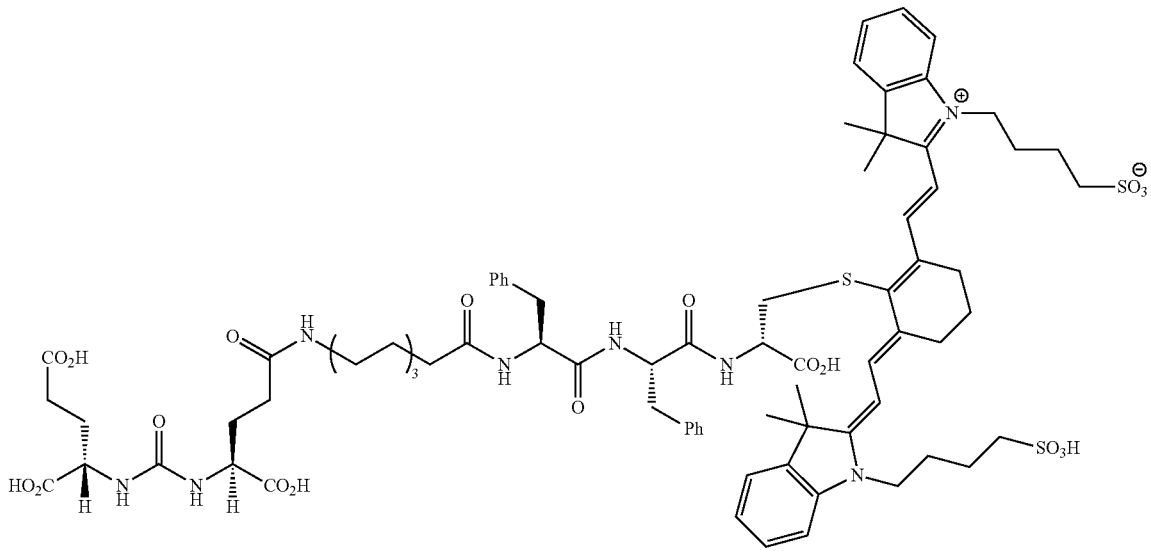
In some aspects the present invention includes a compound that has the structural formula:

(65)
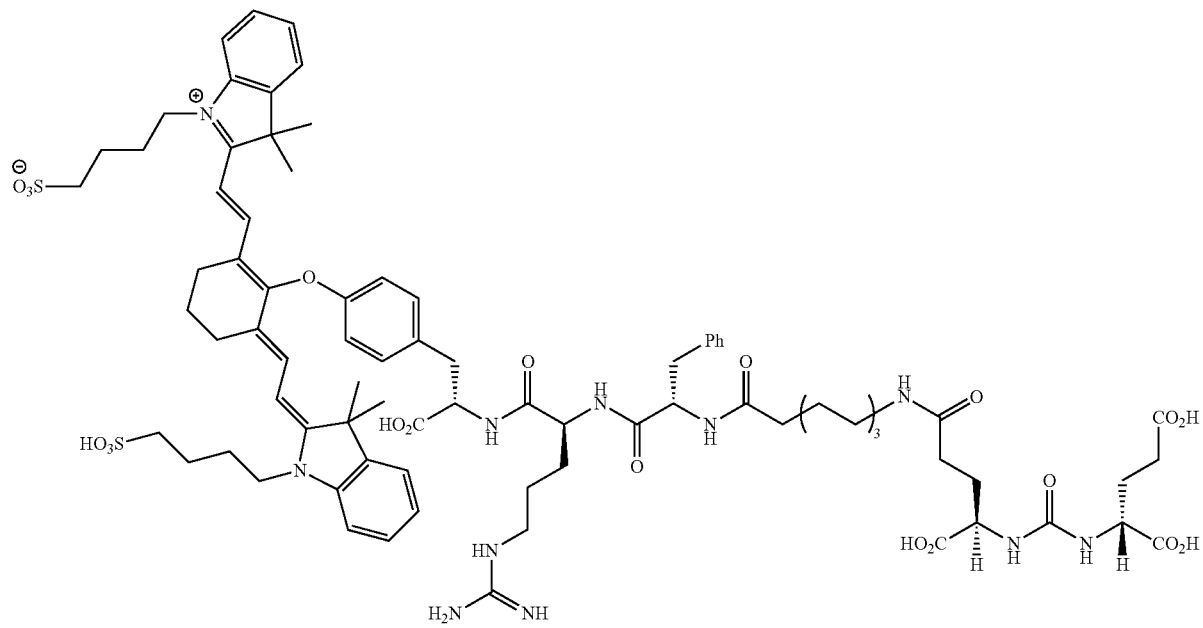
In some aspects the present invention includes a compound that has the structural formula:
(66)
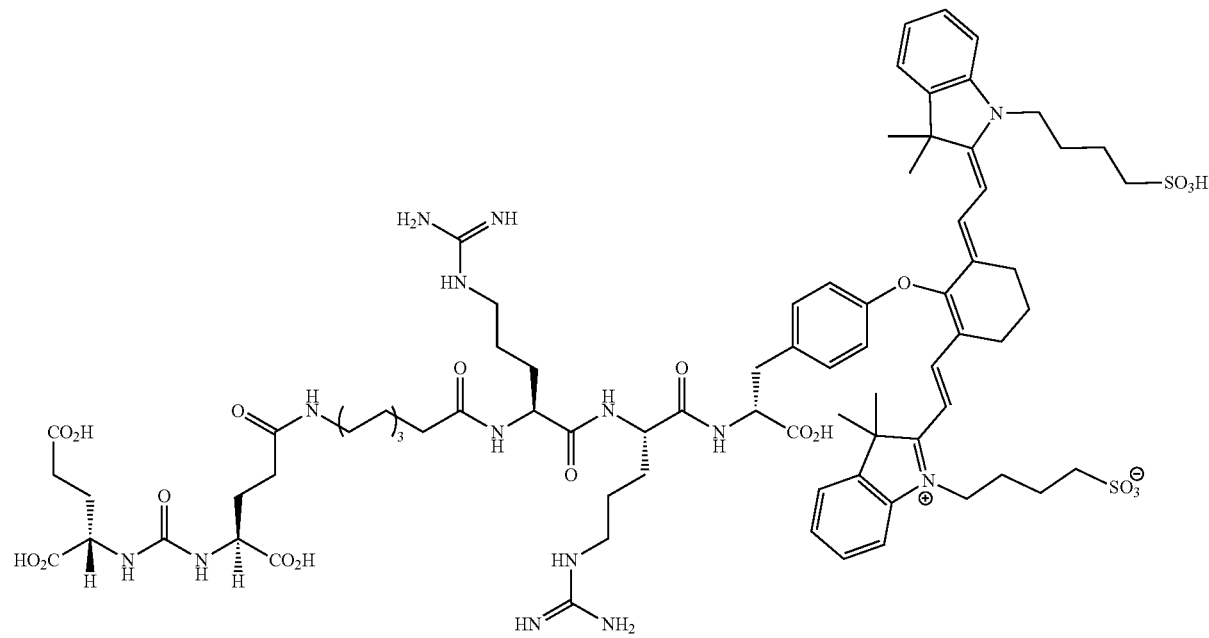
In some aspects the present invention includes a compound that has the structural formula:

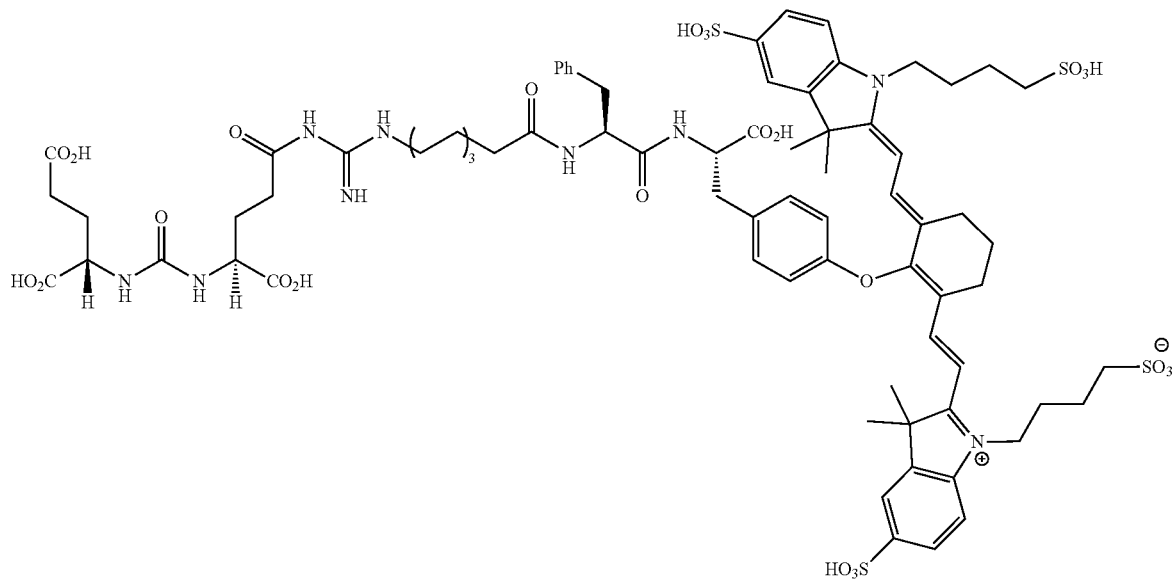
(67)
In some aspects the present invention includes a compound that has the structural formula:
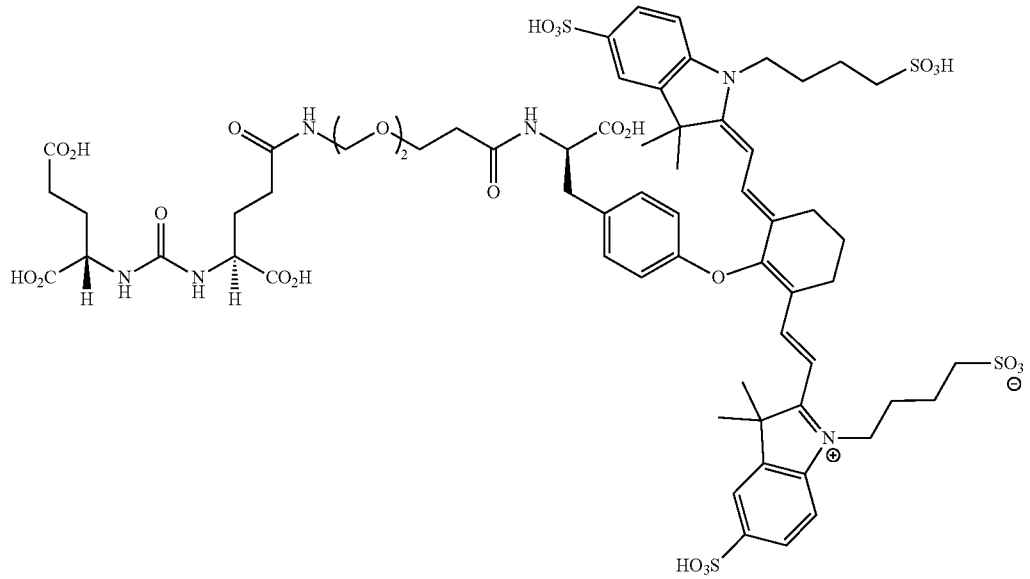
(68)
In some aspects the present invention includes a compound that has the structural formula:

(69)
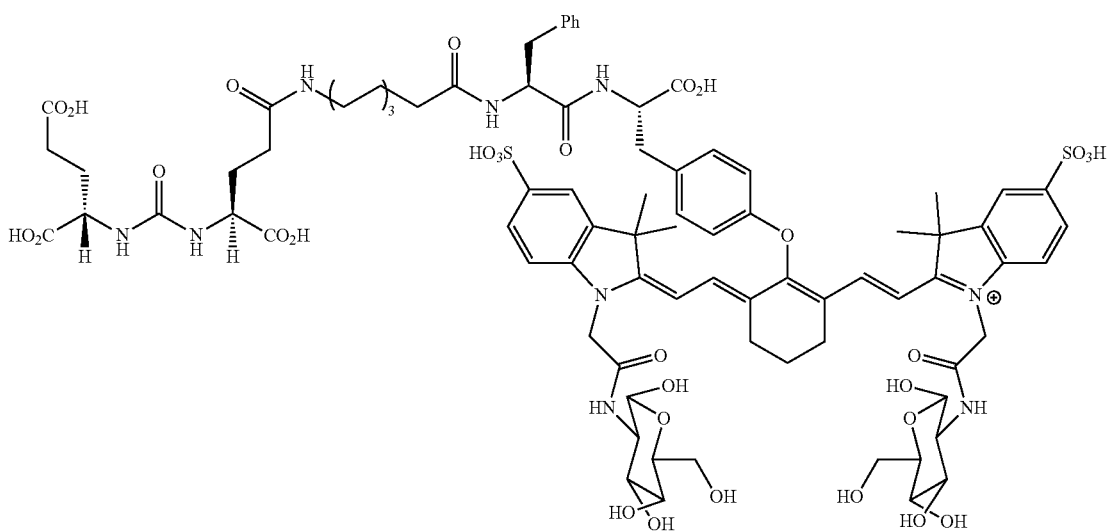
In some aspects the present invention includes a compound that has the structural formula:
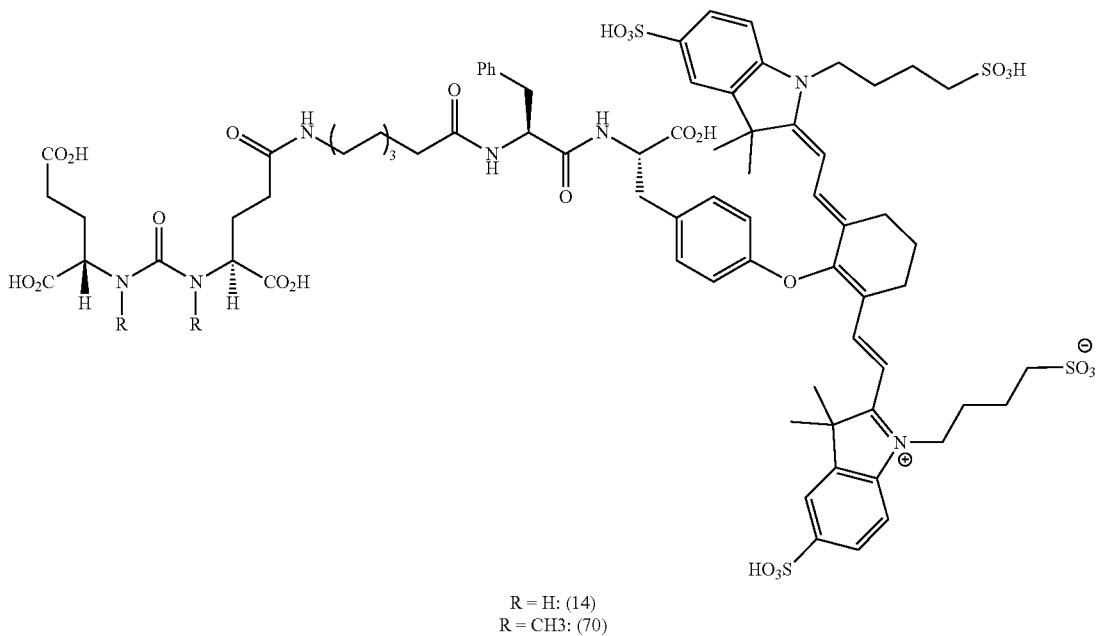
R = H: (14)
R = CH3: (70)
In some aspects the present invention includes a compound that has the structural formula:

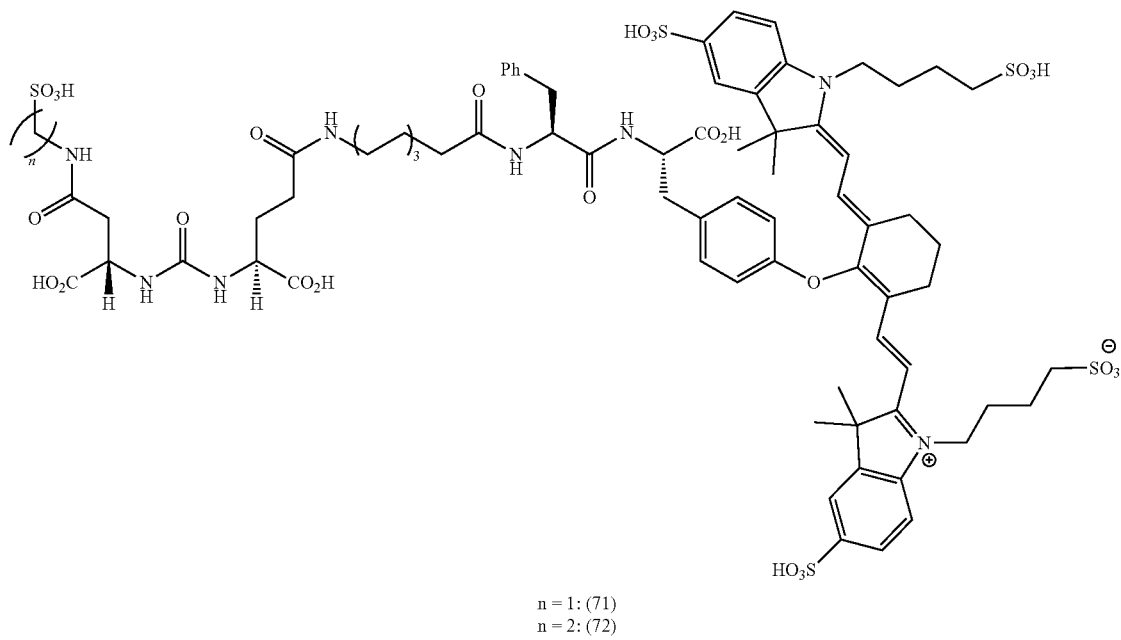
n = 1: (71)
n = 2: (72)
In some aspects the present invention includes a compound that has the structural formula:
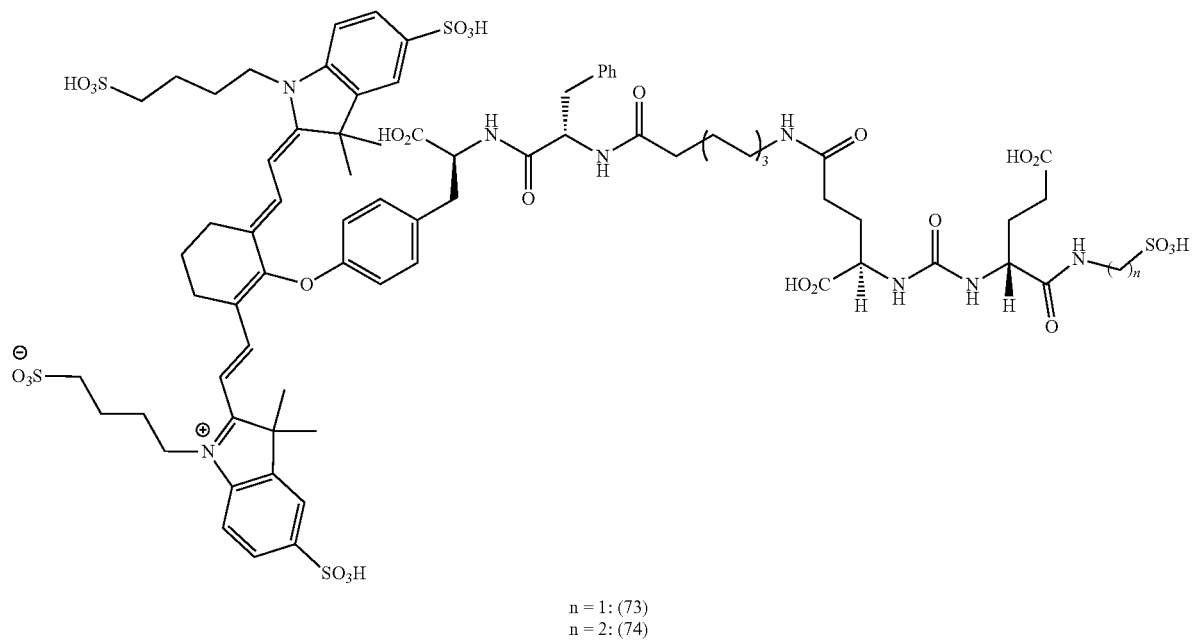
n = 1: (73)
n = 2: (74)
In some aspects the present invention includes a compound that has the structural formula:

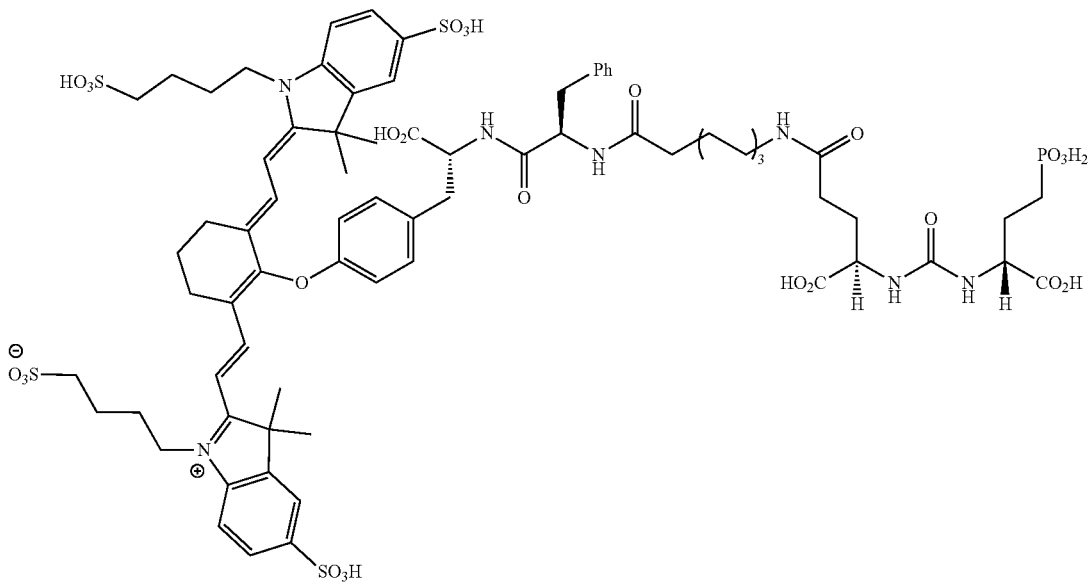
(75)
In some aspects the present invention includes a compound that has the structural formula:
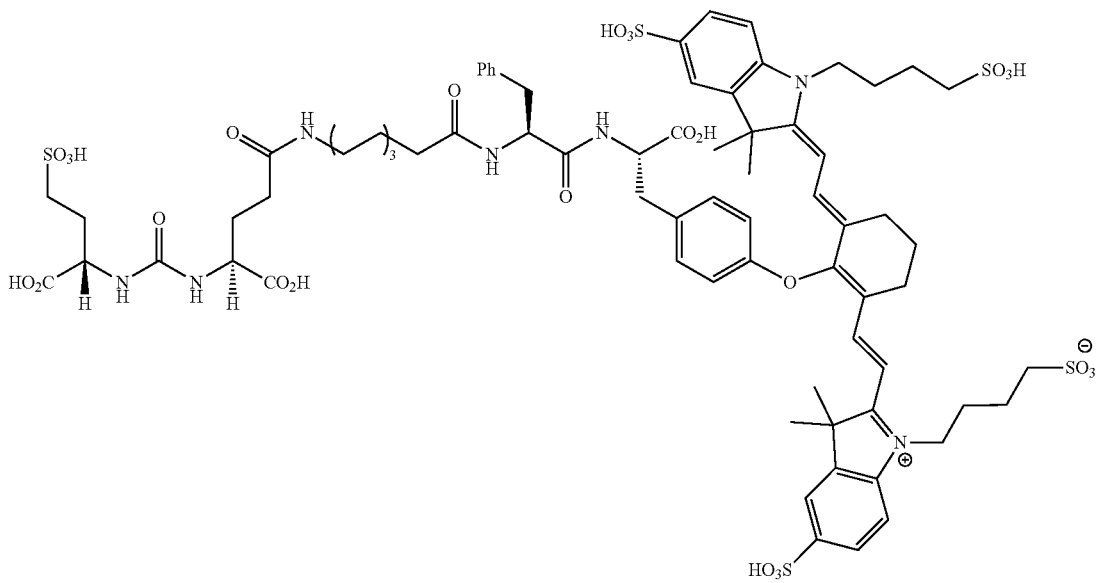
(76)
In some aspects the present invention includes a compound that has the structural formula:

(77)
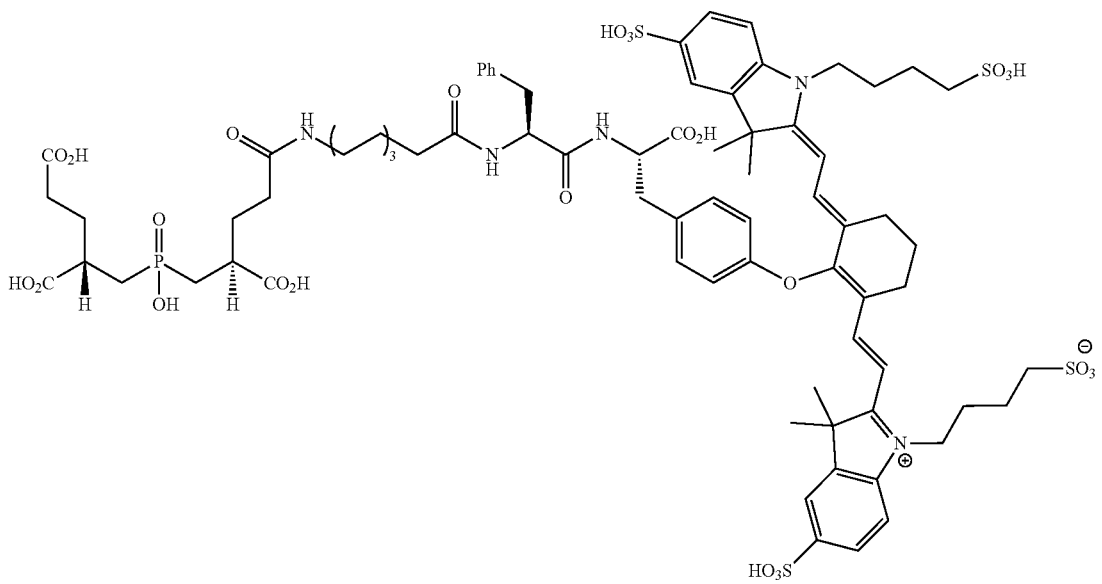
In some aspects the present invention includes a compound that has the structural formula:
(78)
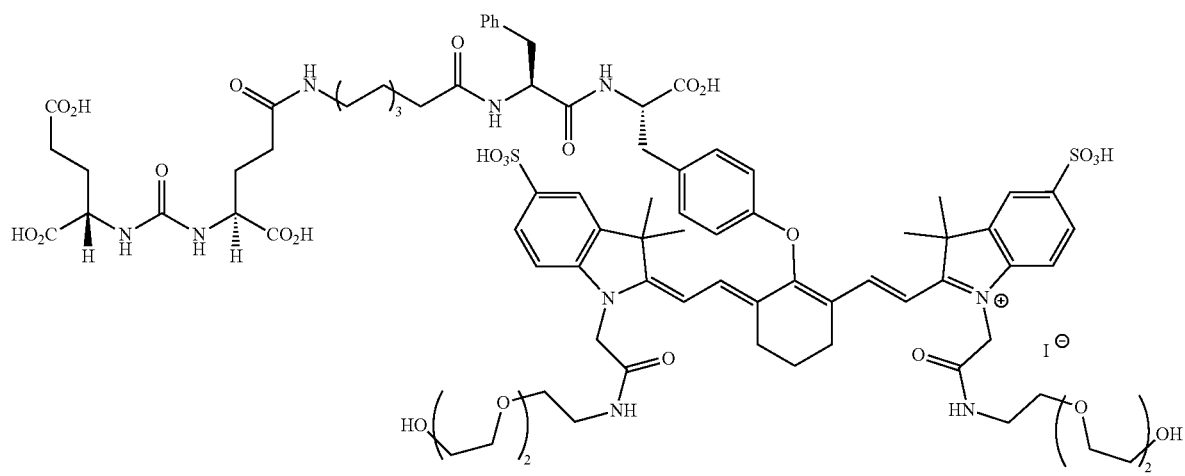
In some aspects the present invention includes a compound that has the structural formula:

(79)
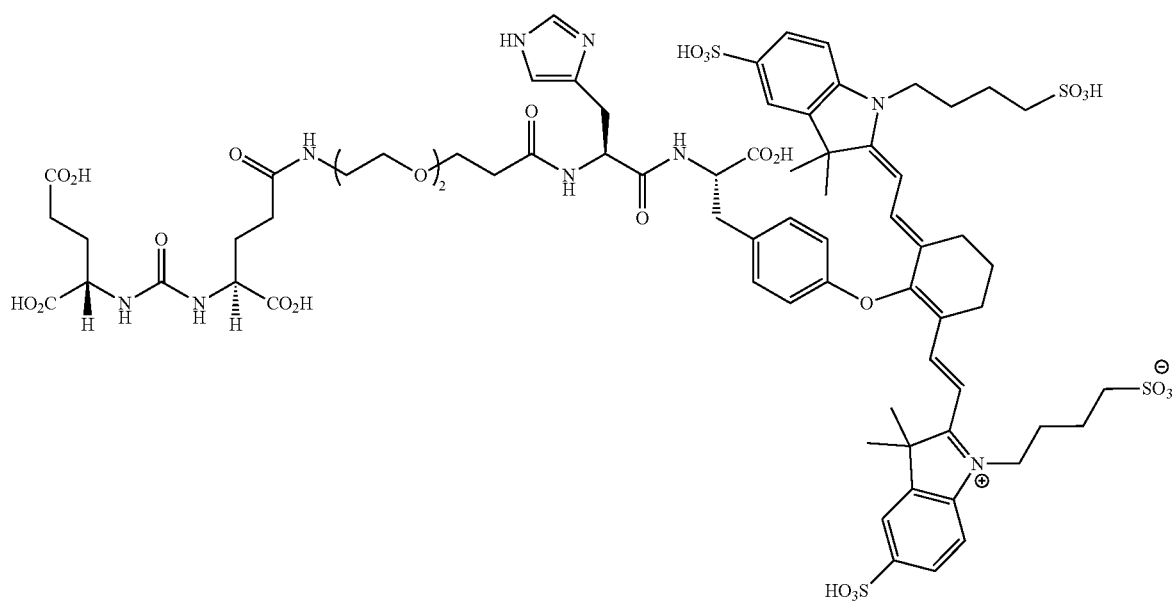
In some aspects the present invention includes a compound that has the structural formula:
(80)
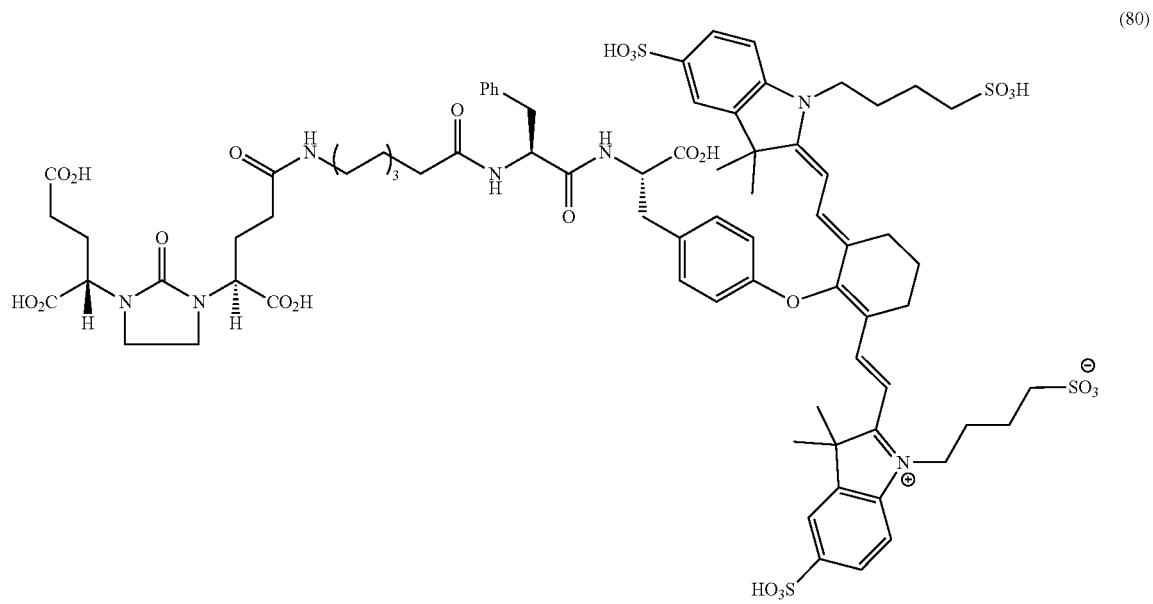
In some aspects the present invention includes a compound that has the structural formula:

(81)
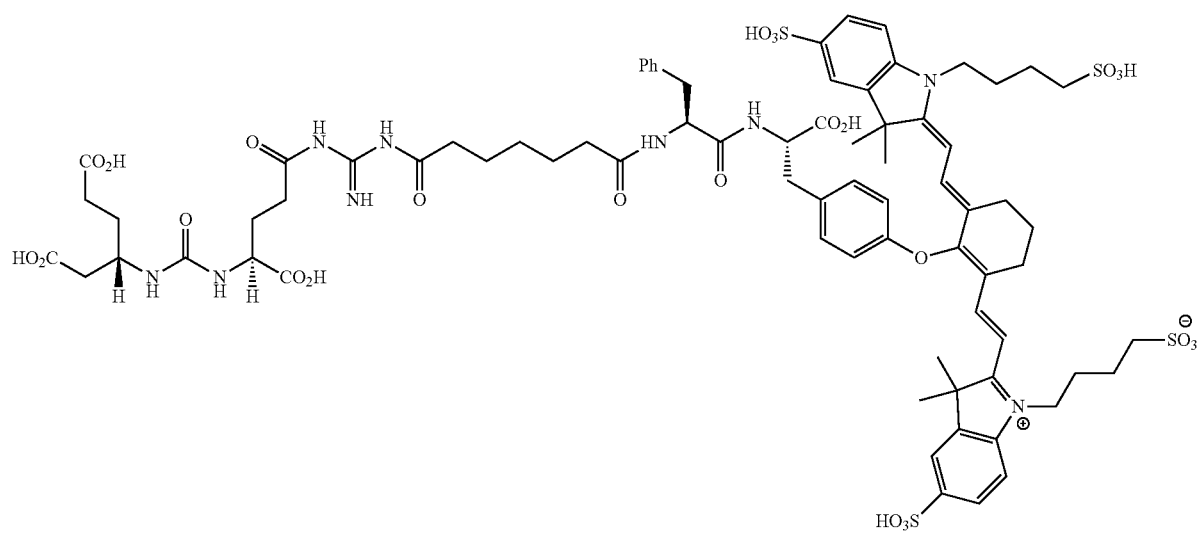
In some aspects the present invention includes a compound that has the structural formula:
(82)
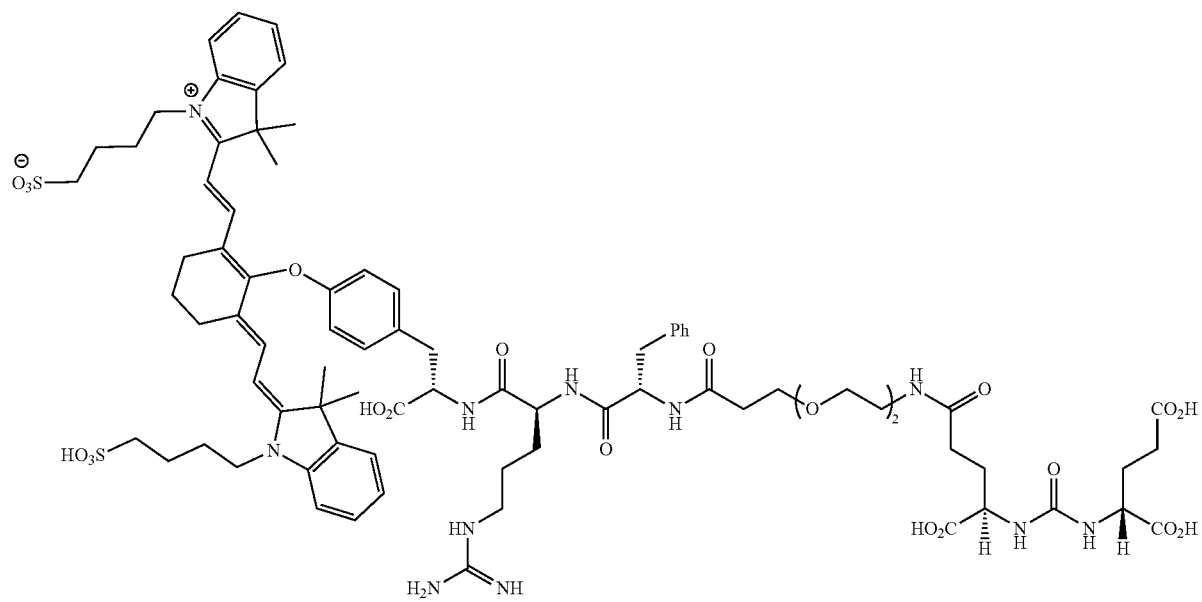
In some aspects the present invention includes a compound that has the structural formula:

(83)
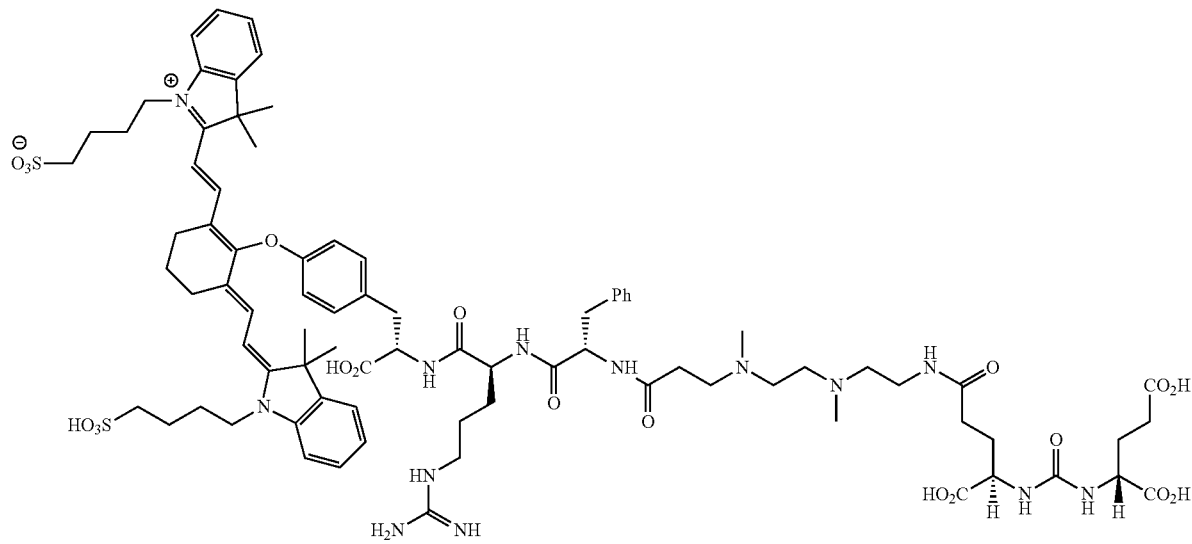
In some aspects the present invention includes a compound that has the structural formula:
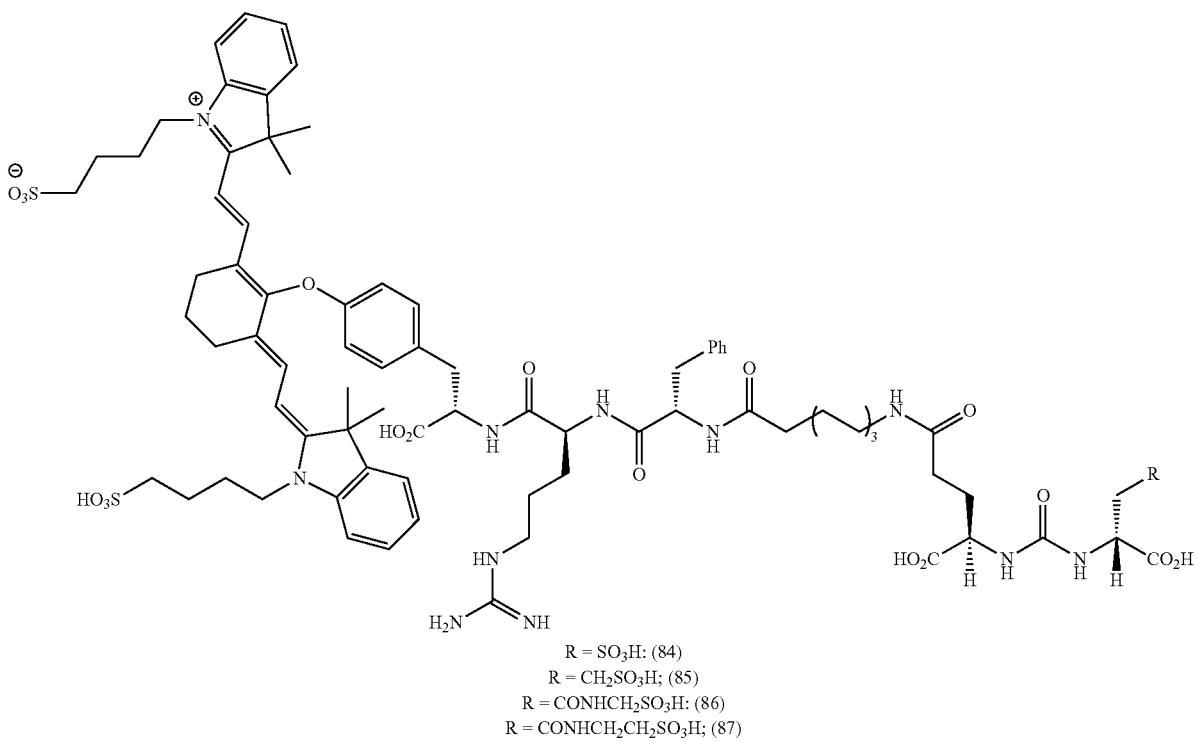
R = SO₃H: (84)
R = CH₂SO₃H; (85)
R = CONHCH₂SO₃H; (86)
R = CONHCH₂CH₂SO₃H; (87)
In some aspects the present invention includes a compound that has the structural formula:

(88)
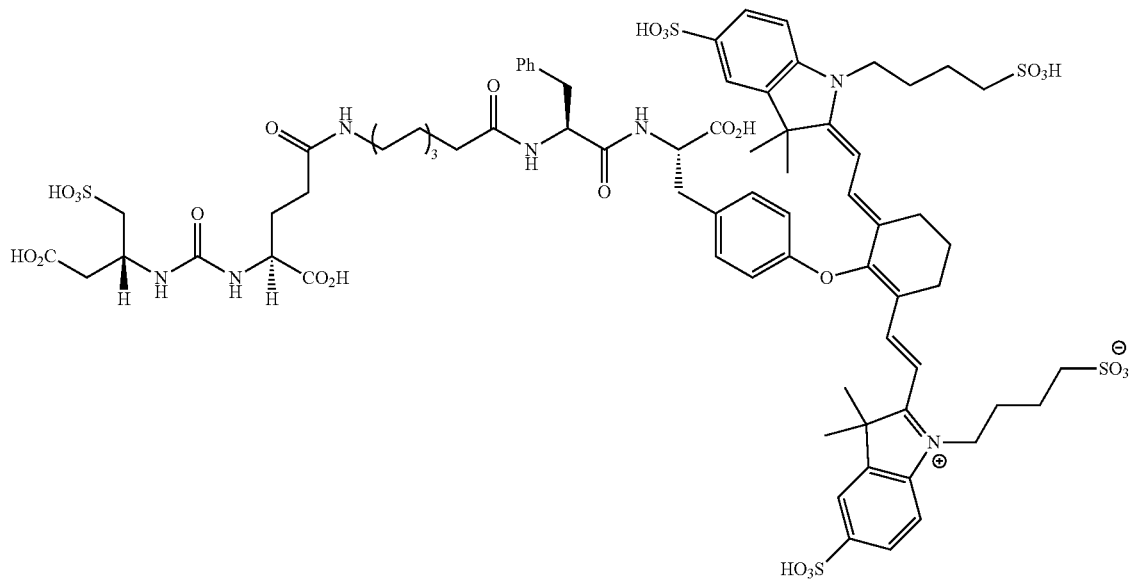
In some aspects the present invention includes a compound that has the structural formula:
(89)
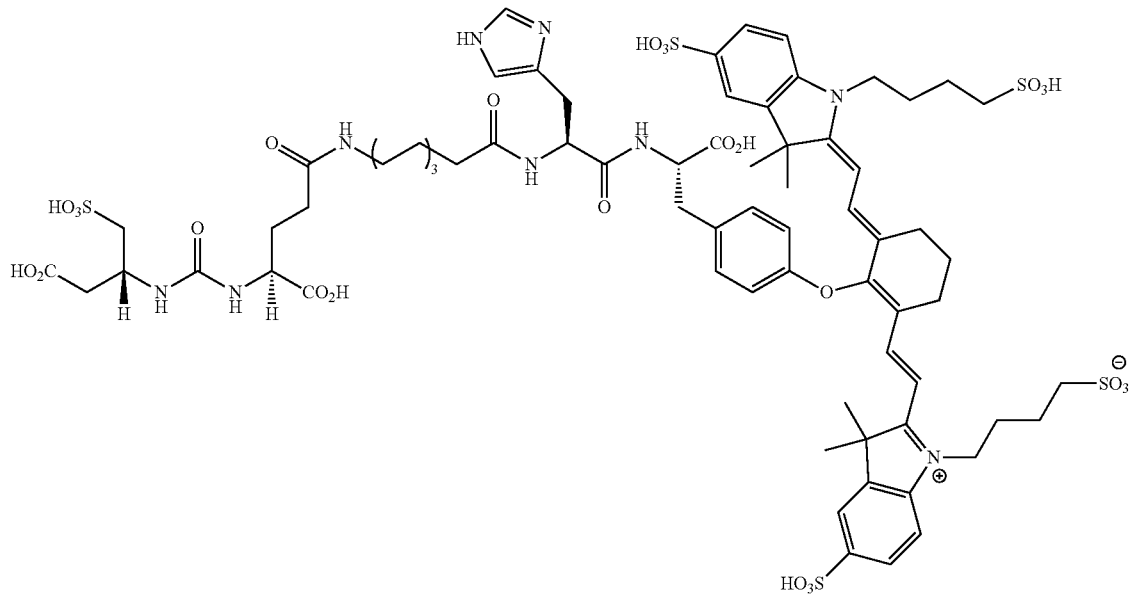
In some aspects the present invention includes a compound that has the structural formula:

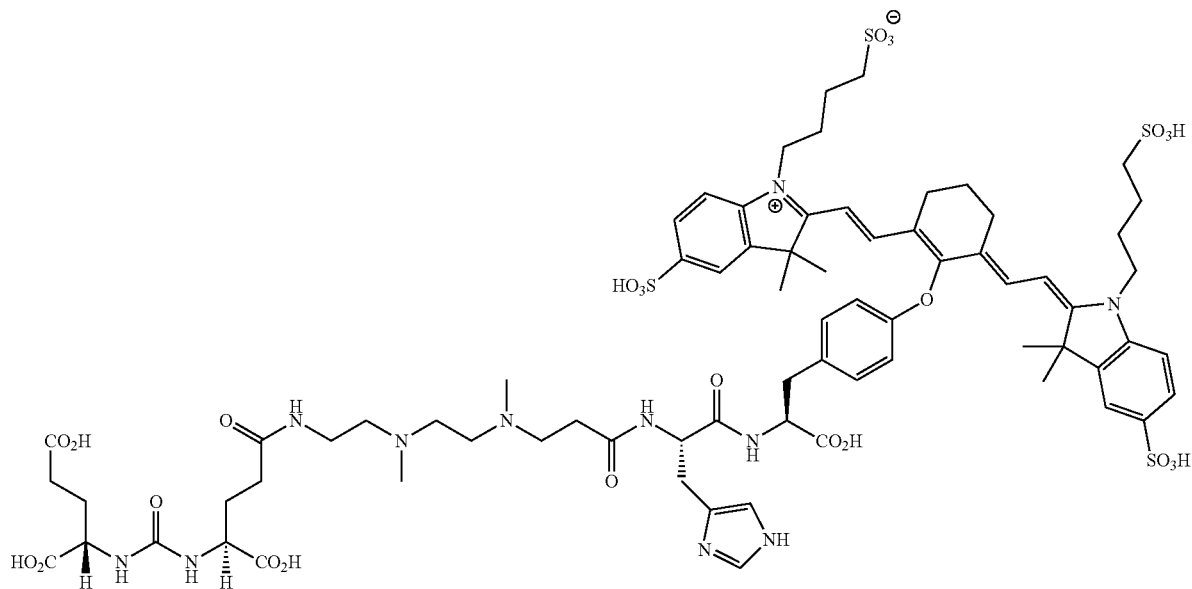
(90)
In some aspects the present invention includes a compound that has the structural formula:
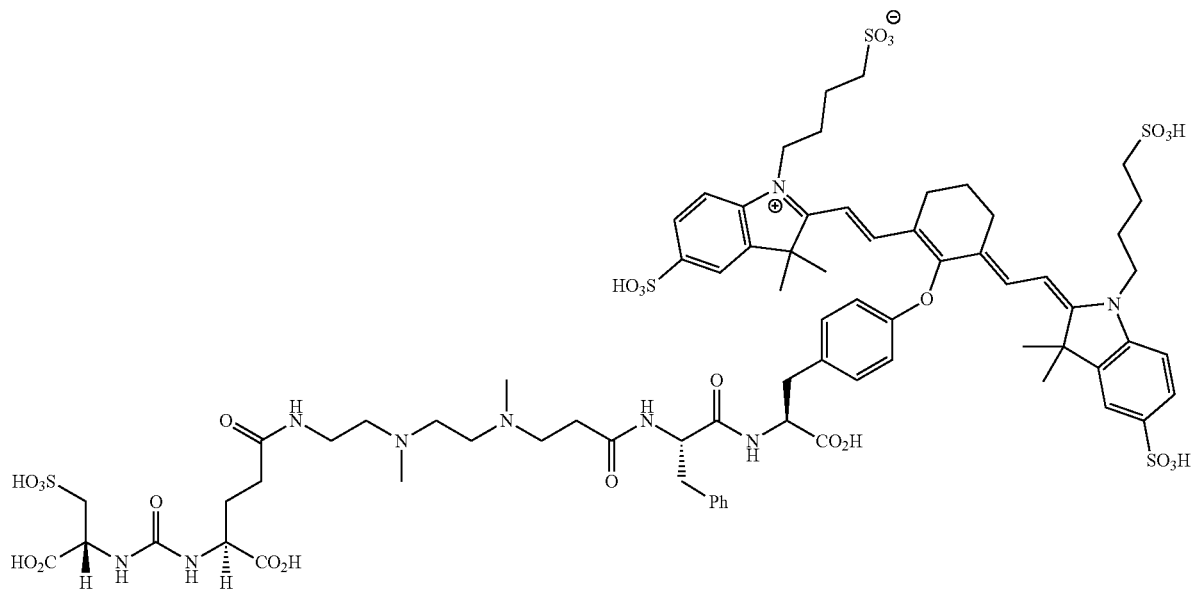
(91)
In some aspects the present invention includes a compound that has the structural formula:

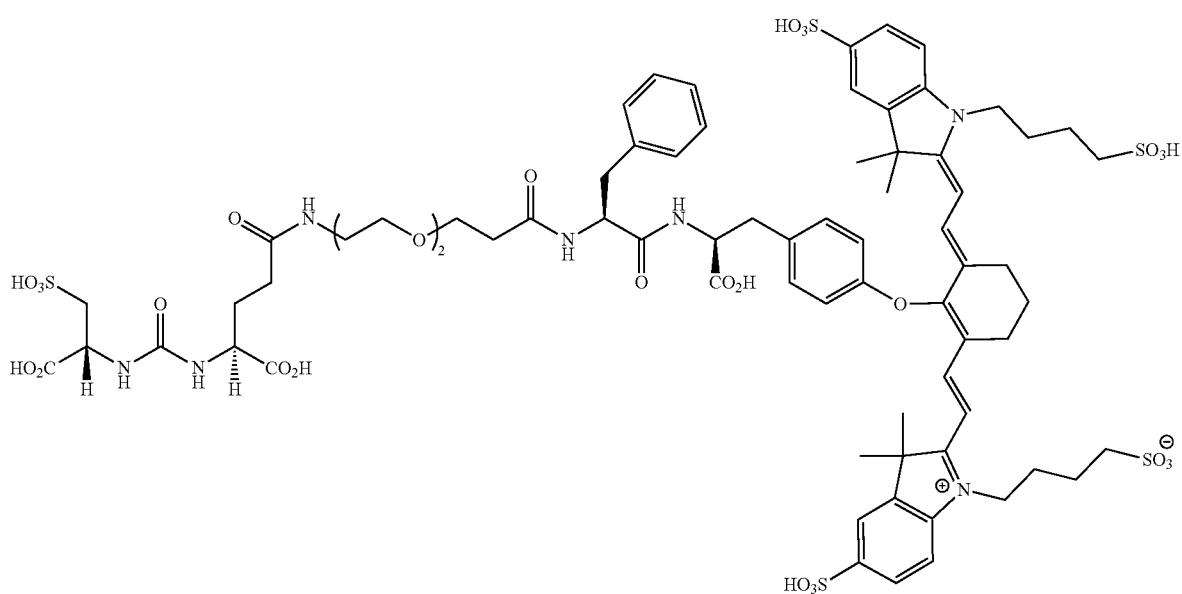
(92)
Additional preferred compounds of the invention include the following:
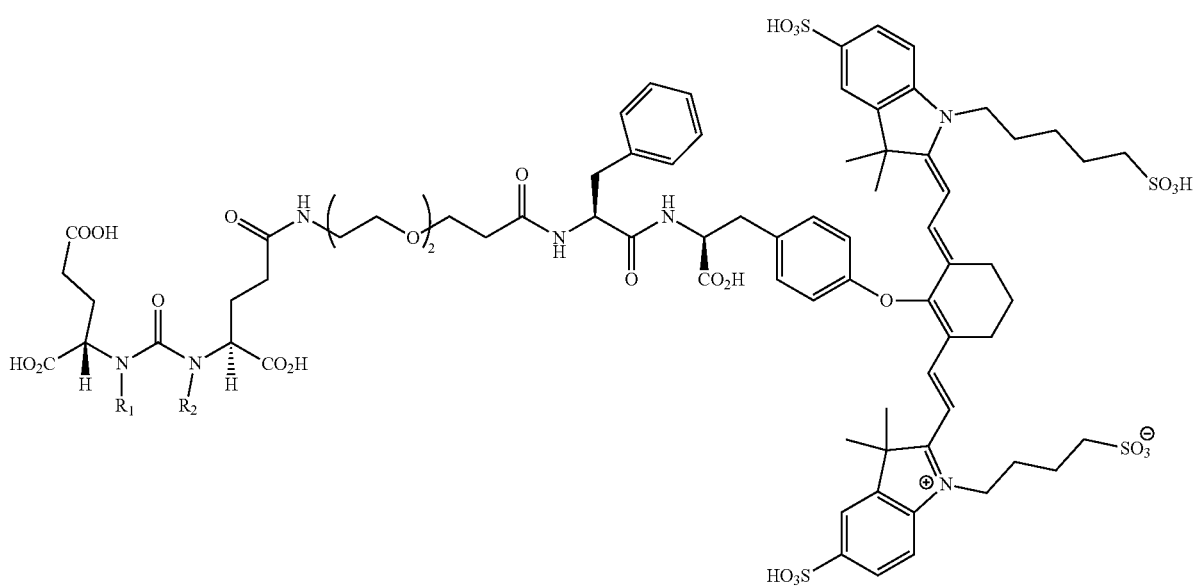
R1 = CH3, R2 = H: (93)
R1 = H, R2 = CH3: (94)
R1 = CH2COOH, R2 = H: (95)
R1 = H, R2 = CH2COOH: (96)
R1 = R2 = CH2COOH: (97)

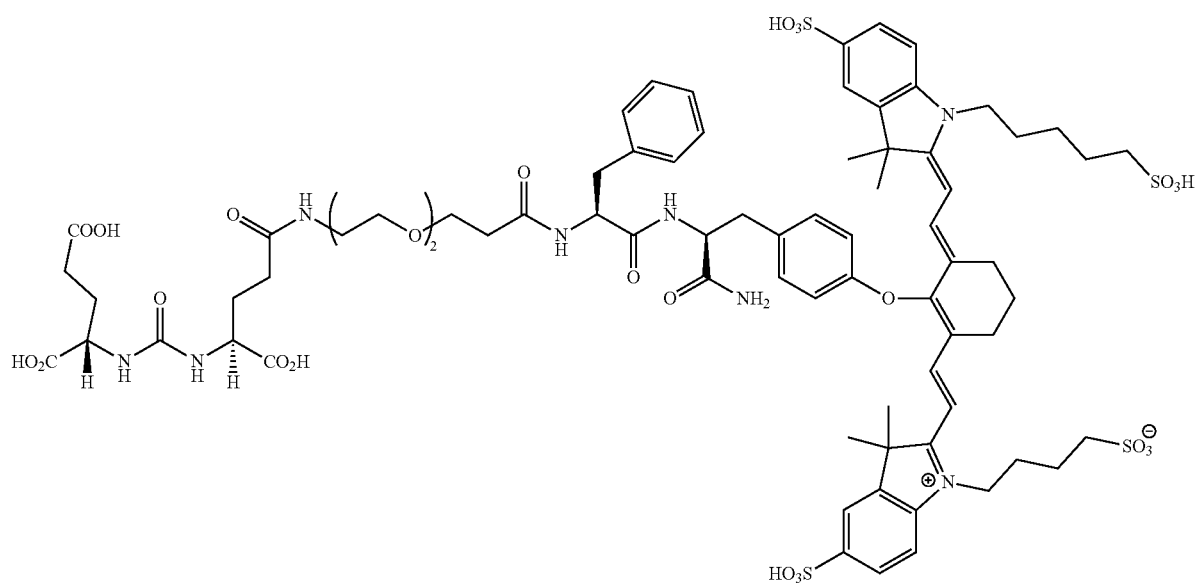
(98)
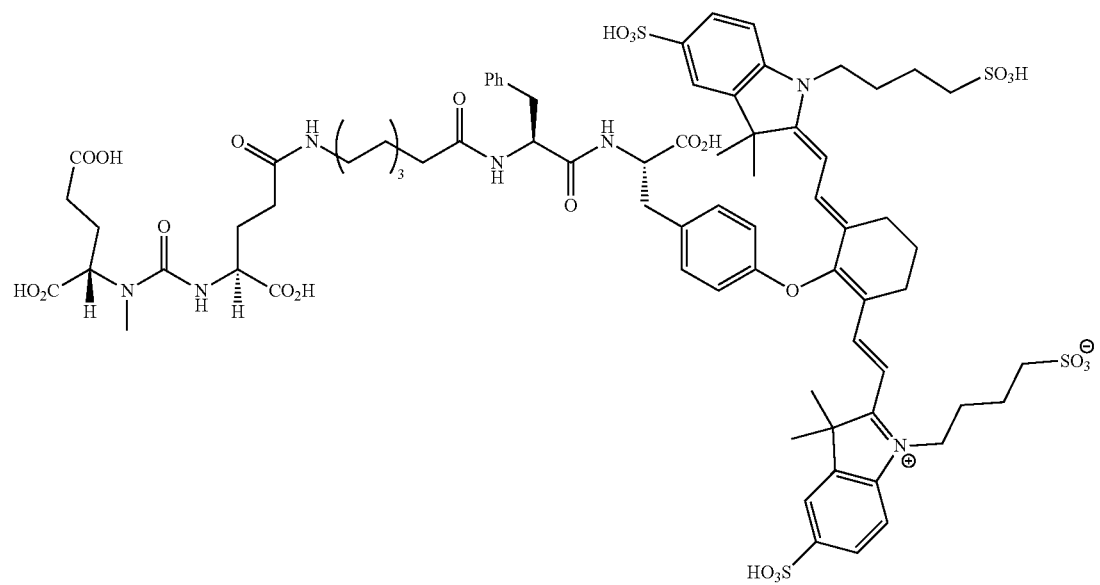
(99)

-continued
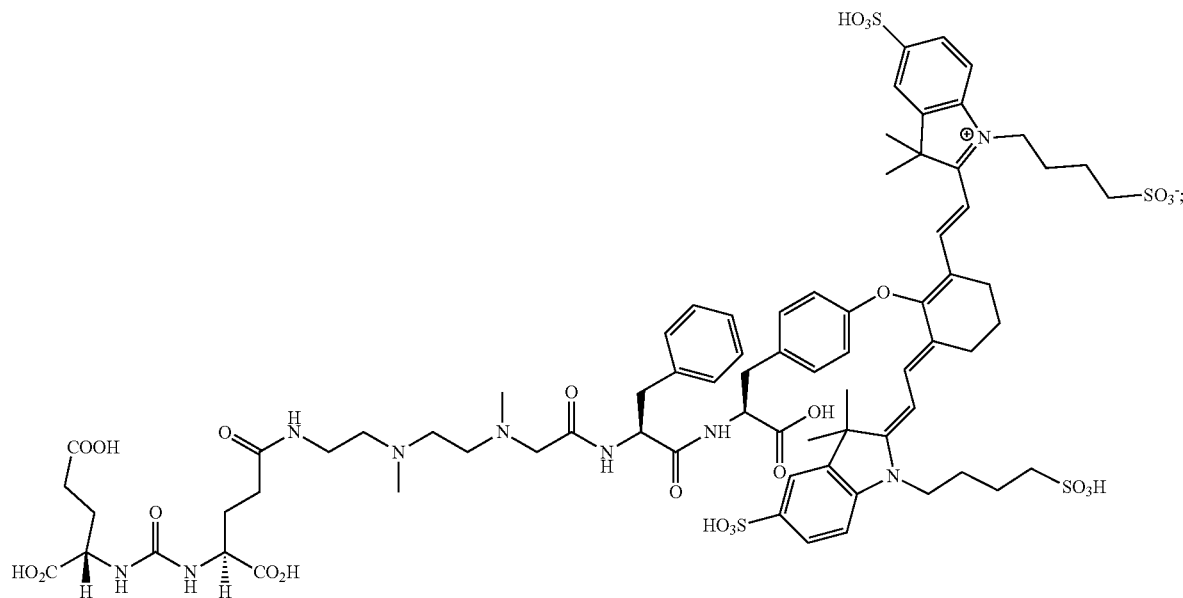
(100)
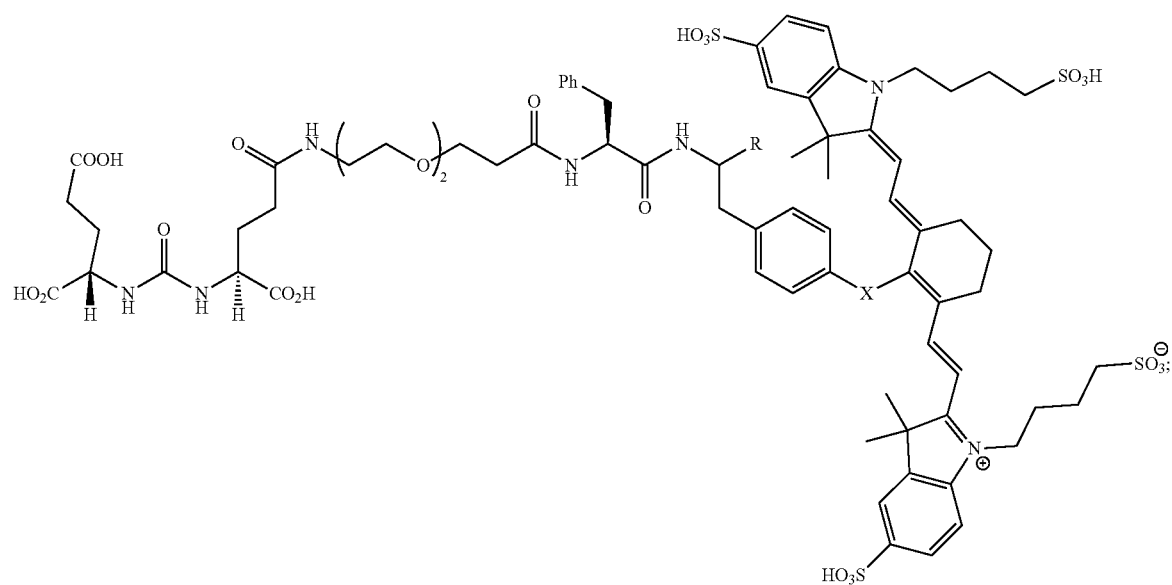
R = CO₂H, X = O: (35)
R = H, X = O: (101)
R = H, X = N: (102)
R = H, X = S: (103)

-continued
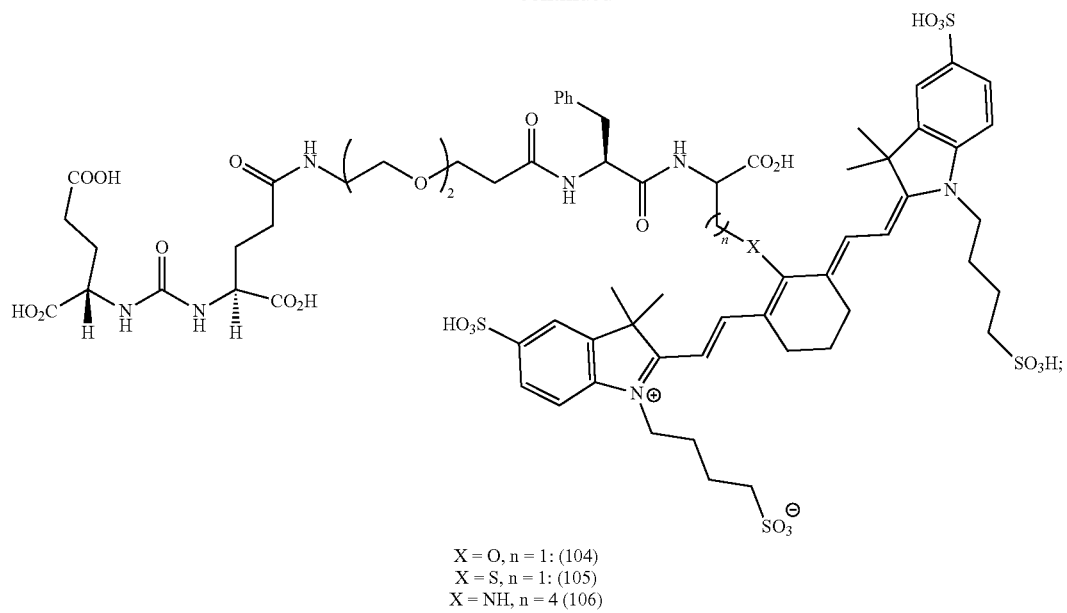
X = O, n = 1: (104)
X = S, n = 1: (105)
X = NH, n = 4 (106)
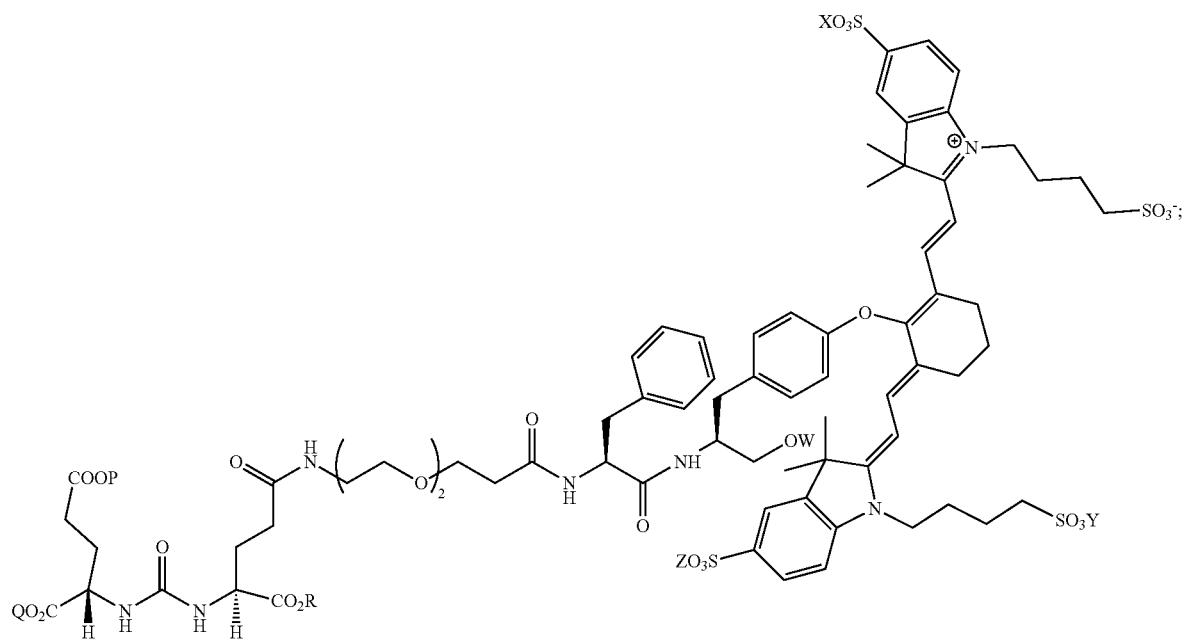
(107)
P, Q, R, W, X, Y, Z can be H (35), Na, K, NH₄

(108)
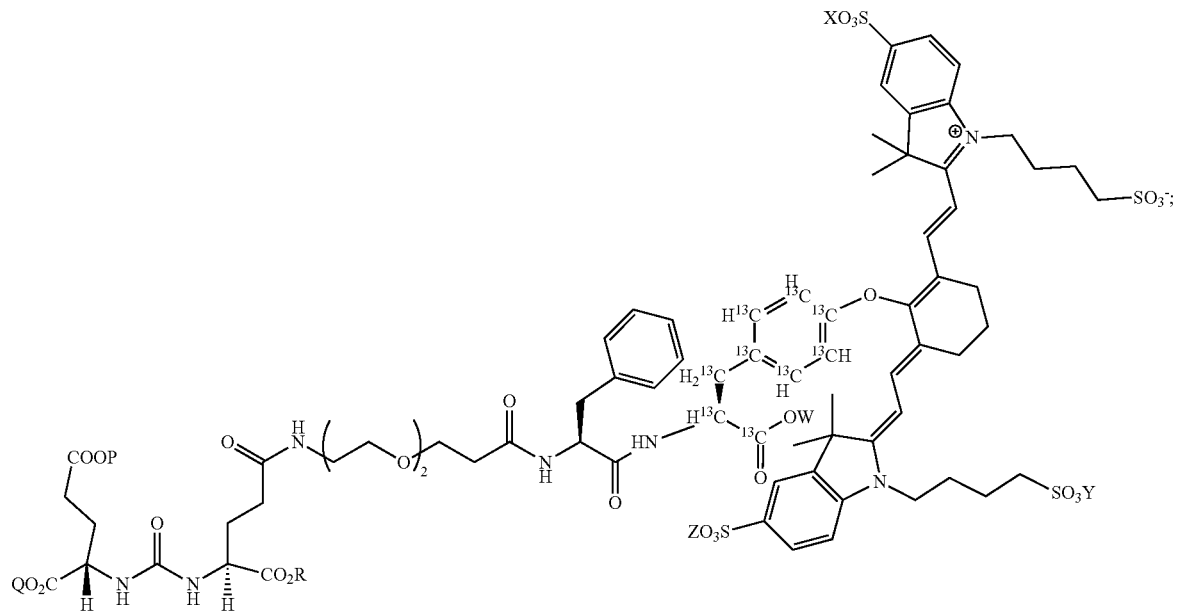
P, Q, R, W, X, Y, Z can be H, Na, K, NH$_4$
(109)
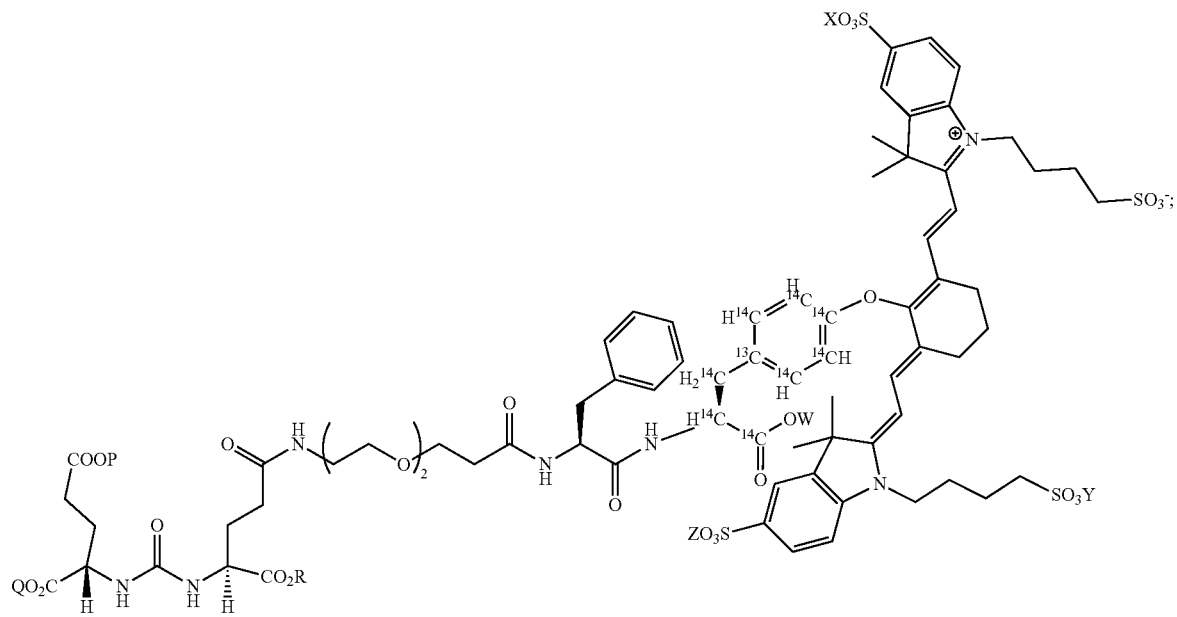
P, Q, R, W, X, Y, Z can be H, Na, K, NH$_4$

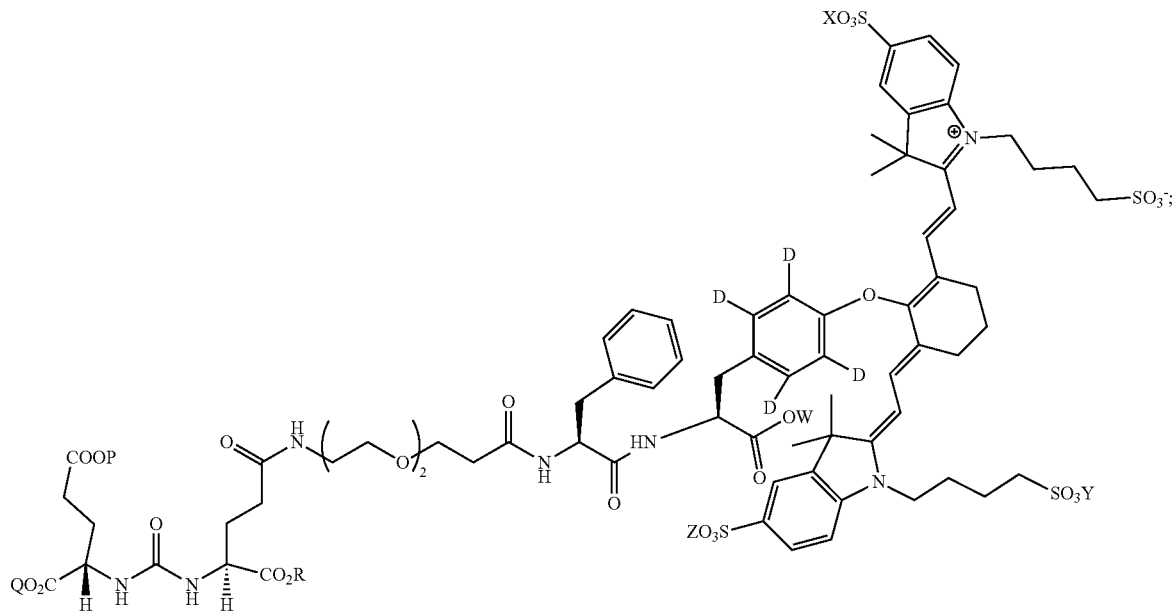
(110)
P, Q, R, W, X, Y, Z can be H, Na, K, NH₄
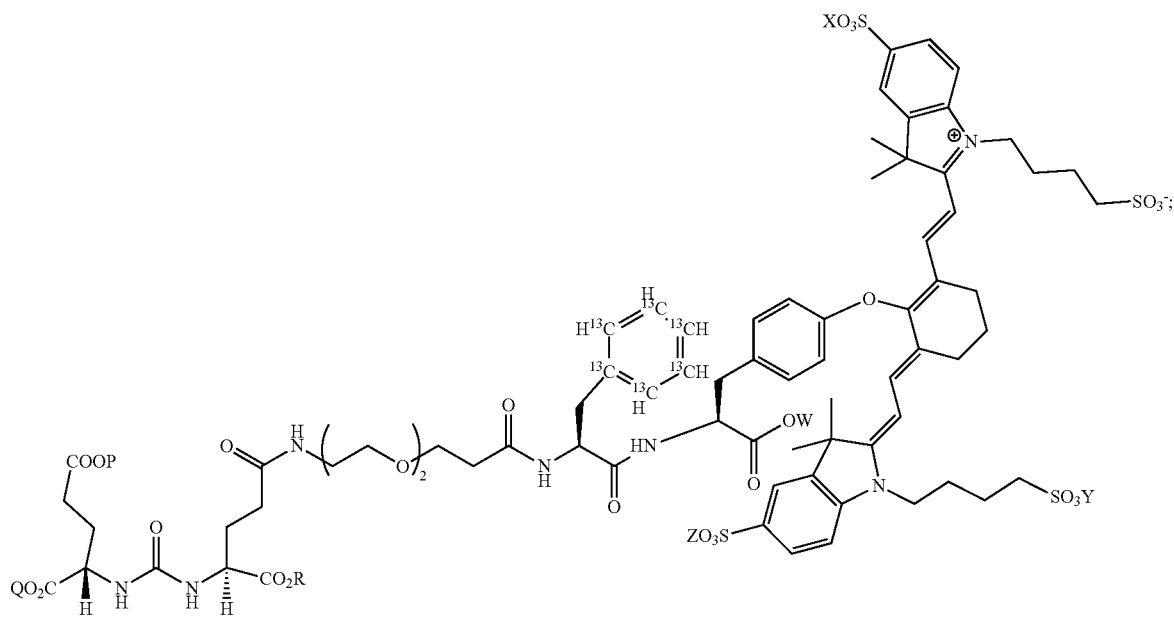
(111)
P, Q, R, W, X, Y, Z can be H, Na, K, NH₄

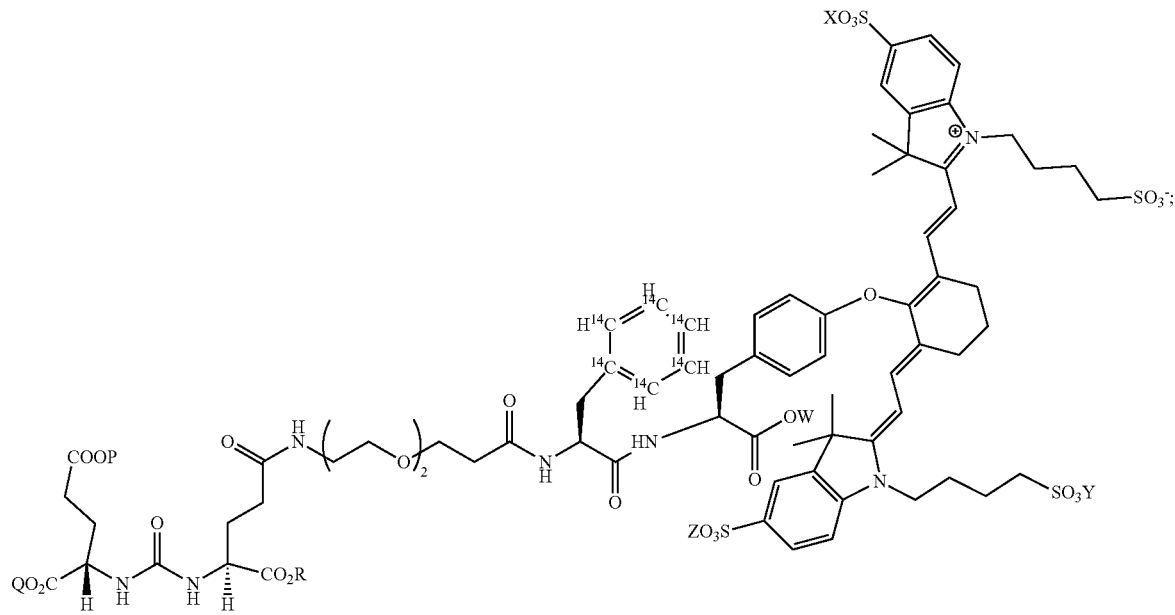
(112)
P, Q, R, W, X, Y, Z can be H, Na, K, NH₄
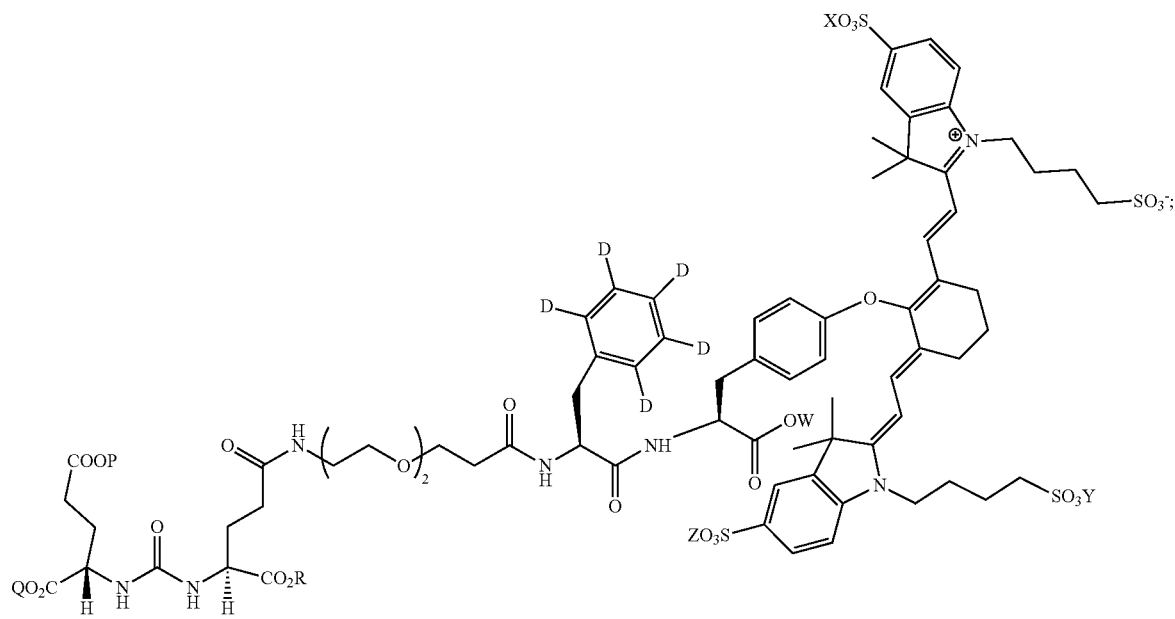
(113)
P, Q, R, W, X, Y, Z can be H, Na, K, NH₄
and
A compound of structure 35 is particularly preferred in the present invention.

(35)
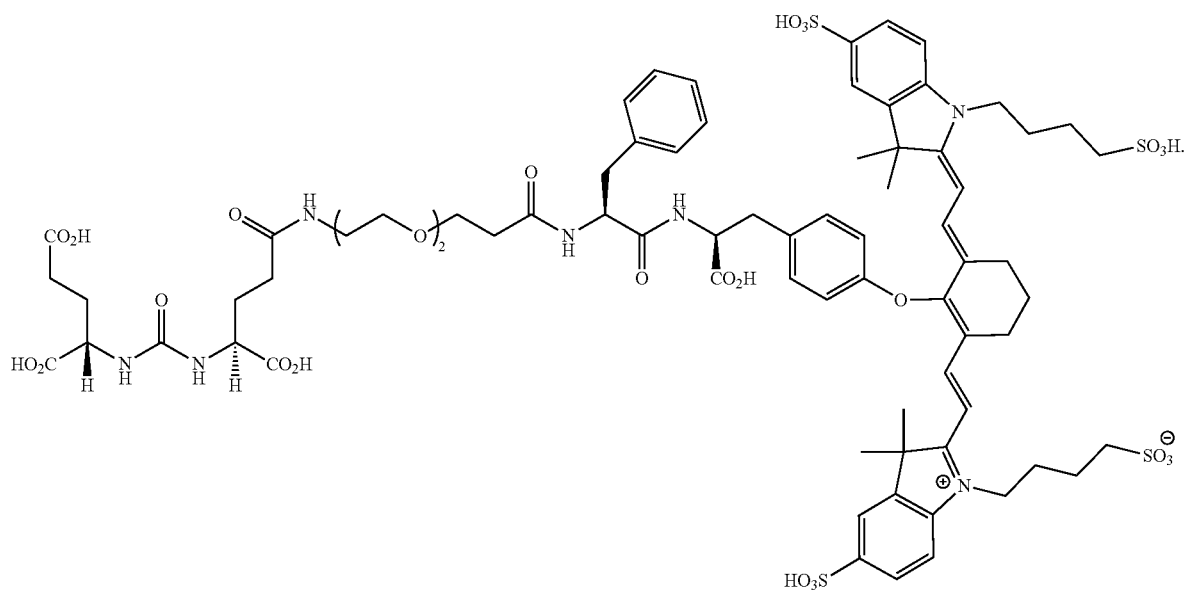
In addition, stereoisomers of compound 35 such as those shown in the following table also are contemplated to be useful PSMA-targeted near-infra red (NIR) dyes for use in the methods of the present invention.
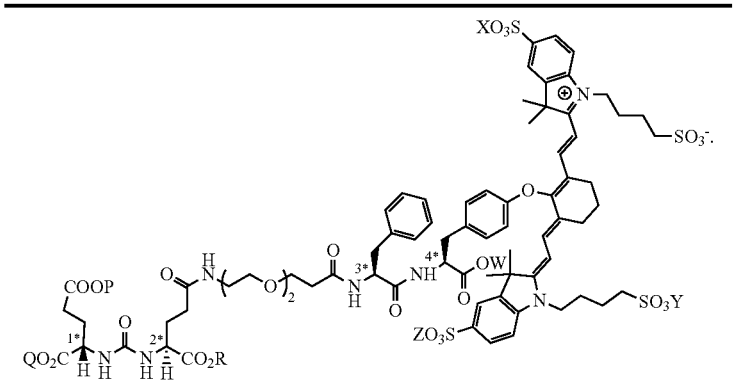
| Compound | Chiral Center | | | |
|---|---|---|---|---|
| | 1* | 2* | 3* | 4* |
| 35 | L | L | L | L |
| 114 | L | L | L | D |
| 115 | L | L | D | L |
| 116 | L | L | D | D |
| 117 | L | D | L | L |
| 118 | L | D | L | D |
| 119 | L | D | D | L |
| 120 | L | D | D | D |
| 121 | D | L | L | L |
| 122 | D | L | L | D |
| 123 | D | L | D | L |
| 124 | D | L | D | D |
| 125 | D | D | L | L |
| 126 | D | D | L | D |
| 127 | D | D | D | L |
| 128 | D | D | D | D. |
Note:
Chiral center is indicated as *

Additional preferred compounds of the invention include the following:

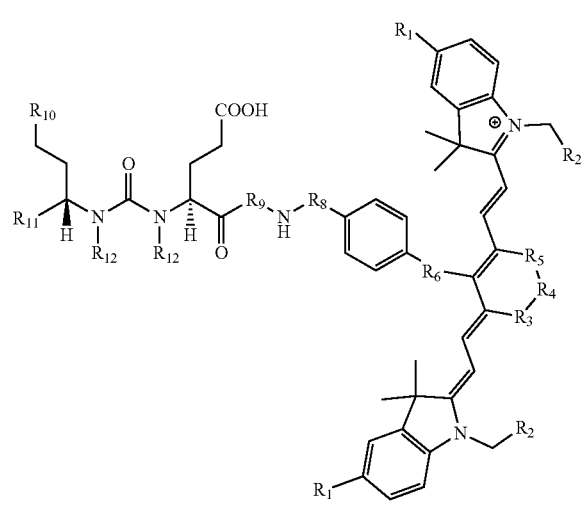

or a pharmaceutically acceptable salt thereof, or isotopes thereof, wherein:

$R_1$ represents a hydrogen or $SO_3H$;

$R_2$ represents a hydrogen, or $CH_3$, or $C_3H_6SO_3$, or $C_3H_6SO_3H$ or $C_4H_8SO_3$, or $C_4H_8SO_3H$ or $C_3H_6N^+(CH_3)_3$;

$R_3$, and $R_5$ each represents a carbon, optionally one or more sharing bonds, or oxygen, or sulfur, or nitrogen $R_4$ represents a carbon with optionally one or more sharing bonds;

$R_6$ represents nitrogen, oxygen, or sulfur or no atom (direct C—C bond between aromatic ring and vinyl ring);

$R_7$ is optional and when present represents electron donating aromatic substitution group;

$R_8$ is optional and when present represents linkers with aromatic amino acids such as Phe, Trp, His, Tyr, or derivative of them, and/or cationic amino acids such Arg, Lys, or derivative of them, and/or anionic amino acids such as Asp, Glu or derivative of them, and/or unnatural amino acids of aromatic/cationic/anionic acids or derivative;

$R_9$ is optional and when present represents a linear carbon chain, or polyethylene glycol linkers, polyethylene amine linkers, cationic linker, or derivative of them;

$R_{10}$ represents a $CO_2H$, $PO_3H_2$, $SO_3H$, $CH_2SO_3H$, $CH_2CONHCH_2SO_3H$, $CH_2CONHCH_2CH_2SO_3H$;

$R_{11}$ represents $CO_2H$, $SO_3H$, $CH_2CONHCH_2SO_3H$, $CH_2CONHCH_2CH_2SO_3H$; and $R_{12}$ represents independently represents a hydrogen, a methyl group, $CH_2COOH$, a $CH_2$ and may optionally represent each a $CH_2$ sharing a bond.

Additional preferred compounds of the invention include the following:

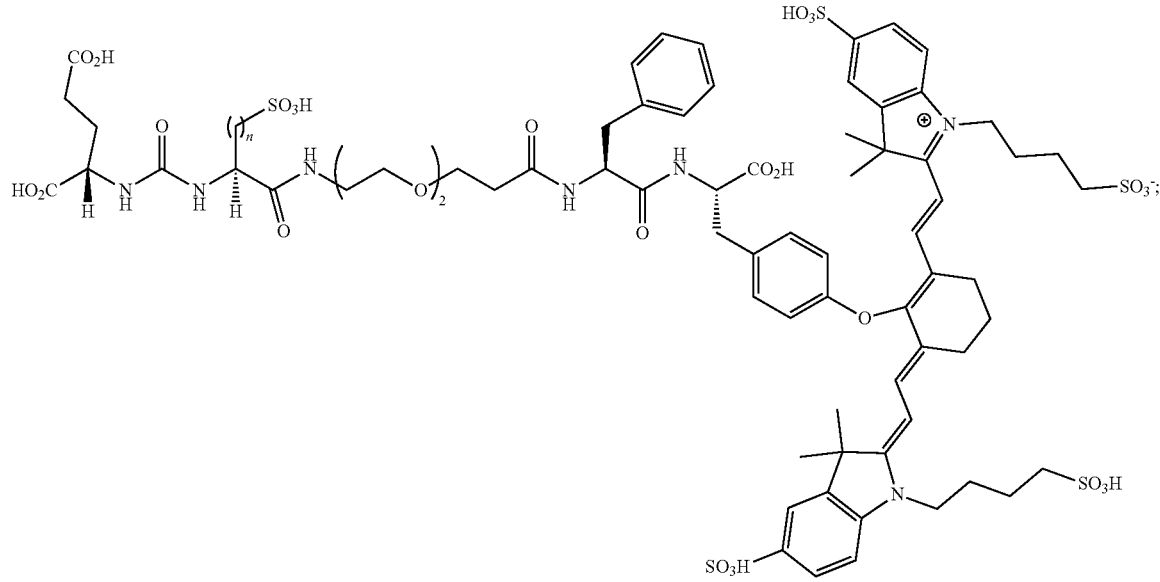

n = 1:129
n = 2:130

-continued
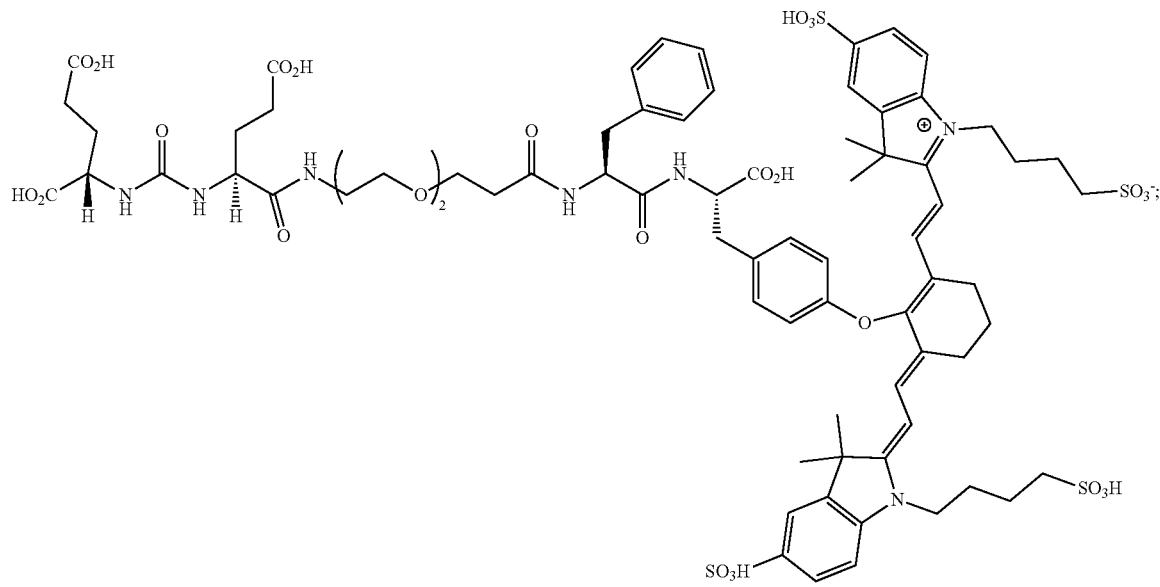
131
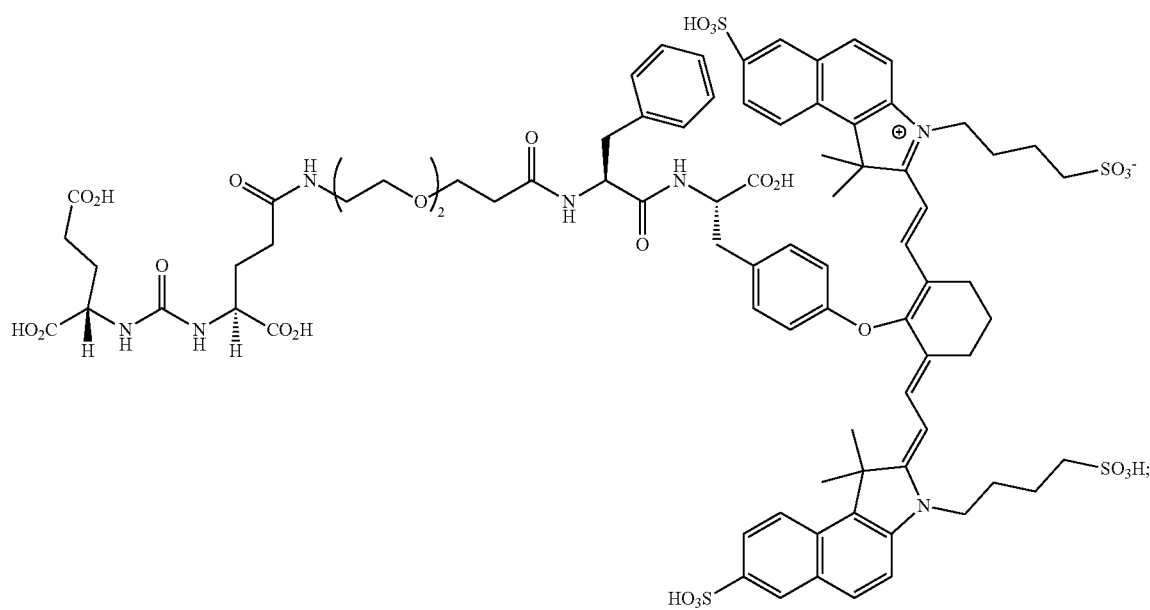
132

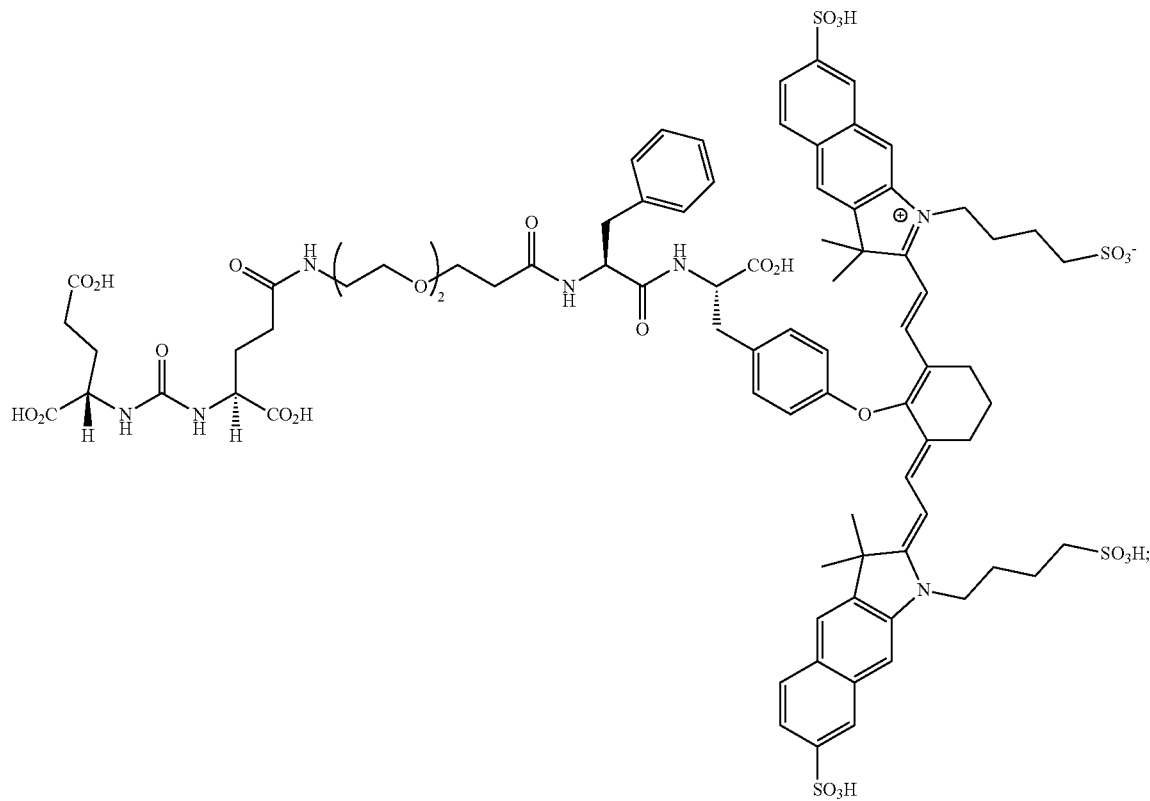
133
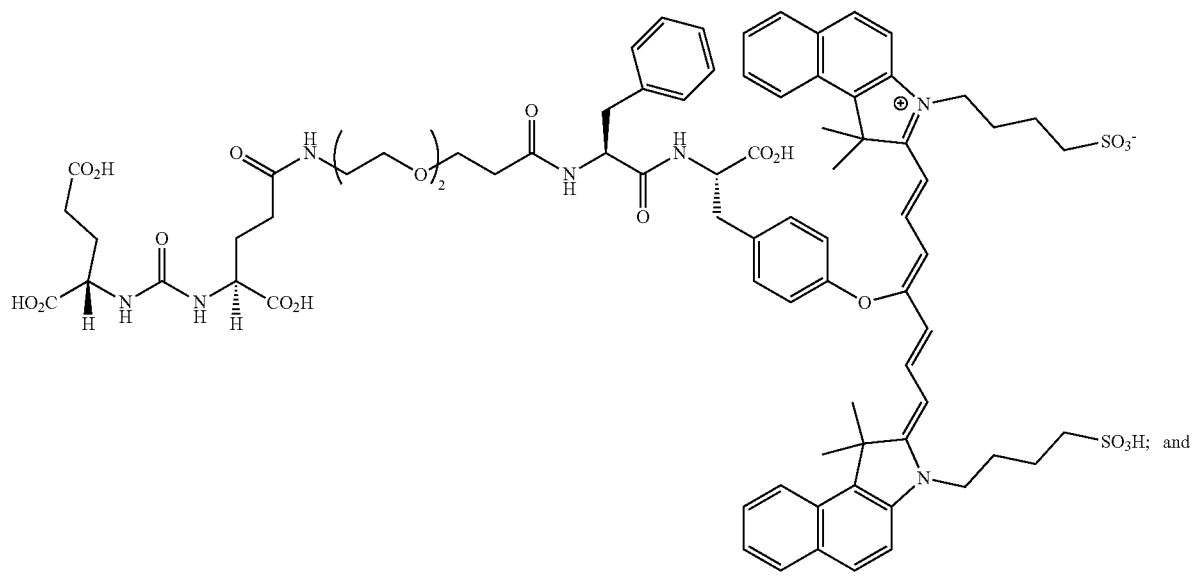
134

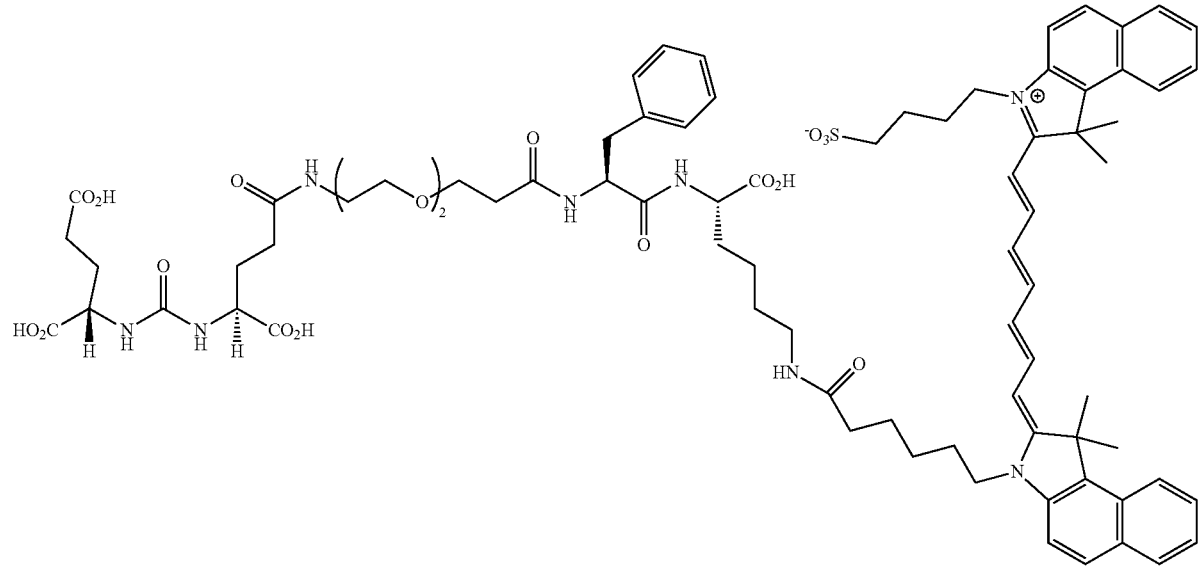
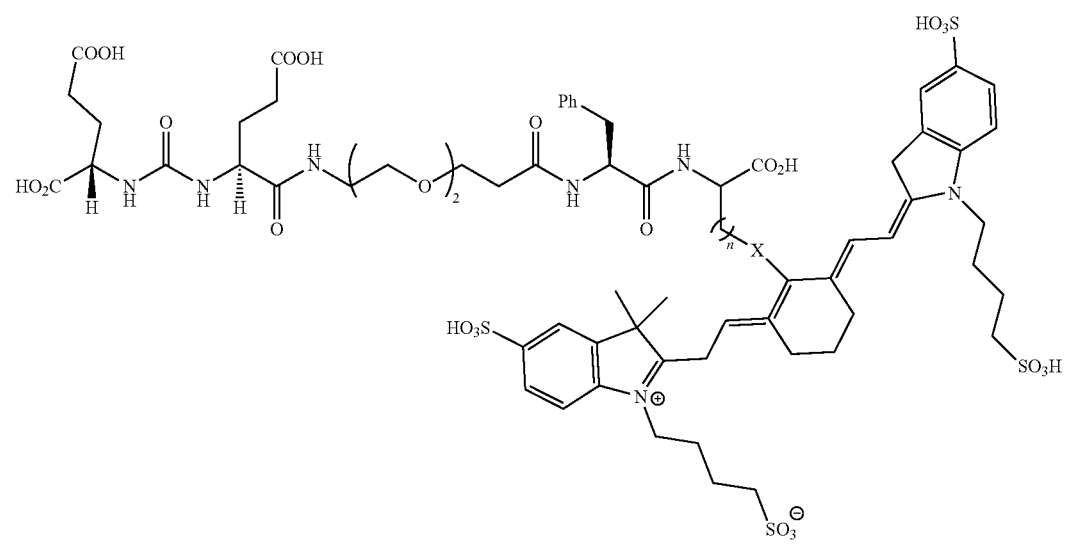
X = O, n = 1: (136)
X = S, n = 1: (137)
X = NH, n = 4 (138)

117 118
-continued
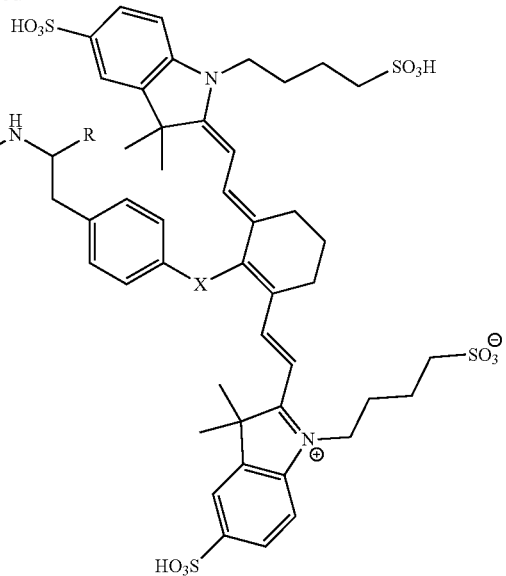
R = CO₂H, X = O: (139)
R = H, X = O: (140)
R = H, X = N: (141)
R = H, X = S: (142)
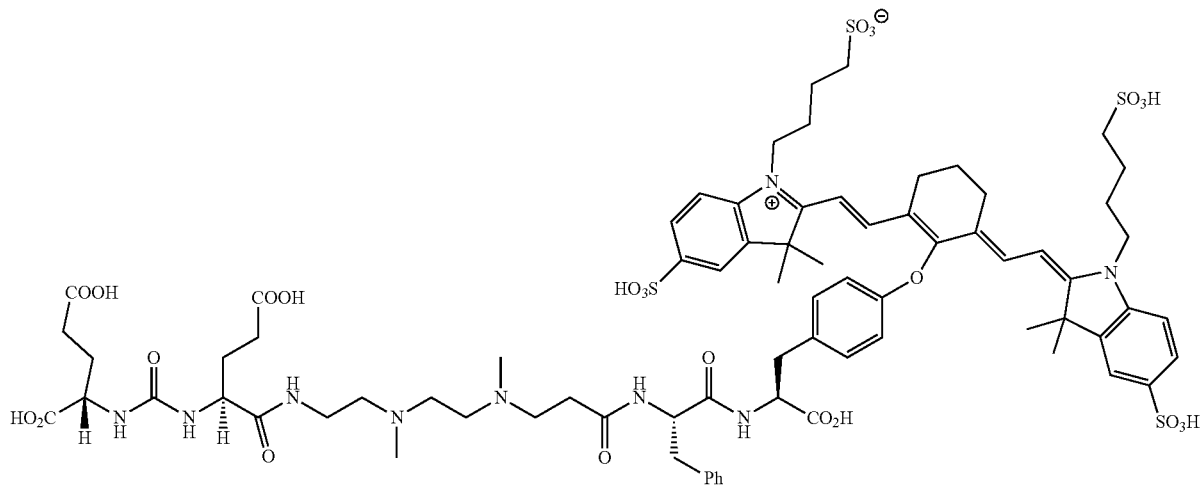
(143)
Additional preferred compounds of the invention include the following:

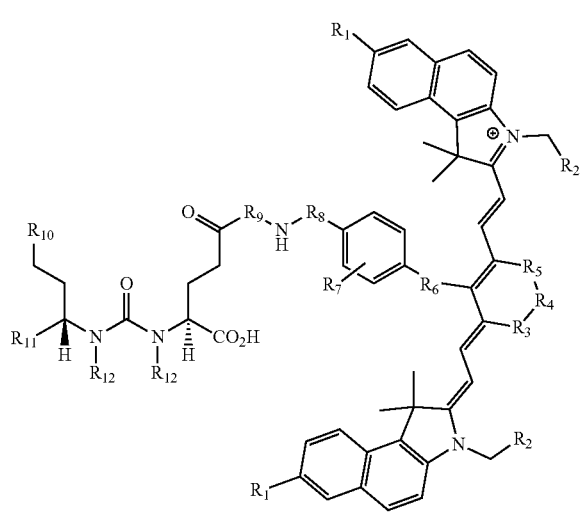

or a pharmaceutically acceptable salt thereof, or isotopes thereof, wherein:

$R_1$ represents a hydrogen or $SO_3H$;

$R_2$ represents a hydrogen, or $CH_3$, or $C_3H_6SO_3$, or $C_3H_6SO_3H$ or $C_4H_8SO_3$, or $C_4H_8SO_3H$ or $C_3H_6N^+(CH_3)_3$;

$R_3$, and $R_5$ each represents a carbon, optionally one or more sharing bonds, or oxygen, or sulfur, or nitrogen $R_4$ represents a carbon with optionally one or more sharing bonds;

$R_6$ represents nitrogen, oxygen, or sulfur or no atom (direct C—C bond between aromatic ring and vinyl ring);

$R_7$ is optional and when present represents electron donating aromatic substitution group;

$R_8$ is optional and when present represents linkers with aromatic amino acids such as Phe, Trp, His, Tyr, or derivative of them, and/or cationic amino acids such Arg, Lys, or derivative of them, and/or anionic amino acids such as Asp, Glu or derivative of them, and/or unnatural amino acids of aromatic/cationic/anionic acids or derivative;

$R_9$ is optional and when present represents a linear carbon chain, or polyethylene glycol linkers, polyethylene amine linkers, cationic linker, or derivative of them;

$R_{10}$ represents a $CO_2H$, $PO_3H_2$, $SO_3H$, $CH_2SO_3H$, $CH_2CONHCH_2SO_3H$, $CH_2CONHCH_2CH_2SO_3H$;

$R_{11}$ represents $CO_2H$, $SO_3H$, $CH_2CONHCH_2SO_3H$, $CH_2CONHCH_2CH_2SO_3H$; and $R_{12}$ represents independently represents a hydrogen, a methyl group, $CH_2COOH$, a $CH_2$ and may optionally represent each a $CH_2$ sharing a bond.

Additional preferred compounds of the invention include the following:

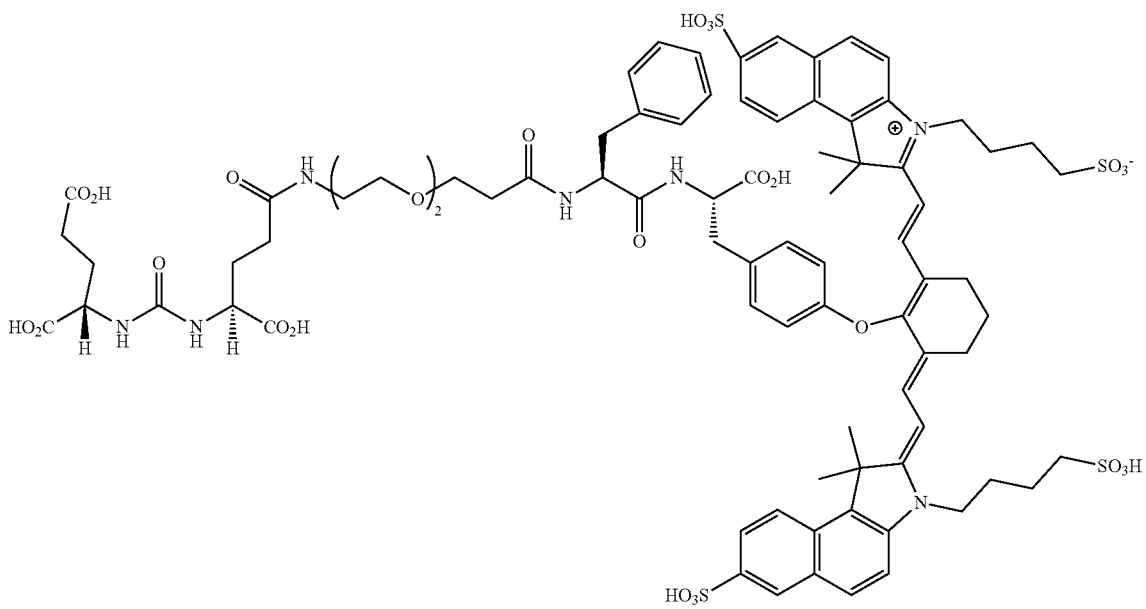

145
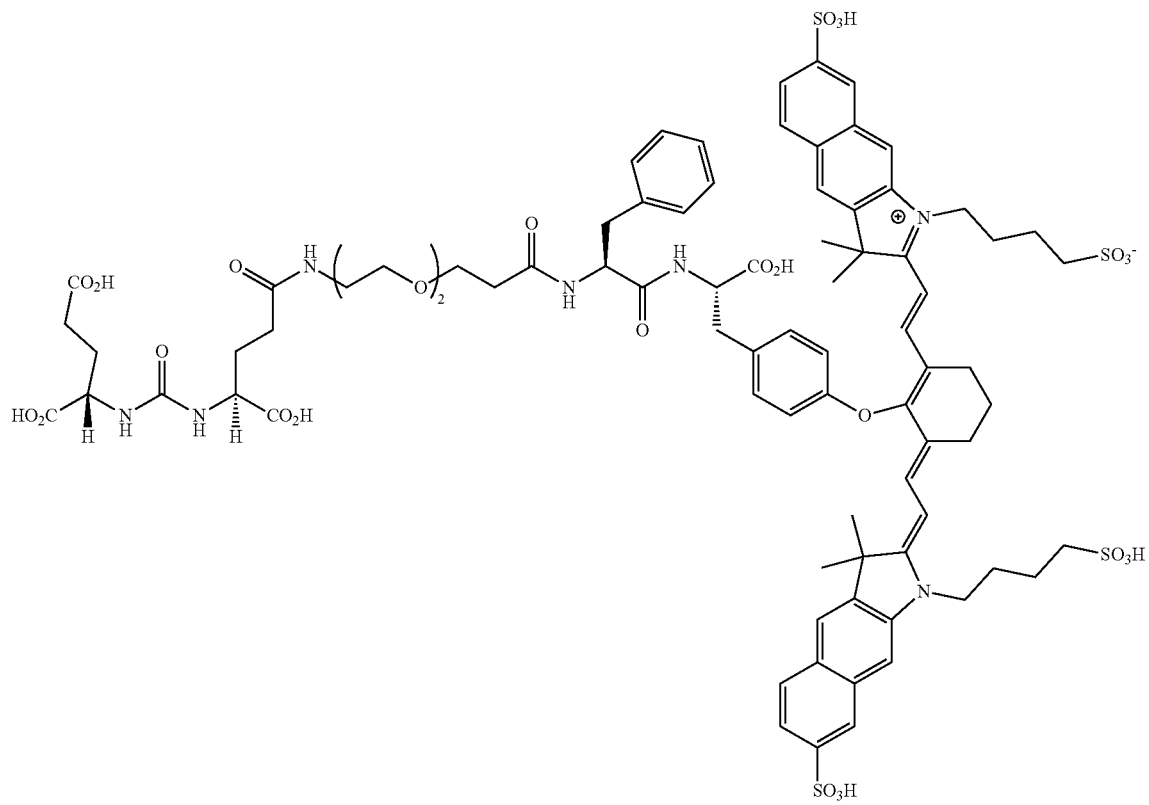
146
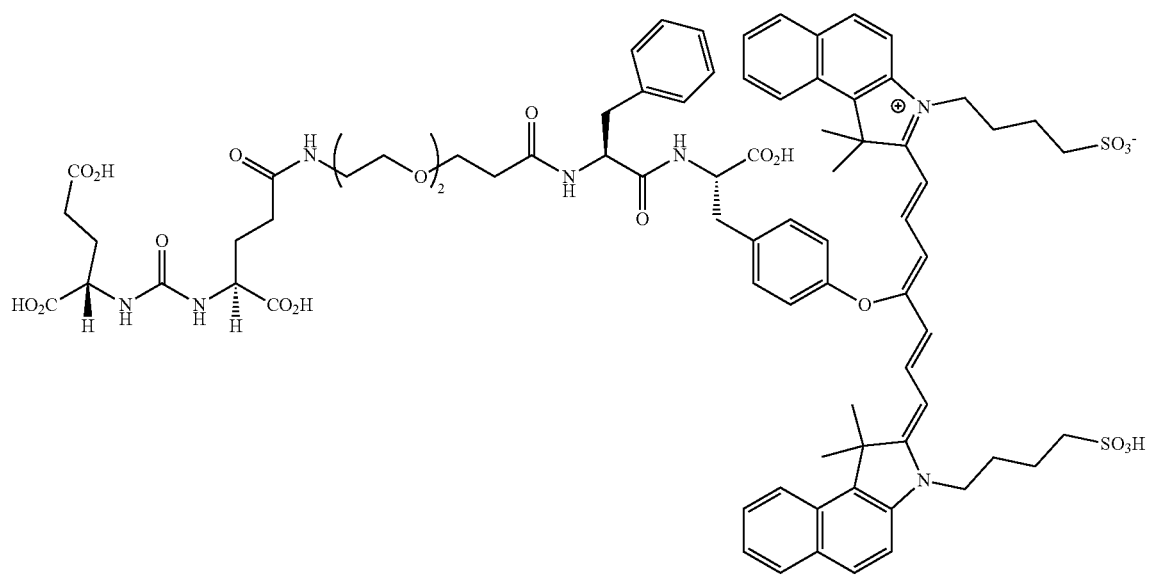
and

147

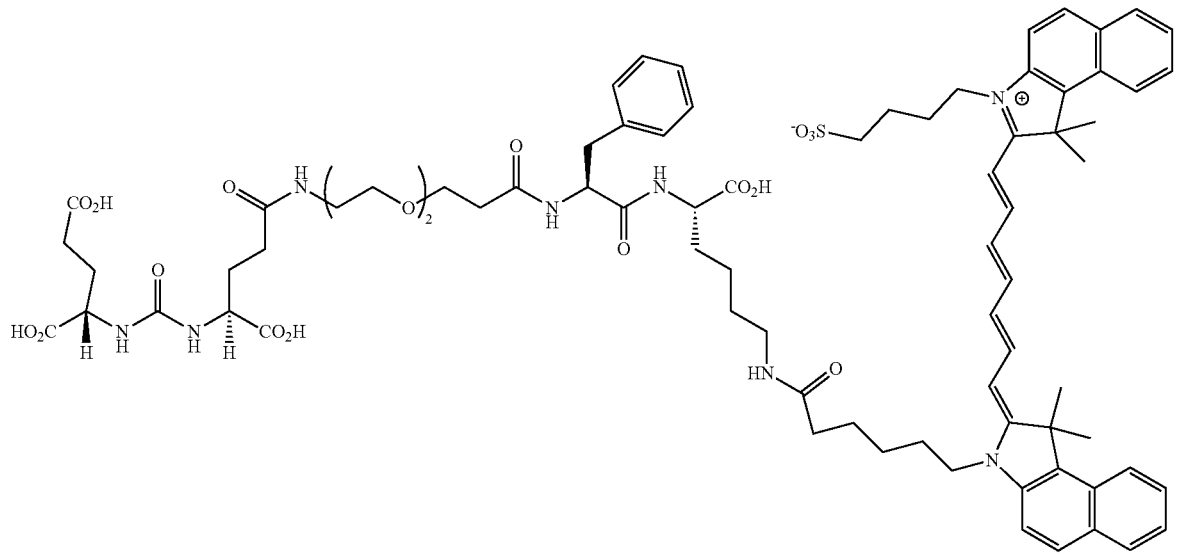

In some aspects compounds of the present invention have an absorption and emission maxima between about 500 nm and about 900 nm. In some aspects compounds of the present invention have an absorption and emission maxima between about 600 nm and 800 nm.

In some aspects compounds of the present invention are made to fluoresce after distribution thereof in the tissue cells. In some aspects compounds of the present invention are made to fluoresce by subjecting the compounds to excitation light of near infrared wavelength. In some aspects compounds of the present invention have a binding affinity to PSMA that is similar to the binding affinity of DUPA. In some aspects compounds of the present invention are highly selective for targeting to a tumor cell.

In certain aspects compounds of the present invention are administered to a subject in need thereof and in some aspects the administered composition comprises, in addition to the compound, a pharmaceutically acceptable carrier, excipient or diluent.

Some aspects of the present invention provide methods of optical imaging of PSMA-expressing biological tissue, said method comprising:
(a) contacting the biological tissue with a composition comprising a PSMA-targeted NIR dye compound,
(b) allowing time for the compound in the composition to distribute within the biological target;
(c) illuminating the tissue with an excitation light of a wavelength absorbable by the compound; and
(d) detecting the optical signal emitted by the compound.

In some aspects, these methods are used in detection of diseases associated with high PSMA expression. In some aspects, further comprising the step of constructing an image from the signal emitted in (d). In some aspects, the invention provides the aforementioned method wherein step (a) includes two or more fluorescent compounds whose signal properties are distinguishable are contacted with the tissue, and optionally the tissue is in a subject. In some aspects the present invention provides use of an endoscope, catheter, tomographic system, hand-held optical imaging system, surgical goggles, or intra-operative microscope for the illuminating and/or detecting method steps.

In some aspects, compositions and methods of the present invention are used to treat cancer. In some aspects, the cancer is selected from the group consisting of prostate cancer, bladder cancer, pancreatic cancer, liver cancer, lung cancer, kidney cancer, sarcoma, breast cancer, brain cancer, neuroendocrine carcinoma, colon cancer, testicular cancer or melanoma. In some aspects, PSMA-targeted NIR dye compounds of the present invention are used for imaging of PSMA-expressing cells. In certain aspects those cells are chosen from the group consisting of prostate cells, prostate cancer cells, bladder cancer cells, pancreatic cancer cells, liver cancer cells, lung cancer cells, kidney cancer cells, sarcoma cells, breast cancer cells, brain cancer cells, neuroendocrine carcinoma cells, colon cancer cells, testicular cancer cells or melanoma cells;

The present invention also provides methods of targeting a cell type in a biological sample comprising: a) contacting the biological sample with a PSMA-targeted NIR dye compound for a time and under conditions that allow for binding of the compound to at least one cell of the target cell type; and b) optically detecting the presence or absence of the compound of in the biological sample, wherein presence of the compound in detecting step c) indicates that the target cell type is present in the biological sample. In some aspects the present invention provides methods for optical detection of PSMA-expressing cells comprising administering PSMA-targeting NIR dye compounds of the present invention and subjecting the compound to an excitation light source and detecting fluorescence from the compound. In some aspects, the excitation light source is near-infrared wavelength light. In some aspects the excitation light wavelength is within a range from about 600 to 1000 nanometers. In some aspects the excitation light wavelength is within a range from about 670 to 850 nanometers.

In certain aspects the present invention provides methods of performing image guided surgery on a subject comprising:
a) administering a composition comprising a PSMA-targeting NIR dye compound under conditions and for a time sufficient for the compound to accumulate at a given surgical site;

b) illuminating the compound to visualize the compound using infrared light; and
c) performing surgical resection of the areas that fluoresce upon excitation by the infrared light.

In some aspects methods of the present invention the infrared light wavelength is within a range from about 600 to 1000 nanometers. In some aspects methods of the present invention use an infrared light wavelength is within a range from about 670 to 850 nanometers.

Some aspects of the present invention provide a method of diagnosing a disease in a subject comprising:
a) administering to a subject in need of diagnosis an amount of a PSMA-targeted NIR dye compound for a time and under conditions that allow for binding of the compound to at least one PSMA-expressing cell or tissues (PSMA also express in neo-vasculature of most of the solid tumors);
b) measuring the signal from the compound of present in the biological sample;
c) comparing the signal measured in b) with at least one control data set, wherein the at least one control data set comprises signals from the compound of claim 1 contacted with a biological sample that does not comprise the target cell type; and
d) providing a diagnosis of disease wherein the comparison in step c) indicates the presence of the disease.

Some aspects of the present invention provide a kit comprising a PSMA-targeting NIR dye compound. In some aspects, the kit is used for the imaging of PSMA-expressing cells or tissues. In some aspects the PSMA-expressing cells are tumor cells. In some aspects the PSMA-expressing cells are non-prostate cancer cells. In certain aspects the PSMA-expressing cells are prostate tumor cells. In certain aspects the PSMA-expressing cells are cancer cells. In some aspects the present invention is used for detection of metastatic disease. In some aspects compounds of the present invention are used for improved surgical resection and/or improved prognosis. In some aspects methods of the present invention provide cleaner surgical margins than non-NIR conjugated fluorescing dyes. In some aspects PSMA-targeted NIR dye compounds of the present invention have an improved tumor-to-background ratio.

In other aspects compounds of the present invention are used to image, diagnose, or detect non-prostate cancer cells chosen from the group consisting of bladder cancer cells, pancreatic cancer cells, liver cancer cells, lung cancer cells, kidney cancer cells, sarcoma cells, breast cancer cells, brain cancer cells, neuroendocrine carcinoma cells, colon cancer cells, testicular cancer cells or melanoma cells. In other aspects, the cells being detected are more than 5 mm below the skin. In some aspects, the tissue being detected is more than 5 mm below the skin. In other aspects, the tumor being detected is more than 5 mm below the skin. In some aspects, the cells being detected are more than 6 mm, 7 mm, 8 mm, 9 mm, or 10 mm below the subject's skin. In some aspects of the present invention dye probes that are detectable outside of the visible light spectrum. In some aspects dye probes greater than the visible light spectrum are used. In some aspects compounds of the present invention comprise dye probes sensitive to wavelengths between 650 nm and 900 nm. In some aspects the PSMA-targeted NIR dye compounds of the present invention have maximum light absorption wavelengths in the near infrared region of between about 650 nm and 1000 nm, for example and in one aspect, at approximately 800 nm.

In still another aspect of the methods provided, the non-prostate cancer is bladder cancer, pancreatic cancer, liver cancer, lung cancer, kidney cancer, sarcoma, breast cancer, brain cancer, neuroendocrine carcinoma, colon cancer, testicular cancer or melanoma.

In a further aspect of the methods provided, the PSMA-expressing cancer cells are of a tumor. In still a further aspect of the methods provided, the PSMA-expressing cancer is a tumor. In some aspects, the volume of the tumor is at least 1000 mm$^3$. In some aspects, the volume of the tumor is less than 1000 mm$^3$. In some aspects, the volume of the tumor is less than 950 mm$^3$. In some aspects, the volume of the tumor is less than 900 mm$^3$. In some aspects, the volume of the tumor is less than 850 mm$^3$. In some aspects, the volume of the tumor is less than 800 mm$^3$. In some aspects, the volume of the tumor is less than 750 mm$^3$. In some aspects, the volume of the tumor is less than 700 mm$^3$. In some aspects, the volume of the tumor is less than 650 mm$^3$. In some aspects, the volume of the tumor is less than 600 mm$^3$. In some aspects, the volume of the tumor is less than 550 mm$^3$. In some aspects, the volume of the tumor is less than 500 mm$^3$. In some aspects, the volume of the tumor is less than 450 mm$^3$. In some aspects, the volume of the tumor is less than 400 mm$^3$. In some aspects, the volume of the tumor is less than 350 mm$^3$. In some aspects, the volume of the tumor is less than 300 mm$^3$. In some aspects, the volume of the tumor is less than 250 mm$^3$. In some aspects, the volume of the tumor is less than 200 mm$^3$. In some aspects, the volume of the tumor is less than 150 mm$^3$. In some aspects, the volume of the tumor is less than 100 mm$^3$. In one aspect, the volume of the tumor is at least 75 mm$^3$. In another aspect, the volume of the tumor is less than 75 mm$^3$. In another aspect, the volume of the tumor is less than 70 mm$^3$. In another aspect, the volume of the tumor is less than 65 mm$^3$. In another aspect, the volume of the tumor is less than 60 mm$^3$. In another aspect, the volume of the tumor is less than 55 mm$^3$. In one aspect, the volume of the tumor is at least 50 mm$^3$. In other aspects, the tumor is less than 50 mm$^3$. In another aspect, the volume of the tumor is less than 45 mm$^3$. In other aspects, the volume of the tumor is less than 40 mm$^3$. In another aspect, the volume of the tumor is less than 35 mm$^3$. In still another aspect, the volume of the tumor is less than 30 mm$^3$. In another aspect, the volume of the tumor is less than 25 mm$^3$. In still another aspect, the volume of the tumor is less than 20 mm$^3$. In another aspect, the volume of the tumor is less than 15 mm$^3$. In still another aspect, the volume of the tumor is less than 10 mm$^3$. In still another aspect, the volume of the tumor is less than 12 mm$^3$. In still another aspect, the volume of the tumor is less than 9 mm$^3$. In still another aspect, the volume of the tumor is less than 8 mm$^3$. In still another aspect, the volume of the tumor is less than 7 mm$^3$. In still another aspect, the volume of the tumor is less than 6 mm$^3$. In still another aspect, the volume of the tumor is less than 5 mm$^3$.

In one aspect, the tumor has a length of at least 5 mm prior to surgical precision using a PSMA-targeted NIR dye compound of the present invention. In one aspect, these methods detect tumors less than 5 mm. In other aspects the methods herein detect tumors less than 4 mm. In some aspects, the methods herein detect tumors less than 3 mm. In another aspect, the tumor has a length of at least 6 mm. In still another aspect, the tumor has a length of at least 7 mm. In yet another aspect, the tumor has a length of at least 8 mm. In another aspect, the tumor has a length of at least 9 mm. In still another aspect, the tumor has a length of at least 10 mm. In yet another aspect, the tumor has a length of at least 11 mm. In a further aspect, the tumor has a length of at least 12 mm. In still a further aspect, the tumor has a length of at least 13 mm. In still a further aspect, the tumor has a length of at least 14 mm. In another aspect, the tumor has a length of at least 15 mm. In yet another aspect, the tumor has a length of at least 16 mm. In still another aspect, the tumor has a length of at least 17 mm. In a further aspect, the tumor has a length of at least 18 mm. In yet a further aspect, the tumor has a length of at least 19 mm. In still a further aspect, the tumor has a length of at least 20 mm. In another aspect, the tumor has a length of at least 21 mm. In still another aspect, the tumor has a length of at least 22 mm. In yet another aspect, the tumor has a length of at least 23 mm. In a further aspect, the tumor has a length of at least 24 mm. In still a further aspect, the tumor has a length of at least 25 mm. In yet a further aspect, the tumor has a length of at least 30 mm.

In some aspects the present disclosure relates to prostate specific membrane antigen (PSMA) targeted compounds conjugated to near-infra red (NIR) dyes and methods for their therapeutic and diagnostic use. More specifically, this disclosure provides compounds and methods for diagnosing and treating diseases associated with cells expressing prostate specific membrane antigen (PSMA), such as prostate cancer and related diseases. The disclosure further describes methods and compositions for making and using the compounds, methods incorporating the compounds, and kits incorporating the compounds. It has been discovered that a PSMA-targeted compound, such as DUPA or conjugating PSMA-targeting ligand to an NIR dye via a linker (L) may be useful in the imaging, diagnosis, and/or treatment of prostate cancer, and related diseases that involve pathogenic cell populations expressing or over-expressing PSMA. PSMA is a cell surface protein that is internalized in a process analogous to endocytosis observed with cell surface receptors, such as vitamin receptors. PSMA also express in the neo-vasculature of most of solid tumors. Accordingly, it has been discovered that certain conjugates that include a linker having a predetermined length, and/or a predetermined diameter, and/or preselected functional groups along its length may be used to treat, image, and/or diagnose such diseases.

In one illustrative aspect, the linker L may be a releasable or non-releasable linker. In one aspect, the linker L is at least about 7 atoms in length. In one variation, the linker L is at least about 10 atoms in length. In one variation, the linker L is at least about 14 atoms in length. In another variation, the linker L is between about 7 and about 22, between about 7 and about 24, or between about 7 and about 20 atoms in length. In another variation, the linker L is between about 14 and about 31, between about 14 and about 24, or between about 14 and about 20 atoms in length.

In an alternative aspect, the linker L is at least about 10 angstroms (A) in length.

In one variation, the linker L is at least about 15 A in length. In another variation, the linker L is at least about 20 A in length. In another variation, the linker L is in the range from about 10 A to about 30 A in length.

In an alternative aspect, at least a portion of the length of the linker L is about 5 A in diameter or less at the end connected to the binding ligand B. In one variation, at least a portion of the length of the linker L is about 4 A or less, or about 3 A or less in diameter at the end connected to the binding ligand B. It is appreciated that the illustrative aspects that include a diameter requirement of about 5 A or less, about 4 A or less, or about 3 A or less may include that requirement for a predetermined length of the linker, thereby defining a cylindrical-like portion of the linker. Illustratively, in another variation, the linker includes a cylindrical portion at the end connected to the binding ligand that is at least about 7 A in length and about 5 A or less, about 4 A or less, or about 3 A or less in diameter.

In another aspect, the linker L includes one or more hydrophilic linkers capable of interacting with one or more residues of PSMA, including amino acids that have hydrophilic side chains, such as Ser, Thr, Cys, Arg, Orn, Lys, Asp, Glu, Gln, and like residues. In another aspect, the linker L includes one or more hydrophobic linkers capable of interacting with one or more residues of PSMA, including amino acids that have hydrophobic side chains, such as Val, Leu, Phe, Tyr, Met, and like residues. It is to be understood that the foregoing aspects and aspects may be included in the linker L either alone or in combination with each other. For example, linkers L that are at least about 7 atoms in length and about 5 Å, about 4 Å or less, or about 3 Å or less in diameter or less are contemplated and described herein, and also include one or more hydrophilic linkers capable of interacting with one or more residues of PSMA, including Val, Leu, Phe, Tyr, Met, and like residues are contemplated and described herein.

In another aspect, one end of the linker is not branched and comprises a chain of carbon, oxygen, nitrogen, and sulfur atoms. In one aspect, the linear chain of carbon, oxygen, nitrogen, and sulfur atoms is at least 5 atoms in length. In one variation, the linear chain is at least 7 atoms, or at least 10 atoms in length. In another aspect, the chain of carbon, oxygen, nitrogen, and sulfur atoms are not substituted. In one variation, a portion of the chain of carbon, oxygen, nitrogen, and sulfur atoms is cyclized with a divalent fragment. For example, a linker (L) comprising the dipeptide Phe-Phe may include a piperazin-1,4-diyl structure by cyclizing two nitrogens with an ethylene fragment, or substituted variation thereof.

In another aspect, pharmaceutical compositions are described herein, where the pharmaceutical composition includes the conjugates described herein in amounts effective to treat diseases and disease states, diagnose diseases or disease states, and/or image tissues and/or cells that are associated with pathogenic populations of cells expressing or over expressing PSMA. Illustratively, the pharmaceutical compositions also include one or more carriers, diluents, and/or excipients.

In another aspect, methods for treating diseases and disease states, diagnosing diseases or disease states, and/or imaging tissues and/or cells that are associated with pathogenic populations of cells expressing or over expressing PSMA are described herein. Such methods include the step of administering the conjugates described herein, and/or pharmaceutical compositions containing the conjugates described herein, in amounts effective to treat diseases and disease states, diagnose diseases or disease states, and/or image tissues and/or cells that are associated with pathogenic populations of cells expressing or over expressing PSMA.

In some aspects, it is shown herein that such PSMA-targeted NIR dye conjugates bind to PSMA expressing tumor cells within a tissue. Moreover, the intensity of the fluorescence in greater than the intensity of previously observed with other near infrared dyes that are targeted with folate for folate receptor positive tumors. This increased intensity allows the targeting and clear identification of smaller areas of biological samples (e.g., smaller tumors) from a tissue being monitored. In addition, the increased intensity of the compounds of the present invention provides the added advantage that lower doses/quantities of the dye can be administered and still produces meaningful results. Thus, the compounds of the present invention lead to more economical imaging techniques. Moreover, there is an added advantaged that a lower dose of the compounds of the invention as compared to conventional imaging compounds minimizes the toxicity and other side effects that are attendant with administration of foreign materials to a body.

Furthermore, identification of small tumors will lead to a more accurate and more effective resection of the primary tumor to produce negative margins, as well as accurate identification and removal of the lymph nodes harboring metastatic cancer cells and identification of satellite disease. Each of these advantages positively correlates with a better clinical outcome for the patient being treated.

In specific aspects, it is contemplated that in addition to tyrosine and tyrosine derivatives, a PSMA-targeted conjugate of a near infrared dye with cysteine or cysteine derivatives also may be useful. Furthermore, it is contemplated that a direct linkage of the PSMA-targeted moiety to the dye or linkage of the dye to DUPA or a PSMA-targeted ligand through an amine linker also produces a loss of intensity of the fluorescence from the conjugate whereas the presence of the tyrosine or tyrosine derivative as the linking moiety between enhances the fluorescence of the conjugated compound as a result of the fact that the tyrosine-based compounds of the invention do not require an extra amine linker to conjugate the SO456 and further because conjugation through the phenol moiety of the tyrosine leads to enhanced fluorescence.

The compounds can be used with fluorescence-mediated molecular tomographic imaging systems, such as those designed to detect near-infrared fluorescence activation in deep tissues. The compounds provide molecular and tissue specificity, yield high fluorescence contrast, brighter fluorescence signal, and reduce background autofluorescence, allowing for improved early detection and molecular target assessment of diseased tissue in vivo (e.g., cancers). The compounds can be used for deep tissue three dimensional imaging, targeted surgery, and methods for quantifying the amount of a target cell type in a biological sample.

In specific aspects, the linker is less than ten atoms. In other aspects, the linker is less than twenty atoms. In some aspects, the linker is less than 30 atoms. In some aspects, the linker is defined by the number of atoms separating the PSMA-targeting compound and the NIR dye. In another aspect, linkers have a chain length of at least 7 atoms. In some aspects, linkers have a chain length of at least 14 atoms. In another aspect, linkers have a chain length in the range from 7 atoms to 20 atoms. In another aspect, linkers have a chain length in the range of 14 atoms to 24 atoms.

PSMA-targeting compounds suitable for use in the present invention can be selected, for example, based on the following criteria, which are not intended to be exclusive: binding to live cells expressing PSMA; binding to neovasculature expressing PSMA; high affinity of binding to PSMA; binding to a unique epitope on PSMA (to eliminate the possibility that antibodies with complimentary activities when used in combination would compete for binding to the same epitope); opsonization of cells expressing PSMA; mediation of growth inhibition, phagocytosis and/or killing of cells expressing PSMA in the presence of effector cells; modulation (inhibition or enhancement) of NAALADase, folate hydrolase, dipeptidyl peptidase IV and/or γ-glutamyl hydrolase activities; growth inhibition, cell cycle arrest and/or cytotoxicity in the absence of effector cells; internalization of PSMA; binding to a conformational epitope on PSMA; minimal cross-reactivity with cells or tissues that do not express PSMA; and preferential binding to dimeric forms of PSMA rather than monomeric forms of PSMA.

PSMA-targeting compounds, PSMA antibodies and antigen-binding fragments thereof provided herein typically meet one or more, and in some instances, more than five of the foregoing criteria. In some aspects, the PSMA-targeting compounds of the present invention meet six or more of the foregoing criteria. In some aspects, the PSMA-targeting compounds of the present invention meet seven or more of the foregoing criteria. In some aspects, the PSMA-targeting compounds of the present invention meet eight or more of the foregoing criteria. In some aspects, the PSMA-targeting compounds of the present invention meet nine or more of the foregoing criteria. In some aspects, the PSMA-targeting compounds of the present invention meet ten or more of the foregoing criteria. In some aspects, the PSMA-targeting compounds of the present invention meet all of the foregoing criteria.

Examples of tumors that can be imaged with the PSMA-targeted compounds of the present invention (e.g., PSMA-targeted NIR dye conjugates) provided herein, include any tumor that expresses PSMA such as, e.g., prostate, bladder, pancreas, lung, colon, kidney, melanomas and sarcomas. A tumor that expresses PSMA includes tumors with neovasculature expressing PSMA.

In some aspects, a PSMA-targeted molecules bind to PSMA and are internalized with PSMA expressed on cells. Thus, a PSMA ligand conjugate comprising a internalized with PSMA expressed on cells. The mechanism by which this internalization occurs is not critical to the practice of the present invention.

In some aspects, the PSMA targeting compounds bind to a conformational epitope within the extracellular domain of the PSMA molecule. In other aspects, a PSMA-targeting compound binds to a dimer-specific epitope on PSMA. Generally, the compound that binds to a dimer-specific epitope preferentially binds the PSMA dimer rather than the PSMA monomer. In some aspects of the present invention, the PSMA-targeting compound preferentially binds to the PSMA dimer. In some aspects of the present invention, the PSMA-targeting compound has a low affinity for the monomeric PSMA protein.

In some aspects, the PSMA-targeting compound is a ligand. In some aspects, the PSMA-targeting compound is 2-[3-(1,3-dicarboxypropyl)ureido] pentanedioic acid (DUPA). In some aspects, the PSMA-targeting compound is DUPA or derivative of DUPA, ligand, inhibitor, or agonist that binds to PSMA-expressing live cells.

The PSMA-targeting NIR dye of the present invention produces a tumor-to-background signal ratio that is higher than the tumor-to-background signal ratio of the PSMA-targeting compound conjugated to a non-NIR dye or non-targeted NIR dye. In some aspects, the improvement is 10-fold. In some aspects, the tumor-to-background signal ratio is at least a 4-fold improvement. In some aspects, the tumor-to-background ratio is increased by at least 1.5-fold. In some aspects, the PSMA-targeted NIR dye background signal is half the background signal of the PSMA-targeted compound conjugated to a fluorescent dye reactive to light less than 600 nm in wavelength. In some aspects of the present invention, methods using the PSMA-targeted NIR dye on live cells produces a background signal less than half the background signal of the PSMA-targeted compound conjugated to a fluorescent dye reactive to light less than 600 nm in wavelength. In some aspects of the present invention, methods using the PSMA-targeted NIR dye on live cells produces a background signal less than half the background signal of the PSMA-targeted compound conjugated to a fluorescent dye reactive to light less than 500 nm in wavelength. In some aspects of the present invention, methods using the PSMA-targeted NIR dye on live cells produces a background signal less than one third of the background signal of the PSMA-targeted compound conjugated to a fluorescent dye reactive to light less than 600 nm in wavelength. In some aspects of the present invention, methods using the PSMA-targeted NIR dye on live cells produces a background signal less than one third of the background signal of the PSMA-targeted compound conjugated to a fluorescent dye reactive to light less than 500 nm in wavelength. In some aspects of the present invention, methods using the PSMA-targeted NIR dye on live cells produces a background signal less than one fourth the background signal of the PSMA-targeted compound conjugated to a fluorescent dye reactive to light less than 600 nm in wavelength. In some aspects of the present invention, methods using the PSMA-targeted NIR dye on live cells produces a background signal less than one fourth the background signal of the PSMA-targeted compound conjugated to a fluorescent dye reactive to light less than 500 nm in wavelength. In some aspects of the present invention, methods using the PSMA-targeted NIR dye on live cells produces a background signal less than one fifth the background signal of the PSMA-targeted compound conjugated to a fluorescent dye reactive to light less than 600 nm in wavelength. In some aspects of the present invention, methods using the PSMA-targeted NIR dye on live cells produces a background signal less than one fifth the background signal of the PSMA-targeted compound conjugated to a fluorescent dye reactive to light less than 500 nm in wavelength. In some aspects of the present invention, methods using the PSMA-targeted NIR dye on live cells produces a background signal less than one eighth the background signal of the PSMA-targeted compound conjugated to a fluorescent dye reactive to light less than 600 nm in wavelength. In some aspects of the present invention, methods using the PSMA-targeted NIR dye on live cells produces a background signal less than one eighth the background signal of the PSMA-targeted compound conjugated to a fluorescent dye reactive to light less than 500 nm in wavelength. In some aspects of the present invention, methods using the PSMA-targeted NIR dye on live cells produces a background signal less than one tenth the background signal of the PSMA-targeted compound conjugated to a fluorescent dye reactive to light less than 600 nm in wavelength. In some aspects of the present invention, methods using the PSMA-targeted NIR dye on live cells produces a background signal less than one tenth the background signal of the PSMA-targeted compound conjugated to a fluorescent dye reactive to light less than 500 nm in wavelength.

In some aspects, the PSMA-targeting compound is a small molecule ligand that binds specifically PSMA. Such small molecule ligands may bind to the enzymatic site of PSMA in its native conformation. Also, such small molecule ligands may possess any one or more of the characteristics for PSMA antibody ligands.

This disclosure also provides methods for synthesizing amino acid linking groups that are conjugated to a PSMA-targeting compound used for the targeted imaging of PSMA-expressing cells, tissues, or tumors. In certain aspects, this disclosure relates to a compound or a salt derivative thereof, that comprises a PSMA-targeting compound, a linking group, and an NIR dye. In certain aspects, the linking group can be an amino acid, an isomer, a derivative, or a racemic mixture thereof. In some aspects, the dye is selected from the group consisting of LS288, IR800, SP054, S0121, KODAK, S2076, S0456 and/or the dyes selected from group consisting of.

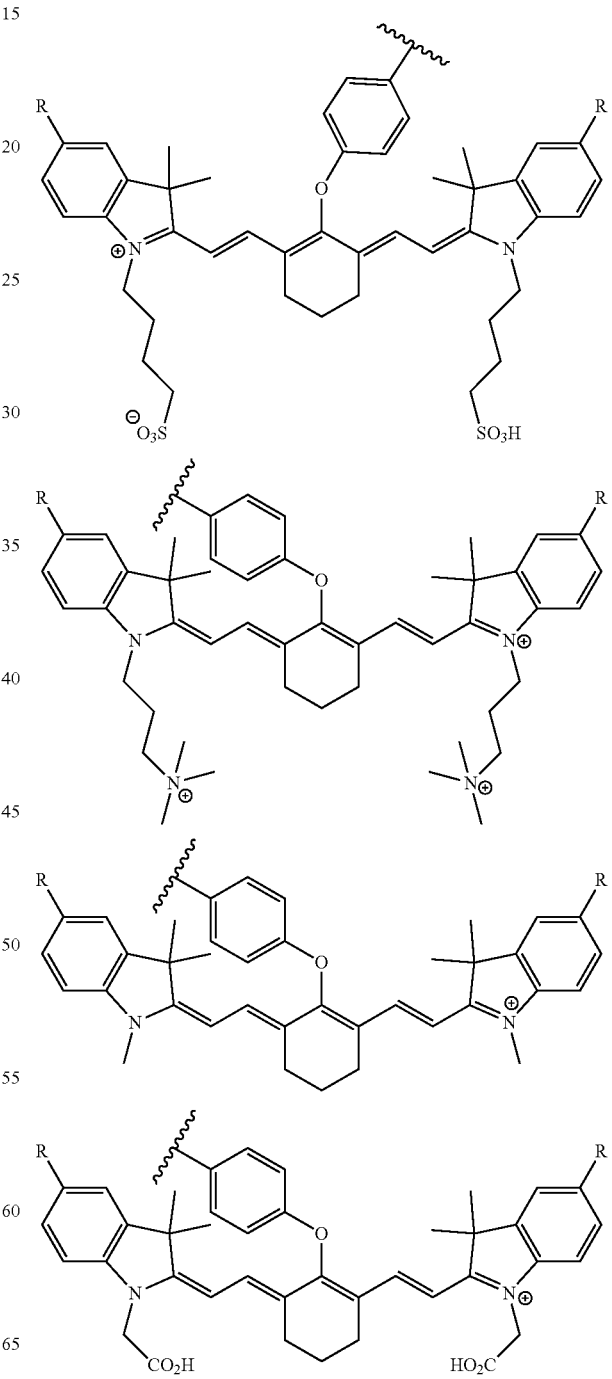

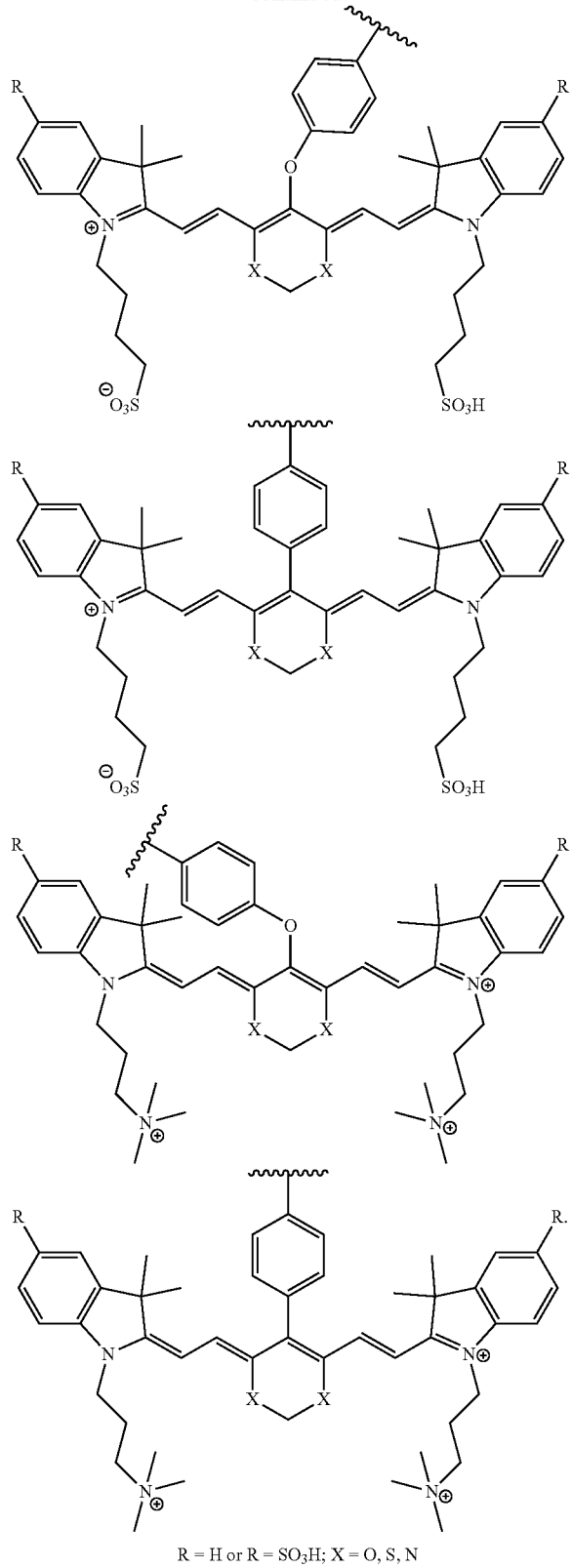

R = H or R = SO₃H; X = O, S, N

In some aspects, this disclosure provides a method of conjugating an amino acid linking group to an NIR dye, wherein the amino acid can be tyrosine, theronine, lysine, arginine, asparagine, glutamine, cysteine, selenocysteine, isomers, and the derivatives thereof. In certain aspects, the amino acid, isomers, or the derivatives thereof, contain an —OH, —NH₂, or —SH functional group that upon addition of the fluorescent dye in slight molar excess produces the conjugation of fluorescent group with the amino acid, isomer, or the derivatives thereof. In other aspects, the amino acid, isomers, or the derivatives thereof, contains an —OH functional group that upon synthesis generates an ether bond with the dye that increases the brightness and detection of the compound. In some aspects, this disclosure relates to the conjugation of the amino acid linking group with the NIR dye, wherein the amino acid, isomers, or the derivatives thereof, contains an —SH, —SeH, —PoH, or —TeH functional group that upon synthesis generates a C—S, C—Se, C—Po, or C—Te bond with the dye. In some aspects, this disclosure relates to the conjugation of the amino acid linking group to a dye that has an absorption and emission maxima between about 500 nm and about 900 nm. In other aspects, the amino acid linking group is conjugated to a fluorescent dye that has an absorption and emission maxima between about 600 nm and about 800 nm.

In additional aspects, this disclosure provides a method for conjugating the amino acid linking group to a PSMA ligand, wherein the amino acid linking group is tyrosine, serine, threonine, lysine, arginine, asparagine, glutamine, cysteine, selenocysteine, isomers or the derivatives thereof, and is conjugated to folate through a dipeptide bond. In additional aspects, this disclosure provides a method of conjugating the linking group with a folate ligand, wherein the linking group is tyrosine, serine, threonine, lysine, arginine, asparagine, glutamine, cysteine, selenocysteine, isomers, or the derivatives thereof. In other aspects, this disclosure relates to a method of conjugating a pteroyl ligand to an amino acid linking group, wherein the linking group is tyrosine, serine, threonine, lysine, arginine, asparagine, glutamine, cysteine, selenocysteine, isomers or the derivatives thereof. In certain aspects, the carboxylic acid of the linking group is bound to the alpha carbon of any amino acid, hence increasing the specificity of the compound for targeted receptors. In some aspects, the charge of the linker contributes specificity to the compound, wherein the observed binding affinity of the compound to targeted receptors is at least 15 nM.

In other aspects, this disclosure relates to the use of a compound designated, DUPA-EAOA-Tyr-S0456, wherein EAOA is eight aminooctonoic acid, for image guided surgery, tumor imaging, prostate imaging, PSMA-expressing tissue imaging, PSMA-expressing tumor imaging, infection diseases, or forensic applications. In other aspects, the compound is a DUPA-EAOA-Tyr-S0456 derivative selected from the group consisting of DUPA-EAOA-(D)Tyr-S0456, DUPA-EAOA-homoTyr-S0456, DUPA-EAOA-beta-homo-Tyr-S0456, DUPA-EAOA-(NMe)-Tyr-S0456, DUPA-EAOA-Tyr(OMe)-S0456, DUPA-EAOA-Tyr(OBn)-S0456, DUPA-EAOA-NHNH-Tyr-OAc-S0456, salts, and derivatives thereof.

In some aspects, the PSMA-targeted compound of the present invention is a small molecule ligand of PSMA.

Some aspects of the present invention relates to a method of imaging a disease comprising the steps of (a) administering to a subject in need of an effective amount of a compound capable of binding to a cell expressing prostate specific membrane antigen having the formula

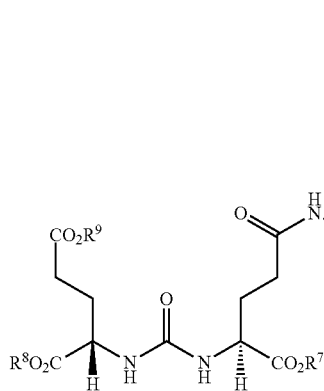
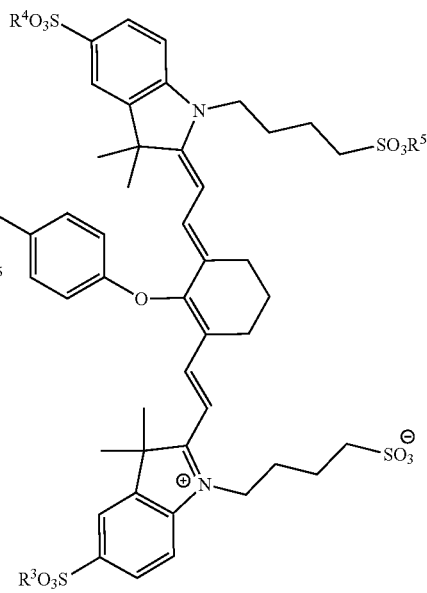

a salt thereof, or isotope thereof, wherein n is 0, 1, 2, 3, or 4, wherein $R^3$, $R^4$, $R^5$, $R^6$, $R^7$, $R^8$, and $R^9$ are independently selected from the group consisting of $H^+$, $Na^+$, $K^+$, and $NH_4^+$, and (b) fluorescent imaging of an area of the disease in the subject's body where the compound has been bound to a cell expressing prostate specific membrane antigen.

In another aspect the salt is a pharmaceutically acceptable salt.

In another aspect, n is 2. In yet another aspect the compound capable of binding to a cell expressing prostate specific membrane antigen has the formula

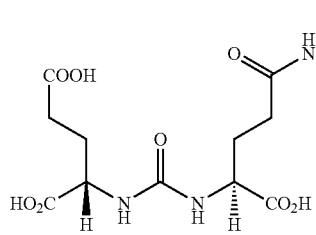
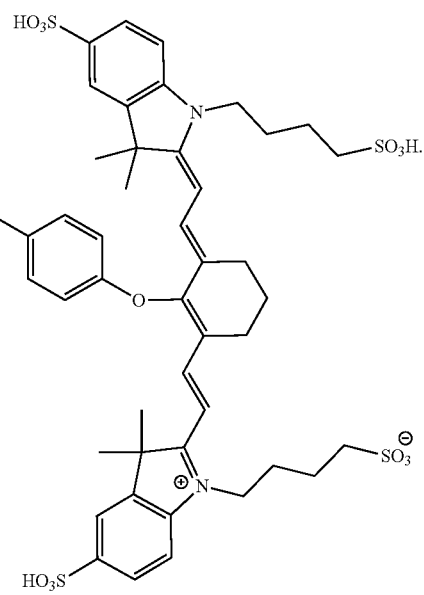

In some aspects, the compound is formulated for intravenous, intraperitoneal, intramuscular, intradermal, or oral administration.

In some aspects, the compound is administered to the subject under conditions and for a time sufficient for the compound to accumulate at the given area of the disease. In another aspect, the time sufficient is at least about 20 minutes. In another aspect, the time sufficient is about 20 minutes to about 4 hours. In yet another aspect the time sufficient is about 30 minutes, alternatively about 40 minutes, alternatively about 50 minutes, alternatively about 60 minutes, alternatively about 70 minutes, alternatively about 80 minutes, alternatively about 90 minutes, alternatively about 100 minutes, alternatively about 110 minutes, alternatively about 120 minutes, alternatively about 130 minutes, alternatively about 140 minutes, alternatively about 150 minutes, alternatively about 160 minutes, alternatively about 170 minutes, alternatively about 180 minutes, alternatively about 190 minutes, alternatively about 200 minutes, alternatively about 210 minutes, alternatively about 220 minutes, alternatively about 230 minutes, alternatively about 240 minutes. In yet another aspect, the time sufficient is about 2 hours.

In some aspects, the imaged disease is cancer. In another aspect, the cancer is selected from the group consisting of prostate cancer, bladder cancer, pancreatic cancer, liver cancer, lung cancer, kidney cancer, sarcoma, breast cancer, brain cancer, neuroendocrine carcinoma, colon cancer, testicular cancer, pituitary cancer, head and neck cancer, ovarian cancer, thyroid cancer, esophageal cancer, and melanoma.

In some aspects the imaged disease is expressed in any primary solid tumors, metastasis tumors, secondary tumors in the lungs, secondary tumors in bones, secondary tumors in seminal vesicles, lymph nodes, subcutaneous tumors, orthotopic tumors, or spontaneous tumors. In another aspect, the metastasis tumors are located in seminal vesicles. In yet another aspect, the imaged disease is expressed in neovasculature of the solid tumor.

In some aspects, the cell expressing prostate specific membrane antigen is selected from the group consisting of prostate cells, prostate cancer cells, bladder cancer cells, pancreatic cancer cells, liver cancer cells, lung cancer cells, kidney cancer cells, sarcoma cells, breast cancer cells, brain cancer cells, neuroendocrine carcinoma cells, colon cancer cells, testicular cancer cells, ovarian cancer cells, pituitary cancer cells, head and neck cancer cells, thyroid cancer cells, esophageal cancer cells, and melanoma cells.

In some aspects, the cell expressing prostate-specific membrane antigen a PCa cell line. In yet another aspect, the PCa cell line is selected from the group consisting of LNCaP, 22Rv1, C4-2, DU145, TSu-Pr1, ALVA, ARCaP, PPC-1, LAPC3, P69SV40T, RWPE-2, CA-HPV-10, PZ-HPV-7, PC-3.

In some aspects, the cells expressing prostate-specific membrane antigen is in xenograft tumor. In another aspect, the xenograft is subcutaneous tumor or orthotopic tumor.

In some aspects, the cells expressing prostate-specific membrane antigen is an alveolar basal epithelial carcinoma cell line. In another aspect, the cell line is A549.

In some aspects, the compound is capable of or adapted to enhance the fluorescence and/or binding affinity of a dye. In another aspect, the dye is S0456.

PSMA-Targeted NIR Dye Conjugates and their Synthesis

The following schemes show the synthesis of PSMA-targeted NIR dye conjugates of the present invention.

Scheme 1

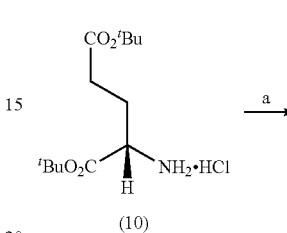

(10)

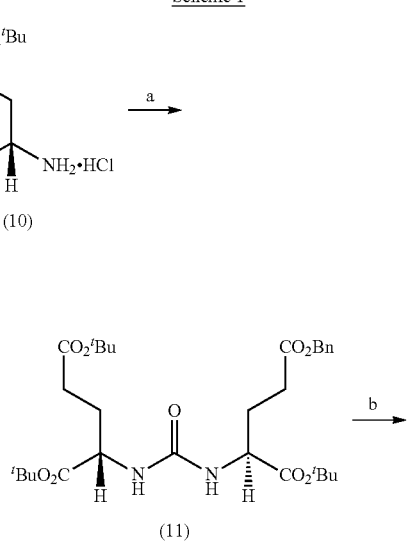

Reagents and conditions: (a) (i) triphosgene, TEA/DCM, -78° C.; (ii) H-L-Glu(OBn)-O'Bu•HCl; (b) H₂; Pd-C/DCM Scheme 2

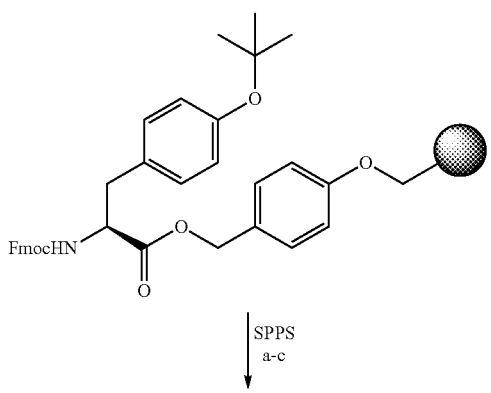

SPPS
a-c

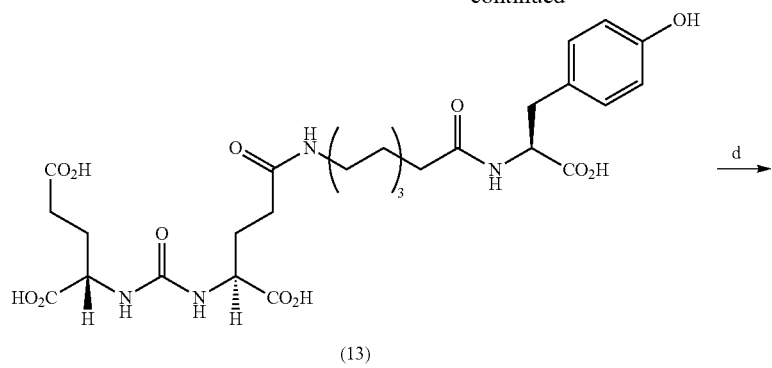
(13)
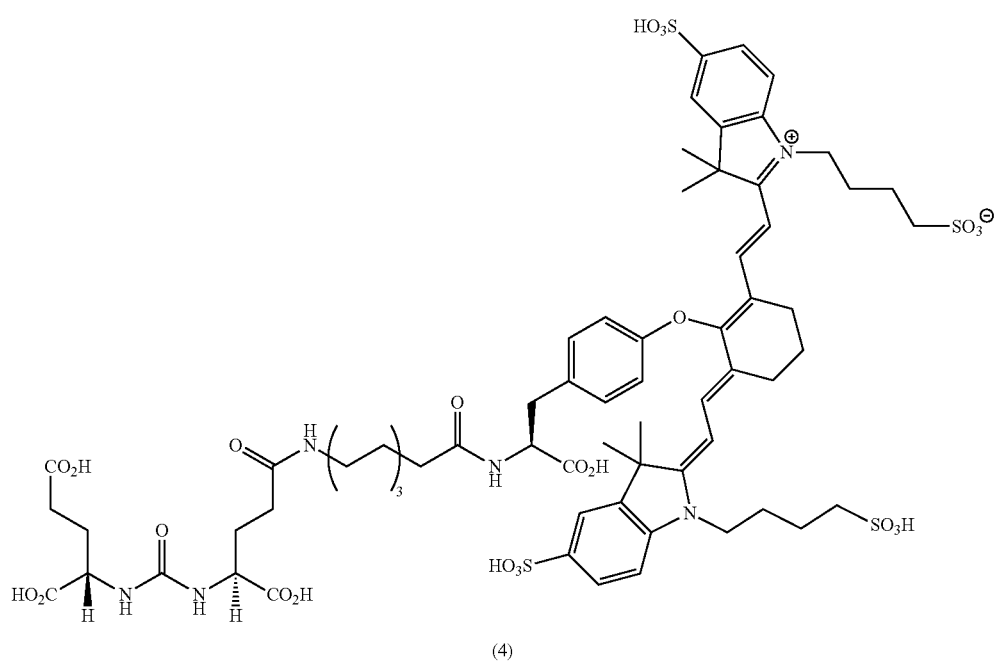
(4)
Reagents and conditions: (a) (i) 20% piperidine/DMF, r.t., 10 min; (ii) Fmoc-Eightaminooctanoic acid-OH, HATU, DMF/DIPEA, 2 h; b) (i) 20% piperidine/DMF, r.t., 10 min; (ii) 12, HATU, DMF/DIPEA, 2 h; c) TFA:H$_2$O:TIPS (95:2.5:2.5) 1 h; (d) (i) H$_2$O, aq. NaOH/pH = 9.5, r.t.; (ii) S0456, H$_2$O, 100° C., 15 min.

Scheme 3
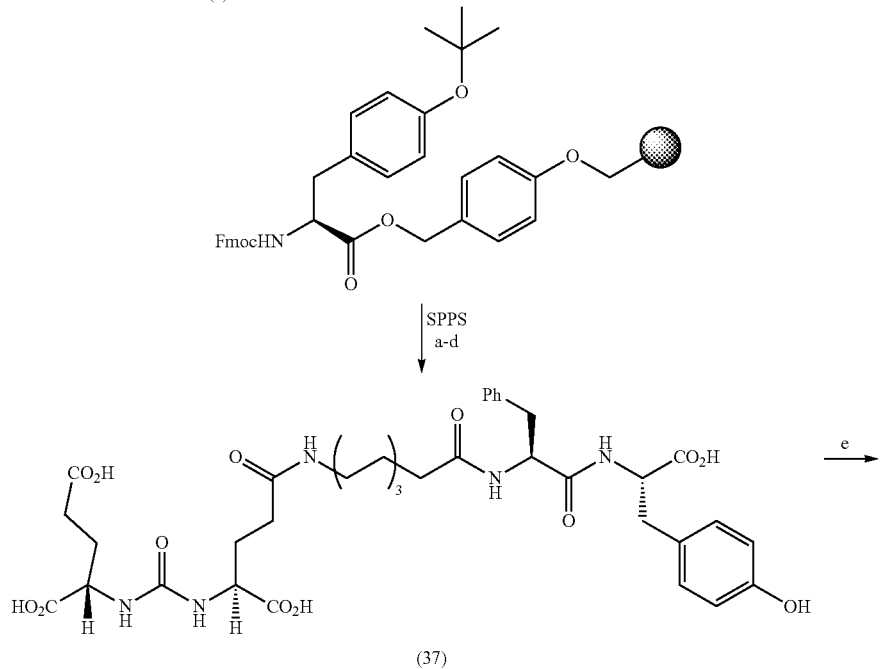
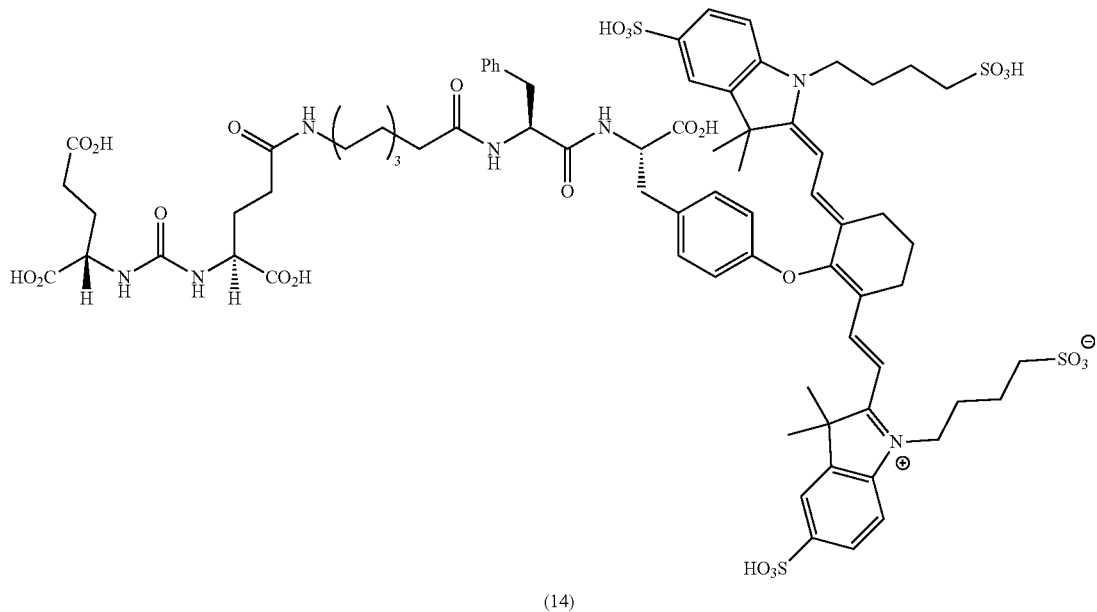
Reagents and conditions: (a) (i) 20% piperidine/DMF, r.t., 10 min; (ii) Fmoc-Phe-OH, HATU, DMF/DIPEA, 2 h; (b) (i) 20% piperidine/DMF, r.t., 10 min; (ii) Fmoc-Eightaminooctanoic acid-OH, HATU, DMF/DIPEA, 2 h; (c) (i) 20% piperidine/DMF, r.t., 10 min; (ii) 12, HATU, DMF/DIPEA, 2 h; d) TFA:H₂O:TIPS (95:2.5:2.5), 1 h; (e) (i) H₂O, aq. NaOH/pH = 9.5, r.t. (ii) S0456, H₂O, 100° C., 15 min.

Scheme 4
(a)
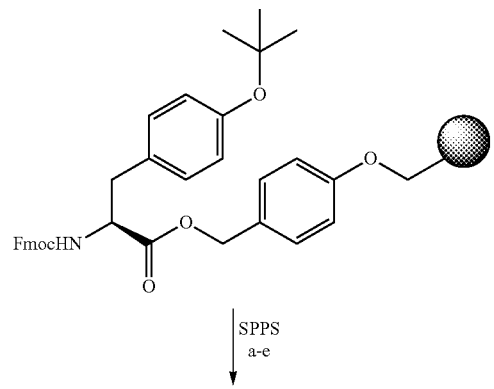
↓ SPPS a-e
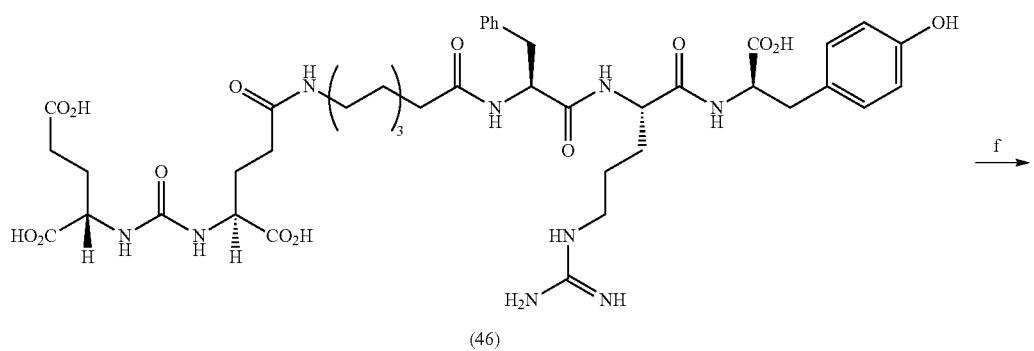
(46)
→ f
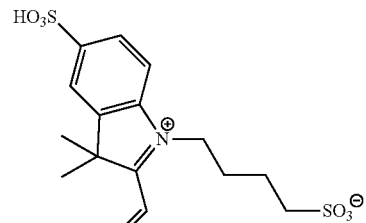
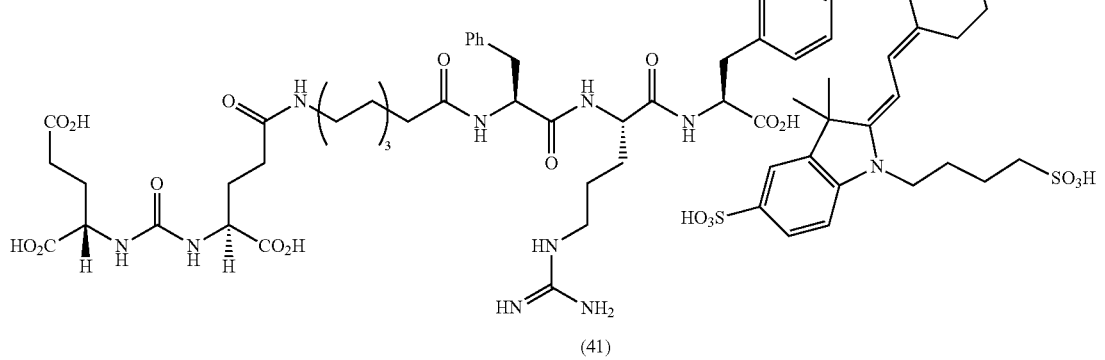
(41)
Reagents and conditions: (a) (i) 20% piperidine/DMF, r.t., 10 min; (ii) Fmoc-Arg(Pbf)-OH, HATU, DMF/DIPEA, 2 h; (b) (i) 20% piperidine/DMF, r.t., 10 min; (ii) Fmoc-Phe-OH, HATU, DMF/DIPEA, 2 h; (c) (i) 20% piperidine/DMF, r.t., 10 min; (ii) Fmoc-Eightaminooctanoic acid-OH, HATU, DMF/DIPEA, 2 h; (d) (i) 20% piperidine/DMF, r.t., 10 min; 12, HATU, DMF/DIPEA, 2 h; (e) TFA:H₂O:TIPS (95:2.5:2.5) 1 h; (f) (i) H₂O, aq. NaOH/pH = 9.5, r.t.; (ii) S0456, H₂O, 100° C., 15 min.

Scheme 5

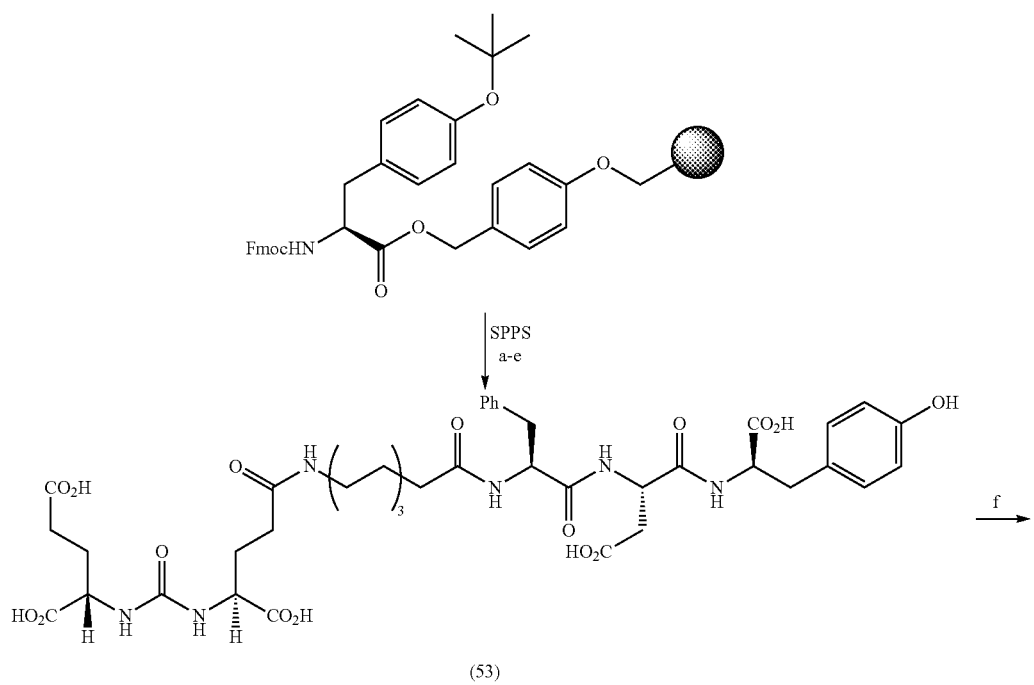

(53)

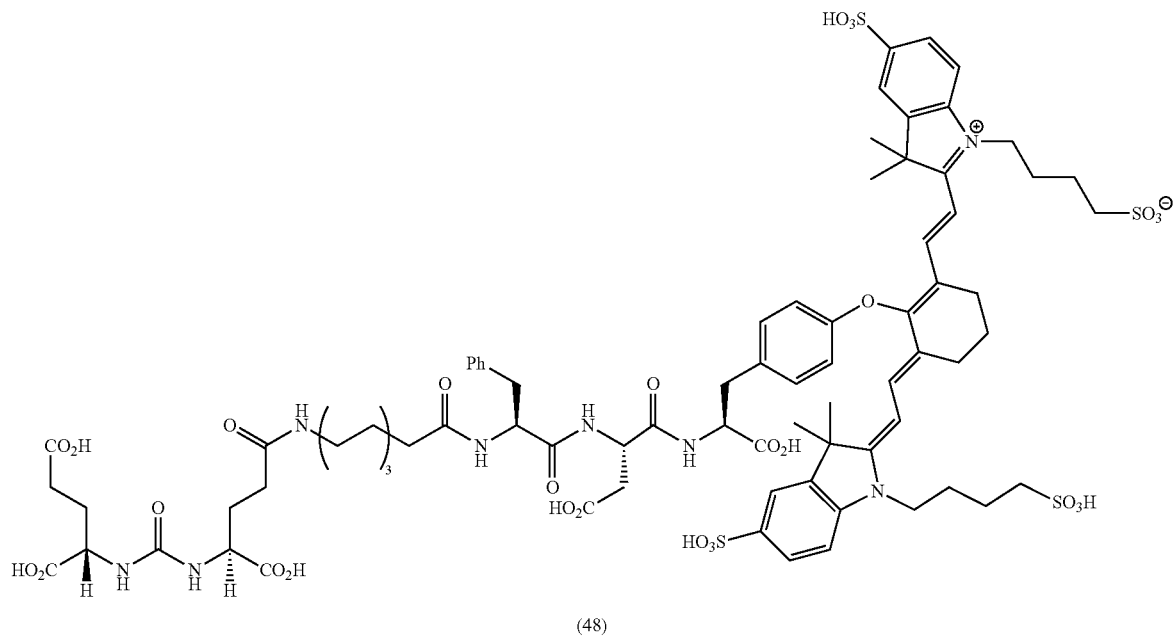

(48)

Reagents and conditions: (a) (i) 20% piperidine/DMF, r.t., 10 min; (ii) Fmoc-Asp(O$^t$Bu)-OH, HATU, DMF/DIPEA, 2 h; (b) (i) 20% piperidine/DMF, r.t., 10 min; (ii) Fmoc-Phe-OH, HATU, DMF/DIPEA, 2 h; (c) (i) 20% piperidine/DMF, r.t., 10 min; (ii) Fmoc-Eightaminooctanoic acid-OH, HATU, DMF/DIPEA, 2 h; (d) (i) 20% piperidine/DMF, r.t., 10 min; 12, HATU, DMF/DIPEA, 2 h; (e) TFA:H$_2$O:TIPS (95:2.5:2.5) 1 h; (f) (i) H$_2$O, aq. NaOH/pH = 9.5, r.t.; (ii) S0456, H$_2$O, 100° C., 15 min.

The examples that follow are merely provided for the purpose of illustrating particular aspects of the disclosure and are not intended to be limiting to the scope of the appended claims. As discussed herein, particular features of the disclosed compounds and methods can be modified in various ways that are not necessary to the operability or advantages they provide. For example, the compounds can incorporate a variety of amino acids and amino acid derivatives as well as targeting ligands depending on the particular use for which the compound will be employed. One of skill in the art will appreciate that such modifications are encompassed within the scope of the appended claims.

EXAMPLES
Example (1): Pre-Clinical Evaluation of PSMA-Targeted NIR Dye Conjugates with Random Variation of Length of the Linker/Spacer Between the Ligand and the NIR Dye
Scheme 1
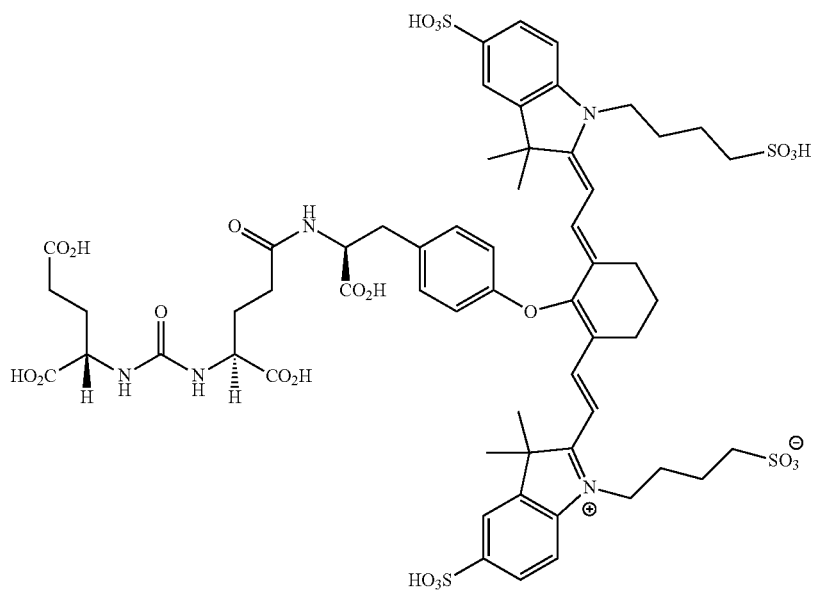
(1)
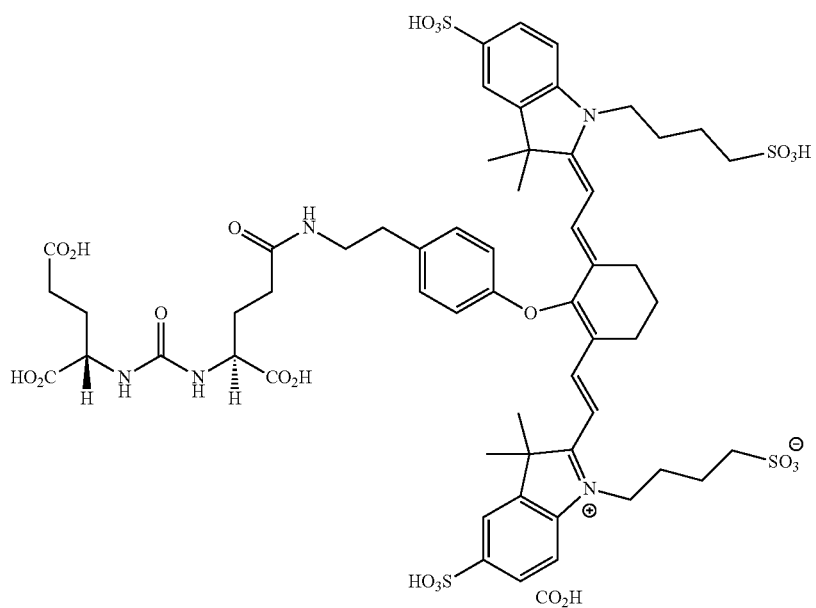
(2)

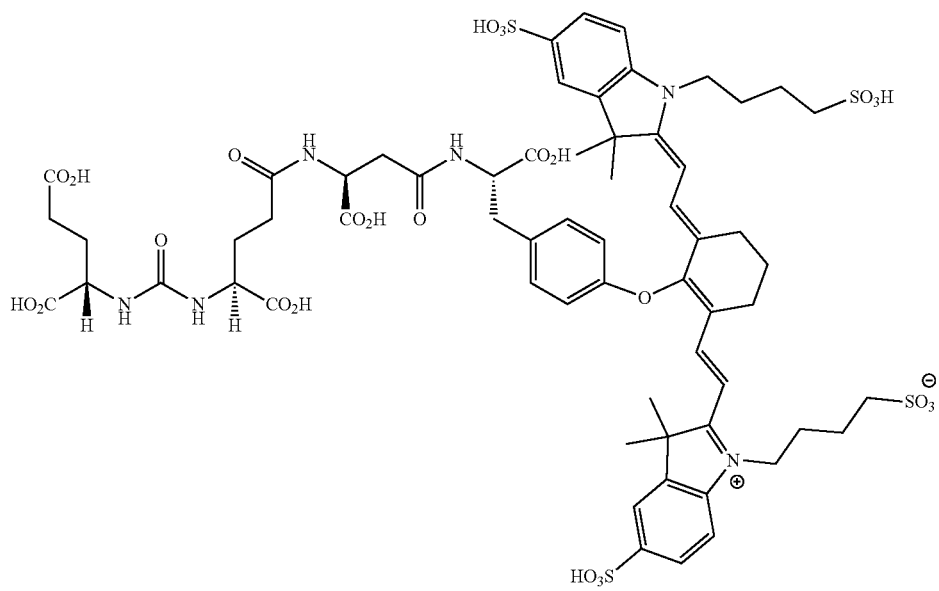
(3)
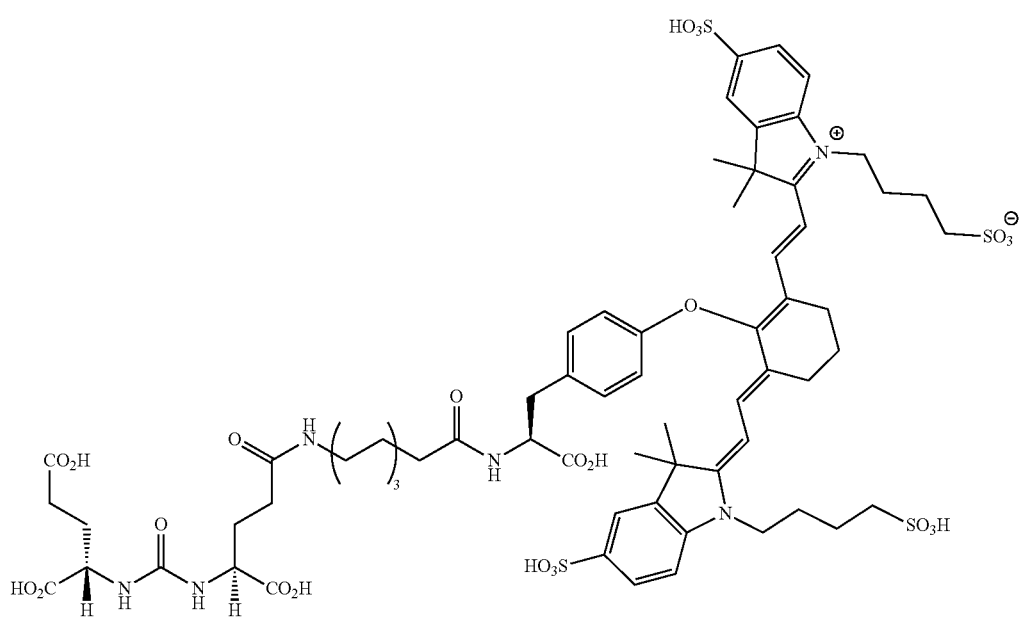
(4)

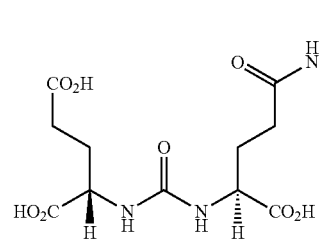
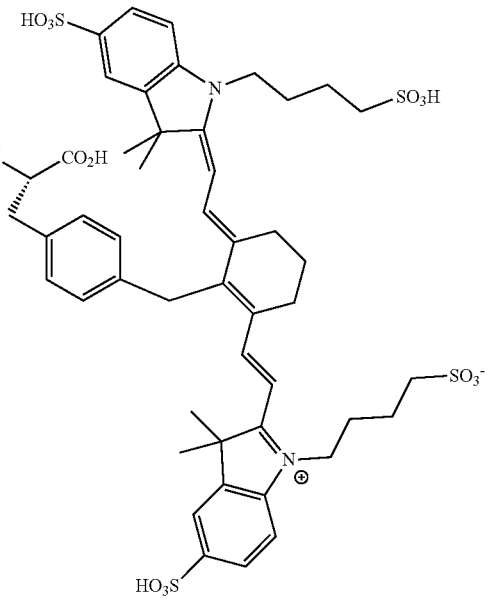
(5)
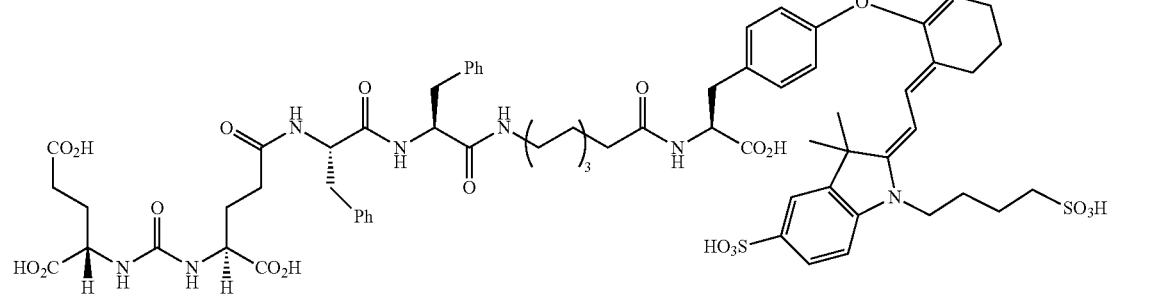
(6)

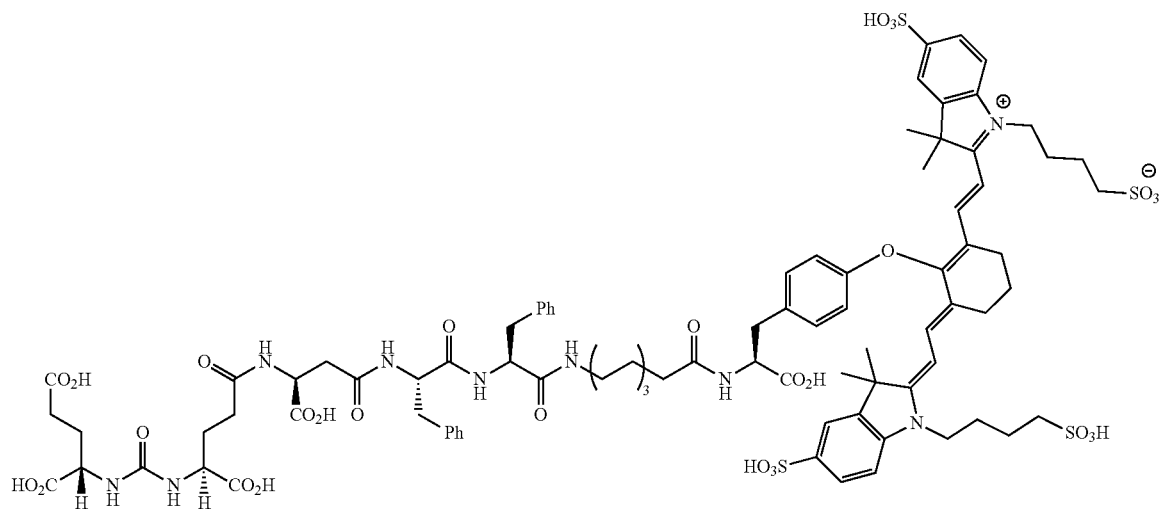
(7)
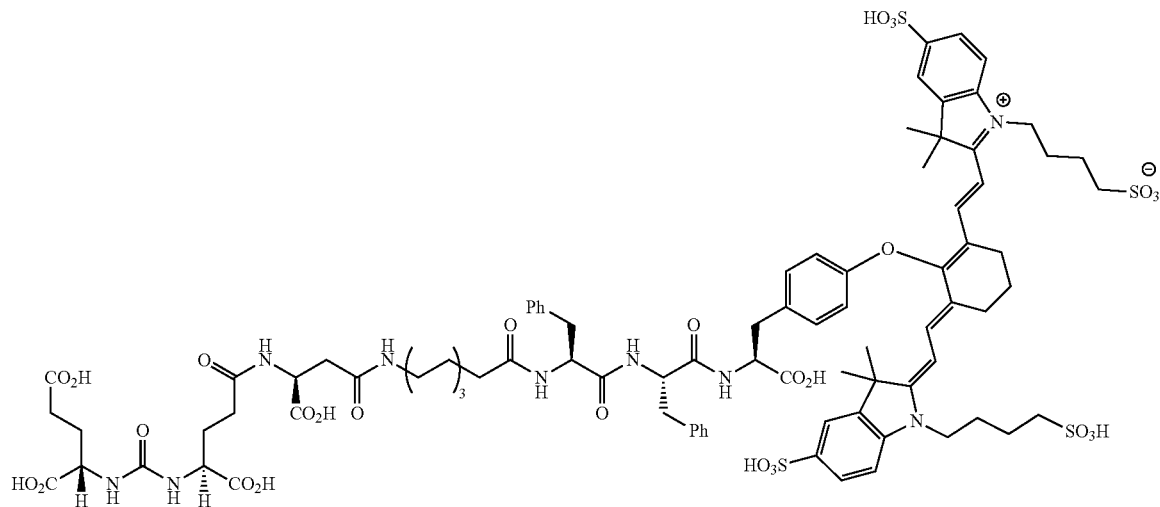
(8)

(9)
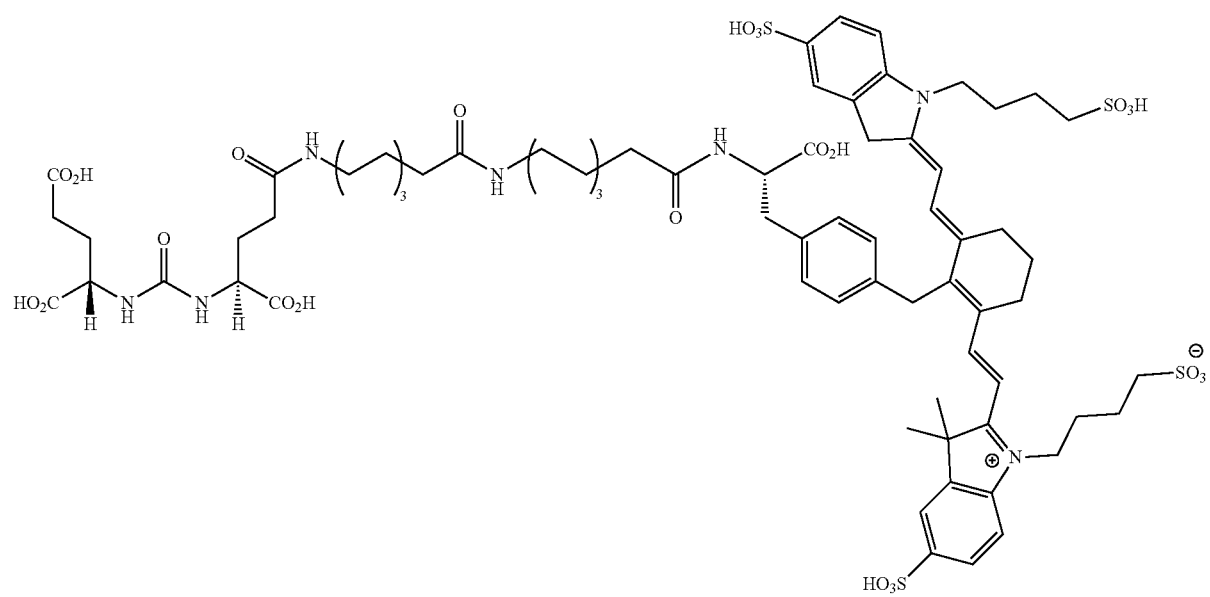
Reagents and conditions: (a) (i) triphosgene, TEA/DCM, -78° C.; (ii) H-L-Glu(OBn)-O^tBu·HCl; (b) H₂; Pd-C/DCM
Scheme 2
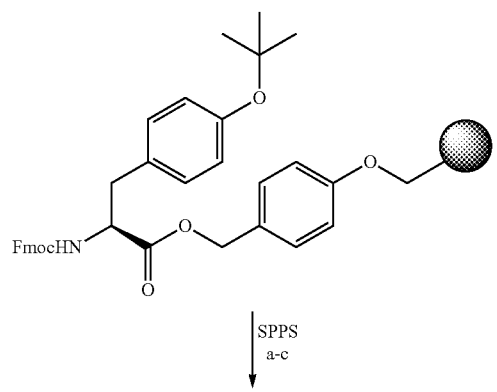
↓ SPPS
a-c
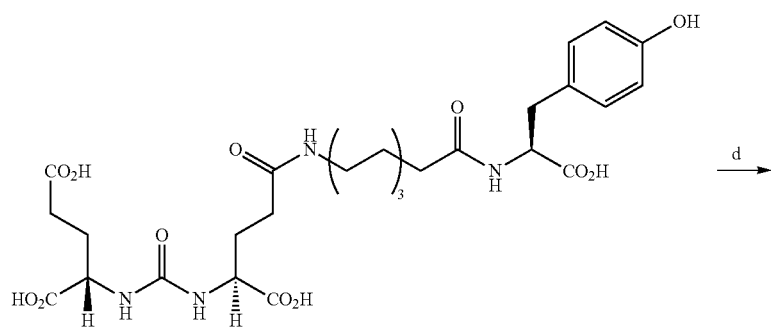
(13)

-continued

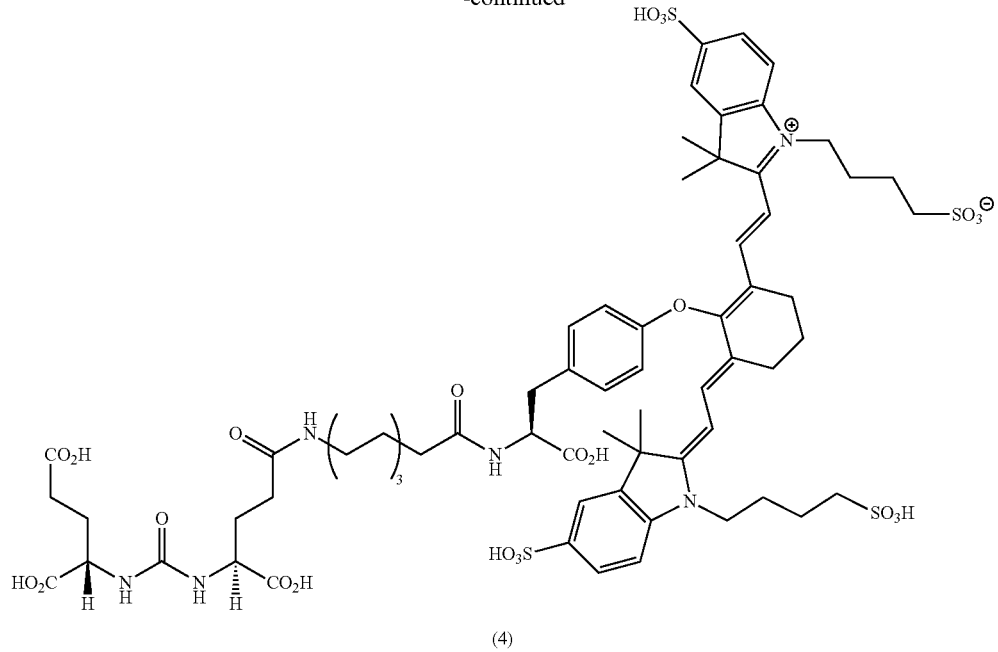

(4)

Reagents and conditions: (a) (i) 20% piperidine/DMF, r.t., 10 min; (ii) Fmoc-Eightaminooctanoic acid-OH, HATU, DMF/DIPEA, 2 h; b) (i) 20% piperidine/DMF, r.t., 10 min; (ii) 12, HATU, DMF/DIPEA, 2 h; c) TFA:$H_2O$:TIPS (95:2.5:2.5) 1 h; (d) (i) $H_2O$, aq. NaOH/pH = 9.5, r.t.; (ii) S0456, $H_2O$, 100° C., 15 min.

(a) In Vitro Studies.

FIG. 2 shows Structure of PSMA-targeted DUPA-FITC (Fluorescein isothiocyanate) conjugate (14) and its binding affinity ($K_D$) and specificity on PSMA-positive 22Rv1 human prostate cancer cells and on PSMA-negative A549 human alveolar basal epithelial cells in culture. DUPA-FITC dissolved in RPMI medium was added at the indicated concentrations to 22Rv1 or A549 cells in RPMI culture media and allowed to incubate for 1 h at 37° C. Media was then removed, washed with fresh media (3×), and replaced with PBS (phosphate buffered saline). Samples were analyzed using flow cytometry. Error bars represent SD (n=3).  does not bind to A549 cells FIG. 3** Relative binding affinities of DUPA-NIR conjugates 1-9 with respect to DUPA-FITC (14). PSMA-positive 22Rv1 human prostate cancer cells were incubated for 1 h at 37° C. in the presence of 100 nM DUPA-FITC with increasing concentrations of DUPA-NIR conjugates. Media was then removed, washed with fresh media (3×), and replaced with PBS. Cell bound fluorescence was assayed as using flow cytometry.

The binding affinity of the DUPA-NIR conjugates was monitored and the data are shown in Table 1.

TABLE 1

Binding affinity of DUPA-NIR conjugates with variable length spacers to PSMA-positive 22Rv1 human prostate cancer cells.

| Compound | Number of atoms between DUPA and NIR agent | $K_D$ (nM) |
| --- | --- | --- |
| 1 | 3 | 141.9 |
| 2 | 3 | 112.7 |
| 3 | 7 | 9.71 |
| 4 | 12 | 15.2 |
| 5 | 15 | 12.2 |
| 6 | 18 | 35.7 |
| 7 | 22 | 26.8 |

TABLE 1-continued

Binding affinity of DUPA-NIR conjugates with variable length spacers to PSMA-positive 22Rv1 human prostate cancer cells.

| Compound | Number of atoms between DUPA and NIR agent | $K_D$ (nM) |
| --- | --- | --- |
| 8 | 22 | 23.2 |
| 9 | 21 | 17.2 |

In vivo studies. For in vivo analysis, the tissue distribution of DUPA-NIR conjugates was monitored and is shown in FIG. 4. More specifically, biodistribution of DUPA-NIR conjugates 1-9 was monitored using fluorescence imaging of mice bearing human prostate tumor xenografts (22Rv1 cells). Male nude mice with 22Rv1 tumor xenografts were injected with DUPA-NIR dye conjugates via tail vein. The mice were euthanized 2 h after administration of the DUPA-NIR dye conjugate, selected tissues were harvested, and tissues were imaged with IVIS imager (ex=745 nm, em=ICG, exposure time=1 s). The results are shown in FIG. 4.

The conjugates were also tested to show the ratio of tumor-to-tissue fluorescence. FIG. 5 shows the tumor-to-tissue fluorescence ratio from tissue biodistribution data of PSMA-targeted DUPA-NIR conjugates 1-9. After imaging, fluorescence within a Region of interest (ROI) was measured for each tissue using In Vivo imaging software and tumor-to-tissue fluorescence was then calculated Conclusion: The in vitro binding affinity data showed that the compounds 3 (7 atom spacer), 4 (12 atom spacer), and 5 (15 atom spacer) have very high affinity for PSMA whereas the compounds 1 (3 atom spacer) and 2 (3 atom spacer) have low affinity for PSMA. The above data show that the PMSA-targeted NIR dye need a minimum length of a 7 atom spacer between DUPA and NIR agent to have optimal effective binding affinity.

Compound 4, DUPA-EAOA-Tyr-S0456, (EAOA—Eight aminooctonoic acid) showed the best tumor-to-background ratio (TBR) out of all compounds evaluated. Compound 4 also showed higher fluorescence intensity in the tumor.

Compounds 6 and 7 showed the second and third best TBR amongst the compound evaluated in this example. However, fluorescence intensity in the tumor for compound 6 and 7 was lower as compared to that of compound 3, 4, and 5. After considering affinity and specificity for PSMA expressing prostate cancer cells and tumor tissues, fluorescence intensity in the tumor, tumor-to-background ratio, etc., it appears that Compound 4 can be considered as a suitable clinical candidate although the other compounds also may provide some valuable insights in the clinic as well as in experimental conditions.

Example 2: Pre-Clinical Evaluation of PSMA-Targeted NIR Conjugates with Aromatic Amino Acid Linkers Between the Ligand and the NIR Dye FIG. 6 shows the structures of PSMA-targeted DUPA-Linker-NIR imaging agents with aromatic amino acid linkers between the ligand and the NIR dye. The synthesis scheme is shown in scheme 3.

(b) Synthesis

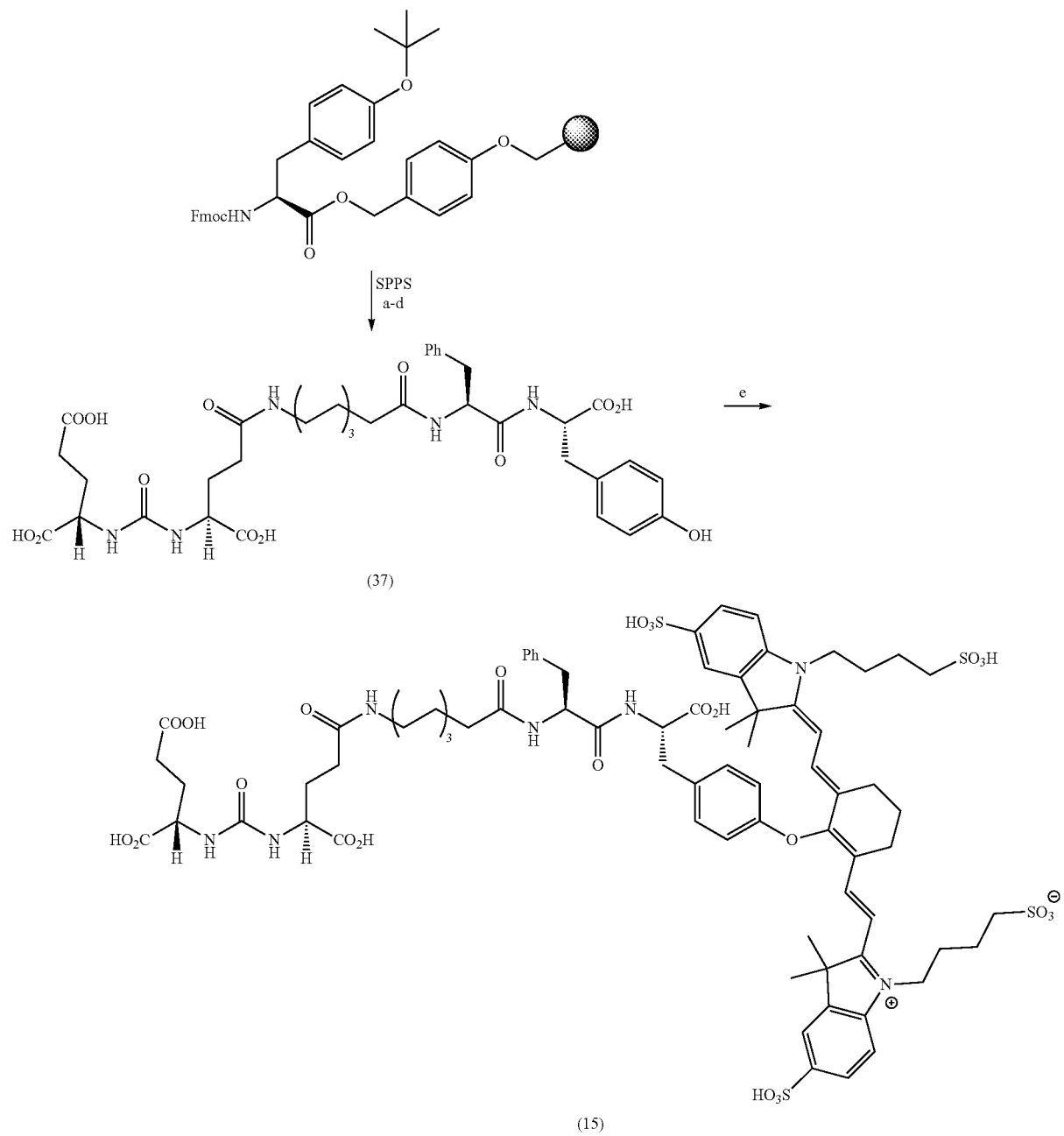

Scheme 3

Reagents and conditions: (a) (i) 20% piperidine/DMF, r.t., 10 min; (ii) Fmoc-Phe-OH, HATU, DMF/DIPEA, 2 h; (b) (i) 20% piperidine/DMF, r.t., 10 min; (ii) Fmoc-Eightaminooactanoic acid-OH, HATU, DMF/DIPEA, 2 h; (c) (i) 20% piperidine/DMF, r.t., 10 min; (ii) 12, HATU, DMF/DIPEA, 2 h; d) TFA:H2O:TIPS (95:2.5:2.5), 1 h; (e) (i) H2O, aq. NaOH/pH = 9.5, r.t.; (ii) S0456, H2O, 100° C., 15 min.

in vitro studies. FIG. 7 shows the Relative binding affinities of DUPA-NIR conjugates with aromatic amino acids linkers with respect to DUPA-FITC (14). PSMA-positive 22Rv1 human prostate cancer cells were incubated for 1 h at 37° C. in the presence of 100 nM DUPA-FITC with increasing concentrations of DUPA-NIR conjugates. Media was then removed, washed with fresh media (3×), and replaced with PBS. Cell bound fluorescence was assayed as using flow cytometry.

Table 2 shows data of the binding affinity of DUPA-NIR conjugates with aromatic linkers to PSMA-positive 22Rv1 human prostate cancer cells.

| Compound | $K_D$ (nM) |
|---|---|
| 15 | 4.9 |
| 23 | 7.5 |
| 25 | 6.3 |
| 27 | 22.2 |
| 32 | 32 |
| 33 | 16 |
| 34 | 34.9 |
| 35 | 23.9 |
| 36 | 13.4 | in vivo studies. FIG. 8 shows Tissue biodistribution analysis and tumor-to-tissue ratio of DUPA-NIR conjugates 15 and 23 using fluorescence imaging of mice bearing human prostate tumor xenografts (22Rv1 cells). Male nude mice with 22Rv1 tumor xenografts were injected with DUPA-NIR dye conjugates via tail vein. The mice were euthanized 2 h after administration of the DUPA-NIR dye conjugate, selected tissues were harvested, and tissues were imaged with IVIS imager (ex=745 nm, em=ICG, exposure time=1 s). After imaging, fluorescence within a Region of interest (ROI) was measured for each tissue using In Vivo imaging software and tumor-to-tissue fluorescence was then calculated.

FIG. 9 shows an overlay of whole or half body fluorescence image over white light images after adjusting the threshold. 22Rv1 human prostate tumor xenograft bearing mouse was injected with 20 nmol of 15 and imaged with IVIS imager (ex=745 nm, em=ICG, exposure time=1 s) at different time intervals.

FIG. 10 shows an overlay of whole or half body fluorescence image over white light images after adjusting the threshold. 22Rv1 human prostate tumor xenograft bearing mouse was injected with 20 nmol of 23 and imaged with IVIS imager (ex=745 nm, em=ICG, exposure time=1 s) at different time intervals.

FIG. 11 shows an overlay of whole body or half body fluorescence image over white light images after adjusting the threshold. 22Rv1 human prostate tumor xenograft bearing mouse was injected with 20 nmol of 25 and imaged with IVIS imager (ex=745 nm, em=ICG, exposure time=1 s) at different time intervals FIG. 12 shows an overlay of whole body or half body fluorescence image over white light images after adjusting the threshold. 22Rv1 human prostate tumor xenograft bearing mouse was injected with 6 nmol of 35 and imaged with IVIS imager (ex=745 nm, em=ICG, exposure time=1 s) at different time intervals.

FIG. 13 shows an overlay of whole body or half body fluorescence image over white light images after adjusting the threshold. 22Rv1 human prostate tumor xenograft bearing mouse was injected with 6 nmol of 36 and imaged with IVIS imager (ex=745 nm, em=ICG, exposure time=1 s) at different time intervals.

Conclusion: These in vitro binding affinity data showed that compounds 15, 23, 25 and 36 have very high affinity for PSMA. Moreover, compounds 15, 23, 25, 35, and 36 showed very good whole-body imaging data within 2-4 hours after administering to the animal. In addition, compounds 15 and 35 showed excellent tumor-to-background ratio (TBR). After considering affinity and specificity for PSMA expressing prostate cancer cells and tumor tissues, fluorescence intensity in the tumor, tumor-to-background ratio, ease synthesis and availability of starting materials for low cost, compound 15 and 35 can be considered as excellent clinical candidates, although the other compounds also may be useful both as clinical and/or experimental candidates.

Example 3: Pre-Clinical Evaluation of PSMA-Targeted NIR Conjugates with a Positive Charge Linker Between the Ligand and the NIR Dye FIG. 14 shows the structures of PSMA-targeted DUPA-Linker-NIR imaging agents with positive charge linkers between the ligand and the NIR dye and the synthesis scheme for these agents is shown in Scheme 4:

Scheme 4

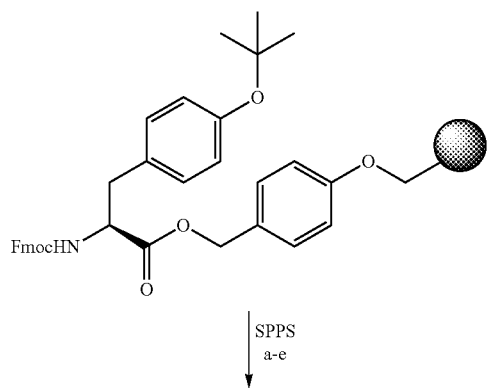

-continued

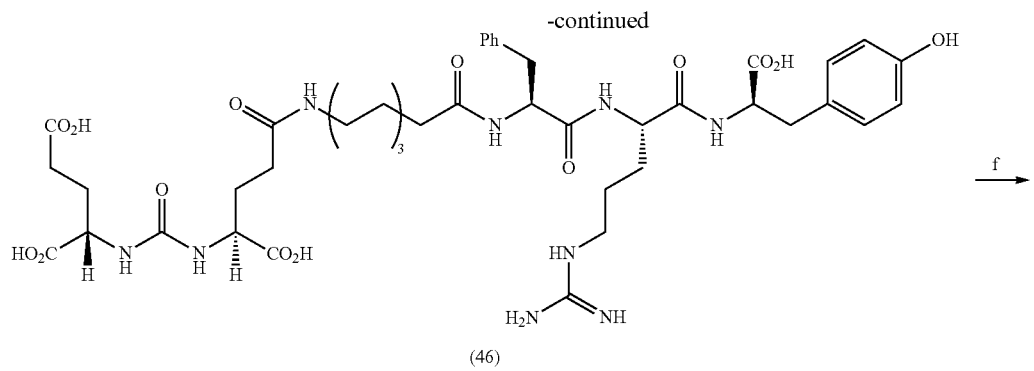

(46)

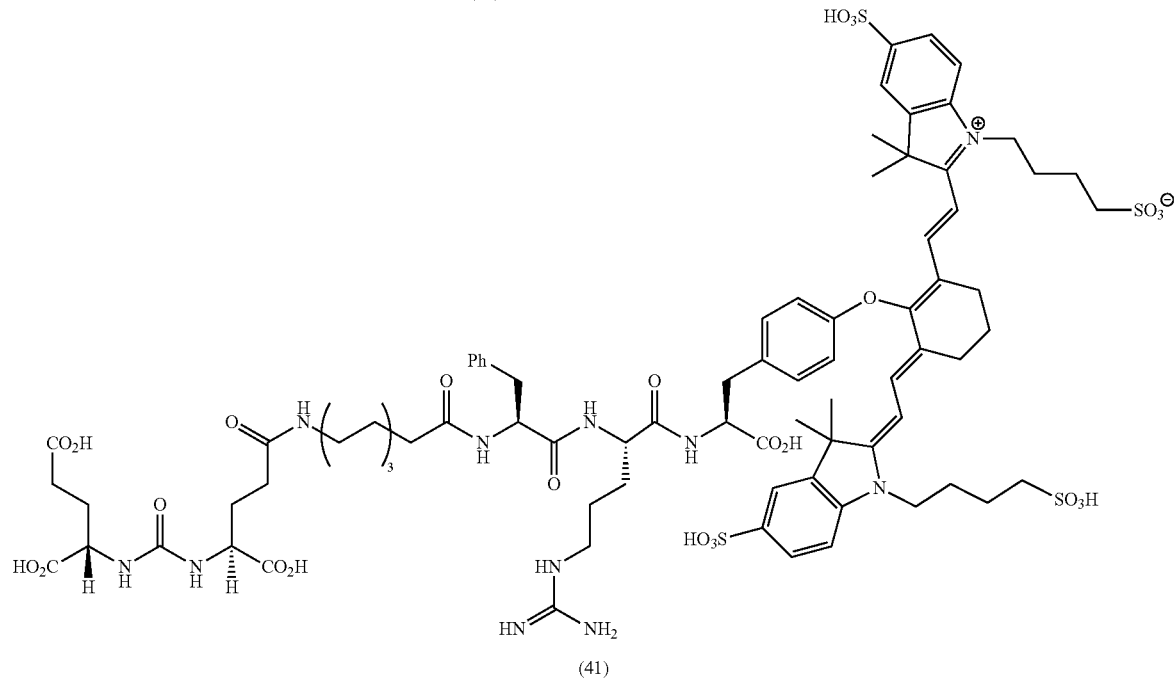

(41)

Reagents and conditions: (a) (i) 20% piperidine/DMF, r.t., 10 min; (ii) Fmoc-Arg(Pbf)-OH, HATU, DMF/DIPEA, 2 h; (b) (i) 20% piperidine/DMF, r.t., 10 min; (ii) Fmoc-Phe-OH, HATU, DMF/DIPEA, 2 h; (c) (i) 20% piperidine/DMF, r.t., 10 min; (ii) Fmoc-Eightaminooctanoic acid-OH, HATU, DMF/DIPEA, 2 h; (d) (i) 20% piperidine/DMF, r.t., 10 min; 12, HATU, DMF/DIPEA, 2 h; (e) TFA:$H_2O$:TIPS (95:2.5:2.5) 1 h; (f) (i) $H_2O$, aq. NaOH/pH = 9.5, r.t.; (ii) S0456, $H_2O$, 100° C., 15 min.

FIG. 15 shows the relative binding affinities of DUPA-NIR conjugates with respect to DUPA-FITC (14). PSMA-positive 22Rv1 human prostate cancer cells were incubated for 1 h at 37° C. in the presence of 100 nM DUPA-FITC with increasing concentrations of DUPA-NIR conjugates. Media was then removed, washed with fresh media (3×), and replaced with PBS. Cell bound fluorescence was assayed as using flow cytometry.

In vivo studies: FIG. 16 shows the tumor to tissue ratio of DUPA-NIR conjugates 39 and 41 using fluorescence imaging of mice bearing human prostate tumor xenografts (22 Rv1 cells). Male nude mice with 22Rv1 tumor xenografts were injected with DUPA-NIR dye conjugates via tail vein. The mice were euthanized 2 h after administration of the DUPA-NIR dye conjugate, selected tissues were harvested, and tissues were imaged with IVIS imager (ex=745 nm, em=ICG, exposure time=1 s). After imaging, fluorescence within a Region of interest (ROI) was measured for each tissue using In Vivo imaging software and tumor-to-tissue fluorescence was then calculated.

FIG. 17 shows an overlay of whole body or half body fluorescence image over white light images after adjusting the threshold. 22Rv1 human prostate tumor xenograft bearing mouse was injected with 20 nmol of 39 and imaged with IVIS imager (ex=745 nm, em=ICG, exposure time=1 s) at different time intervals.

FIG. 18 shows and overlay of whole body or half body fluorescence image over white light images after adjusting the threshold. 22Rv1 human prostate tumor xenograft bearing mouse was injected with 20 nmol of 40 and imaged with IVIS imager (ex=745 nm, em=ICG, exposure time=1 s) at different time intervals.

FIG. 19 shows an overlay of whole body or half body fluorescence image over white light images after adjusting the threshold. 22Rv1 human prostate tumor xenograft bearing mouse was injected with 20 nmol of 41 and imaged with IVIS imager (ex=745 nm, em=ICG, exposure time=1 s) at different time intervals.

Conclusion: These in vitro binding affinity data showed that the compound 41 has very high affinity for PSMA.

Compounds 39, 40 and 41 showed very good whole-body imaging and fast skin clearance in time dependent imaging studies. Adding Arg to the linker between the ligand-eight aminooctonoic acid linker and NIR dye, increased the number of positive charges and decreased the total negative charge of the overall molecule. Although having Arg moieties decreased the affinity of the molecule to PSMA, these compounds showed fast skin clearance. After considering affinity and specificity for PSMA expressing prostate cancer cells and tumor tissues, fast skin clearance, the compound 41 can be considered as a clinical candidate, although the other compounds also may be useful both as clinical and/or experimental candidates.

Example (4): Pre-Clinical Evaluation of PSMA-Targeted NIR Conjugates with a Negative Charge Linker Between the Ligand and the NIR Dye FIG. 20 shows Structures of PSMA-targeted DUPA-Linker-NIR imaging agents with negative charge linkers between the ligand and the NIR dye. The synthesis scheme is shown in Scheme 5.

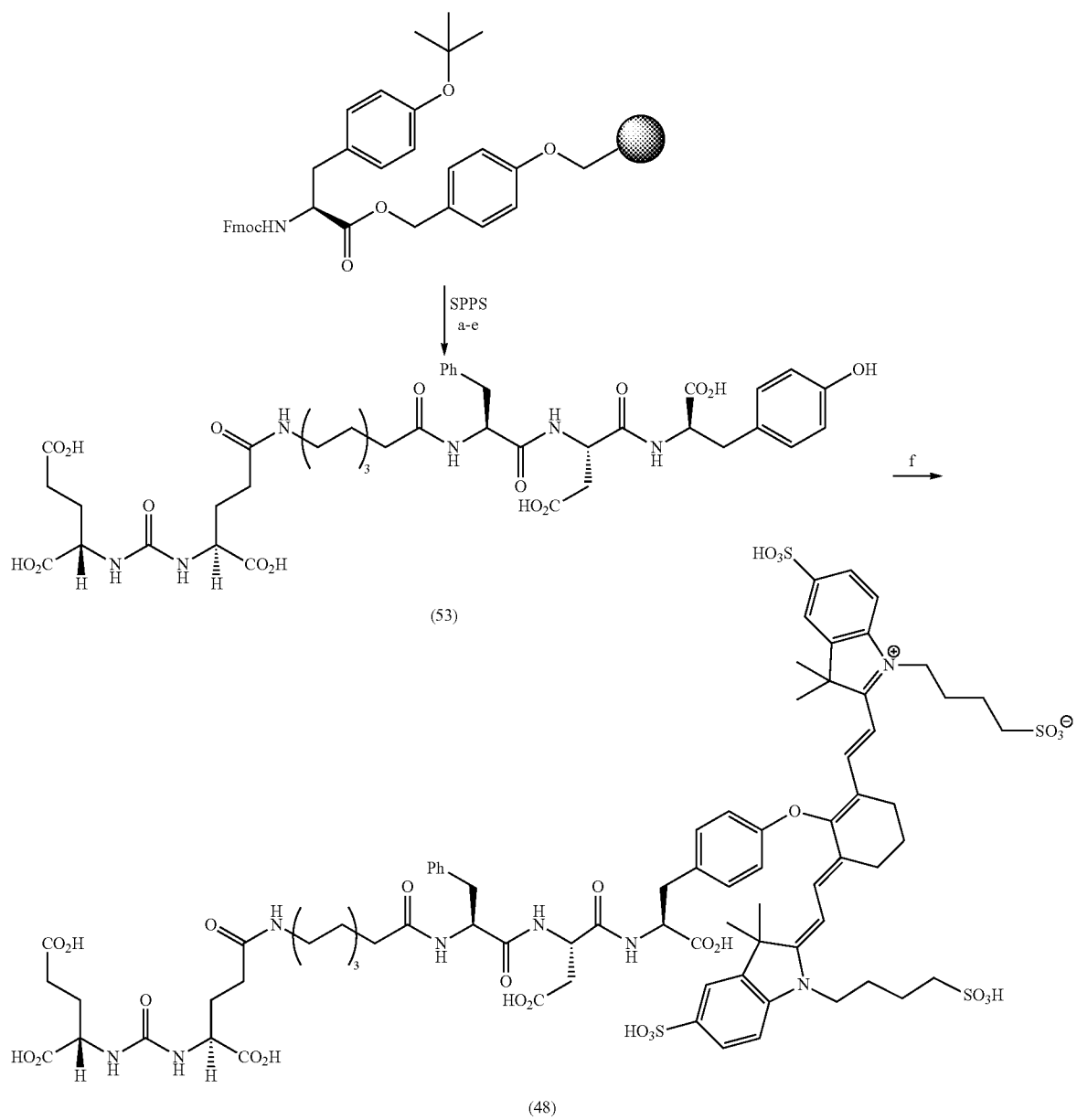

Reagents and conditions: (a) (i) 20% piperidine/DMF, r.t., 10 min; (ii) Fmoc-Asp(O$^t$Bu)-OH, HATU, DMF/DIPEA, 2 h; (b) (i) 20% piperidine/DMF, r.t., 10 min; (ii) Fmoc-Phe-OH, HATU, DMF/DIPEA, 2 h; (c) (i) 20% piperidine/DMF, r.t., 10 min; (ii) Fmoc-Eightaminooctanoic acid-OH, HATU, DMF/DIPEA, 2 h; (d) (i) 20% piperidine/DMF, r.t., 10 min; 12, HATU, DMF/DIPEA, 2 h; (e) TFA:H$_2$O:TIPS (95:2.5:2.5) 1 h; (f) (i) H$_2$O, aq. NaOH/pH = 9.5, r.t.; (ii) S0456, H$_2$O, 100° C., 15 min.

In vitro studies: FIG. 21 Relative binding affinities of DUPA-NIR conjugates of 49 and 50 with respect to DUPA-FITC (14). PSMA-positive 22Rv1 human prostate cancer cells were incubated for 1 h at 37° C. in the presence of 100 nM DUPA-FITC with increasing concentrations of DUPA-NIR conjugates. Media was then removed, washed with fresh media (3x), and replaced with PBS. Cell bound fluorescence was assayed as using flow cytometry.

In vivo studies. FIG. 22 shows Tissue biodistribution analysis and tumor-to-tissue ratio of DUPA-NIR conjugates 49 and 50 using fluorescence imaging of mice bearing human prostate tumor xenografts (22Rv1 cells). Male nude mice with 22Rv1 tumor xenografts were injected with DUPA-NIR dye conjugates via tail vein. The mice were euthanized 2 h after administration of the DUPA-NIR dye conjugate, selected tissues were harvested, and tissues were imaged with IVIS imager (ex=745 nm, em=ICG, exposure time=1 s). After imaging, fluorescence within a Region of interest (ROI) was measured for each tissue using In Vivo imaging software and tumor-to-tissue fluorescence was then calculated.

Conclusion: While it had low binding affinity for PSMA, the compound 49 has very high tumor accumulation (high fluorescence intensity) and good tumor-to-background ratio Example 5: Pre-Clinical Evaluation of PSMA-Targeted NIR Dye Conjugates with Variation of Charge of the NIR Dye Molecule FIG. 23 shows structures of PSMA-targeted DUPA-Linker-NIR imaging agents with variably charged NIR dye molecule.

FIG. 24: Relative binding affinities of DUPA-NIR conjugates with respect to DUPA-FITC (14). PSMA-positive 22Rv1 human prostate cancer cells were incubated for 1 h at 37° C. in the presence of 100 nM DUPA-FITC with increasing concentrations of DUPA-NIR conjugates. Media was then removed, washed with fresh media (3x), and replaced with PBS. Cell bound fluorescence was assayed as using flow cytometry.

| Compound | $K_D$ (nM) |
|---|---|
| 15 | 4.9 |
| 54 | 2.6 |
| 55 | 7.3 |
| 56 | 3.7 |
| 59 | 60.9 |
| 60 | 5.4 |

FIG. 25: Overlay of whole body or half body fluorescence image over white light images after adjusting the threshold. 22Rv1 human prostate tumor xenograft bearing mouse was injected with 20 nmol of 54 and imaged with IVIS imager (ex=745 nm, em=ICG, exposure time=1 s) at different time intervals.

FIG. 26 shows overlay of whole body or half body fluorescence image over white light images after adjusting the threshold. 22Rv1 human prostate tumor xenograft bearing mouse was injected with 20 nmol of 55 and imaged with IVIS imager (ex=745 nm, em=ICG, exposure time=1 s) at different time intervals.

FIG. 27 shows Overlay of whole body or half body fluorescence image over white light images after adjusting the threshold. 22Rv1 human prostate tumor xenograft bearing mouse was injected with 20 nmol of 56 and imaged with IVIS imager (ex=745 nm, em=ICG, exposure time=1 s) at different time intervals.

FIG. 28 shows overlay of whole body or half body fluorescence image over white light images after adjusting the threshold. 22Rv1 human prostate tumor xenograft bearing mouse was injected with 20 nmol of 57 and imaged with IVIS imager (ex=745 nm, em=ICG, exposure time=1 s) at different time intervals FIG. 29 shows overlay of whole body or half body fluorescence image over white light images after adjusting the threshold. 22Rv1 human prostate tumor xenograft bearing mouse was injected with 20 nmol of 58 and imaged with IVIS imager (ex=745 nm, em=ICG, exposure time=1 s) at different time intervals FIG. 30 shows overlay of whole body or half body fluorescence image over white light images after adjusting the threshold. 22Rv1 human prostate tumor xenograft bearing mouse was injected with 20 nmol of 60 and imaged with IVIS imager (ex=745 nm, em=ICG, exposure time=1 s) at different time intervals.

Conclusion: These in vitro binding affinity data showed that the compounds 15, 55, 56, and 60 have very high affinity for PSMA. Compounds 15, 54, 57 and 60 showed very good whole-body imaging and fast skin clearance in time dependent imaging studies. Therefore, reducing negative charge by removal of sulfonic acid groups (SO3H) from the NIR dye helped in producing fast skin clearance and fast tumor accumulation. After considering affinity and specificity for PSMA expressing prostate cancer cells and tumor tissues, fast skin clearance, the compounds 54, 57, and 60 can be considered as clinical candidates.

Example 6: Pre-Clinical Evaluation of PSMA-Targeted NIR Dye Conjugates: Miscellaneous DUPA-NIR Conjugates FIG. 31: Structures of PSMA-targeted DUPA-Linker-NIR imaging agents with miscellaneous linkers and NIR dyes.

FIG. 32 shows the relative binding affinities of DUPA-NIR conjugates with respect to DUPA-FITC (14). PSMA-positive 22Rv1 human prostate cancer cells were incubated for 1 h at 37° C. in the presence of 100 nM DUPA-FITC with increasing concentrations of DUPA-NIR conjugates. Media was then removed, washed with fresh media (3x), and replaced with PBS. Cell bound fluorescence was assayed as using flow cytometry

| Compound | $K_D$ (nM) |
|---|---|
| 15 | 4.9 |
| 54 | 2.6 |
| 55 | 7.3 |
| 56 | 3.7 |
| 59 | 60.9 |
| 60 | 5.4 | in vivo studies. FIG. 33 shows overlay of whole body or half body fluorescence image over white light images after adjusting the threshold. 22Rv1 human prostate tumor xenograft bearing mouse was injected with 20 nmol of 63 and imaged with IVIS imager (ex=745 nm, em=ICG, exposure time=1 s) at different time intervals.

FIG. 34 shows overlay of whole body or half body fluorescence image over white light images after adjusting the threshold. 22Rv1 human prostate tumor xenograft bearing mouse was injected with 6 nmol of 63 and imaged with IVIS imager (ex=745 nm, em=ICG, exposure time=1 s) at different time intervals.

FIG. 35 shows Overlay of whole body or half body fluorescence image over white light images after adjusting the threshold. 22Rv1 human prostate tumor xenograft bearing mouse was injected with 20 nmol of 64 and imaged with IVIS imager (ex=745 nm, em=ICG, exposure time=1 s) at different time intervals.

Conclusion: These in vitro binding affinity data showed that the compounds 62, 64, 65, and 66 have low affinity for PSMA. However, Compounds 63 and 64 also showed very good whole-body imaging and fast skin clearance in time dependent imaging studies. Therefore, the compounds 63 and 64 can be considered as particularly preferred clinical candidates, although the other compounds also may be useful both as clinical and/or experimental candidates.

Example 7: Pre-Clinical Evaluation of PSMA-Targeted NIR Dye Conjugates: Alternative Ligands for DUPA FIG. 36 shows Structures of PSMA-targeted NIR imaging agents with different ligand.

FIG. 37 shows relative binding affinities of PSMA-targeted NIR conjugates 15 with respect to DUPA-FITC (14) for PSMA-positive 22Rv1 and for PSMA-negative A549 cells. Cancer cells were incubated for 1 h at 37° C. in the presence of 100 nM DUPA-FITC with increasing concentrations of compound 15. Media was then removed, washed with fresh media (3×), and replaced with PBS. Cell bound fluorescence was assayed as using flow cytometry.

FIG. 38 shows overlay of whole body or half body fluorescence image over white light images after adjusting the threshold. 22Rv1 human prostate tumor xenograft bearing mouse was injected with 6 nmol of 15 and imaged with IVIS imager (ex=745 nm, em=ICG, exposure time=1 s) at different time intervals.

Conclusion: While alternative ligands for DUPA that have higher affinity for PSMA when compared to DUPA have been synthesized, this example shows that the compound 15 has a very high affinity for PSMA-positive 22Rv1 cells but not for PSMA-negative A549 cells indicating the compound 15 is highly specific for PSMA. Time dependent whole-body imaging studies showed that the compound 15 accumulated in PSMA-positive tumors and kidneys of the mouse, again demonstrating that compound 15 is an excellent clinical candidate.

Example 8: General Methods

Cell culture: LNCaP, 22Rv1 and PC3 (human prostate cancer cell lines) and A549 (a alveolar basal epithelial carcinoma cell line) cells were obtained from American Type Culture Collection (ATCC) (Rockville, Md., 2014) and grown as a monolayer using normal 1640 RPMI-medium (Gibco, N.Y.) containing 10% heat-inactivated fetal bovine serum (Atlanta Biological, GA) and 1% penicillin streptomycin (Gibco, N.Y.) in a 5% carbon dioxide: 95% air-humidified atmosphere at 37° C. for at least 4 passages before they were used for the assays.

Animal: Athymic male nude (nu/nu) (7 weeks old, 20-25 g) were purchased from Invigo (Indianapolis, Ind.) and maintained on normal diet. Animals were housed 5/cage in a barrier, pathogen-free cloaked rack. Autoclaved tap water and food were given as needed. The animals were housed in a sterile environment on a standard 12 h light-dark cycle for the duration of the study. All animal procedures were approved by Purdue Animal Care and Use Committee. Animal care and studies were performed according to national and international guidelines for the humane treatment of animals.

Animal imaging experiments were performed using a Caliper IVIS Lumina II Imaging Station with Living Image 4.0 software (PerkinElmer Inc, MA) using imager parameters as ex=745 nm, em=ICG, and exposure time=1 s. ROI calculations were conducted using Living Image 4.0 software.

Human blood: Collection of blood samples from human subjects and further studies were done according to a Purdue University approved Institutional Review Board protocol.

Example 9: In Vitro Binding and Specificity of OTL78

Experimental Procedures

In vitro binding: For OTL78 relative affinity (IC50), 22Rv1 or PC3 cells were plated into a T75 flask and allowed to form a monolayer over 48 h. After trypsin digestion, released cells were transferred into centrifuge tubes (1×106 cells/tube) and centrifuged. Spent medium in each tube was replaced with 100 nM DUPA-FITC in the presence of increasing concentration (0.001 nM-10 µM) of OTL78 in fresh medium (0.5 mL). After incubating for 30 min at 4° C., cells were rinsed with culture medium (2×1.0 mL) and saline (1×1.0 mL) to remove any unbound DUPA-FITC. Cells were then re-suspended in saline (0.5 mL) and cell bound fluorescence was quantified using a flow cytometer. The relative affinities were calculated using a plot of percent cell bound fluorescence versus the log concentration of OTL78 using GraphPad Prism 6.

For OTL78 binding affinity, 22Rv1 or PC3 cells were seeded into a T75 flask and allowed to form a monolayer over 48 h. After trypsin digestion, cells were transferred into centrifuge tubes (1×106 cells/tube) and centrifuged. The medium was replaced with fresh medium containing increasing concentration of OTL78 and incubated for 30 min at 4° C. After rinsing with fresh medium (2×1.0 mL) and saline (1×1.0 mL), cells were lysed with 1% SDS with in saline (1.0 mL) and cell bound fluorescence was analyzed using a fluorometer (Cary Eclipse, Agilent Technologies). The binding affinity (Kd) was calculated using a plot of percent cell bound fluorescence versus concentration using GraphPad Prism 6.

Confocal Microscopy: 22Rv1, LNCaP, or PC3 cells (50,000 cells/well in 1 mL) were seeded into poly-D-lysine microwell Petri dishes and allowed cells to form monolayers over 12 h. Spent medium was replaced with fresh medium containing OTL78 (100 nM) and cells were incubated for 1 h at 37° C. or 4° C. After rinsing with fresh medium (2×1.0 mL) and saline (lx 1.0 mL), fluorescence images were acquired using an epi-microscopy.

Results and Conclusions: In an effort to improve limitations in current clinical practice of radical prostatectomy and tumor-specific imaging agents that are in the preclinical stages, OTL78 was assembled using: (i) a high affinity PSMA-targeting ligand (coined DUPA), (ii) a rationally designed 14 atoms long polyethylene glycol-dipeptide linker, and (iii) an inexpensive NIR dye (>$400/gram) named S0456 (see FIG. 38A for the chemical structure). The dipeptide consisting of phenylalanine-tyrosine was designed to fit to the contours and chemistry of the tunnel accessing the binding pocket of the PSMA protein. Upon conjugation of DUPA-PEG-dipeptide to S0456, the dipeptide is not only improved the binding affinity of OTL78 but also enhanced the fluorescence of S0456 by ≥2 at the same concentration (see FIG. 38B & FIG. 39A showing excitation & emission spectra of OTL78 at 1 μM and S0456 at 1 μM in 1 mL of PBS obtained using fluorometer).

In an effort to evaluate specificity of OTL78 for PCa, PSMA expression in LNCaP, 22Rv1, PC3 (three human PCa cell lines) and A549 (a human alveolar basal epithelial carcinoma cell line), as a negative control, was first examined by flow cytometry. PSMA expression was highest in LNCaP followed by 22Rv1 and negligible in PC3 and A549 (FIG. 38C). These results were agreeing with number of PSMA molecules per LNCaP, 22Rv1, and PC3 cells reported by Wang and colleagues (35). Due to moderate PSMA expression levels and better tumorigenic capacity with low necrosis, 22Rv1 was selected as the primary cell line to characterize OTL78.

The affinity of OTL78 for PSMA was first screened by competing with DUPA-FITC. The absolute binding affinity (Kd) and specificity of DUPA-FITC for PSMA (Kd=6 nM, FIG. 38D) was first established using PSMA+22Rv1 and PSMA-negative PC3 cells. OTL78 was able to compete with DUPA-FITC for PSMA on 22Rv1 cells with IC50 of 7 nM (FIG. 38E). The affinity and specificity of OTL78 was then evaluated by incubating increasing concentrations of OTL78 with either 22Rv1 or PC3 cells and analyzing for cell bound fluorescence by Fluorometer. OTL78 was able to bind to PSMA on 22Rv1 cells with very high affinity (Kd=4.7 nM) whereas it did not bind to PSMA-negative PC3 cells confirming specificity of OTL78 to PSMA (FIG. 39B).

PSMA-mediate internalization of OTL78 was next evaluated by incubating OTL78 with 22Rv1 and PC3 cells. Analysis of fluorescence microscopy images indicate that OTL78 was able to efficiently label 22Rv1 and LNCaP cells [(FIG. 39C (i & ii)] but not PC3 cells [(FIG. 39C (iii & vi)] indicating PSMA-mediated uptake of OTL78. Fluorescence was detected throughout the cytoplasm of 22Rv1 and LNCaP cells at 37° C. Moreover, we also observed that OTL78 is highly concentrated and entrapped in the certain regions of 22Rv1 and LNCaP cells. Labelling of 22Rv1 and LNCaP cells with OTL78 in the presence a nuclear staining dye (DAPI) at 4° C. was also conducted to decrease the endocytosis and recycling of PSMA [FIG. 39Ff(i & ii)]. Epi-fluorescence images from this study indicated that OTL78 binds to PSMA on the cell surface. Therefore, we assume that OTL78 first binds to PSMA on the cell surface and then it undergoes receptor-mediated endocytosis. We further assume that OTL78 is entrapped in the acidic endosomes within PCa cells.

Example 10: In Vivo Specificity in Different Tumor Models

Experimental Procedures

Whole body Imaging & Tissue biodistribution: Seven-week-old male nu/nu mice were inoculated subcutaneously with 5.0×106 22Rv1, LNCaP, PC3 or A549 cells/mouse in 50% high concentrated matrigel with RPMI1640 medium on the shoulder. Growth of the tumors was measured in perpendicular directions every 2 days using a caliper (body weights were monitored on the same schedule), and the volumes of the tumors were calculated as 0.5×L×W2 (L=longest axis and W=axis perpendicular to L in millimeters). Once tumors reached approximately 300-400 mm3 in volume, animals (3-5 mice/group) were intravenously injected with appropriate dose of OTL78 in saline.

For orthotopic tumors, 2×105 22Rv1 cells/mouse in 10% high concentrated (HC) matrigel with RPMI1640 medium were surgically implanted in the prostate of seven-week-old male SCID mice. Briefly, seven-week-old male SCID mice were given 1-5% isoflurane for anesthesia and subcutaneous injection of 5 mg/kg meloxicam preoperatively for analgesia. The mice were placed dorsal side up and washed above the prostate with a chlorhexidine scrub to ensure a sterile area for incision. After an insertion was made using scalpel through the skin, the peritoneal lining was lifted to make a small incision using a scissor and widened using forceps. Dorsal lobes were exteriorized and gently stabilized with a wet (PBS) cotton swab. 22Rv1 cells (in 10 μL of 10% HC-matrigel) were injected the prostate using a 28-gage needle. After placing the prostate back into the peritoneum, the abdominal wall was sutured, the body wall was closed using 3-0 or 4-0 vicryl and the skin was closed using staples. Animals were monitored until use them for the studies. After one month, the animals were administered with OTL78 (10 nmol in 100 μL saline per mouse), euthanized after 2 h by CO2 asphyxiation, and imaged using AMI image system.

For whole body imaging and biodistribution studies, animals were euthanized after 2 h of administration of OTL78 by CO2 asphyxiation. For time dependent studies, animals were imaged under anesthesia using isoflurane. Imaging experiments were then performed using IVIS or AMI image systems. Following whole body imaging, animals were dissected and selected tissues were analyzed for fluorescence activity using IVIS or AMI image system and ROI of the tissues were calculated using Living Image 4.0 software or AMIView Image Analysis Software.

For ImageJ analysis, whole body imaging was acquired in gray scale and processed in ImageJ software. Either a line across the tumor or box around the tumor was drawn to define the fluorescence to be quantitated. The tumor-to-muscle ratio was analyzed using a plot of the fluorescence gray value versus distance.

Results and Conclusions: The ability of OTL78-mediated imaging of PCa was next established by conducting a series of experiments in mouse models. First, the optimal dose for tumor imaging was determined by administering increasing concentrations of OTL78 (0.3-120 nmol/mouse) to mice bearing 22Rv1 tumor xenografts followed by ex vivo tissue biodistribution analysis. The IVIS image analysis obtained at 2 hour time point indicated that OTL78 provided excellent TBR at dose range between 1-30 nmol per mouse with the best TBR occurring at ~3-10 nmol/mouse (FIG. 40A-B).

We next evaluated in vivo tumor specificity of OTL78 by administering 10 nmol of OTL78 to mice bearing subcutaneous 22Rv1, LNCaP, PC3 or A549 tumor xenografts followed by conducting whole body imaging and ex vivo tissue biodistribution using either IVIS or AMI image systems. Both studies demonstrated that OTL78 accumulated predominantly in PSMA expressing 22Rv1 (FIG. 41A, D and FIG. 42A, D) and LNCaP (FIG. 42B, E) tumors, with no substantial fluorescence activity in other tissues except kidneys. Although tumor accumulated fluorescence was not seen in PC3 and A549 tumors at higher threshold (FIGS. 40B-C & E-F), uptake of OTL78 was observed in both tumors at lower threshold (FIG. 40E-F: Lower panel). While fluorescence intensities of PC3 and A549 tumors were ~6 folds less compared to 22Rv1 tumors (FIG. 40A, D), fluorescence accumulation in PC3 and A549 tumors was higher than rest of the tissues except kidneys and skin (FIG. 43A-B). We therefore assume that the observed fluorescence in PC3 and A549 tumors maybe due to accumulation of OTL78 via PSMA in the neovasculature of PC3 and A549 solid tumors. This further suggests that OTL78 will be able to detect tumors with low PSMA expression levels. OTL78 also had a significant kidney uptake due to high PSMA expression in murine kidneys and clearance of OTL78 through the kidneys. More importantly, fluorescence in the kidneys were clearly visible in whole body images collected from AMI imager demonstrating penetrating ability of OTL78 to locate buried PSMA+ tissues. We assume that observed skin uptake maybe due to non-specific uptake of S0456 moiety of OTL78 molecule. Although skin uptake clears within 4-5 h, skin will not be interfered with open or robotic surgery because the camera will be directly focusing to the prostate in both techniques.

We then examined the ability of OTL78 to detect primary tumors in the prostate and regional metastasis in seminal vesicles. In that case, 22Rv1 cells were surgically implanted in the prostate of SCID mice as described in the SI Materials & Methods. Once tumors grow, the animals were imaged using AMI image system 2 h after administering of 10 nmol of OTL78. Orthotopic imaging studies also demonstrated that OTL78 mainly accumulated in prostate tumors with no fluorescence observed in other tissues except kidneys (FIG. 42C, F & FIG. 43C-D). Moreover, OTL78 was able to detect local regional metastasis in seminal vesicles in the presence of primary tumor (FIG. 43G & FIG. 43D) indicating ability of OTL78 locate tumors and lymph nodes that are buried under the prostate.

Following biodistribution studies, specificity of OTL78 for PSMA was quantitated by calculating TBR. In both subcutaneous and orthotopic tumor models, OTL78 displayed excellent TBR (FIG. 44A) ranging from 19:1-25:1 (tumor:muscle), 11:1-14:1 (tumor:lung), 11:1-15:1 (tumor:liver), 14:1-23:1 (tumor:heart), 19:1 (tumor:intestine), 11:1-20:1 (tumor:spleen), 4:1 (tumor:prostate), and 4:1-10:1 (tumor:skin). Observed better TBRs, especially tumor:skin, in orthotopic model compared to subcutaneous model may be due: (a) higher accumulation of OTL78 due to better tumor angiogenesis and (b) less non-specific skin uptake of NIR dye moiety in SCID mice.

Finally, the ability of OTL78 to define the tumor/healthy tissue boundaries was evaluated using ImageJ software analysis. The whole-body image of mice injected with 10 nmol of OTL78 was acquired as fluorescence in a gray scale and either a line or box (FIG. 44B) was drawn to quantitate the fluorescence to be defined in the tumor boundaries. As shown in FIG. 44C-D, OTL78 was able to define tumor boundaries precisely with a TBR of 5:1 suggesting its capability to guide surgeons to accurately detect the tumor margins (acceptable TBR for image-guided surgery is considered to be >1.5).

Example 11: Fluorescence-Guided Surgery of Prostate Tumors

Experimental Procedures

Tumor surgeries: Seven-week-old male nu/nu mice were inoculated subcutaneously with 5.0×106 22Rv1 cells/mouse in 50% high concentrated matrigel with RPMI1640 medium on the shoulder. Growth of the tumors was measured as previously mentioned. After one month, the animals were mixed and divided into 2 groups (n=5 mice/group). Two hours after administering OTL78 (10 nmol in 100 μL saline per mouse), animals were given 1-5% isoflurane for anesthesia and imaged using AMI image system. After an insertion was made using scalpel through the skin, surgical removal of the tumors was performed either following conventional technique (e.g. visualization under white light or palpation) or with the aid of fluorescence guidance (FGS: debulking of visible tumors under conventional method followed by resection of residual fluorescence tissues under image-guided method). After the surgery, the skin was closed using staples and imaged the mice using AMI image system. After imaging, the residual fluorescent tissues from selected mice of conventional surgery group and tissues samples from the tumor beds of selected mice of FGS group were submit for pathological (IHC) analysis. Response to surgical treatment was monitored for over 30 days by imaging using AMI image system 2 h after injecting OTL78 (10 nmol/mouse) and by measuring the growth of the tumor volume using a caliper. Any animal with tumor volume ≥1000 mm3 were euthanized. Tumor-free survival of the mice was documented as % survival vs. time using GraphPad Prism 6. IHC studies were done as explained bellow in the Safety Studies.

Results & Conclusions: The ability of OTL78 to guide surgeons to excise all cancerous tissues with negative tumor margins was next investigated by performing image-guided surgery in tumor bearing mice. Briefly, 10 nmol of OTL78 was administered into mice bearing 22Rv1 tumor xenografts and comparative study was conducted by performing surgeries under conventional (e.g. visualization under white light or palpation) or fluorescence-guided technology (i.e. debulking of visible tumors under conventional method followed by resection of residual fluorescence tissues under image-guided method) at 2 h time point. Preoperative fluorescence images of tumor bearing mice demonstrated that OTL78 able to localized 22Rv1 tumors with high contrast within 2 h (FIG. 45A: first column and FIG. 46). Postoperative fluorescence imagers indicated presence of residual fluorescent in the tumor bed of the conventional cohorts, whereas no significant fluorescence was observed in the FGS cohorts (FIG. 45A: middle column and FIG. 46). Pathological analysis of residual fluorescent tissues from the conventional surgery confirmed that the fluorescence is due to cancer cells (FIG. 45A-B: middle panel). More importantly, no residual tumors were identified in tissues from tumor margin/bed from the FGS cohorts (FIG. 46: right column). Following surgeries, biochemical recurrence (BCR) of the cancer was assessed by monitoring animals for over a month using fluorescence imaging. As anticipated, only the conventional surgery cohort had recurrence at the primary tumor site and no sign of BCR was observed in the FGS cohort during the study (FIG. 45A & FIG. 46). As shown in the survival curve (FIG. 45C), the FGS cohorts were survived during the study with no BCR whereas all mice in the conventional surgery group had to euthanize within 3 weeks. Although the observed BCR rate is higher than the reported values for human and mice, this proof of concept study highlights the importance of excising all cancerous tissues with negative tumor margins to improve the quality of life and life expectancy of the patient.

Example 12: Evaluation of Safety Profile of OTL78

Experimental Procedures

Safety Study: Seven-week-old healthy male Balb/c (5 mice/group) were administered with 6 μmol of freshly prepared OTL78 or saline dissolved in 100 μL of saline via tail vein injection on day zero. Body weights and clinical observations were monitored prior to dosing and daily thereafter from day zero to 14. Any animals with a body weight loss of 20% or more over two consecutive days would be euthanized, but this was not necessary.

For immunohistopathology (IHC) studies, the animals were euthanized by CO2 asphyxiation on the day 14 and selected tissues (brain, heart, lung, liver, spleen, kidney, stomach, small intestine, large intestine, muscle, and skin) were collected into vials containing 4% formalin. Formalin fixed tissues were sectioned into 10 μm thick sections and mounted onto Superfrost Plus™ slides (Fisher Scientific, Pittsburgh Pa.). After staining the slides with H&E, IHC analysis of the tissues was conducted to determine to the toxicity of OTL78.

For clinical pathology studies, the animals were euthanized by CO2 asphyxiation on the day 14 and blood was collected to heparin by cardiac punch and blood work analysis was conducted at Purdue clinical pathology lab.

Tolerability Studies: The blood samples were collected into hirudin tubes and used within an hour of collection. For each donor, 4 different tubes were prepared for allergen, positive controls, and negative control. Samples were analyzed using Flow CAST® high sensitivity Basophil Activation Test (BAT). Briefly, stimulation buffer (100 μL, background) or anti-FcεER antibody (100 μL) or fMLP (100 μL) or OTL78 (75 μM in 100 μL of saline) was added to tubes containing stimulation buffer (200 μL). 100 μL of blood was added to each tube and mixed gently. After adding staining reagent (40 μL) containing anti-CD63-CD203c-PE-DY647 and anti-CCR3-PE, each tube was mixed gently and incubated for 15 minutes at 37° C. Lysing reagent (2 mL) was added to each tube, mixed gently, incubated for 5-10 minutes at room temperature, and centrifuged for 5 minutes at 500×g. The supernatant was discarded and the cells were re-suspended in wash buffer (900 μL) and analyzed using flow cytometry. CD63-CD203c-PE-DY647+/CCR3-PE+ cell population considered as the activated basophils.

Figure 47D:
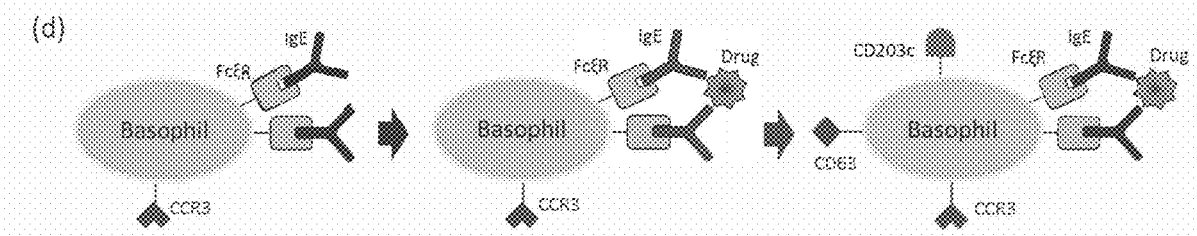
FIG. 47D—Possible mechanism for drug related hypersensitivity reactions due to activation of basophils and mast cells.

Results & Conclusions: Motivated by the specificity and PK properties described above, safety profile of OTL78 was then evaluated using ex vivo and in vivo models. The acute maximum tolerance dose of OTL78 was initially determined by injecting 6 μmol/mouse (600× of normal dose) to healthy Balb/c mice. Body weights and clinical observations were monitored during the study and histopathological analysis on selected tissues was then conducted on day 14 of post-injection. The animals were active after administration of OTL78 and behaved normally throughout the study. As shown in the FIG. 47A, body weights over the course of the study remained unchanged (<5% increase), suggesting that OTL78 is not grossly toxic to the animals. Moreover, no obvious pathological changers were detected in hematoxylin and eosin (H&E) staining conducted on any of the tissues (FIG. 47B and FIGS. 48A-48L). No noticeable toxicities were also noticed in clinical pathology analysis on blood samples collected from mice injected with OTL78 (6 μmol/mouse).

Possible OTL78-related hypersensitivity in human was next examined using basophil activation assay. Drug related hypersensitivity is mainly due to immune response caused by cross-linking of immunoglobulin E (IgE) expressed on mast cells and basophils (FIG. 47D) resulting in activation and subsequent degranulation to release vasoactive amines, prostaglandins, and cytokines (29). Since cross-linking of IgE can be due to aggregates, concentration dependent UV spectrometric studies were conducted to determine higher order aggregates of OTL78. As shown in the FIG. 47C, there were no noticeable higher order aggregates observed with OTL78 whereas the positive control (i.e. OTL38) (30) exhibited concentration dependent aggregation peak at λmax ~700 nm at 75 μM in saline.

Since basophils are readily available from blood samples when compared to tissue-resident mast cells, we then evaluated drug-related hypersensitivity due to monomer and low order aggregates (if present) of OTL78 using basophil activation test in human blood samples as described in the Method section. Briefly, 75 μM of OTL78 was first added to a tube containing whole blood from donors and stimulating buffer. After labeling with anti-CCR3 (CD193)-phycoerythrin and anti-CD63-CD203c-PE-DY647, the percentage of activated basophils was quantitated using flow cytometric analysis (31). As shown in the FIG. 47E and Table 2, no obvious differences in percentage activated basophils were seen between the OTL78 treated sample and negative control resulting in stimulated index of 1, whereas stimulated index is defined as the ratio of % basophil activation by the allergen: % basophil activation by background and stimulated index ≥2 considered as positive response (31). However, when similar assays were conducted using fMLP (a non-specific basophil activator) or anti-FcεER antibody, positive response of 73.5% (stimulated index=29.5) or 6.49% (stimulated index=2.6) was observed.

TABLE 2

Percent of basophile activation in healthy subjects

| Sample | Subject 1 | Subject 2 | Subject 3 | Avg | SI = Avg/background |
|---|---|---|---|---|---|
| fMLP | 73.5 | 55.9 | 50.6 | 60 | 23.1 |
| Anti-Fc$^e$R | 6.49 | 6.04 | 5.88 | 6.1 | 2.4 |
| OTL78 | 2.64 | 2.67 | 3.14 | 2.8 | 1.1 |
| Background | 2.50 | 2.65 | 2.76 | 2.6 | 1.0 |

Note:
fMLP = N-formylmethionyl-leucyl-phenylalanine is a non-specific cell activator, anti-FcεR = a high affinity monoclonal antibody binding to IgE, and stimulation index (SI) is defined as the ratio of % basophil activation by the allergen: % basophil activation by the background While this disclosure has been described as having an exemplary design, the present disclosure may be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains.

What is claimed is:

1. A method of optical or diagnostic imaging of lung tissue that express prostate specific membrane antigen (PSMA) in a subject, wherein the lung tissue is selected from the group consisting of diseased lung tissue, abnormal lung tissue, lung tumor lesions, lymph nodes with metastatic lung tumor cells, primary lung cancer cells, and secondary lung cancer cells, the method comprising:
  contacting the lung tissue with a composition comprising a compound, or a pharmaceutically acceptable salt of the compound, wherein the compound has the formula:
  B—X—Y—Z wherein
  B comprises a compound capable of binding to PSMA;
  X is selected from the group consisting of polyethylene glycol (PEG), N-amino-dPEG$_2$-acid, and polyethylene amine (PEA);
  Y comprises at least one amino acid, or a derivative thereof; and
  Z comprises a near-infrared (NIR) dye;
  illuminating the lung tissue with an excitation light of a wavelength absorbed by the compound; and detecting the optical signal emitted by the compound in the lung tissue.

2. The method of claim 1, wherein B is selected from the group consisting of a small molecule, ligand, inhibitor, agonist, and a derivative thereof.

3. The method of claim 1, wherein B is 2-[3-(1,3-dicarboxypropyl)-ureido]pentanedioic acid (DUPA) or derivative thereof.

4. The method of claim 1, wherein X is a length from 7 atoms to 30 atoms.

5. The method of claim 1 wherein Y comprises aromatic amino acids.

6. The method of claim 1 wherein Y is selected from the group consisting of phenylalanine-tyrosine, phenylalanine-serine, phenylalanine-tyramine, phenylalanine-cysteine, phenylalanine-methionine, phenylalanine-selenocyseteine, histidine-cysteine, phenylalanine-lysine, phenylalanine-ornithine, phenylalanine-arginine, histidine-lysine, phenylalanine-tyrosine, phenylalanine-cysteine, and histidine-tyrosine.

7. The method of claim 1, wherein Z the near-infrared dye is selected from the group consisting of, IR800, SP054, S0121, S2076, S0456,

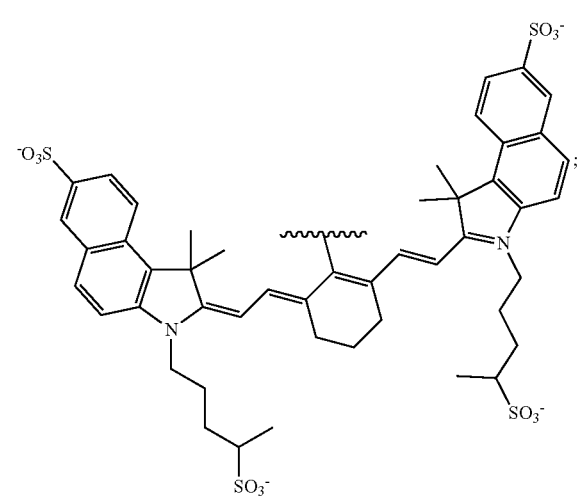

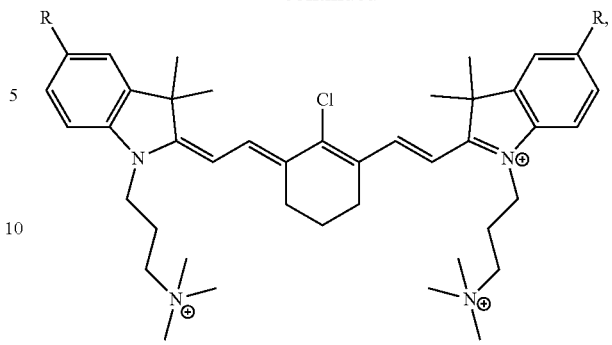

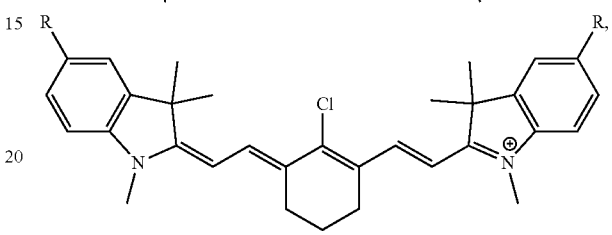

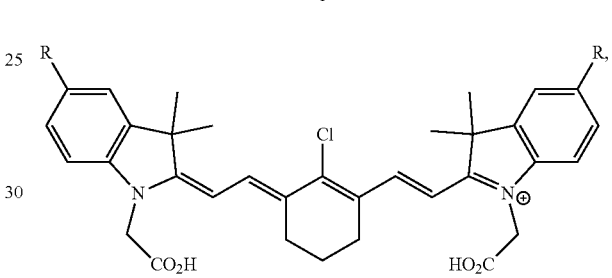

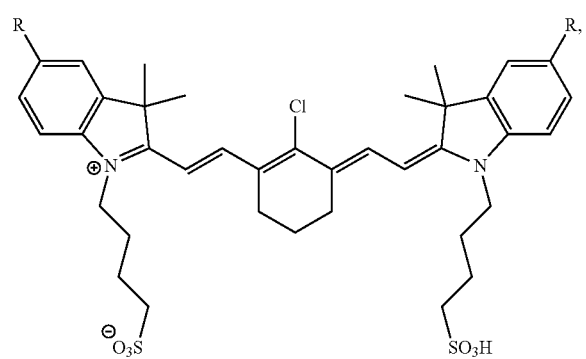

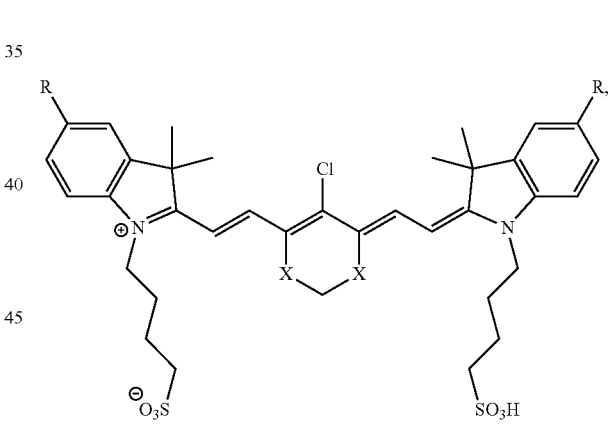

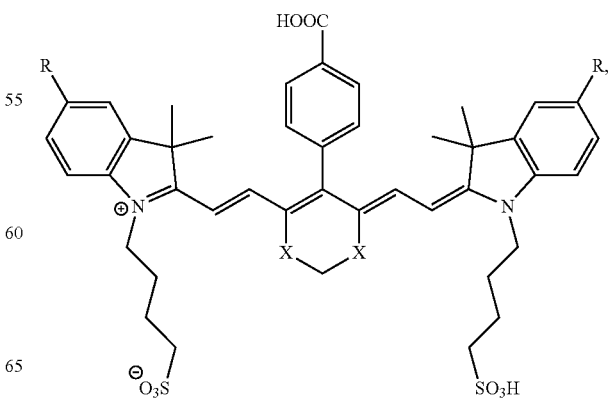

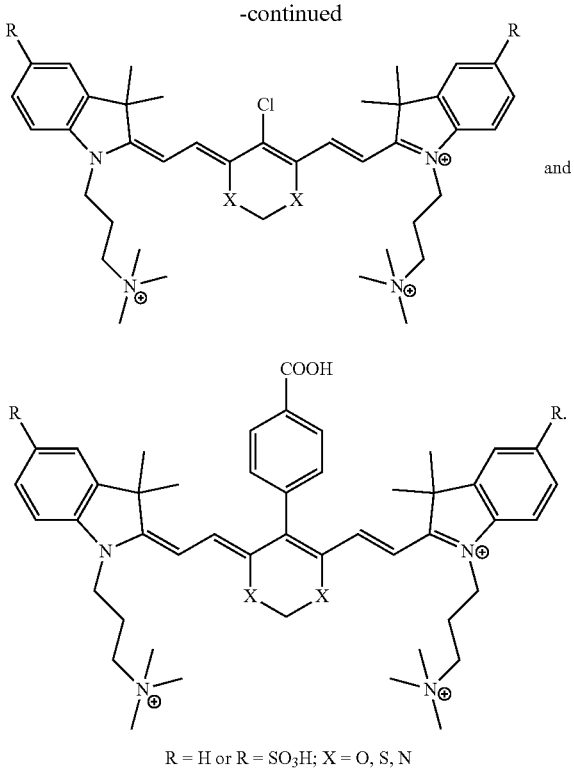

R = H or R = SO₃H; X = O, S, N

8. The method of claim 7, wherein the near-infrared dye is S0456.

9. The method of claim 1, wherein the compound has the formula:

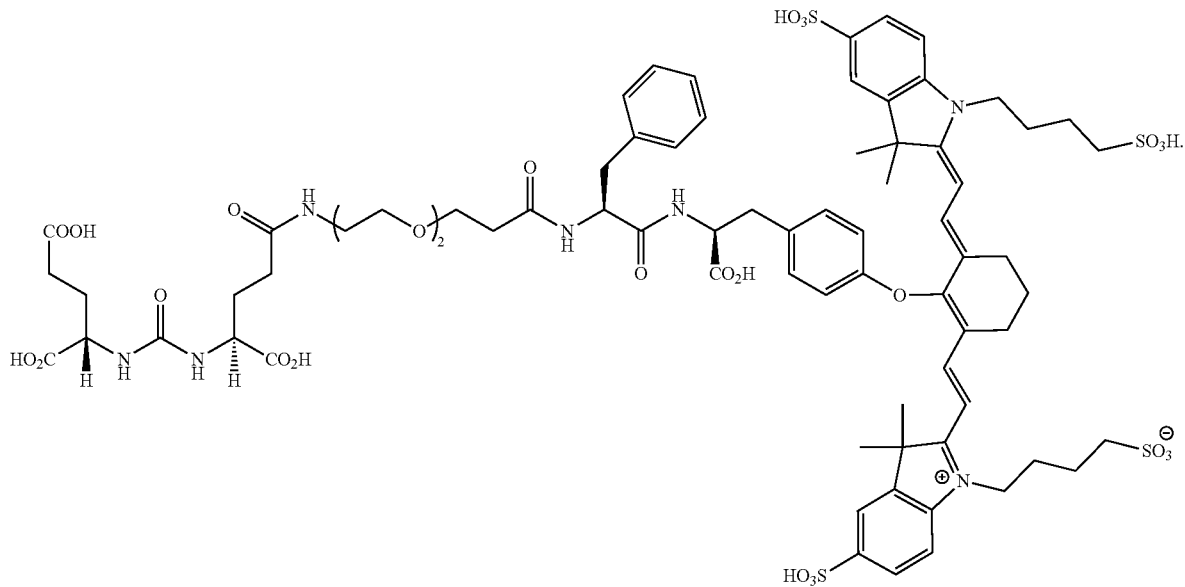

10. The method of claim 1, wherein the pharmaceutically acceptable salt of the compound is a sodium, potassium, and/or ammonium salt.

11. The method of claim 1, wherein the composition further comprises a pharmaceutically acceptable carrier, excipient, or diluent.

12. The method of claim 1, wherein diagnostic imaging of the lung tissue further comprises:
   diagnosing the subject with lung cancer.

13. The method of claim 1, wherein optical or diagnostic imaging is fluorescence-guided surgery or image-guided surgery.

14. The method of claim 1, wherein the primary lung cancer is non-small cell lung cancer, small cell lung cancer, carcinoid tumor, or a neuroendocrine tumor.

15. The method of claim 14, wherein the primary lung cancer is non-small cell lung cancer and the non-small cell lung cancer is selected from the group consisting of lung adenocarcinoma, squamous cell carcinoma, and large cell lung cancer.

16. The method of claim 1, wherein the lung tissue is secondary lung cancer cells and the secondary lung cancer cells originate from a cancer selected from the group consisting of breast cancer, colon cancer, kidney cancer, testicular cancer, bladder cancer, melanoma, bone cancer, sarcoma, and head and neck cancer.

17. The method of claim 1, wherein the subject is a human.

18. A method of diagnosing lung cancer in a subject, the method comprising:
   a) administering to the subject in need of diagnosis a composition comprising a compound under conditions and for a time sufficient for the compound to bind and accumulate in lung tissue that express prostate specific membrane antigen (PSMA), wherein the lung tissue is selected from the group consisting of diseased lung tissue, abnormal lung tissue, lung tumor lesions, lymph nodes with metastatic lung tumor cells, primary lung cancer cells, and secondary lung cancer cells, the compound having the formula: B—X—Y—Z wherein B comprises a compound capable of binding to PSMA;
X is selected from the group consisting of polyethylene glycol (PEG), N-amino-dPEG₂-acid, and polyethylene amine (PEA);
Y comprises at least one amino acid, or a derivative thereof; and
Z comprises a near-infrared (NIR) dye;

b) illuminating the compound to visualize the compound bound to the lung tissue using infrared light;
c) measuring fluorescent signal from the illuminated compound bound to the lung tissue;
d) comparing the fluorescent signal measured in step c) with at least one control data set, wherein the at least one control data set comprises a fluorescent signal from the compound contacted with a biological sample that does not comprise diseased lung tissue, abnormal lung tissue, lung tumor lesions, lymph nodes with metastatic lung tumor cells, primary lung cancer cells, and secondary lung cancer cells; and
e) diagnosing the subject with lung cancer based on step d).

19. The method of claim 18, wherein the subject is a human.

20. The method of claim 4, wherein X is a length from 7 atoms to 14 atoms.

* * * * *